(12) United States Patent
Hatayama et al.

(10) Patent No.: US 9,453,066 B2
(45) Date of Patent: Sep. 27, 2016

(54) FC BINDING PROTEIN AND METHOD FOR MANUFACTURING SAME

(75) Inventors: Kouta Hatayama, Ayase (JP); Yoshiharu Asaoka, Ayase (JP); Toru Tanaka, Ayase (JP); Teruhiko Ide, Ayase (JP)

(73) Assignees: Sagami Chemical Research Institute, Ayase-shi (JP); TOSOH CORPORATION, Shunan-shi (JP)

( * ) Notice: Subject to any disclaimer, the term of this patent is extended or adjusted under 35 U.S.C. 154(b) by 534 days.

(21) Appl. No.: 13/583,550

(22) PCT Filed: Mar. 10, 2011

(86) PCT No.: PCT/JP2011/001413
§ 371 (c)(1),
(2), (4) Date: Oct. 24, 2012

(87) PCT Pub. No.: WO2011/111393
PCT Pub. Date: Sep. 15, 2011

(65) Prior Publication Data
US 2013/0079499 A1 Mar. 28, 2013

(30) Foreign Application Priority Data

Mar. 10, 2010 (JP) ................................. 2010-052789
Feb. 24, 2011 (JP) ................................. 2011-038500

(51) Int. Cl.
| | |
|---|---|
| C07K 1/00 | (2006.01) |
| A23J 1/00 | (2006.01) |
| C07K 14/735 | (2006.01) |
| C07K 1/22 | (2006.01) |
| C07K 17/08 | (2006.01) |
| C07K 16/00 | (2006.01) |

(52) U.S. Cl.
CPC ........... *C07K 14/70535* (2013.01); *C07K 1/22* (2013.01); *C07K 17/08* (2013.01); *C07K 2319/21* (2013.01)

(58) Field of Classification Search
None
See application file for complete search history.

(56) References Cited

U.S. PATENT DOCUMENTS

| | | | |
|---|---|---|---|
| 6,911,321 B2 * | 6/2005 | Presta et al. ................. | 435/69.1 |
| 7,074,896 B1 | 7/2006 | Sondermann et al. | |
| 2013/0079499 A1 * | 3/2013 | Hatayama et al. ........ | 530/387.1 |

FOREIGN PATENT DOCUMENTS

| | | |
|---|---|---|
| EP | 1 006 183 A1 | 6/2000 |
| JP | 2002-531086 A | 9/2002 |
| JP | 2009-201403 A | 9/2009 |
| WO | 00/32767 A1 | 6/2000 |
| WO | 2009/107682 A1 | 9/2009 |

OTHER PUBLICATIONS

Janet M. Allen et al., "Isolation and Expression of Functional High-Affinity FC Receptor Complementary DNAs," Science, 1989, p. 378-381, vol. 243, No. 4889.
Extended European Search Report dated Sep. 25, 2013, issued in EP Application No. 11753056.8.
Database Geneseq: "Cynomolgus Monkey FcgammaRIalpha-chain protein", Oct. 6, 2003.
Database Geneseq: "Human Fc receptor I", May 10, 1999.
Paetz et al. "Recombinant soluble human Fcgamma receptor I with picomolar affinity for immunoglobulin G", Biochemical and Biophysical Research Communications, Academic Press Inc., Orlando, FL, vol. 338, No. 4 pp. 1811-1817.
Asaoka et al. "Engineering of recombinant human Fc-gamma receptor I by directed evolution", Protein Eng. Des. Sel., vol. 25, No. 12, Sep. 11, 2012, pp. 835-842.

* cited by examiner

*Primary Examiner* — Chun Dahle
(74) *Attorney, Agent, or Firm* — Sughrue Mion, PLLC

(57) ABSTRACT

Disclosed are: an Fc binding protein having increased stability with respect to heat, acid, and/or alkalinity compared with the wild type; a method for producing same; and a method for specifically isolating protein containing an Fc binding protein binding site using said Fc binding protein as a ligand for affinity chromatography.

An Fc binding protein was obtained having increased stability with respect to heat, acid, and/or alkalinity compared with the wild-type human Fc receptor by means of substituting at least one specific amino acid residue in the extracellular domain of the wild-type human Fc receptor with another amino acid residue. The Fc binding protein is useful as a ligand for affinity chromatography for example by immobilizing in a solid phase. Also, when the Fc binding protein is expressed using a host that has been transformed with an expression vector containing a polynucleotide coding for said protein, the amount of produced protein is increased compared with using a wild-type human Fc receptor.

6 Claims, 15 Drawing Sheets

SEQUENCE LISTING

<160> NUMBER OF SEQ ID NOS: 182

<210> SEQ ID NO 1
<211> LENGTH: 374
<212> TYPE: PRT
<213> ORGANISM: Homo sapiens
<300> PUBLICATION INFORMATION:
<308> DATABASE ACCESSION NUMBER: UniProt/P12314
<309> DATABASE ENTRY DATE: 2004-07-19
<313> RELEVANT RESIDUES IN SEQ ID NO: (1)..(374)

<400> SEQUENCE: 1

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
            340                 345                 350

```
Cys Gln Glu Gln Lys Glu Gln Leu Gln Glu Gly Val His Arg Lys
        355                 360                 365
Glu Pro Gln Gly Ala Thr
    370

<210> SEQ ID NO 2
<211> LENGTH: 313
<212> TYPE: PRT
<213> ORGANISM: Artificial sequence
<220> FEATURE:
<223> OTHER INFORMATION: Synthetic peptide

<400> SEQUENCE: 2

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Gln Val Asp Thr Thr Lys Ala Val Ile Thr Leu Gln Pro Pro Trp
        35                  40                  45

Val Ser Val Phe Gln Glu Glu Thr Val Thr Leu His Cys Glu Val Pro
    50                  55                  60

His Leu Pro Gly Ser Ser Ser Thr Gln Trp Phe Leu Asn Gly Thr Ala
65                  70                  75                  80

Ile Gln Thr Ser Thr Pro Ser Tyr Arg Ile Thr Ser Ala Ser Val Asn
                85                  90                  95

Asp Ser Gly Glu Tyr Arg Cys Gln Arg Gly Leu Ser Gly Arg Ser Asp
            100                 105                 110

Pro Ile Gln Leu Glu Ile His Arg Gly Trp Leu Leu Leu Gln Val Ser
        115                 120                 125

Ser Arg Val Leu Thr Glu Gly Glu Pro Leu Ala Leu Arg Cys His Ala
    130                 135                 140

Trp Lys Asp Lys Leu Val Tyr Asn Val Leu Tyr Tyr Arg Asn Gly Lys
145                 150                 155                 160

Ala Phe Lys Phe Phe His Trp Asn Ser Asn Leu Thr Ile Leu Lys Thr
                165                 170                 175

Asn Ile Ser His Asn Gly Thr Tyr His Cys Ser Gly Met Gly Lys His
            180                 185                 190

Arg Tyr Thr Ser Ala Gly Ile Ser Val Thr Val Lys Glu Leu Phe Pro
        195                 200                 205

Ala Pro Val Leu Asn Ala Ser Val Thr Ser Pro Leu Leu Glu Gly Asn
    210                 215                 220

Leu Val Thr Leu Ser Cys Glu Thr Lys Leu Leu Leu Gln Arg Pro Gly
225                 230                 235                 240

Leu Gln Leu Tyr Phe Ser Phe Tyr Met Gly Ser Lys Thr Leu Arg Gly
                245                 250                 255

Arg Asp Thr Ser Ser Glu Tyr Gln Ile Leu Thr Ala Arg Arg Glu Asp
            260                 265                 270

Ser Gly Leu Tyr Trp Cys Glu Ala Ala Thr Glu Asp Gly Asn Val Leu
        275                 280                 285

Lys Arg Ser Pro Glu Leu Glu Leu Gln Val Leu Gly Leu Gln Leu Pro
    290                 295                 300

Thr Pro Val His His His His His
305                 310

<210> SEQ ID NO 3
```

<211> LENGTH: 313
<212> TYPE: PRT
<213> ORGANISM: Artificial sequence
<220> FEATURE:
<223> OTHER INFORMATION: Synthetic peptide

<400> SEQUENCE: 3

```
Met Lys Ile Lys Thr Gly Ala Arg Ile Leu Ala Leu Ser Ala Leu Thr
1               5                   10                  15
Thr Met Met Phe Ser Ala Ser Ala Leu Ala Lys Ile Glu Glu Ala Met
                20                  25                  30
Gly Gln Val Asp Thr Thr Lys Ala Val Ile Thr Leu Gln Pro Pro Trp
            35                  40                  45
Val Ser Val Phe Gln Glu Glu Ser Val Thr Leu His Cys Glu Val Pro
    50                  55                  60
His Leu Pro Gly Ser Ser Ser Thr Gln Trp Phe Leu Asn Gly Thr Ala
65                  70                  75                  80
Ile Gln Thr Ser Thr Pro Ser Tyr Arg Ile Thr Ser Ala Ser Val Asn
                85                  90                  95
Asp Ser Gly Glu Tyr Arg Cys Gln Arg Gly Leu Ser Gly Arg Ser Asp
            100                 105                 110
Pro Ile Gln Leu Glu Val His Arg Gly Trp Leu Leu Leu Gln Val Ser
        115                 120                 125
Ser Arg Val Leu Thr Glu Gly Glu Pro Leu Ala Leu Arg Cys His Ala
    130                 135                 140
Trp Lys Asp Lys Leu Val Tyr Asn Val Leu Tyr Tyr Arg Asn Gly Lys
145                 150                 155                 160
Ala Phe Lys Phe Phe His Trp Asn Ser Asn Leu Thr Ile Leu Lys Thr
                165                 170                 175
Asn Ile Ser His Asn Gly Thr Tyr His Cys Ser Gly Met Gly Lys His
            180                 185                 190
Arg Tyr Thr Ser Ala Gly Ile Ser Val Thr Val Lys Glu Leu Phe Pro
        195                 200                 205
Ala Pro Val Leu Asn Ala Ser Val Thr Ser Pro Leu Leu Glu Gly Asn
    210                 215                 220
Leu Val Thr Leu Ser Cys Glu Thr Lys Leu Leu Leu Gln Arg Pro Gly
225                 230                 235                 240
Leu Gln Leu Tyr Phe Ser Phe Tyr Met Gly Ser Lys Thr Leu Arg Gly
                245                 250                 255
Arg Asp Thr Ser Ser Glu Tyr Gln Ile Leu Thr Ala Arg Arg Glu Asp
            260                 265                 270
Ser Gly Leu Tyr Trp Cys Glu Ala Ala Thr Glu Asp Gly Asn Val Leu
        275                 280                 285
Lys Arg Ser Pro Glu Leu Glu Leu Gln Val Leu Gly Leu Gln Leu Pro
    290                 295                 300
Thr Pro Val His His His His His
305                 310
```

<210> SEQ ID NO 4
<211> LENGTH: 313
<212> TYPE: PRT
<213> ORGANISM: Artificial sequence
<220> FEATURE:
<223> OTHER INFORMATION: Synthetic peptide

<400> SEQUENCE: 4

Met Lys Ile Lys Thr Gly Ala Arg Ile Leu Ala Leu Ser Ala Leu Thr

```
              1               5                  10                 15
            Thr Met Met Phe Ser Ala Ser Ala Leu Ala Lys Ile Glu Glu Ala Met
                           20                  25                 30
            Gly Gln Val Asp Thr Thr Lys Ala Val Ile Thr Leu Gln Pro Pro Trp
                           35                  40                 45
            Val Ser Val Phe Gln Glu Glu Ser Val Thr Leu His Cys Glu Val Pro
             50                  55                 60
            His Leu Pro Gly Ser Ser Thr Gln Trp Phe Leu Asn Gly Thr Ala
             65                  70                 75                 80
            Ile Gln Thr Ser Thr Pro Ser Tyr Arg Ile Thr Ser Ala Ser Val Asn
                           85                  90                 95
            Asp Ser Gly Glu Tyr Arg Cys Gln Arg Gly Leu Ser Gly Arg Ser Asp
                          100                 105                110
            Pro Ile Gln Leu Glu Val His Arg Gly Trp Leu Leu Leu Gln Val Ser
                          115                 120                125
            Ser Arg Val Leu Thr Glu Gly Glu Pro Leu Ala Leu Arg Cys His Ala
                    130                 135                140
            Trp Lys Asp Lys Leu Val Tyr Asn Val Leu Tyr Tyr Arg Asn Gly Lys
            145                 150                 155                160
            Ala Phe Lys Phe Phe His Trp Asn Ser Asn Leu Thr Ile Leu Lys Thr
                          165                 170                175
            Asn Met Ser His Ser Gly Thr Tyr His Cys Ser Gly Met Gly Lys His
                    180                 185                190
            Arg Tyr Thr Ser Ala Gly Ile Ser Val Thr Val Lys Glu Leu Phe Pro
                    195                 200                205
            Ala Pro Val Leu Asn Ala Ser Val Thr Ser Pro Leu Leu Glu Gly Asn
                    210                 215                220
            Leu Val Thr Leu Ser Cys Glu Thr Lys Leu Leu Leu Gln Arg Pro Gly
            225                 230                 235                240
            Leu Gln Leu Tyr Phe Ser Phe Tyr Met Gly Ser Lys Thr Leu Arg Gly
                          245                 250                255
            Arg Asp Thr Ser Ser Glu Tyr Gln Ile Leu Thr Ala Arg Arg Glu Asp
                    260                 265                270
            Ser Gly Leu Tyr Trp Cys Glu Ala Ala Thr Glu Asp Gly Asn Val Leu
                    275                 280                285
            Lys Arg Ser Pro Glu Leu Glu Leu Gln Val Leu Gly Leu Gln Leu Pro
                    290                 295                300
            Thr Pro Val His His His His His
            305                 310

<210> SEQ ID NO 5
<211> LENGTH: 313
<212> TYPE: PRT
<213> ORGANISM: Artificial sequence
<220> FEATURE:
<223> OTHER INFORMATION: Synthetic peptide

<400> SEQUENCE: 5

Met Lys Ile Lys Thr Gly Ala Arg Ile Leu Ala Leu Ser Ala Leu Thr
 1               5                  10                 15

Thr Met Met Phe Ser Ala Ser Ala Leu Ala Lys Ile Glu Glu Ala Met
                20                  25                 30

Gly Gln Val Asp Thr Pro Lys Ala Val Ile Lys Leu Gln Pro Pro Trp
                35                  40                 45

Val Ser Val Phe Gln Glu Glu Ser Val Thr Leu His Cys Glu Val Pro
```

```
                50                  55                  60
His Leu Pro Gly Ser Ser Thr Gln Trp Phe Leu Asn Gly Thr Ala
 65                  70                  75                  80

Ile Gln Thr Ser Thr Pro Thr Tyr His Ile Thr Ser Ala Ser Glu Asp
                 85                  90                  95

Asp Ser Gly Glu Tyr Arg Cys Gln Arg Gly Leu Ser Gly Arg Ser Asp
                100                 105                 110

Pro Ile Gln Leu Glu Val His Arg Gly Trp Leu Leu Gln Val Ser
            115                 120                 125

Ser Arg Val Leu Thr Glu Gly Glu Pro Leu Ala Leu Arg Cys His Ala
        130                 135                 140

Trp Lys Asp Lys Leu Val Tyr Asn Val Leu Tyr Tyr Arg Asn Gly Lys
145                 150                 155                 160

Ala Phe Lys Phe Phe His Trp Asn Ser Asn Leu Thr Ile Leu Lys Thr
                165                 170                 175

Asn Met Ser His Ser Gly Thr Tyr His Cys Ser Gly Met Gly Lys His
            180                 185                 190

Arg Tyr Thr Ser Ala Gly Ile Ser Val Thr Val Lys Glu Leu Phe Pro
        195                 200                 205

Ala Pro Val Leu Thr Ala Ser Val Thr Ser Pro Leu Leu Glu Gly Thr
    210                 215                 220

Pro Val Thr Leu Ser Cys Glu Thr Lys Leu Leu Leu Gln Arg Pro Gly
225                 230                 235                 240

Leu Gln Leu Tyr Phe Ser Phe Tyr Met Gly Ser Lys Thr Leu Arg Gly
                245                 250                 255

Arg Asp Thr Ser Ser Glu Tyr Gln Ile Leu Thr Ala Arg Arg Glu Asp
            260                 265                 270

Ser Gly Leu Tyr Trp Cys Glu Ala Ala Thr Glu Asp Gly Asn Val Leu
        275                 280                 285

Lys Arg Ser Pro Glu Leu Glu Leu Gln Val Leu Gly His Gln Gln Pro
    290                 295                 300

Thr Pro Val His His His His His His
305                 310

<210> SEQ ID NO 6
<211> LENGTH: 939
<212> TYPE: DNA
<213> ORGANISM: Artificial sequence
<220> FEATURE:
<223> OTHER INFORMATION: Synthetic polynucleotide

<400> SEQUENCE: 6
atgaaaataa aaacaggtgc acgcatcctc gcattatccg cattaacgac gatgatgttt      60
tccgcctcgg ctctcgccaa atcgaagaa gccatgggac aagtagatac caccaaagct     120
gtgattacgc tgcaaccacc gtgggtgagc gtgttccagg aagaaaccgt gacgttgcac     180
tgcgaagtac cgcatctgcc tgggtcaagt tcaacccaat ggttcctgaa tggcaccgcg     240
atccagacct ccaccccgtc ttaccgcatt acctccgcga gcgtaaacga ttcgggagaa     300
tatcgttgtc aacgtggcct gagcggccgt agcgatccga taacttgaa aattcatcgt     360 ggctggctgc ttttacaggt tagctcccgc gttttaaccg aaggcgaacc gcttgcatta     420
cgttgccacg catggaaaga taagctggtg tacaacgtgc tttactaccg caacggcaag     480
gcttttaagt tcttccactg gaactccaac ctgaccattc tgaagacgaa catttcccac     540
aacgggacgt accattgctc gggcatgggc aaacatcgtt atacgtcggc gggaatctcg     600
```

```
gtcaccgtca aagaactgtt tcccgcgccc gtgctgaatg cgagtgtgac aagcccgctg      660
cttgaaggca atctggtgac cctgagctgc gaaaccaaac tgctgttaca gcgtcccggc      720
ctgcagctgt atttctcgtt ctatatgggc agcaaaaccc tgcgcggacg cgatacctcg      780
agtgagtatc agattttaac cgcgcgtcgt gaagatagtg ggctgtactg gtgtgaagcg      840
gcgaccgagg atggcaatgt gcttaaacgg agcccagagc ttgagttgca agtgctgggt      900
cttcaactgc cgaccccggt ccatcatcat catcatcat                             939

<210> SEQ ID NO 7
<211> LENGTH: 939
<212> TYPE: DNA
<213> ORGANISM: Artificial sequence
<220> FEATURE:
<223> OTHER INFORMATION: Synthetic polynucleotide

<400> SEQUENCE: 7
atgaaaataa aaacaggtgc acgcatcctc gcattatccg cattaacgac gatgatgttt       60
tccgcctcgg ctctcgccaa aatcgaagaa gccatgggac aagtagatac caccaaagct      120
gtgattacgc tgcaaccacc gtgggtgagc gtgttccagg aagaatccgt gacgttgcac      180
tgcgaagtac cgcatctgcc tgggtcaagt tcaacccaat ggttcctgaa tggcaccgcg      240
atccagacct ccaccccgtc ttaccgcatt acctccgcga gcgtaaacga ttcgggagaa      300
tatcgttgtc aacgtggcct gagcggccgt agcgatccga taacttga agttcatcgt        360 ggctggctgc ttttacaggt tagctcccgc gttttaaccg aaggcgaacc gcttgcatta      420
cgttgccacg catggaaaga taagctggtg tacaacgtgc tttactaccg caacggcaag      480
gcttttaagt tcttccactg gaactccaac ctgaccattc tgaagacgaa catttcccac      540
aacgggacgt accattgctc gggcatgggc aaacatcgtt atacgtcggc gggaatctcg      600
gtcaccgtca aagaactgtt tcccgcgccc gtgctgaatg cgagtgtgac aagcccgctg      660
cttgaaggca atctggtgac cctgagctgc gaaaccaaac tgctgttaca gcgtcccggc      720
ctgcagctgt atttctcgtt ctatatgggc agcaaaaccc tgcgcggacg cgatacctcg      780
agtgagtatc agattttaac cgcgcgtcgt gaagatagtg ggctgtactg gtgtgaagcg      840
gcgaccgagg atggcaatgt gcttaaacgg agcccagagc ttgagttgca agtgctgggt      900
cttcaactgc cgaccccggt ccatcatcat catcatcat                             939

<210> SEQ ID NO 8
<211> LENGTH: 939
<212> TYPE: DNA
<213> ORGANISM: Artificial sequence
<220> FEATURE:
<223> OTHER INFORMATION: Synthetic polynucleotide

<400> SEQUENCE: 8
atgaaaataa aaacaggtgc acgcatcctc gcattatccg cattaacgac gatgatgttt       60
tccgcctcgg ctctcgccaa aatcgaagaa gccatgggac aagtagatac caccaaagct      120
gtgattacgc tgcaaccacc gtgggtgagc gtgttccagg aagaatccgt gacgttgcac      180
tgcgaagtac cgcatctgcc tgggtcaagt tcaacccaat ggttcctgaa tggcaccgcg      240
atccagacct ccaccccgtc ttaccgcatt acctccgcga gcgtaaacga ttcgggagaa      300
tatcgttgtc aacgtggcct gagcggccgt agcgatccga taacttga agttcatcgt        360 ggctggctgc ttttacaggt tagctcccgc gttttaaccg aaggcgaacc gcttgcatta      420
```

| | |
|---|---|
| cgttgccacg catggaaaga taagctggtg tacaacgtgc tttactaccg caacggcaag | 480 |
| gcttttaagt tcttccactg gaactccaac ctgaccattc tgaagacgaa catgtcccac | 540 |
| agcgggacgt accattgctc gggcatgggc aaacatcgtt atacgtcggc gggaatctcg | 600 |
| gtcaccgtca agaactgtt tcccgcgccc gtgctgaatg cgagtgtgac aagcccgctg | 660 |
| cttgaaggca atctggtgac cctgagctgc gaaaccaaac tgctgttaca gcgtcccggc | 720 |
| ctgcagctgt atttctcgtt ctatatgggc agcaaaaccc tgcgcggacg cgatacctcg | 780 |
| agtgagtatc agattttaac cgcgcgtcgt gaagatagtg ggctgtactg gtgtgaagcg | 840 |
| gcgaccgagg atggcaatgt gcttaaacgg agcccagagc ttgagttgca agtgctgggt | 900 |
| cttcaactgc cgaccccggt ccatcatcat catcatcat | 939 |

<210> SEQ ID NO 9
<211> LENGTH: 939
<212> TYPE: DNA
<213> ORGANISM: Artificial sequence
<220> FEATURE:
<223> OTHER INFORMATION: Synthetic polynucleotide

<400> SEQUENCE: 9

| | |
|---|---|
| atgaaaataa aaacaggtgc acgcatcctc gcattatccg cattaacgac gatgatgttt | 60 |
| tccgcctcgg ctctcgccaa aatcgaagaa gccatgggac aagtagatac ccccaaagct | 120 |
| gtgattaagc tgcaaccacc gtgggtgagc gtgttccagg aagaatccgt gacgttgcac | 180 |
| tgcgaagtac cgcatctgcc tgggtcaagt tcaacccaat ggttcctgaa tggcaccgcg | 240 |
| atccagacct ccaccccgac ttaccacatt acctccgcga gcgaagacga ttcgggagaa | 300 |
| tatcgttgtc aacgtggcct gagcggccgt agcgatccga tacaacttga agttcatcgt | 360 |
| ggctggctgc ttttacaggt tagctcccgc gttttaaccg aaggcgaacc gcttgcatta | 420 |
| cgttgccacg catggaaaga taagctggtg tacaacgtgc tttactaccg caacggcaag | 480 |
| gcttttaagt tcttccactg gaactccaac ctgaccattc tgaagacgaa catgtcccac | 540 |
| agcgggacgt accattgctc gggcatgggc aaacatcgtt atacgtcggc gggaatctcg | 600 |
| gtcaccgtca agaactgtt tcccgcgccc gtgctgactg cgagtgtgac aagcccgctg | 660 |
| cttgaaggca ctccggtgac cctgagctgc gaaaccaaac tgctgttaca gcgtcccggc | 720 |
| ctgcagctgt atttctcgtt ctatatgggc agcaaaaccc tgcgcggacg cgatacctcg | 780 |
| agtgagtatc agattttaac cgcgcgtcgt gaagatagtg ggctgtactg gtgtgaagcg | 840 |
| gcgaccgagg atggcaatgt gcttaaacgg agcccagagc ttgagttgca agtgctgggt | 900 |
| catcaacagc cgaccccggt ccatcatcat catcatcat | 939 |

<210> SEQ ID NO 10
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 10

| | |
|---|---|
| atgtggtttc tgaccacgct gttgctgtgg gtgccggt | 38 |

<210> SEQ ID NO 11
<211> LENGTH: 40
<212> TYPE: DNA
<213> ORGANISM: Artificial sequence
<220> FEATURE:
<223> OTHER INFORMATION: Synthetic oligonucleotide

```
<400> SEQUENCE: 11
tttggtggta tctacttggc catcaaccgg cacccacagc                                40

<210> SEQ ID NO 12
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 12
ggccaagtag ataccaccaa agctgtgatt acgctgcaac                                40

<210> SEQ ID NO 13
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 13
ggaacacgct cacccacggt ggttgcagcg taatcacagc                                40

<210> SEQ ID NO 14
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 14
gtgggtgagc gtgttccagg aagaaaccgt gacgttgcac                                40

<210> SEQ ID NO 15
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 15
aggcagatgc agtacttcgc agtgcaacgt cacggtttct                                40

<210> SEQ ID NO 16
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 16
cgaagtactg catctgcctg ggtcaagttc aacccaatgg                                40

<210> SEQ ID NO 17
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 17
gtcgcggtgc cattcaggaa ccattgggtt gaacttgacc                                40

<210> SEQ ID NO 18
```

```
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 18
ctgaatggca ccgcgaccca gacctccacc ccgtcttacc                      40

<210> SEQ ID NO 19
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 19
tttacgctcg cggaggtaat gcggtaagac ggggtggagg                      40

<210> SEQ ID NO 20
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 20
acctccgcga gcgtaaacga ttcgggagaa tatcgttgtc                      40

<210> SEQ ID NO 21
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 21
ggccgctcag gccacgttga caacgatatt ctcccgaatc                      40

<210> SEQ ID NO 22
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 22
gtggcctgag cggccgtagc gatccgatac aacttgaaat                      40

<210> SEQ ID NO 23
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 23
agcagccagc cacgatgaat ttcaagttgt atcggatcgc                      40

<210> SEQ ID NO 24
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 24
```
atcgtggctg gctgctttta caggttagct cccgcgtttt                    40

<210> SEQ ID NO 25
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 25
tgcaagcggt tcgccttcgg taaaaacgcg ggagctaacc                    40

<210> SEQ ID NO 26
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 26
aggcgaaccg cttgcattac gttgccacgc atggaaagat                    40

<210> SEQ ID NO 27
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 27
aagcacgttg tacaccagct tatctttcca tgcgtggcaa                    40

<210> SEQ ID NO 28
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 28
gctggtgtac aacgtgcttt actaccgcaa cggcaaggct                    40

<210> SEQ ID NO 29
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 29
tggagttcca gtggaagaac ttaaaagcct tgccgttgcg                    40

<210> SEQ ID NO 30
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 30
gttcttccac tggaactcca acctgaccat tctgaagacg                    40

<210> SEQ ID NO 31
<211> LENGTH: 40
<212> TYPE: DNA

<213> ORGANISM: Artificial sequence
<220> FEATURE:
<223> OTHER INFORMATION: Synthetic oligonucleotide

<400> SEQUENCE: 31
gtcccgttgt gggaaatgtt cgtcttcaga atggtcaggt                                    40

<210> SEQ ID NO 32
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 32
acatttccca caacgggacg taccattgct cgggcatggg                                    40

<210> SEQ ID NO 33
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 33
ccgccgacgt ataacgatgt ttgcccatgc ccgagcaatg                                    40

<210> SEQ ID NO 34
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 34
catcgttata cgtcggcggg aatctcggtc accgtcaaag                                    40

<210> SEQ ID NO 35
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 35
cacgggcgcg ggaaacagtt ctttgacggt gaccgagatt                                    40

<210> SEQ ID NO 36
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 36
ttcccgcgcc cgtgctgaat gcgagtgtga caagcccgct                                    40

<210> SEQ ID NO 37
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 37
gggtcaccag attgccttca agcagcgggc ttgtcacact                                    40

<210> SEQ ID NO 38
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 38
gaaggcaatc tggtgaccct gagctgcgaa accaaactgc                40

<210> SEQ ID NO 39
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 39
tgcaggccgg gacgctgtaa cagcagtttg gtttcgcagc                40

<210> SEQ ID NO 40
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 40
cgtcccggcc tgcagctgta tttctcgttc tatatgggca                40

<210> SEQ ID NO 41
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 41
ccgcgcaggg ttttgctgcc catatagaac gagaaataca                40

<210> SEQ ID NO 42
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 42
gcaaaaccct gcgcggacgc aatacctcga gtgagtatca                40

<210> SEQ ID NO 43
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 43
cgacgcgcgg ttaaaatctg atactcactc gaggtattgc                40

<210> SEQ ID NO 44
<211> LENGTH: 40
<212> TYPE: DNA
<213> ORGANISM: Artificial sequence
<220> FEATURE:

<223> OTHER INFORMATION: Synthetic oligonucleotide

<400> SEQUENCE: 44
gattttaacc gcgcgtcgtg aagatagtgg gctgtactgg           40

<210> SEQ ID NO 45
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 45
cctcggtcgc cgcttcacac cagtacagcc cactatcttc           40

<210> SEQ ID NO 46
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 46
aagcggcgac cgaggatggc aatgtgctta aacggagccc           40

<210> SEQ ID NO 47
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 47
agcacttgca actcaagctc tgggctccgt ttaagcacat           40

<210> SEQ ID NO 48
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 48
agcttgagtt gcaagtgctg ggtcttcaac tgccgacccc           40

<210> SEQ ID NO 49
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 49
aaacagcaca tgaaaccaga ccggggtcgg cagttgaaga           40

<210> SEQ ID NO 50
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 50
gtctggtttc atgtgctgtt ttacctggct gttgggatca           40

<210> SEQ ID NO 51
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 51
agcaccgtgt tgaccagaaa catgatccca acagccaggt                            40

<210> SEQ ID NO 52
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 52
tctggtcaac acggtgcttt gggtaaccat tcgcaaggaa                            40

<210> SEQ ID NO 53
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 53
cacttcttct tgcgcttcag ttccttgcga atggttaccc                            40

<210> SEQ ID NO 54
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 54
ctgaagcgca agaagaagtg ggacttggag atcagtctgg                            40

<210> SEQ ID NO 55
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 55
tttcttttca tggccgctgt ccagactgat ctccaagtcc                            40

<210> SEQ ID NO 56
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 56
acagcggcca tgaaaagaaa gttatcagca gcttgcagga                            40

<210> SEQ ID NO 57
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 57
cttcctcaag gtgacgatcc tcctgcaagc tgctgataac 40

<210> SEQ ID NO 58
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 58
ggatcgtcac cttgaggaag agctgaagtg ccaagaacaa 40

<210> SEQ ID NO 59
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 59
tcctgcagtt gctcctcttt ttgttcttgg cacttcagct 40

<210> SEQ ID NO 60
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 60
agaggagcaa ctgcaggaag gcgtgcatcg taaggagccg 40

<210> SEQ ID NO 61
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 61
ggtcgcgccc tgcggctcct tacgatgcac 30

<210> SEQ ID NO 62
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 62
tatacatatg aaaataaaaa caggtgcacg catcc 35

<210> SEQ ID NO 63
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 63
gcattaacga cgatgatgtt ttccgcctcg gctctcgcc 39

<210> SEQ ID NO 64
<211> LENGTH: 40

```
<212> TYPE: DNA
<213> ORGANISM: Artificial sequence
<220> FEATURE:
<223> OTHER INFORMATION: Synthetic oligonucleotide

<400> SEQUENCE: 64
atcgtcgtta atgcggataa tgcgaggatg cgtgcacctg                              40

<210> SEQ ID NO 65
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 65
ttgtcccatg gcttcttcga ttttggcgag agccg                                   35

<210> SEQ ID NO 66
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 66
tcagccatgg gacaagtaga taccaccaaa gctgtgatta                              40

<210> SEQ ID NO 67
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 67
ccaagcttaa tgatgatgat gatgatggac cggggtcggc agttgaagac ccag              54

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
taatacgact cactataggg                                                    20

<210> SEQ ID NO 69
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 69
tatgctagtt attgctcag                                                     19

<210> SEQ ID NO 70
<211> LENGTH: 1122
<212> TYPE: DNA
<213> ORGANISM: Artificial sequence
<220> FEATURE:
<223> OTHER INFORMATION: Synthetic polynucleotide

<400> SEQUENCE: 70
```

```
atgtggtttc tgaccacgct gttgctgtgg gtgccggttg atggccaagt agataccacc      60
aaagctgtga ttacgctgca accaccgtgg gtgagcgtgt tccaggaaga aaccgtgacg     120
ttgcactgcg aagtactgca tctgcctggg tcaagttcaa cccaatggtt cctgaatggc     180
accgcgaccc agacctccac cccgtcttac cgcattacct ccgcgagcgt aaacgattcg     240
ggagaatatc gttgtcaacg tggcctgagc ggccgtagcg atccgataca acttgaaatt     300
catcgtggct ggctgctttt acaggttagc tcccgcgttt ttaccgaagg cgaaccgctt     360
gcattacgtt gccacgcatg gaaagataag ctggtgtaca acgtgcttta ctaccgcaac     420
ggcaaggctt ttaagttctt ccactggaac tccaacctga ccattctgaa gacgaacatt     480
tcccacaacg ggacgtacca ttgctcgggc atgggcaaac atcgttatac gtcggcggga     540
atctcggtca ccgtcaaaga actgtttccc gcgcccgtgc tgaatgcgag tgtgacaagc     600
ccgctgcttg aaggcaatct ggtgaccctg agctgcgaaa ccaaactgct gttacagcgt     660
cccggcctgc agctgtattt ctcgttctat atgggcagca aaaccctgcg cggacgcaat     720
acctcgagtg agtatcagat tttaaccgcg cgtcgtgaag atagtgggct gtactggtgt     780
gaagcggcga ccgaggatgg caatgtgctt aaacggagcc agagcttga gttgcaagtg      840
ctgggtcttc aactgccgac cccggtctgg tttcatgtgc tgttttacct ggctgttggg     900
atcatgtttc tggtcaacac ggtgctttgg gtaaccattc gcaaggaact gaagcgcaag     960
aagaagtggg acttggagat cagtctggac agcggccatg aaaagaaagt tatcagcagc    1020
ttgcaggagg atcgtcacct tgaggaagag ctgaagtgcc aagaacaaaa agaggagcaa    1080
ctgcaggaag gcgtgcatcg taaggagccg cagggcgcga cc                       1122
```

<210> SEQ ID NO 71
<211> LENGTH: 374
<212> TYPE: PRT
<213> ORGANISM: Artificial sequence
<220> FEATURE:
<223> OTHER INFORMATION: Synthetic peptide

<400> SEQUENCE: 71

```
Met Trp Phe Leu Thr Thr Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
```

```
                165                 170                 175
Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
            195                 200                 205

Thr Leu Ser Cys Glu Thr Lys Leu Leu Leu Gln Arg Pro Gly Leu Gln
        210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
        355                 360                 365

Glu Pro Gln Gly Ala Thr
        370
```

<210> SEQ ID NO 72
<211> LENGTH: 949
<212> TYPE: DNA
<213> ORGANISM: Artificial sequence
<220> FEATURE:
<223> OTHER INFORMATION: Synthetic polynucleotide

<400> SEQUENCE: 72

```
catatgaaaa taaaaacagg tgcacgcatc ctcgcattat ccgcattaac gacgatgatg      60
ttttccgcct cggctctcgc caaaatcgaa gaagccatgg acaagtagaa taccaccaaa     120
gctgtgatta cgctgcaacc accgtgggtg agcgtgttcc aggaagaaac cgtgacgttg     180
cactgcgaag tactgcatct gcctgggtca agttcaaccc aatggttcct gaatggcacc     240
gcgacccaga cctccacccc gtcttaccgc attacctccg cgagcgtaaa cgattcggga     300
gaatatcgtt gtcaacgtgg cctgagcggc cgtagcgatc cgatacaact tgaaattcat     360
cgtggctggc tgcttttaca ggttagctcc cgcgttttta ccgaaggcga accgcttgca     420
ttacgttgcc acgcatggaa agataagctg gtgtacaacg tgctttacta ccgcaacggc     480
aaggctttta agttcttcca ctggaactcc aacctgacca ttctgaagac gaacatttcc     540
cacaacggga cgtaccattg ctcgggcatg ggcaaacatc gttatacgtc ggcgggaatc     600
tcggtcaccg tcaaagaact gtttcccgcg cccgtgctga atgcgagtgt gacaagcccg     660
ctgcttgaag gcaatctggt gaccctgagc tgcgaaacca aactgctgtt acagcgtccc     720
ggcctgcagc tgtatttctc gttctatatg ggcagcaaaa ccctgcgcgg acgcaatacc     780
tcgagtgagt atcagatttt aaccgcgcgt cgtgaagata gtgggctgta ctggtgtgaa     840
```

```
gcggcgaccg aggatggcaa tgtgcttaaa cggagcccag agcttgagtt gcaagtgctg    900
ggtcttcaac tgccgacccc ggtccatcat catcatcatc attaagctt               949
```

<210> SEQ ID NO 73
<211> LENGTH: 313
<212> TYPE: PRT
<213> ORGANISM: Artificial sequence
<220> FEATURE:
<223> OTHER INFORMATION: Synthetic peptide

<400> SEQUENCE: 73

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Gln Val Asp Thr Thr Lys Ala Val Ile Thr Leu Gln Pro Pro Trp
        35                  40                  45

Val Ser Val Phe Gln Glu Glu Thr Val Thr Leu His Cys Glu Val Leu
    50                  55                  60

His Leu Pro Gly Ser Ser Ser Thr Gln Trp Phe Leu Asn Gly Thr Ala
65                  70                  75                  80

Thr Gln Thr Ser Thr Pro Ser Tyr Arg Ile Thr Ser Ala Ser Val Asn
                85                  90                  95

Asp Ser Gly Glu Tyr Arg Cys Gln Arg Gly Leu Ser Gly Arg Ser Asp
            100                 105                 110

Pro Ile Gln Leu Glu Ile His Arg Gly Trp Leu Leu Leu Gln Val Ser
        115                 120                 125

Ser Arg Val Phe Thr Glu Gly Glu Pro Leu Ala Leu Arg Cys His Ala
    130                 135                 140

Trp Lys Asp Lys Leu Val Tyr Asn Val Leu Tyr Tyr Arg Asn Gly Lys
145                 150                 155                 160

Ala Phe Lys Phe Phe His Trp Asn Ser Asn Leu Thr Ile Leu Lys Thr
                165                 170                 175

Asn Ile Ser His Asn Gly Thr Tyr His Cys Ser Gly Met Gly Lys His
            180                 185                 190

Arg Tyr Thr Ser Ala Gly Ile Ser Val Thr Val Lys Glu Leu Phe Pro
        195                 200                 205

Ala Pro Val Leu Asn Ala Ser Val Thr Ser Pro Leu Leu Glu Gly Asn
    210                 215                 220

Leu Val Thr Leu Ser Cys Glu Thr Lys Leu Leu Leu Gln Arg Pro Gly
225                 230                 235                 240

Leu Gln Leu Tyr Phe Ser Phe Tyr Met Gly Ser Lys Thr Leu Arg Gly
                245                 250                 255

Arg Asn Thr Ser Ser Glu Tyr Gln Ile Leu Thr Ala Arg Arg Glu Asp
            260                 265                 270

Ser Gly Leu Tyr Trp Cys Glu Ala Ala Thr Glu Asp Gly Asn Val Leu
        275                 280                 285

Lys Arg Ser Pro Glu Leu Glu Leu Gln Val Leu Gly Leu Gln Leu Pro
    290                 295                 300

Thr Pro Val His His His His His
305                 310
```

<210> SEQ ID NO 74
<211> LENGTH: 27
<212> TYPE: DNA
<213> ORGANISM: Artificial sequence

```
<220> FEATURE:
<223> OTHER INFORMATION: Synthetic oligonucleotide

<400> SEQUENCE: 74
aggaaccatt gggttgaact tgaccca                                        27

<210> SEQ ID NO 75
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 75
tgggtcaagt tcaacccaat ggttcct                                        27

<210> SEQ ID NO 76
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 76
agcagccagc cacgatgaat ttcaagttgt atcggatcgc                          40

<210> SEQ ID NO 77
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 77
gtggcctgag cggccgtagc gatccgatac aacttgaaat                          40

<210> SEQ ID NO 78
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 78
ccgcgcaggg ttttgctgcc catatagaac gagaaataca                          40

<210> SEQ ID NO 79
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 79
cgtcccggcc tgcagctgta tttctcgttc tatatgggca                          40

<210> SEQ ID NO 80
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 80
tgcaacgtca cggattcttc ctggaa                                         26
```

<210> SEQ ID NO 81
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 81
ttccaggaag aatccgtgac gttgca                    26

<210> SEQ ID NO 82
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 82
cagccagcca cgatgaactt caagtt                    26

<210> SEQ ID NO 83
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 83
aacttgaagt tcatcgtggc tggctg                    26

<210> SEQ ID NO 84
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 84
tacgtcccgc tgtgggacat gttcgtcttc aga             33

<210> SEQ ID NO 85
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 85
tctgaagacg aacatgtccc acagcgggac gta             33

<210> SEQ ID NO 86
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 86
tgcagcttaa tcacagcttt gggggtat                   28

<210> SEQ ID NO 87
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 87 ataccccccaa agctgtgatt aagctgca                                28

<210> SEQ ID NO 88
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 88
cgctcgcgga ggtaatgtgg taagtcgggg t                             31

<210> SEQ ID NO 89
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 89
attacctccg cgagcgaaga cgattcg                                  27

<210> SEQ ID NO 90
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 90
tcaagcagcg ggcttgtcac actcgcagtc agca                          34

<210> SEQ ID NO 91
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 91
acaagcccgc tgcttgaagg cactccggtg a                             31

<210> SEQ ID NO 92
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 92
tcggctgttg atgacccagc acttgcaa                                 28

<210> SEQ ID NO 93
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 93
ttgcaagtgc tgggtcatca acagccga                                 28

<210> SEQ ID NO 94

```
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 94
acgtcacgga ttctccctgg aacacgctca                                    30

<210> SEQ ID NO 95
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 95
tgagcgtgtt ccagggagaa tccgtgacgt                                    30

<210> SEQ ID NO 96
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 96
agacagatgc ggtgcttcgc agtgcaa                                       27

<210> SEQ ID NO 97
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 97
ttgcactgcg aagcaccgca tctgtct                                       27

<210> SEQ ID NO 98
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 98
aacttgaccc agacagatgc ggtactt                                       27

<210> SEQ ID NO 99
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 99
aagtaccgca tctgtctggg tcaagtt                                       27

<210> SEQ ID NO 100
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 100
```

```
gggtggaggc ctggatcgcg gtgtcattca gga                              33

<210> SEQ ID NO 101
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 101
tcctgaatga caccgcgatc caggcctcca ccc                              33

<210> SEQ ID NO 102
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 102
ttgtggtagt aaagcacgtt gtgcaccagc tt                               32

<210> SEQ ID NO 103
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 103
tgcacaacgt gctttactac cacaacggca a                                31

<210> SEQ ID NO 104
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 104
aggttggagt tccggtggaa gaacttaa                                    28

<210> SEQ ID NO 105
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 105
ttaagttctt ccaccggaac tccaacct                                    28

<210> SEQ ID NO 106
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 106
tgtgggacgt gttcgtcttc ggaatggtca                                  30

<210> SEQ ID NO 107
<211> LENGTH: 30
<212> TYPE: DNA
```

<213> ORGANISM: Artificial sequence
<220> FEATURE:
<223> OTHER INFORMATION: Synthetic oligonucleotide

<400> SEQUENCE: 107
tgaccattcc gaagacgaac acgtcccaca                                    30

<210> SEQ ID NO 108
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 108
tcccgccgac gtataacgat gtctgcccat                                    30

<210> SEQ ID NO 109
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 109
acatcgttat acgtcggcgg gaacctcggt ca                                 32

<210> SEQ ID NO 110
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 110
agggtcacct gagtgccttc atgcagcgg                                     29

<210> SEQ ID NO 111
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 111
ccgctgcatg aaggcactca ggtgaccct                                     29

<210> SEQ ID NO 112
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 112
cgcagggttt tgctgccctt atagaacga                                     29

<210> SEQ ID NO 113
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 113
tcgttctata agggcagcaa aaccctgcg                                     29

<210> SEQ ID NO 114
<211> LENGTH: 313
<212> TYPE: PRT
<213> ORGANISM: Artificial sequence
<220> FEATURE:
<223> OTHER INFORMATION: Synthetic peptide

<400> SEQUENCE: 114

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
                20                  25                  30

Gly Gln Val Asp Thr Pro Lys Ala Val Ile Lys Leu Gln Pro Pro Trp
            35                  40                  45

Val Ser Val Phe Gln Gly Glu Ser Val Thr Leu His Cys Glu Ala Pro
50                  55                  60

His Leu Ser Gly Ser Ser Ser Thr Gln Trp Phe Leu Asn Asp Thr Ala
65                  70                  75                  80

Ile Gln Ala Ser Thr Pro Thr Tyr His Ile Thr Ser Ala Ser Glu Asp
                85                  90                  95

Asp Ser Gly Glu Tyr Arg Cys Gln Arg Gly Leu Ser Gly Arg Ser Asp
            100                 105                 110

Pro Ile Gln Leu Glu Val His Arg Gly Trp Leu Leu Leu Gln Val Ser
        115                 120                 125

Ser Arg Val Leu Thr Glu Gly Glu Pro Leu Ala Leu Arg Cys His Ala
130                 135                 140

Trp Lys Asp Lys Leu Val His Asn Val Leu Tyr Tyr His Asn Gly Lys
145                 150                 155                 160

Ala Phe Lys Phe Phe His Arg Asn Ser Asn Leu Thr Ile Pro Lys Thr
                165                 170                 175

Asn Thr Ser His Ser Gly Thr Tyr His Cys Ser Gly Met Gly Arg His
            180                 185                 190

Arg Tyr Thr Ser Ala Gly Thr Ser Val Thr Val Lys Glu Leu Phe Pro
        195                 200                 205

Ala Pro Val Leu Thr Ala Ser Val Thr Ser Pro Leu His Glu Gly Thr
210                 215                 220

Gln Val Thr Leu Ser Cys Glu Thr Lys Leu Leu Leu Gln Arg Pro Gly
225                 230                 235                 240

Leu Gln Leu Tyr Phe Ser Phe Tyr Lys Gly Ser Lys Thr Leu Arg Gly
                245                 250                 255

Arg Asp Thr Ser Ser Glu Tyr Gln Ile Leu Thr Ala Arg Arg Glu Asp
            260                 265                 270

Ser Gly Leu Tyr Trp Cys Glu Ala Ala Thr Glu Asp Gly Asn Val Leu
        275                 280                 285

Lys Arg Ser Pro Glu Leu Glu Leu Gln Val Leu Gly His Gln Gln Pro
    290                 295                 300

Thr Pro Val His His His His His His
305                 310

<210> SEQ ID NO 115
<211> LENGTH: 939
<212> TYPE: DNA
<213> ORGANISM: Artificial sequence
<220> FEATURE:
<223> OTHER INFORMATION: Synthetic polynucleotide

<400> SEQUENCE: 115

```
atgaaaataa aaacaggtgc acgcatcctc gcattatccg cattaacgac gatgatgttt      60
tccgcctcgg ctctcgccaa aatcgaagaa gccatgggac aagtagatac ccccaaagct     120
gtgattaagc tgcaaccacc gtgggtgagc gtgttccagg gagaatccgt gacgttgcac     180
tgcgaagcac cgcatctgtc tgggtcaagt tcaacccaat ggttcctgaa tgacaccgcg     240
atccaggcct ccaccccgac ttaccacatt acctccgcga gcgaagacga ttcgggagaa     300
tatcgttgtc aacgtggcct gagcggccgt agcgatccga taacttgaa gttcatcgt      360
ggctggctgc ttttacaggt tagctcccgc gttttaaccg aaggcgaacc gcttgcatta     420
cgttgccacg catggaaaga taagctggtg cacaacgtgc tttactacca caacggcaag     480
gcttttaagt tcttccaccg gaactccaac ctgaccattc gaagacgaa cacgtcccac      540
agcgggacgt accattgctc gggcatgggc agacatcgtt atacgtcggc gggaacctcg     600
gtcaccgtca aagaactgtt tcccgcgccc gtgctgactg cgagtgtgac aagcccgctg     660
catgaaggca ctcaggtgac cctgagctgc gaaaccaaac tgctgttaca gcgtcccggc     720
ctgcagctgt atttctcgtt ctataagggc agcaaaaccc tgcgcggacg cgataacctcg    780
agtgagtatc agattttaac cgcgcgtcgt gaagatagtg ggctgtactg gtgtgaagcg     840
gcgaccgagg atggcaatgt gcttaaacgg agcccagagc ttgagttgca agtgctgggt     900
catcaacagc cgaccccggt ccatcatcat catcatcat                           939
```

<210> SEQ ID NO 116
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 116

```
atgcggtgct tcgcagtgca tcgtcacgga ttctcccagg aaca                       44
```

<210> SEQ ID NO 117
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 117

```
gacgatgcac tgcgaagcac cgcatctgtc tgggtcaggt tcaa                       44
```

<210> SEQ ID NO 118
<211> LENGTH: 313
<212> TYPE: PRT
<213> ORGANISM: Artificial sequence
<220> FEATURE:
<223> OTHER INFORMATION: Synthetic peptide

<400> SEQUENCE: 118

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Gln Val Asp Thr Pro Lys Ala Val Ile Lys Leu Gln Pro Pro Trp
        35                  40                  45

Val Ser Val Phe Leu Gly Glu Ser Val Thr Met His Cys Glu Ala Pro
    50                  55                  60
```

```
His Leu Ser Gly Ser Gly Ser Thr Gln Trp Phe Leu Asn Asp Thr Ala
 65                  70                  75                  80

Ile Gln Ala Ser Thr Pro Thr Tyr His Ile Thr Ser Ala Ser Glu Asp
                 85                  90                  95

Asp Ser Gly Glu Tyr Arg Cys Gln Arg Gly Leu Ser Gly Arg Ser Asp
            100                 105                 110

Pro Ile Gln Leu Glu Val His Arg Gly Trp Leu Leu Leu Gln Val Ser
        115                 120                 125

Ser Arg Val Leu Thr Glu Gly Glu Pro Leu Ala Leu Arg Cys His Ala
130                 135                 140

Trp Lys Asp Lys Leu Val His Asn Val Leu Tyr Tyr His Asn Gly Lys
145                 150                 155                 160

Ala Phe Lys Phe Phe His Arg Asn Ser Thr Leu Thr Ile Pro Lys Thr
                165                 170                 175

Asn Thr Ser His Ser Gly Thr Tyr His Cys Ser Gly Met Gly Arg His
            180                 185                 190

Arg Tyr Thr Ser Ala Gly Thr Ser Val Thr Val Lys Glu Leu Phe Pro
        195                 200                 205

Ala Pro Val Leu Thr Ala Ser Val Thr Ser Pro Leu His Glu Gly Thr
210                 215                 220

Gln Val Thr Leu Ser Cys Glu Thr Lys Leu Leu Leu Gln Arg Pro Gly
225                 230                 235                 240

Leu Gln Leu Tyr Phe Ser Phe Tyr Lys Gly Ser Lys Thr Leu Arg Gly
                245                 250                 255

Arg Asp Thr Ser Ser Glu Tyr Gln Ile Leu Thr Ala Arg Arg Glu Asp
            260                 265                 270

Ser Gly Leu Tyr Trp Cys Glu Ala Ala Thr Glu Asp Gly Asn Val Leu
        275                 280                 285

Lys Arg Ser Pro Glu Leu Glu Leu Gln Val Leu Gly His Gln Gln Pro
    290                 295                 300

Thr Pro Val His His His His His His
305                 310

<210> SEQ ID NO 119
<211> LENGTH: 939
<212> TYPE: DNA
<213> ORGANISM: Artificial sequence
<220> FEATURE:
<223> OTHER INFORMATION: Synthetic polynucleotide

<400> SEQUENCE: 119
atgaaaataa aaacaggtgc acgcatcctc gcattatccg cattaacgac gatgatgttt      60
tccgcctcgg ctctcgccaa aatcgaagaa gccatgggac aagtagatac ccccaaagct     120
gtgattaagc tgcaaccacc gtgggtgagc gtgttcctgg agaatccgt gacgatgcac      180 tgcgaagcac cgcatctgtc tgggtcaggt tcaacccaat ggttcctgaa tgacaccgcg     240
atccaggcct ccaccccgac ttaccacatt acctccgcga gcgaagacga ttcgggagaa     300
tatcgttgtc aacgtggcct gagcggccgt agcgatccga taacttga agttcatcgt       360 ggctggctgc ttttacaggt tagctcccgc gttttaaccg aaggcgaacc gcttgcatta     420
cgttgccacg catggaaaga taagctggtg cacaacgtgc tttactacca caacggcaag     480
gcttttaagt tcttccaccg gaactccacc ctgaccattc cgaagacgaa cacgtcccac     540
agcgggacgt accattgctc gggcatgggc agacatcgtt atacgtcggc gggaaccccg     600
```

```
gtcaccgtca aagaactgtt tcccgcgccc gtgctgactg cgagtgtgac aagcccgctg    660
catgaaggca ctcaggtgac cctgagctgc gaaaccaaac tgctgttaca gcgtcccggc    720
ctgcagctgt atttctcgtt ctataagggc agcaaaaccc tgcgcggacg cgatacctcg    780
agtgagtatc agattttaac cgcgcgtcgt gaagatagtg ggctgtactg gtgtgaagcg    840
gcgaccgagg atggcaatgt gcttaaacgg agcccagagc ttgagttgca agtgctgggt    900
catcaacagc cgaccccggt ccatcatcat catcatcat                           939
```

<210> SEQ ID NO 120
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 120

```
tcagccatgg gacaagtaga tacccccaaa gctgtgatta                           40
```

<210> SEQ ID NO 121
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 121

```
ccaagcttaa tgatgatgat gatgatggac cggggtcggc tgttgatgac ccag           54
```

<210> SEQ ID NO 122
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 122

```
cagcttatct ctccatgcgt ggcaa                                           25
```

<210> SEQ ID NO 123
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 123

```
ttgccacgca tggagagata agctg                                           25
```

<210> SEQ ID NO 124
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 124

```
acgtgttcgt cctcggaatg gtcagggt                                        28
```

<210> SEQ ID NO 125
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 125
accctgacca ttccgaggac gaacacgt                                              28

<210> SEQ ID NO 126
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 126
acgctgtatc agcagtttgg ttacgcagct ca                                        32

<210> SEQ ID NO 127
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 127
tgagctgcgt aaccaaactg ctgatacagc gt                                        32

<210> SEQ ID NO 128
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 128
acgacgcgcg gctaaaatct gatact                                               26

<210> SEQ ID NO 129
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 129
agtatcagat tttagccgcg cgtcgt                                               26

<210> SEQ ID NO 130
<211> LENGTH: 313
<212> TYPE: PRT
<213> ORGANISM: Artificial sequence
<220> FEATURE:
<223> OTHER INFORMATION: Synthetic peptide

<400> SEQUENCE: 130

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Gln Val Asp Thr Pro Lys Ala Val Ile Lys Leu Gln Pro Pro Trp
        35                  40                  45

Val Ser Val Phe Leu Gly Glu Ser Val Thr Met His Cys Glu Ala Pro
    50                  55                  60

His Leu Ser Gly Ser Gly Ser Thr Gln Trp Phe Leu Asn Asp Thr Ala
65                  70                  75                  80

Ile Gln Ala Ser Thr Pro Thr Tyr His Ile Thr Ser Ala Ser Glu Asp

```
                        85                  90                  95
Asp Ser Gly Glu Tyr Arg Cys Gln Arg Gly Leu Ser Gly Arg Ser Asp
                100                 105                 110

Pro Ile Leu Leu Glu Val His Arg Gly Trp Leu Leu Gln Val Ser
            115                 120                 125

Ser Arg Val Leu Thr Glu Gly Glu Pro Leu Ala Leu Arg Cys His Ala
130                 135                 140

Trp Arg Asp Lys Leu Val His Asn Val Leu Tyr Tyr His Asn Gly Lys
145                 150                 155                 160

Ala Phe Lys Phe Phe His Arg Asn Ser Thr Leu Thr Ile Pro Arg Thr
                165                 170                 175

Asn Thr Ser His Ser Gly Thr Tyr His Cys Ser Gly Met Gly Arg His
                180                 185                 190

Arg Tyr Thr Ser Ala Gly Thr Leu Val Thr Val Lys Glu Leu Phe Pro
            195                 200                 205

Ala Pro Val Leu Thr Ala Ser Val Thr Ser Pro Leu His Glu Gly Thr
            210                 215                 220

Gln Val Thr Leu Ser Cys Val Thr Lys Leu Leu Ile Gln Arg Pro Gly
225                 230                 235                 240

Leu Gln Leu Tyr Phe Ser Phe Tyr Lys Gly Ser Lys Thr Leu Arg Gly
                245                 250                 255

Arg Asp Thr Ser Ser Glu Tyr Gln Ile Leu Ala Ala Arg Arg Glu Asp
                260                 265                 270

Ser Gly Leu Tyr Trp Cys Val Ala Ala Thr Glu Asp Gly Asn Val Leu
            275                 280                 285

Lys Arg Ser Pro Glu Leu Glu Leu Gln Val Leu Gly His Gln Gln Pro
        290                 295                 300

Thr Pro Val His His His His His
305                 310

<210> SEQ ID NO 131
<211> LENGTH: 939
<212> TYPE: DNA
<213> ORGANISM: Artificial sequence
<220> FEATURE:
<223> OTHER INFORMATION: Synthetic polynucleotide

<400> SEQUENCE: 131
atgaaaataa aaacaggtgc acgcatcctc gcattatccg cattaacgac gatgatgttt      60
tccgcctcgg ctctcgccaa atcgaagaa gccatgggac aagtagatac ccccaaagct     120
gtgattaagc tgcaaccacc gtgggtgagc gtgttcctgg agaatccgt gacgatgcac     180 tgcgaagcac cgcatctgtc tgggtcaggt tcaacccaat ggttcctgaa tgacaccgcg     240
atccaggcct ccaccccgac ttaccacatt acctccgcga gcgaagacga ttcgggagaa     300
tatcgttgtc aacgtggcct gagcggccgt agcgatccga tactacttga agttcatcgt     360
ggctggctgc ttttacaggt tagctcccgc gttttaaccg aaggcgaacc gcttgcatta     420
cgttgccacg catggagaga taagctggtg cacaacgtgc tttactacca caacggcaag     480
gcttttaagt tcttccaccg gaactccacc ctgaccattc cgaggacgaa cacgtcccac     540
agcgggacgt accattgctc gggcatgggc agacatcgtt atacgtcggc gggaaccttg     600
gtcaccgtca agaactgttt tcccgcgccc gtgctgactg cgagtgtgac aagcccgctg     660
catgaaggca ctcaggtgac cctgagctgc gtaaccaaac tgctgataca gcgtcccggc     720
ctgcagctgt atttctcgtt ctataagggc agcaaaaccc tgcgcggacg cgataccctcg     780
```

```
agtgagtatc agattttagc cgcgcgtcgt gaagatagtg ggctgtactg gtgtgtagcg    840
gcgaccgagg atggcaatgt gcttaaacgg agcccagagc ttgagttgca agtgctgggt    900
catcaacagc cgaccccggt ccatcatcat catcatcat                           939

<210> SEQ ID NO 132
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 132
gtgcacctgc ttatctctcc atgcgt                                          26

<210> SEQ ID NO 133
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 133
acgcatggag agataagcag gtgcac                                          26

<210> SEQ ID NO 134
<211> LENGTH: 313
<212> TYPE: PRT
<213> ORGANISM: Artificial sequence
<220> FEATURE:
<223> OTHER INFORMATION: Synthetic peptide

<400> SEQUENCE: 134
```

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Gln Val Asp Thr Pro Lys Ala Val Ile Lys Leu Gln Pro Pro Trp
        35                  40                  45

Val Ser Val Phe Leu Gly Glu Ser Val Thr Met His Cys Glu Ala Pro
    50                  55                  60

His Leu Ser Gly Thr Gly Ser Thr Gln Trp Phe Leu Asn Asp Thr Ala
65                  70                  75                  80

Ile Gln Ala Ser Thr Pro Thr Tyr His Ile Thr Ser Ala Ser Glu Asp
                85                  90                  95

Asp Ser Gly Glu Tyr Arg Cys Gln Arg Gly Leu Ser Gly Arg Ser Asp
            100                 105                 110

Pro Ile Leu Leu Glu Val His Arg Gly Trp Leu Leu Leu Gln Val Ser
        115                 120                 125

Ser Arg Val Leu Thr Glu Gly Glu Pro Leu Ala Leu Arg Cys His Ala
    130                 135                 140

Trp Arg Asp Lys Gln Val His Asn Val Leu Phe Tyr His Asn Gly Lys
145                 150                 155                 160

Ala Phe Lys Phe Phe His Arg Asn Ser Thr Leu Thr Ile Pro Arg Thr
                165                 170                 175

Asn Thr Ser His Ser Gly Thr Tyr His Cys Ser Gly Met Gly Arg His
            180                 185                 190

Arg Tyr Thr Ser Ala Gly Thr Leu Val Ser Val Lys Glu Leu Phe Pro
        195                 200                 205

```
Ala Pro Val Leu Thr Ala Ser Val Thr Ser Pro Leu His Glu Gly Thr
    210                 215                 220

Gln Val Thr Leu Ser Cys Val Thr Lys Leu Leu Ile Gln Arg Pro Gly
225                 230                 235                 240

Leu Gln Leu Tyr Phe Ser Phe Tyr Lys Gly Ser Lys Thr Leu Arg Gly
                245                 250                 255

Arg Asp Thr Ser Ser Glu Tyr Gln Ile Leu Ala Ala Arg Arg Glu Asp
                260                 265                 270

Ser Gly Leu Tyr Trp Cys Val Ala Ala Thr Glu Asp Gly Asn Val Leu
                275                 280                 285

Lys Arg Ser Pro Glu Leu Glu Leu Gln Val Leu Gly His Gln Gln Pro
                290                 295                 300

Thr Pro Val His His His His His
305                 310

<210> SEQ ID NO 135
<211> LENGTH: 939
<212> TYPE: DNA
<213> ORGANISM: Artificial sequence
<220> FEATURE:
<223> OTHER INFORMATION: Synthetic polynucleotide

<400> SEQUENCE: 135
atgaaaataa aaacaggtgc acgcatcctc gcattatccg cattaacgac gatgatgttt      60
tccgcctcgg ctctcgccaa atcgaagaa gccatgggac aagtagatac ccccaaagct     120
gtgattaagc tgcaaccacc gtgggtgagc gtgttcctgg agaatccgt gacgatgcac     180 tgcgaagcac cgcatctgtc tgggacaggt tcaacccaat ggttcctgaa tgacaccgcg     240
atccaggcct ccaccccgac ttaccacatt acctccgcga gcgaagacga ttcgggagaa     300
tatcgttgtc aacgtggcct gagcggccgt agcgatccga tactacttga agttcatcgt     360
ggctggctgt ttttacaggt tagctcccgc gttttaaccg aaggcgaacc gcttgcatta     420
cgttgccacg catggagaga taagcaggtg cacaacgtgc ttttctacca caacggcaag     480
gcttttaagt tcttccaccg gaactcaacc ctgaccattc cgaggacgaa cacgtcccac     540
agcgggacgt accattgctc gggcatgggc agacatcgtt atacgtcggc gggaaccttg     600
gtctccgtca agaactgtt tcccgcgccc gtgctgactg cgagtgtgac aagcccgctg     660
catgaaggca ctcaggtgac cctgagctgc gtaaccaaac tgctgataca gcgtcccggc     720
ctgcagctgt atttctcgtt ctataagggc agcaaaaccc tgcgcggacg cgataccctcg    780 agtgagtatc agattttagc cgcgcgtcgt gaagatagtg ggctgtactg gtgtgtagcg     840
gcgaccgagg atggcaatgt gcttaaacgg agcccagagc ttgagttgca agtgctgggt     900
catcaacagc cgacccggt ccatcatcat catcatcat                              939

<210> SEQ ID NO 136
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 136
cttcgcagag catcgtcacg gattct                                            26

<210> SEQ ID NO 137
<211> LENGTH: 26
```

```
<212> TYPE: DNA
<213> ORGANISM: Artificial sequence
<220> FEATURE:
<223> OTHER INFORMATION: Synthetic oligonucleotide

<400> SEQUENCE: 137
agaatccgtg acgatgctct gcgaag                                            26

<210> SEQ ID NO 138
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 138
tcgctcgcgg aggcaatgtg gtaagt                                            26

<210> SEQ ID NO 139
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 139
acttaccaca ttgcctccgc gagcga                                            26

<210> SEQ ID NO 140
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 140
tggcaacgta atacaagcgg ttcgcct                                           27

<210> SEQ ID NO 141
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 141
aggcgaaccg cttgtattac gttgcca                                           27

<210> SEQ ID NO 142
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 142
tggtcagggt tgtgttccgg tggaagaa                                          28

<210> SEQ ID NO 143
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 143
```

-continued

```
ttcttccacc ggaacacaac cctgacca                                              28
```

<210> SEQ ID NO 144
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 144

```
tccgcgcagg gtttcgctgc ccttata                                               27
```

<210> SEQ ID NO 145
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 145

```
tataagggca gcgaaaccct gcgcgga                                               27
```

<210> SEQ ID NO 146
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 146

```
tgggctccgt ttaaccacat tgccat                                                26
```

<210> SEQ ID NO 147
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 147

```
atggcaatgt ggttaaacgg agccca                                                26
```

<210> SEQ ID NO 148
<211> LENGTH: 313
<212> TYPE: PRT
<213> ORGANISM: Artificial sequence
<220> FEATURE:
<223> OTHER INFORMATION: Synthetic peptide

<400> SEQUENCE: 148

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Gln Val Asp Thr Pro Lys Ala Val Ile Lys Leu Gln Pro Pro Trp
        35                  40                  45

Val Ser Val Phe Leu Gly Glu Ser Val Thr Met Leu Cys Glu Val Pro
    50                  55                  60

His Leu Ser Gly Ala Gly Ser Thr Gln Trp Phe Leu Asn Asp Thr Ala
65                  70                  75                  80

Ile Gln Ala Ser Thr Pro Thr Tyr His Ile Ala Ser Ala Ser Glu Asp
                85                  90                  95

Asp Ser Gly Glu Tyr Arg Cys Gln Arg Gly Leu Ser Gly Arg Ser Asp
```

```
                100                 105                 110
Pro Ile Leu Leu Glu Val His Arg Gly Trp Leu Leu Gln Val Ser
            115                 120                 125

Ser Arg Val Leu Thr Glu Gly Glu Pro Leu Val Leu Arg Cys His Ala
    130                 135                 140

Trp Arg Asp Lys Gln Val His Asn Val Leu Phe Tyr His Asn Gly Lys
145                 150                 155                 160

Ala Phe Lys Phe Phe His Arg Asn Thr Thr Leu Thr Ile Pro Arg Thr
                165                 170                 175

Asn Thr Ser His Ser Gly Thr Tyr His Cys Ser Gly Met Gly Arg His
            180                 185                 190

Arg Tyr Thr Ser Ala Gly Thr Leu Val Ser Val Lys Glu Leu Phe Pro
    195                 200                 205

Ala Pro Val Leu Thr Ala Ser Val Ala Ser Pro Leu His Glu Gly Thr
210                 215                 220

Gln Val Thr Leu Ser Cys Val Thr Lys Leu Leu Ile Gln Arg Pro Gly
225                 230                 235                 240

Leu Gln Leu Tyr Phe Ser Phe Tyr Lys Gly Ser Glu Thr Leu Arg Gly
                245                 250                 255

Arg Asp Thr Ser Ser Glu Tyr Gln Ile Leu Ala Ala Arg Arg Glu Asp
            260                 265                 270

Ser Gly Leu Tyr Trp Cys Val Ala Ala Thr Glu Asp Gly Asn Val Val
    275                 280                 285

Lys Arg Ser Pro Glu Leu Glu Leu Gln Val Leu Gly His Gln Gln Pro
290                 295                 300

Thr Pro Val His His His His His His
305                 310

<210> SEQ ID NO 149
<211> LENGTH: 939
<212> TYPE: DNA
<213> ORGANISM: Artificial sequence
<220> FEATURE:
<223> OTHER INFORMATION: Synthetic polynucleotide

<400> SEQUENCE: 149
atgaaaataa aaacaggtgc acgcatcctc gcattatccg cattaacgac gatgatgttt      60
tccgcctcgg ctctcgccaa aatcgaagaa gccatgggac aagtagatac ccccaaagct     120
gtgattaagc tgcaaccacc gtgggtgagc gtgttcctgg agaatccgt gacgatgctc      180
tgcgaagtac cgcatctgtc tggggcagga tcaacccaat ggttcctgaa tgacaccgcg     240
atccaggcct ccaccccgac ttaccacatt gcctccgcga gcgaagacga ttcgggagaa     300
tatcgttgtc aacgtggcct gagcggccgt agcgatccga tactacttga agttcatcgt     360
ggctggctgc ttttacaggt tagctcccgc gttttaaccg aaggcgaacc gcttgtatta     420
cgttgccacg catggagaga taagcaggtg cacaacgtgc ttttctacca caacggcaag     480
gcttttaagt tcttccaccg gaacacaacc ctgaccattc cgaggacgaa cacgtcccac     540
agcgggacgt accattgctc gggcatgggc agacatcgtt atcgtcggc gggaaccttg      600
gtctccgtca agaactgttt tcccgcgccc gtgctgactg cgagtgtggc aagcccgctg     660
catgaaggca ctcaggtgac cctgagctgc gtaaccaaac tgctgataca gcgtcccggc     720
ctgcagctgt atttctcgtt ctataagggc agcgaaaccc tgcgcggacg cgataccctcg    780
agtgagtatc agatttttagc cgcgcgtcgt gaagatagtg gctgtactg gtgtgtagcg     840
```

```
gcgaccgagg atggcaatgt ggttaaacgg agcccagagc ttgagttgca agtgctgggt    900
catcaacagc cgaccccggt ccatcatcat catcatcat                           939
```

<210> SEQ ID NO 150
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 150

```
aaacgcgggc gctaacctgt aaaagca                                        27
```

<210> SEQ ID NO 151
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 151

```
tgcttttaca ggttagcgcc cgcgttt                                        27
```

<210> SEQ ID NO 152
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 152

```
tcggtcgccg cttcacacca gtaca                                          25
```

<210> SEQ ID NO 153
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 153

```
tgtactggtg tgaagcggcg accga                                          25
```

<210> SEQ ID NO 154
<211> LENGTH: 313
<212> TYPE: PRT
<213> ORGANISM: Artificial sequence
<220> FEATURE:
<223> OTHER INFORMATION: Synthetic peptide

<400> SEQUENCE: 154

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Gln Val Asp Thr Pro Lys Ala Val Ile Lys Leu Gln Pro Pro Trp
        35                  40                  45

Val Ser Val Phe Leu Gly Glu Ser Val Thr Met Leu Cys Glu Val Pro
    50                  55                  60

His Leu Ser Gly Ala Gly Ser Thr Gln Trp Phe Arg Asn Asp Thr Ala
65                  70                  75                  80

Ile Gln Ala Ser Thr Pro Thr Tyr His Ile Ala Ser Ala Ser Glu Asp
                85                  90                  95

Asp Ser Gly Glu Tyr Arg Cys Gln Arg Gly Leu Ser Gly Arg Ser Asp
            100                 105                 110

Pro Ile Leu Leu Glu Val His Arg Gly Trp Leu Leu Gln Val Ser
        115                 120                 125

Ala Arg Val Leu Ile Glu Gly Glu Pro Leu Val Leu Arg Cys His Ala
    130                 135                 140

Trp Arg Asp Lys Gln Val His Asn Val Leu Phe Tyr His Asn Gly Lys
145                 150                 155                 160

Ala Phe Lys Phe Phe His Arg Asn Thr Thr Leu Thr Ile Pro Arg Thr
                165                 170                 175

Asn Thr Ser His Ser Gly Thr Tyr His Cys Ser Gly Met Gly Arg His
            180                 185                 190

Arg Tyr Thr Ser Ala Gly Thr Leu Val Ser Val Lys Glu Leu Phe Pro
        195                 200                 205

Ala Pro Val Leu Thr Ala Ser Val Ala Ser Pro Leu His Glu Gly Thr
    210                 215                 220

Gln Val Thr Leu Ser Cys Val Thr Lys Leu Leu Ile Gln Arg Pro Gly
225                 230                 235                 240

Leu Gln Leu Tyr Phe Ser Phe Tyr Lys Gly Ser Glu Thr Leu Arg Gly
                245                 250                 255

Arg Asp Thr Ser Ser Glu Tyr Gln Ile Leu Ala Ala Arg Arg Glu Asp
            260                 265                 270

Ser Gly Leu Tyr Trp Cys Glu Ala Ala Thr Glu Asp Gly Asn Val Val
        275                 280                 285

Lys Arg Ser Pro Glu Leu Glu Leu Gln Val Leu Gly His Gln Gln Pro
    290                 295                 300

Thr Pro Val His His His His His
305                 310

<210> SEQ ID NO 155
<211> LENGTH: 939
<212> TYPE: DNA
<213> ORGANISM: Artificial sequence
<220> FEATURE:
<223> OTHER INFORMATION: Synthetic polynucleotide

<400> SEQUENCE: 155
atgaaaataa aaacaggtgc acgcatcctc gcattatccg cattaacgac gatgatgttt      60
tccgcctcgg ctctcgccaa aatcgaagaa gccatgggac aagtagatac ccccaaagct     120
gtgattaagc tgcaaccacc gtgggtgagc gtgttcctgg gagaatccgt gacgatgctc     180
tgcgaagtac cgcatctgtc tggggcagga tcaacccaat ggttccggaa tgacaccgcg     240
atccaggcct ccaccccgac ttaccacatt gcctccgcga gcgaagacga ttcgggagaa     300
tatcgttgtc aacgtggcct gagcggccgt agcgatccga tactacttga agttcatcgt     360
ggctggctgc ttttacaggt tagcgcccgc gttttaatcg aaggcgaacc gcttgtatta     420
cgttgccacg catggagaga taagcaggtg cacaacgtgc ttttctacca caacggcaag     480
gcttttaagt tcttccaccg gaacacaacc ctgaccattc cgaggacgaa cacgtcccac     540
agcgggacgt accattgctc gggcatgggc agacatcgtt atacgtcggc gggaaccttg     600
gtctccgtca agaactgttt tccgcgcccc gtgctgactg cgagtgtggc aagcccgctg     660
catgaaggca ctcaggtgac cctgagctgc gtaaccaaac tgctgataca gcgtcccggc     720
ctgcagctgt atttctcgtt ctataagggc agcgaaaccc tgcgcggacg cgatacctcg     780

```
agtgagtatc agattttagc cgcgcgtcgt gaagatagtg ggctgtactg gtgtgaagcg      840
gcgaccgagg atggcaatgt ggttaaacgg agcccagagc ttgagttgca agtactgggt      900
catcaacagc cgaccccggt ccatcatcat catcatcat                            939

<210> SEQ ID NO 156
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 156
aggcaatgtg gaaagtcggg gtgga                                            25

<210> SEQ ID NO 157
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 157
tccaccccga ctttccacat tgcct                                            25

<210> SEQ ID NO 158
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 158
agctcagggt caccggagtg ccttca                                           26

<210> SEQ ID NO 159
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 159
tgaaggcact ccggtgaccc tgagct                                           26

<210> SEQ ID NO 160
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 160
gcccttaaag aacgagaaat acagct                                           26

<210> SEQ ID NO 161
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 161
agctgtattt ctcgttcttt aagggc                                           26
```

```
<210> SEQ ID NO 162
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 162
tccgcgcagg gtttcgccgc cctta                                           25

<210> SEQ ID NO 163
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 163
taagggcggc gaaaccctgc gcgga                                           25

<210> SEQ ID NO 164
<211> LENGTH: 313
<212> TYPE: PRT
<213> ORGANISM: Artificial sequence
<220> FEATURE:
<223> OTHER INFORMATION: Synthetic peptide

<400> SEQUENCE: 164
```

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Gln Val Asp Thr Pro Lys Ala Val Ile Lys Leu Gln Pro Pro Trp
        35                  40                  45

Val Ser Val Phe Leu Gly Glu Ser Val Thr Met Leu Cys Glu Val Pro
    50                  55                  60

His Leu Ser Gly Ala Gly Ser Thr Gln Trp Phe Arg Asn Asp Thr Ala
65                  70                  75                  80

Ile Gln Ala Ser Thr Pro Thr Phe His Ile Ala Ser Ala Ser Glu Asp
                85                  90                  95

Asp Ser Gly Glu Tyr Arg Cys Gln Arg Gly Leu Ser Gly Arg Ser Asp
            100                 105                 110

Pro Ile Leu Leu Glu Val His Arg Gly Trp Leu Leu Leu Gln Val Ser
        115                 120                 125

Ala Arg Val Leu Ile Glu Gly Glu Pro Leu Val Leu Arg Cys His Ala
    130                 135                 140

Trp Arg Asp Lys Leu Val His Asn Val Leu Phe Tyr His Asn Gly Lys
145                 150                 155                 160

Ala Phe Lys Phe Phe His Arg Asn Thr Thr Leu Thr Ile Pro Arg Thr
                165                 170                 175

Asn Thr Ser His Ser Gly Thr Tyr His Cys Ser Gly Met Gly Arg His
            180                 185                 190

Arg Tyr Thr Ser Ala Gly Thr Leu Val Ser Val Lys Glu Leu Phe Pro
        195                 200                 205

Ala Pro Val Leu Thr Ala Ser Val Ala Ser Pro Leu Glu Gly Thr
    210                 215                 220

Pro Val Thr Leu Ser Cys Val Thr Lys Leu Leu Ile Gln Arg Pro Gly
225                 230                 235                 240

Leu Gln Leu Tyr Phe Ser Phe Phe Lys Gly Gly Glu Thr Leu Arg Gly

```
                        245                 250                 255
Arg Asp Thr Ser Ser Glu Tyr Gln Ile Leu Ala Ala Arg Arg Glu Asp
        260                 265                 270

Ser Gly Leu Tyr Trp Cys Glu Ala Ala Thr Glu Asp Gly Asn Val Val
            275                 280                 285

Lys Arg Ser Pro Glu Leu Glu Leu Gln Val Leu Gly His Gln Gln Pro
        290                 295                 300

Thr Pro Val His His His His His His
305                 310

<210> SEQ ID NO 165
<211> LENGTH: 939
<212> TYPE: DNA
<213> ORGANISM: Artificial sequence
<220> FEATURE:
<223> OTHER INFORMATION: Synthetic polynucleotide

<400> SEQUENCE: 165
atgaaaataa aaacaggtgc acgcatcctc gcattatccg cattaacgac gatgatgttt      60
tccgcctcgg ctctcgccaa aatcgaagaa gccatgggac aagtagatac ccccaaagct     120
gtgattaagc tgcaaccacc gtgggtgagc gtgttcctgg gagaatccgt gacgatgctc     180
tgcgaagtac cgcatctgtc tggggcagga tcaacccaat ggttccggaa tgacaccgcg     240
atccaggcct ccaccccgac tttccacatt gcctccgcga gcgaagacga ttcgggagaa     300
tatcgttgtc aacgtggcct gagcggccgt agcgatccga tactacttga agttcatcgt     360
ggctggctgc ttttacaggt tagcgcccgc gttttaatcg aaggcgaacc gcttgtatta     420
cgttgccacg catggagaga taagctggtg cacaacgtgc ttttctacca caacggcaag     480
gcttttaagt tcttccaccg gaacacaacc ctgaccattc gaggacgaa cacgtcccac      540 agcgggacgt accattgctc gggcatgggc agacatcgtt atacgtcggc gggaaccttg     600
gtctccgtca aagaactgtt tcccgcgccc gtgctgactg cgagtgtggc aagcccgctg     660
cttgaaggca ctccggtgac cctgagctgc gtaaccaaac tgctgataca gcgtcccggc     720
ctgcagctgt atttctcgtt ctttaagggc ggcgaaaccc tgcgcggacg cgatacctcg     780
agtgagtatc agatttttagc cgcgcgtcgt gaagatagtg ggctgtactg gtgtgaagcg     840
gcgaccgagg atggcaatgt ggttaaacgg agcccagagc ttgagttgca agtactgggt     900
catcaacagc cgaccccggt ccatcatcat catcatcat                           939

<210> SEQ ID NO 166
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 166
tacaagcggg tcgccttcga ttaaa                                           25

<210> SEQ ID NO 167
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 167
tttaatcgaa ggcgacccgc ttgta                                           25
```

<210> SEQ ID NO 168
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 168
ggctaaaatc ttatactcac tcgag                                                25

<210> SEQ ID NO 169
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 169
ctcgagtgag tataagattt tagcc                                                25

<210> SEQ ID NO 170
<211> LENGTH: 313
<212> TYPE: PRT
<213> ORGANISM: Artificial sequence
<220> FEATURE:
<223> OTHER INFORMATION: Synthetic peptide

<400> SEQUENCE: 170

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Gln Val Asp Thr Pro Lys Ala Val Ile Lys Leu Gln Pro Pro Trp
        35                  40                  45

Val Ser Val Phe Leu Gly Glu Ser Val Thr Met Leu Cys Glu Val Pro
    50                  55                  60

His Leu Ser Gly Ala Gly Ser Thr Gln Trp Phe Arg Asn Asp Thr Ala
65                  70                  75                  80

Ile Gln Ala Ser Thr Pro Thr Phe His Ile Ala Ser Ala Ser Glu Asp
                85                  90                  95

Asp Ser Gly Glu Tyr Arg Cys Gln Arg Gly Leu Ser Gly Arg Ser Asp
            100                 105                 110

Pro Ile Leu Leu Glu Val His Arg Gly Trp Leu Leu Leu Gln Val Ser
        115                 120                 125

Ala Arg Val Leu Ile Glu Gly Asp Pro Leu Val Leu Arg Cys His Ala
    130                 135                 140

Trp Arg Asp Lys Leu Val His Asn Val Leu Phe Tyr His Asn Gly Lys
145                 150                 155                 160

Ala Phe Lys Phe Phe His Arg Asn Thr Thr Leu Thr Ile Pro Arg Thr
                165                 170                 175

Asn Thr Ser His Ser Gly Met Tyr His Cys Ser Gly Met Gly Arg His
            180                 185                 190

Arg Tyr Thr Ser Ala Gly Thr Leu Val Ser Val Lys Glu Leu Phe Pro
        195                 200                 205

Ala Pro Val Leu Thr Ala Ser Val Ala Ser Pro Leu Leu Glu Gly Thr
    210                 215                 220

Pro Val Thr Leu Ser Cys Val Thr Lys Leu Leu Ile Gln Arg Pro Gly
225                 230                 235                 240

```
Leu Gln Leu Tyr Phe Ser Phe Lys Gly Gly Glu Thr Leu Arg Gly
            245                 250                 255

Arg Asp Thr Ser Ser Glu Tyr Lys Ile Leu Ala Ala Arg Glu Asp
        260                 265                 270

Ser Gly Leu Tyr Trp Cys Glu Ala Ala Thr Gly Asp Gly Asn Val Val
        275                 280                 285

Lys Arg Ser Pro Glu Leu Glu Leu Gln Val Leu Gly His Gln Gln Pro
    290                 295                 300

Thr Pro Asp His His His His His His
305                 310
```

<210> SEQ ID NO 171
<211> LENGTH: 939
<212> TYPE: DNA
<213> ORGANISM: Artificial sequence
<220> FEATURE:
<223> OTHER INFORMATION: Synthetic polynucleotide

<400> SEQUENCE: 171

| | |
|---|---:|
| atgaaaataa aaacaggtgc acgcatcctc gcattatccg cattaacgac gatgatgttt | 60 |
| tccgcctcgg ctctcgccaa aatcgaagaa gccatgggac aagtagatac ccccaaagct | 120 |
| gtgattaagc tgcaaccacc gtgggtgagc gtgttcctgg gagaatccgt gacgatgctc | 180 |
| tgcgaagtac gcatctgtc tggggcagga tcaacccaat ggttccggaa tgacaccgcg | 240 |
| atccaggcct ccaccccgac tttccacatt gcctccgcga gcgaagacga ttcgggagaa | 300 |
| tatcgttgtc aacgtggcct gagcggccgt agcgatccga tactacttga agttcatcgt | 360 |
| ggctggctgc ttttacaggt tagcgcccgc gttttaatcg aaggcgaccc gcttgtatta | 420 |
| cgttgccacg catggagaga taagctggtg cacaacgtgc ttttctacca caacggcaag | 480 |
| gcttttaagt tcttccaccg gaacacaacc ctgaccattc cgaggacgaa cacgtcccac | 540 |
| agcgggatgt accattgctc gggcatgggc agacatcgtt atacgtcggc gggaaccttg | 600 |
| gtctccgtca agaactgtt tcccgcgccc gtgctgactg cgagtgtggc tagcccgctg | 660 |
| cttgaaggca ctccggtgac cctgagctgc gtaaccaaac tgctgataca gcgtcccggc | 720 |
| ctgcagctgt atttctcgtt cttttaagggc ggcgaaaccc tgcgcggacg cgatacctcg | 780 |
| agtgagtata agattttagc cgcgcgtcgt gaagatagtg ggctgtactg gtgtgaagcg | 840 |
| gcgaccgagg atggcaatgt ggttaaacgg agcccagagc ttgagttgca agtactgggt | 900 |
| catcaacagc cgaccccgga ccatcatcat catcatcat | 939 |

<210> SEQ ID NO 172
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 172

| | |
|---|---:|
| agcaatggta catcccgctg tggga | 25 |

<210> SEQ ID NO 173
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 173
tcccacagcg ggatgtacca ttgct          25

<210> SEQ ID NO 174
<211> LENGTH: 313
<212> TYPE: PRT
<213> ORGANISM: Artificial sequence
<220> FEATURE:
<223> OTHER INFORMATION: Synthetic peptide

<400> SEQUENCE: 174

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
                20                  25                  30

Gly Gln Val Asp Thr Pro Lys Ala Val Ile Lys Leu Gln Pro Pro Trp
            35                  40                  45

Val Ser Val Phe Leu Gly Glu Ser Val Thr Met Leu Cys Glu Val Pro
        50                  55                  60

His Leu Ser Gly Ala Gly Ser Thr Gln Trp Phe Arg Asn Asp Thr Ala
65                  70                  75                  80

Ile Gln Ala Ser Thr Pro Thr Phe His Ile Ala Ser Ala Ser Glu Asp
                85                  90                  95

Asp Ser Gly Glu Tyr Arg Cys Gln Arg Gly Leu Ser Gly Arg Ser Asp
            100                 105                 110

Pro Ile Leu Leu Glu Val His Arg Gly Trp Leu Leu Leu Gln Val Ser
        115                 120                 125

Ala Arg Val Leu Ile Glu Gly Glu Pro Leu Val Leu Arg Cys His Ala
130                 135                 140

Trp Arg Asp Lys Leu Val His Asn Val Leu Phe Tyr His Asn Gly Lys
145                 150                 155                 160

Ala Phe Lys Phe Phe His Arg Asn Thr Thr Leu Thr Ile Pro Arg Thr
                165                 170                 175

Asn Thr Ser His Ser Gly Met Tyr His Cys Ser Gly Met Gly Arg His
            180                 185                 190

Arg Tyr Thr Ser Ala Gly Thr Leu Val Ser Val Lys Glu Leu Phe Pro
        195                 200                 205

Ala Pro Val Leu Thr Ala Ser Val Ala Ser Pro Leu Leu Glu Gly Thr
    210                 215                 220

Pro Val Thr Leu Ser Cys Val Thr Lys Leu Gln Ile Gln Arg Pro Gly
225                 230                 235                 240

Leu Gln Leu Tyr Phe Ser Phe Phe Lys Gly Glu Thr Leu Arg Gly
                245                 250                 255

Arg Asp Thr Ser Ser Glu Tyr Gln Ile Leu Ala Ala Arg Arg Glu Asp
            260                 265                 270

Ser Gly Leu Tyr Trp Cys Glu Ala Ala Thr Glu Asp Gly Asn Val Val
        275                 280                 285

Lys Arg Ser Pro Glu Leu Glu Leu Gln Val Leu Gly His Gln Gln Pro
    290                 295                 300

Thr Pro Asp His His His His His
305                 310

<210> SEQ ID NO 175
<211> LENGTH: 939
<212> TYPE: DNA
<213> ORGANISM: Artificial sequence
<220> FEATURE:

<223> OTHER INFORMATION: Synthetic polynucleotide

<400> SEQUENCE: 175

```
atgaaaataa aaacaggtgc acgcatcctc gcattatccg cattaacgac gatgatgttt    60
tccgcctcgg ctctcgccaa aatcgaagaa gccatgggac aagtagatac ccccaaagct   120
gtgattaagc tgcaaccacc gtgggtgagc gtgttcctgg agaatccgt gacgatgctc    180
tgcgaagtac cgcacctgtc tggggcagga tcaacccaat ggttccggaa tgacaccgcg   240
atccaggcct ccaccccgac tttccacatt gcctccgcga gcgaagacga ttcgggagaa   300
tatcgttgtc aacgtggcct gagcggccgt agcgatccga tactacttga agttcatcgt   360
ggctggctgc ttttacaggt tagcgcccgc gttttaatcg aaggcgaacc gcttgtatta   420
cgttgccacg catggagaga taagctggtg cacaacgtgc ttttctacca caacggcaag   480
gcttttaagt tcttccaccg gaacacaacc ctgaccattc cgaggacgaa cacgtcccac   540
agcgggatgt accattgctc gggcatgggc agacatcgtt atacgtcggc gggaaccttg   600
gtctccgtca agaactgttt tcccgcgccc gtgctgactg cgagtgtggc aagcccgctg   660
cttgaaggca ctccggtgac cctgagctgc gtaaccaaac tgcagataca gcgtcccggc   720
ctgcagctgt atttctcgtt cttttaagggc ggcgaaaccc tgcgcggacg cgatacctcg   780
agtgagtatc agattttagc cgcgcgtcgt gaagatagtg ggctgtactg gtgtgaagcg   840
gcgaccgagg atggcaatgt ggttaaacgg agcccagagc ttgagttgca agtactgggt   900
catcaacagc cgaccccgga ccatcatcat catcatcat                          939
```

<210> SEQ ID NO 176
<211> LENGTH: 313
<212> TYPE: PRT
<213> ORGANISM: Artificial sequence
<220> FEATURE:
<223> OTHER INFORMATION: Synthetic peptide

<400> SEQUENCE: 176

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
                20                  25                  30

Gly Gln Val Asp Thr Pro Lys Ala Val Ile Lys Leu Gln Pro Pro Trp
            35                  40                  45

Val Ser Val Phe Leu Gly Glu Ser Val Thr Met Leu Cys Glu Val Pro
        50                  55                  60

His Leu Ser Gly Ala Gly Ser Thr Gln Trp Phe Arg Asn Asp Thr Ala
65                  70                  75                  80

Ile Gln Ala Ser Thr Pro Thr Phe His Ile Ala Ser Ala Ser Glu Asp
                85                  90                  95

Asp Ser Gly Glu Tyr Arg Cys Gln Arg Gly Leu Ser Gly Arg Ser Asp
            100                 105                 110

Pro Ile Leu Leu Glu Val His Arg Gly Trp Leu Leu Leu Gln Val Ser
        115                 120                 125

Ala Arg Val Leu Ile Glu Gly Asp Pro Leu Val Leu Arg Cys His Ala
    130                 135                 140

Trp Arg Asp Lys Leu Val His Asn Val Leu Phe Tyr His Asn Gly Lys
145                 150                 155                 160

Ala Phe Lys Phe Phe His Arg Asn Thr Thr Leu Thr Ile Pro Arg Thr
                165                 170                 175
```

Asn Thr Ser His Ser Gly Met Tyr His Cys Ser Gly Met Gly Arg His
            180                 185                 190

Arg Tyr Thr Ser Ala Gly Thr Leu Val Ser Val Lys Glu Leu Phe Pro
        195                 200                 205

Ala Pro Val Leu Thr Ala Ser Val Ala Ser Pro Leu Leu Glu Gly Thr
    210                 215                 220

Pro Val Thr Leu Ser Cys Val Thr Lys Leu Gln Ile Gln Arg Pro Gly
225                 230                 235                 240

Leu Gln Leu Tyr Phe Ser Phe Phe Lys Gly Gly Glu Thr Leu Arg Gly
                245                 250                 255

Arg Asp Thr Ser Ser Glu Tyr Lys Ile Leu Ala Ala Arg Arg Glu Asp
            260                 265                 270

Ser Gly Leu Tyr Trp Cys Glu Ala Ala Thr Glu Asp Gly Asn Val Val
        275                 280                 285

Lys Arg Ser Pro Glu Leu Glu Leu Gln Val Leu Gly His Gln Gln Pro
    290                 295                 300

Thr Pro Asp His His His His His His
305                 310

<210> SEQ ID NO 177
<211> LENGTH: 939
<212> TYPE: DNA
<213> ORGANISM: Artificial sequence
<220> FEATURE:
<223> OTHER INFORMATION: Synthetic polynucleotide

<400> SEQUENCE: 177
atgaaaataa aaacaggtgc acgcatcctc gcattatccg cattaacgac gatgatgttt       60
tccgcctcgg ctctcgccaa aatcgaagaa gccatgggac aagtagatac ccccaaagct      120
gtgattaagc tgcaaccacc gtgggtgagc gtgttcctgg gagaatccgt gacgatgctc      180
tgcgaagtac cgcatctgtc tggggcagga tcaacccaat ggttccggaa tgacaccgcg      240
atccaggcct ccaccccgac tttccacatt gcctccgcga gcgaagacga ttcgggagaa      300
tatcgttgtc aacgtggcct gagcggccgt agcgatccga tactacttga agttcatcgt      360
ggctggctgc ttttacaggt tagcgcccgc gttttaatcg aaggcgaccc gcttgtatta      420
cgttgccacg catggagaga taagctggtg cacaacgtgc ttttctacca caacggcaag      480
gcttttaagt tcttccaccg gaacacaacc ctgaccattc cgaggacgaa cacgtcccac      540
agcgggatgt accattgctc gggcatgggc agacatcgtt atacgtcggc gggaaccttg      600
gtctccgtca agaactgttt tcccgcgccc gtgctgactg cgagtgtggc aagcccgctg      660
cttgaaggca ctccggtgac cctgagctgc gtaaccaaac tgcagataca gcgtcccggc      720
ctgcagctgt atttctcgtt ctttaagggc ggcgaaaccc tgcgcggacg cgataccctcg     780 agtgagtata agattttagc cgcgcgtcgt gaagatagtg ggctgtactg gtgtgaagcg      840
gcgaccgagg atggcaatgt ggttaaacga agcccagagc ttgagttgca agtactgggt      900
catcaacagc cgaccccgga ccatcatcat catcatcat                             939

<210> SEQ ID NO 178
<211> LENGTH: 33
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (19)..(19)

```
<223> OTHER INFORMATION: n stands for any base
<220> FEATURE:
<221> NAME/KEY: misc_feature
<222> LOCATION: (20)..(20)
<223> OTHER INFORMATION: n stands for any base
<220> FEATURE:
<221> NAME/KEY: misc_feature
<222> LOCATION: (21)..(21)
<223> OTHER INFORMATION: k stands for either g or t

<400> SEQUENCE: 178
acgttgcact gcgaagtann kcatctgcct ggg                                    33

<210> SEQ ID NO 179
<211> LENGTH: 33
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (19)..(19)
<223> OTHER INFORMATION: m stands for either a or c
<220> FEATURE:
<221> NAME/KEY: misc_feature
<222> LOCATION: (20)..(20)
<223> OTHER INFORMATION: n stands for any base
<220> FEATURE:
<221> NAME/KEY: misc_feature
<222> LOCATION: (21)..(21)
<223> OTHER INFORMATION: n stands for any base

<400> SEQUENCE: 179
acttgaccca ggcagatgmn ntacttcgca gtg                                    33

<210> SEQ ID NO 180
<211> LENGTH: 32
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (19)..(19)
<223> OTHER INFORMATION: n stands for any base
<220> FEATURE:
<221> NAME/KEY: misc_feature
<222> LOCATION: (20)..(20)
<223> OTHER INFORMATION: n stands for any base
<220> FEATURE:
<221> NAME/KEY: misc_feature
<222> LOCATION: (21)..(21)
<223> OTHER INFORMATION: k stands for either g or t

<400> SEQUENCE: 180
caggttagct cccgcgttnn kaccgaaggc ga                                     32

<210> SEQ ID NO 181
<211> LENGTH: 32
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (19)..(19)
<223> OTHER INFORMATION: m stands for either a or c
<220> FEATURE:
<221> NAME/KEY: misc_feature
<222> LOCATION: (20)..(20)
<223> OTHER INFORMATION: n stands for any base
<220> FEATURE:
<221> NAME/KEY: misc_feature
```

```
<222> LOCATION: (21)..(21)
<223> OTHER INFORMATION: n stands for any base

<400> SEQUENCE: 181
aagcggttcg ccttcggtmn naacgcggga gc                               32

<210> SEQ ID NO 182
<211> LENGTH: 26
<212> TYPE: PRT
<213> ORGANISM: Escherichia coli
<300> PUBLICATION INFORMATION:
<308> DATABASE ACCESSION NUMBER: UniProt P0AEX9
<309> DATABASE ENTRY DATE: 1986-07-21
<313> RELEVANT RESIDUES IN SEQ ID NO: (1)..(26)

<400> SEQUENCE: 182

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25
```

FC BINDING PROTEIN AND METHOD FOR MANUFACTURING SAME

CROSS REFERENCE TO RELATED APPLICATIONS

This application is a National Stage of International Application No. PCT/JP2011/001413 filed Mar. 10, 2011, claiming priority based on Japanese Patent Application Nos. 2010-052789 filed Mar. 10, 2010 and JP 2011-038500 filed Feb. 24, 2011, the contents of all of which are incorporated herein by reference in their entirety.

TECHNICAL FIELD

The present invention relates to an Fc binding protein having an affinity for an immunoglobulin. More specifically, the present invention relates to an Fc binding protein showing characteristics such as higher thermal stability than a wild-type, which can be used as, for example, an immunoglobulin affinity ligand for affinity chromatography. The present invention also relates to a method for manufacturing the protein, and an adsorbent which uses the protein as a component and adsorbs an immunoglobulin, for example.

BACKGROUND ART

An immune signal from immunoglobulin G (hereinafter, referred to as IgG) is transmitted by binding of IgG after antigen trapping to an Fc receptor on the surface of an immunocyte. The Fc receptor is a group of protein molecules which binds to the Fc region of IgG, and each molecular species has an Fc recognition domain belonging to an immunoglobulin super family and recognizes a single variety of immunoglobulin or the immunoglobulin belonging to the same subtype. This determines which accessory cell is recruited in each immune response (Non-Patent Literature 1). The Fc receptor can be further classified into subtypes and it has been reported that FcγRI, FcγRIIa, FcγRIIb, and FcγRIII exist as receptors for IgG (Non-Patent Literature 1). Especially, the binding affinity of FcγRI to IgG is high and the equilibrium dissociation constant ($K_D$) thereof is $10^{-8}$ M or less (Non-Patent Literature 2).

FcγRI is divided roughly into a signal peptide region, an extracellular region, a transmembrane region, and an intracytoplasmic region. The binding thereof to IgG occurs between the Fc region of IgG and the extracellular region of FcγRI, and subsequently the signal of their binding is transmitted into cytoplasm. FcγRI includes two kinds of subunits, an α chain directly associated with binding to IgG, and a γ chain. The γ chain forms a homodimer with a covalent bond through cysteine on the boundary between the transmembrane region and the extracellular region (Non-Patent Literature 1). The amino acid sequence and the gene base sequence of the α chain of FcγRI have been revealed by Non-Patent Literature 3, and thereafter an example of the expression thereof has been reported by genetic modification techniques with *E. coli* (Patent Literature 1) or animal cells as host cells (Non-Patent Literature 4).

The protein which constitutes the extracellular region of FcγRI (hereinafter, referred to as an Fc binding protein) as described above has excellent ability to identify a human antibody on the basis of high affinity. Based on this high affinity, the method for utilizing the Fc binding protein as a ligand of affinity chromatography used in a process of manufacturing diagnostic reagents, tools for research of antibody drugs, or antibody drugs such as of IgG, has been reported (Patent Literature 1).

The Fc binding protein is a protein originated from a protein which works in a human living body, and it has stronger tendency to be denatured by heat and extreme change of pH, etc. than a protein present outside a living body such as on the outer surface of a bacterial cell. On the other hand, when the Fc binding protein is used as a ligand for affinity chromatography to manufacture IgG, the Fc binding protein is required to have stability to acid since the ligand may be exposed to a solution of low pH, such as a citric acid buffer solution, in eluting adsorbed IgG through chromatography procedure using a gel with the ligand immobilized thereto. In addition, the Fc binding protein is also required to have stability to alkali since the ligand may also be exposed to a solution of high pH, such as a sodium hydroxide solution, when the gel is washed or regenerated. Further, in view of the long-term storage of the gel, the Fc binding protein is also required to have stability to heat.

To industrially utilize a biological substance such as a protein, it may be required that the native structure of the biological substance is modified to newly produce a substance which is stable under the predetermined conditions. Regarding an enzyme protein, etc., many examples have been reported in which a mutation is artificially introduced into a polynucleotide encoding the enzyme protein and a mutant which acquires a desired trait is obtained after screening. However, as for the Fc binding protein which is a receptor protein, no example of modification has been reported in which stability to heat, acid, or alkali is increased and thus no example has been industrially utilized so far.

CITATION LIST

Patent Literature

Patent Literature 1: Japanese Translation of PCT Patent Application No. 2002-531086

Non-Patent Literature

Non-Patent Literature 1: J. V. Ravetch, et al., Annu. Rev. Immunol., 9, 457, 1991
Non-Patent Literature 2: Toshiyuki Takai, Jpn. J. Clin. Immunol., 28, 318, 2005
Non-Patent Literature 3: J. M. Allen, et al., Science, 243, 378, 1989
Non-Patent Literature 4: A. Paetz, et al., Biochem. Biophys. Res. Commun., 338, 1811, 2005
Non-Patent Literature 5: Protein Structure and Function, Medical Sciences International, Ltd., 9, 2005
Non-Patent Literature 6: Molecular Cloning, Cold Spring Horbor Laboratory, 256, 1992

SUMMARY OF INVENTION

Technical Problem

The present invention provides an Fc binding protein having increased stability to heat, acid, and/or alkali compared with a wild-type human Fc receptor FcγRI, and a method for manufacturing the Fc binding protein. The present invention also provides a method for specifically isolating a protein containing an Fc binding protein binding site using the Fc binding protein as a ligand for affinity chromatography.

Solution to Problem

As a result of intensive studies to solve the aforementioned problems, the present inventors has identified an amino acid residue associated with the structural stability in the Fc binding protein, and found that a mutant in which the amino acid residue is substituted by another amino acid residue has excellent stability to heat, acid, and/or alkali and is useful as a ligand for affinity chromatography, thereby completing the present invention.

That is, this application encompasses the aspects described below in (A) to (K):

(A) An Fc binding protein, containing the amino acids at positions 16 to 289 of the amino acid sequence described in SEQ ID NO: 1 and having at least any one of the following amino acid substitutions (1) to (168) in the amino acid sequence from positions 16 to 289:

(1) threonine at position 20 of SEQ ID NO: 1 is substituted by proline;
(2) threonine at position 25 of SEQ ID NO: 1 is substituted by lysine;
(3) threonine at position 38 of SEQ ID NO: 1 is substituted by alanine or serine;
(4) leucine at position 46 of SEQ ID NO: 1 is substituted by arginine or proline;
(5) alanine at position 62 of SEQ ID NO: 1 is substituted by valine;
(6) threonine at position 63 of SEQ ID NO: 1 is substituted by isoleucine;
(7) serine at position 69 of SEQ ID NO: 1 is substituted by phenylalanine or threonine;
(8) arginine at position 71 of SEQ ID NO: 1 is substituted by histidine;
(9) valine at position 77 of SEQ ID NO: 1 is substituted by alanine or glutamic acid;
(10) asparagine at position 78 of SEQ ID NO: 1 is substituted by aspartic acid;
(11) aspartic acid at position 94 of SEQ ID NO: 1 is substituted by glutamic acid;
(12) isoleucine at position 100 of SEQ ID NO: 1 is substituted by valine;
(13) serine at position 110 of SEQ ID NO: 1 is substituted by asparagine;
(14) phenylalanine at position 114 of SEQ ID NO: 1 is substituted by leucine;
(15) histidine at position 125 of SEQ ID NO: 1 is substituted by arginine;
(16) leucine at position 131 of SEQ ID NO: 1 is substituted by arginine or proline;
(17) tryptophan at position 149 of SEQ ID NO: 1 is substituted by leucine;
(18) leucine at position 156 of SEQ ID NO: 1 is substituted by proline;
(19) isoleucine at position 160 of SEQ ID NO: 1 is substituted by methionine;
(20) asparagine at position 163 of SEQ ID NO: 1 is substituted by serine;
(21) asparagine at position 195 of SEQ ID NO: 1 is substituted by threonine;
(22) threonine at position 199 of SEQ ID NO: 1 is substituted by serine;
(23) asparagine at position 206 of SEQ ID NO: 1 is substituted by lysine, serine, or threonine;
(24) leucine at position 207 of SEQ ID NO: 1 is substituted by proline;
(25) leucine at position 218 of SEQ ID NO: 1 is substituted by valine;
(26) asparagine at position 240 of SEQ ID NO: 1 is substituted by aspartic acid;
(27) leucine at position 248 of SEQ ID NO: 1 is substituted by serine;
(28) leucine at position 283 of SEQ ID NO: 1 is substituted by histidine;
(29) leucine at position 285 of SEQ ID NO: 1 is substituted by glutamine;
(30) valine at position 17 of SEQ ID NO: 1 is substituted by glycine or glutamic acid;
(31) threonine at position 19 of SEQ ID NO: 1 is substituted by isoleucine;
(32) threonine at position 20 of SEQ ID NO: 1 is substituted by isoleucine;
(33) threonine at position 25 of SEQ ID NO: 1 is substituted by methionine or arginine;
(34) glutamine at position 27 of SEQ ID NO: 1 is substituted by proline or lysine;
(35) glutamine at position 35 of SEQ ID NO: 1 is substituted by leucine, methionine, or arginine;
(36) glutamic acid at position 36 of SEQ ID NO: 1 is substituted by glycine;
(37) leucine at position 41 of SEQ ID NO: 1 is substituted by methionine;
(38) histidine at position 42 of SEQ ID NO: 1 is substituted by leucine;
(39) glutamic acid at position 44 of SEQ ID NO: 1 is substituted by aspartic acid;
(40) valine at position 45 of SEQ ID NO: 1 is substituted by alanine;
(41) leucine at position 46 of SEQ ID NO: 1 is substituted by alanine, asparagine, aspartic acid, glutamine, glycine, histidine, lysine, serine, or tryptophan;
(42) histidine at position 47 of SEQ ID NO: 1 is substituted by glutamine, leucine, or asparagine;
(43) proline at position 49 of SEQ ID NO: 1 is substituted by serine or alanine;
(44) glycine at position 50 of SEQ ID NO: 1 is substituted by arginine or glutamic acid;
(45) serine at position 51 of SEQ ID NO: 1 is substituted by alanine, threonine, leucine, proline, or valine;
(46) serine at position 52 of SEQ ID NO: 1 is substituted by glycine;
(47) serine at position 53 of SEQ ID NO: 1 is substituted by leucine, threonine, or proline;
(48) glutamine at position 55 of SEQ ID NO: 1 is substituted by arginine;
(49) phenylalanine at position 57 of SEQ ID NO: 1 is substituted by tyrosine;
(50) leucine at position 58 of SEQ ID NO: 1 is substituted by arginine;
(51) glycine at position 60 of SEQ ID NO: 1 is substituted by aspartic acid;
(52) threonine at position 61 of SEQ ID NO: 1 is substituted by alanine or serine;
(53) alanine at position 62 of SEQ ID NO: 1 is substituted by glutamic acid;
(54) threonine at position 63 of SEQ ID NO: 1 is substituted by leucine or phenylalanine;
(55) glutamine at position 64 of SEQ ID NO: 1 is substituted by proline, histidine, leucine or lysine;
(56) threonine at position 65 of SEQ ID NO: 1 is substituted by alanine or valine;
(57) serine at position 66 of SEQ ID NO: 1 is substituted by threonine;
(58) threonine at position 67 of SEQ ID NO: 1 is substituted by alanine or serine;

(59) serine at position 69 of SEQ ID NO: 1 is substituted by alanine;
(60) tyrosine at position 70 of SEQ ID NO: 1 is substituted by histidine or phenylalanine;
(61) arginine at position 71 of SEQ ID NO: 1 is substituted by tyrosine;
(62) threonine at position 73 of SEQ ID NO: 1 is substituted by alanine or serine;
(63) serine at position 74 of SEQ ID NO: 1 is substituted by phenylalanine;
(64) serine at position 76 of SEQ ID NO: 1 is substituted by asparagine;
(65) valine at position 77 of SEQ ID NO: 1 is substituted by aspartic acid or lysine;
(66) asparagine at position 78 of SEQ ID NO: 1 is substituted by serine or glycine;
(67) serine at position 80 of SEQ ID NO: 1 is substituted by alanine;
(68) arginine at position 84 of SEQ ID NO: 1 is substituted by serine;
(69) glycine at position 88 of SEQ ID NO: 1 is substituted by serine;
(70) leucine at position 89 of SEQ ID NO: 1 is substituted by glutamine or proline;
(71) serine at position 90 of SEQ ID NO: 1 is substituted by glycine;
(72) arginine at position 92 of SEQ ID NO: 1 is substituted by cysteine or leucine;
(73) isoleucine at position 96 of SEQ ID NO: 1 is substituted by valine or lysine;
(74) glutamine at position 97 of SEQ ID NO: 1 is substituted by leucine or lysine;
(75) histidine at position 101 of SEQ ID NO: 1 is substituted by leucine;
(76) arginine at position 102 of SEQ ID NO: 1 is substituted by serine or leucine;
(77) glycine at position 103 of SEQ ID NO: 1 is substituted by aspartic acid or serine;
(78) serine at position 111 of SEQ ID NO: 1 is substituted by alanine;
(79) phenylalanine at position 114 of SEQ ID NO: 1 is substituted by alanine, isoleucine, methionine, proline, threonine, or valine;
(80) threonine at position 115 of SEQ ID NO: 1 is substituted by isoleucine or phenylalanine;
(81) glutamic acid at position 118 of SEQ ID NO: 1 is substituted by aspartic acid;
(82) alanine at position 121 of SEQ ID NO: 1 is substituted by threonine or valine;
(83) lysine at position 128 of SEQ ID NO: 1 is substituted by arginine or glycine;
(84) aspartic acid at position 129 of SEQ ID NO: 1 is substituted by glycine;
(85) leucine at position 131 of SEQ ID NO: 1 is substituted by glutamine;
(86) tyrosine at position 133 of SEQ ID NO: 1 is substituted by histidine or arginine;
(87) asparagine at position 134 of SEQ ID NO: 1 is substituted by serine;
(88) tyrosine at position 137 of SEQ ID NO: 1 is substituted by phenylalanine;
(89) tyrosine at position 138 of SEQ ID NO: 1 is substituted by histidine;
(90) arginine at position 139 of SEQ ID NO: 1 is substituted by histidine;
(91) asparagine at position 140 of SEQ ID NO: 1 is substituted by aspartic acid;
(92) glycine at position 141 of SEQ ID NO: 1 is substituted by aspartic acid or valine;
(93) lysine at position 142 of SEQ ID NO: 1 is substituted by glutamic acid or arginine;
(94) phenylalanine at position 144 of SEQ ID NO: 1 is substituted by isoleucine;
(95) phenylalanine at position 147 of SEQ ID NO: 1 is substituted by serine;
(96) histidine at position 148 of SEQ ID NO: 1 is substituted by arginine or glutamine;
(97) tryptophan at position 149 of SEQ ID NO: 1 is substituted by arginine;
(98) serine at position 151 of SEQ ID NO: 1 is substituted by threonine;
(99) asparagine at position 152 of SEQ ID NO: 1 is substituted by threonine, isoleucine, or proline;
(100) threonine at position 154 of SEQ ID NO: 1 is substituted by serine;
(101) leucine at position 156 of SEQ ID NO: 1 is substituted by histidine;
(102) lysine at position 157 of SEQ ID NO: 1 is substituted by arginine;
(103) asparagine at position 159 of SEQ ID NO: 1 is substituted by threonine or aspartic acid;
(104) isoleucine at position 160 of SEQ ID NO: 1 is substituted by threonine, valine, or leucine;
(105) serine at position 161 of SEQ ID NO: 1 is substituted by threonine;
(106) threonine at position 165 of SEQ ID NO: 1 is substituted by methionine;
(107) methionine at position 171 of SEQ ID NO: 1 is substituted by threonine;
(108) lysine at position 173 of SEQ ID NO: 1 is substituted by arginine;
(109) histidine at position 174 of SEQ ID NO: 1 is substituted by glutamine;
(110) threonine at position 177 of SEQ ID NO: 1 is substituted by serine;
(111) isoleucine at position 181 of SEQ ID NO: 1 is substituted by threonine;
(112) serine at position 182 of SEQ ID NO: 1 is substituted by threonine, leucine, valine, or glutamic acid;
(113) threonine at position 184 of SEQ ID NO: 1 is substituted by serine;
(114) proline at position 190 of SEQ ID NO: 1 is substituted by serine;
(115) valine at position 193 of SEQ ID NO: 1 is substituted by leucine;
(116) asparagine at position 195 of SEQ ID NO: 1 is substituted by alanine;
(117) alanine at position 196 of SEQ ID NO: 1 is substituted by serine;
(118) valine at position 198 of SEQ ID NO: 1 is substituted by glycine or methionine;
(119) threonine at position 199 of SEQ ID NO: 1 is substituted by alanine;
(120) serine at position 200 of SEQ ID NO: 1 is substituted by glycine or arginine;
(121) leucine at position 202 of SEQ ID NO: 1 is substituted by methionine;
(122) leucine at position 203 of SEQ ID NO: 1 is substituted by histidine, glutamine, tyrosine, arginine or proline;
(123) glutamic acid at position 204 of SEQ ID NO: 1 is substituted by valine;
(124) leucine at position 207 of SEQ ID NO: 1 is substituted by glutamine, histidine, or arginine;

(125) threonine at position 209 of SEQ ID NO: 1 is substituted by alanine;
(126) serine at position 211 of SEQ ID NO: 1 is substituted by arginine or glycine;
(127) glutamic acid at position 213 of SEQ ID NO: 1 is substituted by valine or isoleucine;
(128) lysine at position 215 of SEQ ID NO: 1 is substituted by arginine or glutamic acid;
(129) leucine at position 217 of SEQ ID NO: 1 is substituted by arginine or glutamine;
(130) leucine at position 218 of SEQ ID NO: 1 is substituted by isoleucine, methionine, or lysine;
(131) glutamine at position 219 of SEQ ID NO: 1 is substituted by proline or arginine;
(132) leucine at position 223 of SEQ ID NO: 1 is substituted by arginine, glutamine, or methionine;
(133) glutamine at position 224 of SEQ ID NO: 1 is substituted by arginine;
(134) leucine at position 225 of SEQ ID NO: 1 is substituted by glutamine;
(135) phenylalanine at position 227 of SEQ ID NO: 1 is substituted by isoleucine;
(136) tyrosine at position 230 of SEQ ID NO: 1 is substituted by histidine or phenylalanine;
(137) methionine at position 231 of SEQ ID NO: 1 is substituted by lysine or arginine;
(138) serine at position 233 of SEQ ID NO: 1 is substituted by glycine or asparagine;
(139) lysine at position 234 of SEQ ID NO: 1 is substituted by glutamic acid;
(140) asparagine at position 240 of SEQ ID NO: 1 is substituted by glycine;
(141) glutamic acid at position 244 of SEQ ID NO: 1 is substituted by valine;
(142) tyrosine at position 245 of SEQ ID NO: 1 is substituted by histidine or glutamic acid;
(143) glutamine at position 246 of SEQ ID NO: 1 is substituted by arginine or lysine;
(144) leucine at position 248 of SEQ ID NO: 1 is substituted by isoleucine;
(145) threonine at position 249 of SEQ ID NO: 1 is substituted by alanine or serine;
(146) alanine at position 250 of SEQ ID NO: 1 is substituted by valine;
(147) arginine at position 251 of SEQ ID NO: 1 is substituted by serine;
(148) arginine at position 252 of SEQ ID NO: 1 is substituted by histidine;
(149) glutamic acid at position 253 of SEQ ID NO: 1 is substituted by glycine;
(150) leucine at position 257 of SEQ ID NO: 1 is substituted by arginine or glutamine;
(151) glutamic acid at position 261 of SEQ ID NO: 1 is substituted by valine or alanine;
(152) alanine at position 262 of SEQ ID NO: 1 is substituted by valine;
(153) alanine at position 263 of SEQ ID NO: 1 is substituted by serine;
(154) threonine at position 264 of SEQ ID NO: 1 is substituted by serine;
(155) glutamic acid at position 265 of SEQ ID NO: 1 is substituted by alanine or glycine;
(156) asparagine at position 268 of SEQ ID NO: 1 is substituted by serine, isoleucine, or threonine;
(157) leucine at position 270 of SEQ ID NO: 1 is substituted by histidine, arginine, or valine;
(158) lysine at position 271 of SEQ ID NO: 1 is substituted by arginine;
(159) arginine at position 272 of SEQ ID NO: 1 is substituted by glutamine;
(160) glutamic acid at position 277 of SEQ ID NO: 1 is substituted by valine;
(161) glutamine at position 279 of SEQ ID NO: 1 is substituted by arginine or histidine;
(162) glycine at position 282 of SEQ ID NO: 1 is substituted by aspartic acid;
(163) leucine at position 283 of SEQ ID NO: 1 is substituted by proline;
(164) leucine at position 285 of SEQ ID NO: 1 is substituted by arginine or histidine;
(165) proline at position 286 of SEQ ID NO: 1 is substituted by glutamine, arginine or glutamic acid;
(166) threonine at position 287 of SEQ ID NO: 1 is substituted by isoleucine, proline, alanine, or valine;
(167) proline at position 288 of SEQ ID NO: 1 is substituted by alanine, serine, or threonine; and
(168) valine at position 289 of SEQ ID NO: 1 is substituted by alanine, aspartic acid, glycine, leucine, or isoleucine.

(B) The Fc binding protein described in (A), having at least the amino acid substitution described above in any one of (4), (14), (41), and (79) in the aforementioned amino acid sequence from positions 16 to 289.

(C) The Fc binding protein described in (B), containing the amino acids from positions 34 to 307 in the amino acid sequence described in any one of SEQ ID NOS: 2, 3, 4, 5, 114, 118, 130, 134, 148, 154, 164, 170, 174, and 176.

(D) The Fc binding protein described in (B), comprising the amino acid sequence described in any one of SEQ ID NOS: 2, 3, 4, 5, 114, 118, 130, 134, 148, 154, 164, 170, 174, and 176.

(E) A polynucleotide, encoding the Fc binding protein described in any one of (A) to (D).

(F) An expression vector, containing the polynucleotide described in (E).

(G) A transformant obtained by transforming a host with the expression vector described in (F).

(H) The transformant described in (G), wherein the host is *Escherichia coli*.

(I) A method for manufacturing an Fc binding protein, comprising culturing the transformant described in (G) or (H) to produce the Fc binding protein, and recovering the produced Fc binding protein from its culture.

(J) An adsorbent for a protein containing an Fc binding protein binding site, the adsorbent obtained by immobilizing to a solid phase the Fc binding protein described in any one of (A) to (D).

(K) An antibody purification method including: (1) adding a solution containing an antibody to an adsorbent for a protein containing an Fc binding protein binding site to cause the antibody to be adsorbed to the adsorbent, the adsorbent obtained by immobilizing to a solid phase an Fc binding protein including the amino acid sequence described in any one of SEQ ID NOS: 114, 118, 130, 134, 148, 154, 164, 170, 174, and 176; and (2) eluting the antibody adsorbed to the adsorbent with a buffer solution of pH 3.0 to pH 4.5.

Advantageous Effects of the Invention

The Fc binding protein of the present invention is a protein in which at least one specific amino acid residue in the extracellular region of the wild-type human Fc receptor FcγRI is substituted by another amino acid. The protein has increased stability to heat, acid, and/or alkali as compared with the wild-type human FcγRI. Accordingly, an antibody such as human IgG can be stably purified by using the Fc binding protein of the present invention as a ligand for affinity chromatography.

In the method for manufacturing the Fc binding protein, which includes culturing the transformant obtained by transforming a host with the expression vector containing the polynucleotide encoding the Fc binding protein to produce the Fc binding protein, and recovering the produced Fc binding protein from the culture, protein productivity will increase when the Fc binding protein of the present invention is used as an Fc binding protein. Accordingly, the present invention is also useful in industrial manufacture of the Fc binding protein.

Furthermore, the Fc binding protein of the present invention has increased stability to heat, acid, and/or alkali as compared with the wild-type human FcγRI. Accordingly, with regard to the adsorbent for the protein containing the Fc binding protein binding site, the adsorbent obtained by immobilizing to the solid phase the Fc binding protein of the present invention, adsorption performance is hardly decreased, for example, even when the adsorbent is regenerated by an alkali treatment (for example, a 100 mM sodium hydroxide aqueous solution). Thus, it can be said that the adsorbent of the present invention is especially preferred in the application of bulk purification of antibodies such as human IgG.

DESCRIPTION OF EMBODIMENTS

The Fc binding protein of the present embodiment will be described below in detail.

Figure 1:
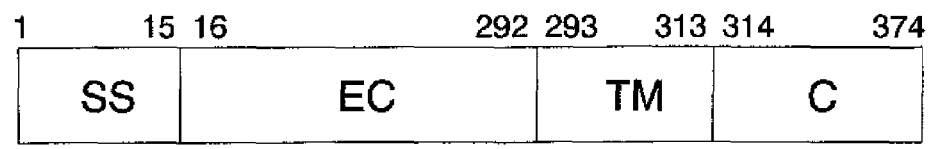
FIG. 1 is a schematic diagram of the structure of the human Fc receptor FcγRI.

FIG. 1 shows the structure of the α chain of the human Fc receptor FcγRI. The α chain of the human Fc receptor FcγRI comprises the signal peptide region including 15 amino acids from the N-terminal side (SS, the region from positions 1 to 15 in the amino acid sequence described in SEQ ID NO: 1), the extracellular region including 277 amino acids (EC, the region from positions 16 to 292 in the amino acid sequence described in SEQ ID NO: 1), the transmembrane region including 21 amino acids (TM, the region from positions 293 to 313 in the amino acid sequence described in SEQ ID NO: 1), and the intracellular region including 61 amino acids (C, the region from positions 314 to 374 in amino acid sequence described in SEQ ID NO: 1).

The Fc binding protein of the present embodiment contains at least the region from glutamine at position 16 to valine at position 289 in the extracellular region (EC region in FIG. 1) from glutamine at position 16 to histidine at position 292 in the amino acid sequence described in SEQ ID NO: 1. The Fc binding protein of the present embodiment may contain all or a part of the signal peptide region (SS region in FIG. 1) at the N-terminal side of the EC region, or may include the transmembrane region (TM region in FIG. 1) or the intracellular region (C region in FIG. 1) at the C-terminal side of the EC region. Further, the Fc binding protein of the present embodiment may have a tag peptide, such as a polyhistidine tag, for purification or others added to the N-terminal side or the C terminal side.

The Fc binding protein of the present embodiment is a polypeptide in which at least one amino acid residue in the region from glutamine at position 16 to valine at position 289, which is a part of the extracellular region (EC region in FIG. 1) in the amino acid sequence described in SEQ ID NO: 1 is substituted by another amino acid residue. The substitution allows the Fc binding protein of the present embodiment to have significantly increased thermal stability, acid stability, and/or alkali stability as compared to wild-type human FcγRI including the amino acid sequence described in SEQ ID NO: 1, and thereby to become useful as a ligand for affinity chromatography. For example, the Fc binding protein illustrated in Example possesses the antibody binding activity more than or equal to the wild-type human FcγRI which does not have any amino acid substitution, even if subjected to a heat-treatment at 43° C. for 10 minutes, a heat-treatment at 70° C. for 20 minutes, a treatment under the acidic conditions of pH 3.0 for 24 hours, or a treatment under the alkaline conditions of pH 10 at 53° C. for 20 minutes.

Specifically, the Fc binding protein of the present embodiment contains at least the amino acid sequence of the region from glutamine at position 16 to valine at position 289 in the amino acid sequence described in SEQ ID NO: 1. Further, the amino acid sequence is a polypeptide which has any one or more of the following substitutions: Thr20Pro (This letter means that threonine at position 20 of SEQ ID NO: 1 is substituted by proline. The same applies to the following letters.), Thr25Lys, Thr38Ala, Thr38Ser, Leu46Arg, Leu46Pro, Ala62Val, Thr63Ile, Ser69Phe, Ser69Thr, Arg71His, Val77Ala, Val77Glu, Asn78Asp, Asp94Glu, Ile100Val, Ser110Asn, Phe114Leu, His125Arg, Leu131Arg, Leu131Pro, Trp149Leu, Leu156Pro, Ile160Met, Asn163Ser, Asn195Thr, Thr199Ser, Asn206Lys, Asn206Ser, Asn206Thr, Leu207Pro, Leu218Val, Asn240Asp, Leu248Ser, Leu283His, Leu285Gln, Val17Gly, Val17Glu, Thr19Ile, Thr20Ile, Thr25Met, Thr25Arg, Gln27Pro, Gln27Lys, Gln35Leu, Gln35Met, Gln35Arg, Glu36Gly, Leu41Met, His42Leu, Glu44Asp, Val45Ala, Leu46Ala, Leu46Asn, Leu46Asp, Leu46Gln, Leu46Gly, Leu46His, Leu46Lys, Leu46Ser, Leu46Trp, His47Gln, His47Leu, His47Asn, Pro49Ser, Pro49Ala, Gly50Arg, Gly50Glu, Ser51Ala, Ser51Thr, Ser51Leu, Ser51Pro, Ser51Val, Ser52Gly, Ser53Leu, Ser53Thr, Ser53Pro, Gln55Arg, Phe57Tyr, Leu58Arg, Gly60Asp, Thr61Ala, Thr61Ser, Ala62Glu, Thr63Leu, Thr63Phe, Gln64Pro, Gln64His, Gln64Leu, Gln64Lys, Thr65Ala, Thr65Val, Ser66Thr, Thr67Ala, Thr67Ser, Ser69Ala, Tyr70His, Tyr70Phe, Arg71Tyr, Thr73Ala, Thr73Ser, Ser74Phe, Ser76Asn, Val77Asp, Val77Lys, Asn78Ser, Asn78Gly, Ser80Ala, Arg84Ser, Gly88Ser, Leu89Gln, Leu89Pro, Ser90Gly, Arg92Cys, Arg92Leu, Ile96Val, Ile96Lys, Gln97Leu, Gln97Lys, His101Leu, Arg102Ser, Arg102Leu, Gly103Asp, Gly103Ser, Ser111Ala, Phe114Ala, Phe114Ile, Phe114Met, Phe114Pro, Phe114Thr, Phe114Val, Thr115Ile, Thr115Phe, Glu118Asp, Ala121Thr, Ala121Val, Lys128Arg, Lys128Gly, Asp129Gly, Leu131Gln, Tyr133His, Tyr133Arg, Asn134Ser, Tyr137Phe, Tyr138His, Arg139His, Asn140Asp, Gly141Asp, Gly141Val, Lys142Glu, Lys142Arg, Phe144Ile, Phe147Ser, His148Arg, His148Gln, Trp149Arg, Ser151Thr, Asn152Thr, Asn152Ile, Asn152Pro, Thr154Ser, Leu156His, Lys157Arg, Asn159Thr, Asn159Asp, Ile160Thr, Ile160Val, Ile160Leu, Ser161Thr, Thr165Met, Met171Thr, Lys173Arg, His174Gln, Thr177Ser, Ile181Thr, Ser182Thr, Ser182Leu, Ser182Val, Ser182Glu, Thr184Ser, Pro190Ser, Val193Leu, Asn195Ala, Ala196Ser, Val198Gly, Val198Met, Thr199Ala, Ser200Gly, Ser200Arg, Leu202Met, Leu203His, Leu203Gln, Leu203Tyr, Leu203Arg, Leu203Pro, Glu204Val, Leu207Gln, Leu207His, Leu207Arg, Thr209Ala, Ser211Arg, Ser211Gly, Glu213Val, Glu213Ile, Lys215Arg, Lys215Glu, Leu217Arg, Leu217Gln, Leu218Ile, Leu218Met, Leu218Lys, Gln219Pro, Gln219Arg, Leu223Arg, Leu223Gln, Leu223Met, Gln224Arg, Leu225Gln, Phe227Ile, Tyr230His, Tyr230Phe, Met231Lys, Met231Arg, Ser233Gly, Ser233Asn, Lys234Glu, Asn240Gly, Glu244Val, Tyr245His, Tyr245Glu, Gln246Arg, Gln246Lys, Leu248Ile, Thr249Ala, Thr249Ser, Ala250Val, Arg251Ser, Arg252His, Glu253Gly, Leu257Arg, Leu257Gln, Glu261Val, Glu261Ala, Ala262Val, Ala263Ser, Thr264Ser, Glu265Ala, Glu265Gly, Asn268Ser, Asn268Ile, Asn268Thr, Leu270His, Leu270Arg, Leu270Val, Lys271Arg, Arg272Gln, Glu277Val, Gln279Arg, Gln279His, Gly282Asp, Leu283Pro, Leu285Arg, Leu285His, Pro286Gln, Pro286Arg, Pro286Glu, Thr287Ile, Thr287Pro, Thr287Ala, Thr287Val, Pro288Ala, Pro288Ser, Pro288Thr, Val289Ala, Val289Asp, Val289Gly, Val289Leu, and Val289Ile.

Moreover, among the aforementioned substitutions, the amino acid sequence preferably has any one or more of the following substitutions to further increase thermal stability: Thr20Pro, Thr25Lys, Thr38Ser, Leu46Pro, Thr63Ile, Ser69Thr, Arg71His, Val77Glu, Asn78Asp, Ile100Val, Phe114Leu, Ile160Met, Asn163Ser, Asn195Thr, Asn206Thr, Leu207Pro, Asn240Asp, Leu283His, and Leu285Gln.

Furthermore, among the aforementioned substitutions, the amino acid sequence preferably has any one or more of the following substitutions to further increase stability of the Fc binding protein to heat, acid, and alkali: Leu46Arg, Leu46Pro, Leu46Ala, Leu46Asn, Leu46Asp, Leu46Gln, Leu46Gly, Leu46His, Leu46Lys, Leu46Ser, Leu46Trp, Phe114Leu, Phe114Ala, Phe114Ile, Phe114Met, Phe114Pro, Phe114Thr, and Phe114Val.

When the Fc binding protein of the present embodiment is produced by causing the amino acid substitution, the amino acid at a specific position may be substituted by an amino acid other than that in the substitution described above as long as the Fc binding protein has the antibody binding activity. Examples thereof include a conserved substitution which is a substitution between amino acids having both or either of similar physical properties and chemical properties. It is known by a person skilled in the art that the conserved substitution generally can keep the function of proteins between those with substitution and those without substitution not only for the Fc binding protein. Examples of the conserved substitution include the substitution between glycine and alanine, between aspartic acid and glutamic acid, between serine and proline, or between glutamic acid and alanine (Non-Patent Literature 5).

In the Fc binding protein of the present embodiment, the number of the amino acid to be substituted is not particularly limited. Examples include the following substitution products (a) to (n). Among these substitution products, particularly, the substitution products described in (c) to (n) are preferred in terms of further increased stability to heat, acid, and alkali.

(a) the tetrasubstitution product (the Fc binding protein containing the amino acid sequence from positions 34 to 307 in the amino acid sequence described in SEQ ID NO: 2) having the substitutions of Leu46Pro, Thr63Ile, Phe114Leu, and Asn240Asp, (b) the hexasubstitution product (the Fc binding protein containing the amino acid sequence from positions 34 to 307 in the amino acid sequence described in SEQ ID NO: 3) having the substitutions of Thr38Ser, Leu46Pro, Thr63Ile, Ile100Val, Phe114Leu, and Asn240Asp, (c) the octasubstitution product (the Fc binding protein containing the amino acid sequence from positions 34 to 307 in the amino acid sequence described in SEQ ID NO: 4) having the substitutions of Thr38Ser, Leu46Pro, Thr63Ile, Ile100Val, Phe114Leu, Ile160Met, Asn163Ser, and Asn240Asp, (d) the nonadecasubstitution product (the Fc binding protein containing the amino acid sequence from positions 34 to 307 in the amino acid sequence described in SEQ ID NO: 5) having the substitutions of Thr20Pro, Thr25Lys, Thr38Ser, Leu46Pro, Thr63Ile, Ser69Thr, Arg71His, Val77Glu, Asn78Asp, Ile100Val, Phe114Leu, Ile160Met, Asn163Ser, Asn195Thr, Asn206Thr, Leu207Pro, Asn240Asp, Leu283His, and Leu285Gln, (e) the dotriacontasubstitution product (the Fc binding protein containing the amino acid sequence from positions 34 to 307 in the amino acid sequence described in SEQ ID NO: 114) having the substitutions of Thr20Pro, Thr25Lys, Glu36Gly, Thr38Ser, Val45Ala, Leu46Pro, Pro49Ser, Gly60Asp, Thr63Ile, Thr65Ala, Ser69Thr, Arg71His, Val77Glu, Asn78Asp, Ile100Val, Phe114Leu, Tyr133His, Arg139His, Trp149Arg, Leu156Pro, Ile160Thr, Asn163Ser, Lys173Arg, Ile181Thr, Asn195Thr, Leu203His, Asn206Thr, Leu207Gln, Met231Lys, Asn240Asp, Leu283His, and Leu285Gln, (f) the hexatriacontasubstitution product (the Fc binding protein containing the amino acid sequence from positions 34 to 307 in the amino acid sequence described in SEQ ID NO: 118) having the substitutions of Thr20Pro, Thr25Lys, Gln35Leu, Glu36Gly, Thr38Ser, Leu41Met, Val45Ala, Leu46Pro, Pro49Ser, Ser52Gly, Gly60Asp, Thr63Ile, Thr65Ala, Ser69Thr, Arg71His, Val77Glu, Asn78Asp, Ile100Val, Phe114Leu, Tyr133His, Arg139His, Trp149Arg, Asn152Thr, Leu156Pro, Ile160Thr, Asn163Ser, Lys173Arg, Ile181Thr, Asn195Thr, Leu203His, Asn206Thr, Leu207Gln, Met231Lys, Asn240Asp, Leu283His, and Leu285Gln, (g) the tetratetracontasubstitution product (the Fc binding protein containing the amino acid sequence from positions 34 to 307 in the amino acid sequence described in SEQ ID NO: 130) having the substitutions of Thr20Pro, Thr25Lys, Gln35Leu, Glu36Gly, Thr38Ser, Leu41Met, Val45Ala, Leu46Pro, Pro49Ser, Ser52Gly, Gly60Asp, Thr63Ile, Thr65Ala, Ser69Thr, Arg71His, Val77Glu, Asn78Asp, Gln97Leu, Ile100Val, Phe114Leu, Lys128Arg, Tyr133His, Arg139His, Trp149Arg, Asn152Thr, Leu156Pro, Lys157Arg, Ile160Thr, Asn163Ser, Lys173Arg, Ile181Thr, Ser182Leu, Asn195Thr, Leu203His, Asn206Thr, Leu207Gln, Glu213Val, Leu218Ile, Met231Lys, Asn240Asp, Thr249Ala, Glu261Val, Leu283His, and Leu285Gln, (h) the octatetracontasubstitution product (the Fc binding protein containing the amino acid sequence from positions 34 to 307 in the amino acid sequence described in SEQ ID NO: 134) having the substitutions of Thr20Pro, Thr25Lys, Gln35Leu, Glu36Gly, Thr38Ser, Leu41Met, Val45Ala, Leu46Pro, Pro49Ser, Ser51Thr, Ser52Gly, Gly60Asp, Thr63Ile, Thr65Ala, Ser69Thr, Arg71His, Val77Glu, Asn78Asp, Gln97Leu, Ile100Val, Phe114Leu, Lys128Arg, Leu131Gln, Tyr133His, Tyr137Phe, Arg139His, Trp149Arg, Asn152Thr, Leu156Pro, Lys157Arg, Ile160Thr, Asn163Ser, Lys173Arg, Ile181Thr, Ser182Leu, Thr184Ser, Asn195Thr, Leu203His, Asn206Thr, Leu207Gln, Glu213Val, Leu218Ile, Met231Lys, Asn240Asp, Thr249Ala, Glu261Val, Leu283His, and Leu285Gln, (i) the tetrapentacontasubstitution product (the Fc binding protein containing the amino acid sequence from positions 34 to 307 in the amino acid sequence described in SEQ ID NO: 148) having the substitutions of Thr20Pro, Thr25Lys, Gln35Leu, Glu36Gly, Thr38Ser, Leu41Met, His42Leu, Leu46Pro, Pro49Ser, Ser51Ala, Ser52Gly, Gly60Asp, Thr63Ile, Thr65Ala, Ser69Thr, Arg71His, Thr73Ala, Val77Glu, Asn78Asp, Gln97Leu, Ile100Val, Phe114Leu, Ala121Val, Lys128Arg, Leu131Gln, Tyr133His, Tyr137Phe, Arg139His, Trp149Arg, Ser151Thr, Asn152Thr, Leu156Pro, Lys157Arg, Ile160Thr, Asn163Ser, Lys173Arg, Ile181Thr, Ser182Leu, Thr184Ser, Asn195Thr, Thr199Ala, Leu203His, Asn206Thr, Leu207Gln, Glu213Val, Leu218Ile, Met231Lys, Lys234Glu, Asn240Asp, Thr249Ala, Glu261Val, Leu270Val, Leu283His, and Leu285Gln, (j) the hexapentacontasubstitution product (the Fc binding protein containing the amino acid sequence from positions 34 to 307 in the amino acid sequence described in SEQ ID NO: 154) having the substitutions of Thr20Pro, Thr25Lys, Gln35Leu, Glu36Gly, Thr38Ser, Leu41Met, His42Leu, Leu46Pro, Pro49Ser, Ser51Ala, Ser52Gly, Leu58Arg, Gly60Asp, Thr63Ile, Thr65Ala, Ser69Thr, Arg71His, Thr73Ala, Val77Glu, Asn78Asp, Gln97Leu, Ile100Val, Ser111Ala, Phe114Leu, Thr115Ile, Ala121Val, Lys128Arg, Leu131Gln, Tyr133His, Tyr137Phe, Arg139His, Trp149Arg, Ser151Thr, Asn152Thr, Leu156Pro, Lys157Arg, Ile160Thr, Asn163Ser, Lys173Arg, Ile181Thr, Ser182Leu, Thr184Ser, Asn195Thr, Thr199Ala, Leu203His, Asn206Thr, Leu207Gln, Glu213Val, Leu218Ile, Met231Lys, Lys234Glu, Asn240Asp, Thr249Ala, Leu270Val, Leu283His, and Leu285Gln, (k) the heptapentacontasubstitution product (the Fc binding protein containing the amino acid sequence from positions 34 to 307 in the amino acid sequence described in SEQ ID NO: 164) having the substitutions of Thr20Pro, Thr25Lys, Gln35Leu, Glu36Gly, Thr38Ser, Leu41Met, His42Leu, Leu46Pro, Pro49Ser, Ser51Ala, Ser52Gly, Leu58Arg, Gly60Asp, Thr63Ile, Thr65Ala, Ser69Thr, Tyr70Phe, Arg71His, Thr73Ala, Val77Glu, Asn78Asp, Gln97Leu, Ile100Val, Ser111Ala, Phe114Leu, Thr115Ile, Ala121Val, Lys128Arg, Tyr133His, Tyr137Phe, Arg139His, Trp149Arg, Ser151Thr, Asn152Thr, Leu156Pro, Lys157Arg, Ile160Thr, Asn163Ser, Lys173Arg, Ile181Thr, Ser182Leu, Thr184Ser, Asn195Thr, Thr199Ala, Asn206Thr, Leu207Pro, Glu213Val, Leu218Ile, Tyr230Phe, Met231Lys, Ser233Gly, Lys234Glu, Asn240Asp, Thr249Ala, Leu270Val, Leu283His, and Leu285Gln, (l) the hexacontasubstitution product (the Fc binding protein containing the amino acid sequence from positions 34 to 307 in the amino acid sequence described in SEQ ID NO: 174) having the substitutions of Thr20Pro, Thr25Lys, Gln35Leu, Glu36Gly, Thr38Ser, Leu41Met, His42Leu, Leu46Pro, Pro49Ser, Ser51Ala, Ser52Gly, Leu58Arg, Gly60Asp, Thr63Ile, Thr65Ala, Ser69Thr, Tyr70Phe, Arg71His, Thr73Ala, Val77Glu, Asn78Asp, Gln97Leu, Ile100Val, Ser111Ala, Phe114Leu, Thr115Ile, Ala121Val, Lys128Arg, Tyr133His, Tyr137Phe, Arg139His, Trp149Arg, Ser151Thr, Asn152Thr, Leu156Pro, Lys157Arg, Ile160Thr, Asn163Ser, Thr165Met, Lys173Arg, Ile181Thr, Ser182Leu, Thr184Ser, Asn195Thr, Thr199Ala, Asn206Thr, Leu207Pro, Glu213Val, Leu217Gln, Leu218Ile, Tyr230Phe, Met231Lys, Ser233Gly, Lys234Glu, Asn240Asp, Thr249Ala, Leu270Val, Leu283His, Leu285Gln, and Val289Asp, (m) the henhexacontasubstitution product (the Fc binding protein containing the amino acid sequence from positions 34 to 307 in the amino acid sequence described in SEQ ID NO: 170) having the substitutions of Thr20Pro, Thr25Lys, Gln35Leu, Glu36Gly, Thr38Ser, Leu41Met, His42Leu, Leu46Pro, Pro49Ser, Ser51Ala, Ser52Gly, Leu58Arg, Gly60Asp, Thr63Ile, Thr65Ala, Ser69Thr, Tyr70Phe, Arg71His, Thr73Ala, Val77Glu, Asn78Asp, Gln97Leu, Ile100Val, Ser111Ala, Phe114Leu, Thr115Ile, Glu118Asp, Ala121Val, Lys128Arg, Tyr133His, Tyr137Phe, Arg139His, Trp149Arg, Ser151Thr, Asn152Thr, Leu156Pro, Lys157Arg, Ile160Thr, Asn163Ser, Thr165Met, Lys173Arg, Ile181Thr, Ser182Leu, Thr184Ser, Asn195Thr, Thr199Ala, Asn206Thr, Leu207Pro, Glu213Val, Leu218Ile, Tyr230Phe, Met231Lys, Ser233Gly, Lys234Glu, Asn240Asp, Gln246Lys, Thr249Ala, Leu270Val, Leu283His, Leu285Gln, and Val289Asp, (n) the dohexacontasubstitution product (the Fc binding protein containing the amino acid sequence from positions 34 to 307 in the amino acid sequence described in SEQ ID NO: 176) having the substitutions of Thr20Pro, Thr25Lys, Gln35Leu, Glu36Gly, Thr38Ser, Leu41Met, His42Leu, Leu46Pro, Pro49Ser, Ser51Ala, Ser52Gly, Leu58Arg, Gly60Asp, Thr63Ile, Thr65Ala, Ser69Thr, Tyr70Phe, Arg71His, Thr73Ala, Val77Glu, Asn78Asp, Gln97Leu, Ile100Val, Ser111Ala, Phe114Leu, Thr115Ile, Glu118Asp, Ala121Val, Lys128Arg, Tyr133His, Tyr137Phe, Arg139His, Trp149Arg, Ser151Thr, Asn152Thr, Leu156Pro, Lys157Arg, Ile160Thr, Asn163Ser, Thr165Met, Lys173Arg, Ile181Thr, Ser182Leu, Thr184Ser, Asn195Thr, Thr199Ala, Asn206Thr, Leu207Pro, Glu213Val, Leu217Gln, Leu218Ile, Tyr230Phe, Met231Lys, Ser233Gly, Lys234Glu, Asn240Asp, Gln246Lys, Thr249Ala, Leu270Val, Leu283His, Leu285Gln, and Val289Asp.

Examples of the methods for manufacturing the polynucleotide having the nucleotide sequence encoding the Fc binding protein of the present embodiment (hereinafter, simply referred to as the polynucleotide of the present embodiment) include, the methods (I) and (II) described below.

(I) The method for converting the amino acid sequence of the Fc binding protein of the present embodiment to a nucleotide sequence to artificially synthesize the polynucleotide including the nucleotide sequence.

(II) The method for preparing the polynucleotide including the whole or a partial sequence of human FcγRI directly and artificially or using a DNA amplification method, such as a PCR method, from human FcγRI cDNA, etc., to link the prepared polynucleotides together in a suitable manner.

In addition, the amino acid sequence is preferably converted to the nucleotide sequence in consideration of the frequency in use of codons in a host to be transformed. As an example, in the case of E. coli (Escherichia coli) as a host, AGA/AGG/CGG/CGA in arginine (Arg), ATA in isoleucine (Ile), CTA in leucine (Leu), GGA in glycine (Gly), and CCC in proline (Pro) are less frequently used (so-called rare codons) respectively, and thus these codons may be avoided in conversion. The frequency in use of codons can be also analyzed by utilizing public databases (for example, Codon Usage Database in the homepage of Kazusa DNA Research Institute, etc.).

When a mutation is introduced into the polynucleotide of the present embodiment by the method (II), a so-called error-prone PCR method can also be used as a DNA amplification method. The reaction conditions in the error-prone PCR method are not particularly limited as long as a desired mutation can be introduced into the polynucleotide encoding human FcγRI. For example, a mutation can be introduced into the polynucleotide by making uneven concentration of four kinds of deoxynucleotide (dATP/dTTP/dCTP/dGTP) which is a substrate, and adding MnCl$_2$ with a concentration of 0.01 to 10 mM (preferably 0.1 to 1 mM) to a PCR solution to perform PCR.

Moreover, the methods for introducing a mutation into the polynucleotide of the present embodiment also include the method (III) described below.

(III) the method for causing a drug to be a mutagen to contact and act on the polynucleotide including the whole or a partial sequence of human FcγRI, or irradiating the polynucleotide with ultraviolet light to introduce a mutation to the polynucleotide. As the drug to be a mutagen, the mutagenic drugs which are generally used by a person skilled in the art may be used, such as hydroxylamine, N-methyl-N'-nitro-N-nitrosoguanidine, nitrous acid, sulfurous acid, and hydrazine.

The 5' terminal side of the polynucleotide of the present embodiment, which is produced by the method (I), (II), or (III), may have the polynucleotide encoding a signal peptide added. In the case of E. coli as a host, the signal peptide includes signal peptides causing the periplasm such as pelB, DsbA, MalE (SEQ ID NO: 182), and TorT to secrete proteins (Japanese Patent Application No. 2009-256180).

In the case of transformation of a host using the polynucleotide of the present embodiment, the polynucleotide of the present embodiment itself may be used, but an expression vector (for example, a bacteriophage, a cosmid, or a plasmid which is generally used for transformation of a prokaryotic cell or an eukaryotic cell, etc.) having the polynucleotide of the present embodiment inserted at a suitable position is more preferably used. The expression vector is not particularly limited as long as it is stable and can be replicated in a host to be transformed. In the case of E. coli as a host, examples of the expression vector include a pET plasmid vector, a pUC plasmid vector, a pTrc plasmid vector, a pCDF plasmid vector, and a pBBR plasmid vector. The suitable position means the position at which the region associated with replication function of the expression vector, a desired antibiotic marker and transmissibility is not destroyed. In inserting the polynucleotide of the present embodiment into the expression vector, the polynucleotide is preferably inserted into the expression vector with being linked to a functional polynucleotide such as a promoter necessary for expression. Examples of the promoter include, in the case of E. coli as a host, a trp promoter, a tac promoter, a trc promoter, a lac promoter, a T7 promoter, a recA promoter, a lpp promoter, as well as a λPL promoter and a λPR promoter of a λ phage.

Transformation of a host with the expression vector produced by the aforementioned method and having the polynucleotide of the present embodiment inserted may be carried out by the methods which are generally used by a person skilled in the art. For example, when microorganisms belonging to genus Escherichia (E. coli JM 109 strain, BL21 (DE3) strain, etc.) are selected as a host, transformation may be carried out by the methods such as described in Non-Patent Literature 6. The transformants obtained by transformation with such a method are screened by a suitable method to obtain a transformant which expresses the Fc binding protein of the present embodiment having increased stability to heat, acid, and alkali. From this transformant, the expression vector having the polynucleotide of the present embodiment inserted may be prepared using an alkaline extraction method, or a commercially available extraction kit such as QIAprep Spin Miniprep kit (produced by QIAGEN). The transformant which expresses the Fc binding protein of the present embodiment can be screened, for example, by determining the binding activity of antibodies to the Fc binding protein expressed. The binding activity of antibodies, for example, to IgG can be determined by ELISA or surface plasmon resonance, etc. IgG used for determining the binding activity is preferably human IgG, and particularly preferably human IgG1.

The Fc binding protein of the present embodiment can be manufactured by culturing the host (transformant) which is transformed with the expression vector containing the polynucleotide of the present embodiment. The method for manufacturing the Fc binding protein, specifically, includes culturing the transformant, and recovering the Fc binding proteins of the present embodiment from the culture. In this specification, the culture conceptually refers to not only the cell itself of the cultured transformant but also the medium used for culturing, etc. Recovery can be carried out by, for example, extracting the Fc binding protein from the culture. The transformant used in the method for manufacturing the Fc binding protein of the present embodiment may be cultured in a medium suitable for culturing a target host, and, in the case of *E. coli* as a host, a LB (Luria-Bertani) medium supplemented with essential nutrients is included as an example of a preferable medium. In order to make possible selective growth of the transformant according to the presence or absence of introduction of the expression vector containing the polynucleotide of the present embodiment, it is preferable that the drug corresponding to a drug resistance gene included in the expression vector be added to a medium for culturing. For example, when the expression vector includes the kanamycin resistant gene, kanamycin may be added to a medium. To a medium, sources of carbon, nitrogen, and an inorganic salt as well as suitable nutrients may be added. The medium, if desired, may include one or more kinds of reducing agents selected from the group consisting of glutathione, cysteine, cystamine, thioglycolate, and dithiothreitol. Furthermore, the reagent, such as glycine, for enhancing protein secretion of the transformant to a broth medium may be added and, specifically, it is preferable that glycine be added at 2% (w/v) or less to a medium in the case of *E. coli* as a host.

The incubation temperature, in the case of *E. coli* as a host, is generally 10° C. to 40° C., preferably 25° C. to 35° C., and more preferably around 30° C., but may be selected according to characteristics of the Fc binding protein to be expressed. The pH of a medium, in the case of *E. coli* as a host, is pH 6.8 to pH 7.4, and preferably around pH 7.0.

When an inducible promoter is included in the expression vector containing the polynucleotide of the present embodiment, it may be induced under the conditions such that the polypeptide containing the Fc binding protein of the present embodiment can be favorably expressed. Exemplary inducers include IPTG (isopropyl-β-D-thiogalactopyranoside). In the case of *E. coli* as a host, the turbidity (the absorbance at 600 nm) of a broth medium is determined and, when it is from about 0.5 to 1.0, an adequate amount of IPTG is added to the broth medium, and subsequent culture can induce expression of the Fc binding protein of the present embodiment. The concentration of IPTG added may be properly selected from the range of 0.005 mM to 1.0 mM, preferably in the range of 0.01 mM to 0.5 mM. Various conditions about IPTG induction may be in accordance with the conditions which are well-known in the art.

In order to extract the Fc binding protein from the broth medium of the transformant of the present embodiment, an extraction method may be properly selected according to the form of expression. When the Fc binding protein is expressed in a culture supernatant, bacterial cells may be separated by centrifugation to extract the Fc binding protein from the obtained culture supernatant. On the other hand, when the Fc binding protein is intracellularly expressed (including a periplasm in a procaryote), bacterial cells may be collected by centrifugation and then lysed by adding an enzyme treatment agent or a surfactant, etc. to extract the Fc binding protein.

Isolation and purification of the Fc binding protein from the extracted protein may be carried out using well-known methods in the art. Examples thereof include isolation and purification using liquid chromatography. Examples of liquid chromatography include ion exchange chromatography, hydrophobic interaction chromatography, gel filtration chromatography, and affinity chromatography. Purification procedure in combination with these chromatographies allows high purity of the Fc binding protein of the present embodiment to be prepared.

The Fc binding protein of the present embodiment is, for example, useful as a ligand for affinity chromatography to isolate and purify the protein containing an Fc binding protein binding site. In application of the Fc binding protein of the present embodiment to the aforementioned chromatography, for example, it can be used in the mode of an adsorbent with the Fc binding protein of the present embodiment immobilized to the solid phase, which adsorbs the protein containing an Fc binding protein binding site (hereinafter, simply referred to as the adsorbent of the present embodiment).

Exemplary solid phases to which the Fc binding protein of the present embodiment is immobilized include substances containing hydrophilic vinyl polymer, silica, glass, Sepharose (registered trademark), agarose, cellulose, hydroxyapatite, and polystyrene. The form of the solid phase is preferably the form with pores controlled or the form of a membrane in terms of higher resolution. To immobilize the Fc binding protein of the present embodiment to the solid phase, for example, an active group, such as an epoxy group, a formyl group, an amino group, and a carboxyl group may be introduced into the surface of the solid phase, and subsequently the amino acid residue on the surface of the Fc binding protein of the present embodiment may be covalently bonded to the active group introduced into the surface of the solid phase.

Examples of the protein containing an Fc binding protein binding site to be isolated and purified using the adsorbent of the present embodiment (hereinafter, referred to as the target protein) include the protein containing the constant region of IgG. Specific examples thereof include IgG, and a fused protein of the Fc binding protein binding site of IgG with another protein. The constant region of IgG, as used here, may include, for example, a hinge, or CH2 and CH3 domains which are produced from IgG by protease treatment such as papain. Examples of the target protein to be isolated and purified using the adsorbent of the present embodiment include human IgG, humanized IgG, mouse IgG, rat IgG, rabbit IgG, and camel IgG. Particularly, human IgG or humanized IgG is preferred. Examples of human IgGs to be isolated and purified using the adsorbent of the present embodiment include human IgG1, human IgG2, human IgG3, and human IgG4. Other examples of the target protein to be isolated and purified using the adsorbent of the present embodiment include a monoclonal IgG antibody, a polyclonal IgG antibody, and an IgG fragment.

The method for isolating and purifying the target protein such as an antibody using the adsorbent of the present embodiment comprises, for example, the steps (1) and (2) described below:
(1) causing the target protein to be adsorbed to the adsorbent, by adding a solution containing the target protein to the adsorbent for the protein containing the Fc binding protein binding site, the adsorbent obtained by immobilizing the Fc binding protein of the present embodiment to the solid phase.

(2) eluting the target protein adsorbed to the adsorbent with a suitable eluate.

The target protein, such as an antibody, to be isolated and purified using the adsorbent of the present embodiment can be expressed and produced in animal cells such as CHO cells (Chinese hamster ovary cells), insect cells, bacteria such as *E. coli* and *Bacillus* genus bacteria, yeasts such as baker's yeast (*Saccharomyces cerevisiae*) and pombe yeast (*Schizosaccharomyces pombe*), or filamentous fungi such as *Aspergillus*, using genetic modification technology, for example. When the target protein is produced in the form with a carbohydrate chain required on the surface thereof, animal cells, insect cells, yeasts, and filamentous fungi, which are eukaryotic cells, may be selected, and CHO cells are more preferably used. Examples of the solution containing the target protein to be isolated and purified using the adsorbent of the present embodiment include broth medium of a host (such as animal cells, insect cells, bacteria, yeasts, filamentous fungi) capable of expressing the target protein, a solution of crushed plant capable of expressing the target protein, and milk of an animal such as cow. With respect to broth medium among these examples, a host capable of expressing the target protein may be contained or the host may be removed by a suitable pretreatment. Exemplary suitable pretreatments as used here may include centrifugation, microfiltration membrane and ultrafiltration membrane, and methods well-known to a person skilled in the art in may be adopted.

Examples of the step of causing the target protein to be adsorbed to the adsorbent of the present embodiment include a step of adding the solution containing the target protein directly or with adjusted pH using a liquid delivery system suitable for the column for isolation and purification using the adsorbent of the present embodiment, thereby attaining adsorption of the target protein. The column for isolation and purification can be produced by, for example, filling an empty column of suitable volume with the adsorbent of the present embodiment. For the liquid delivery system, for example, a high-pressure pump and a peristaltic pump which are used in liquid chromatography can be used. When the pH of the solution containing the target protein is adjusted, as long asunder the conditions that do not cause denatured target protein, pH to be adjusted is not particularly limited and may be neutral, acidic, or alkaline. In addition, in the case of normal target protein, pH is adjusted preferably in the range of pH 3 to pH 10, and particularly preferably in the range of pH 4 to pH 8.

When the target protein adsorbed to the adsorbent of the present embodiment is eluted, after the adsorption step, the target protein may be eluted immediately, but preferably eluted after a washing step for removing contaminating proteins using a suitable washing liquid before the elution step. The washing liquid may be any buffer solution having adjusted pH of the conditions under which the target protein is not eluted. Examples of components of the buffer solution used as the washing liquid include acetic acid, citric acid, histidine, phosphoric acid, boric acid, ammonium salts (for example, ammonium acetate and ammonium succinate), MES (2-Morpholinoethanesulfonic acid monohydrate), MOPS (3-Morpholinopropanesulfonic acid), HEPES (2-[4-(2-Hydroxyethyl)-1-piperazinyl]ethanesulfonic acid), Tris (Tris(hydroxymethyl)aminomethane), and combinations thereof. The pH of the buffer solution used as the washing liquid changes depending on the target protein, but generally it is preferably in the range of pH 3 to pH 10, and particularly preferably in the range of pH 4 to pH 8. In addition, the buffer solution used as the washing liquid, if necessary, may contain an additive, including, for example, salts such as sodium chloride, sodium sulfate, and potassium chloride for adjusting ionic strength of the buffer solution, amino acids such as glycine, histidine, and arginine, chaotropic agents such as urea, alcohols such as ethanol, mannitol, glycerol, and benzyl alcohol, carbohydrates such as sucrose, maltose, trehalose, and fructose.

In the step of eluting the target protein adsorbed to the adsorbent of the present embodiment, the target protein is dissociated from the adsorbent with a suitable eluate and recovered in a suitable container. The eluate may be any buffer solution having adjusted pH of the conditions under which the target protein is eluted and not denatured. The pH of the buffer solution used as the eluate changes depending on the target protein, but generally it is preferably in the range of pH 2 to pH 11, particularly preferably in the range of pH 2.5 to pH 6. When the adsorbent of the present embodiment is the adsorbent obtained by immobilizing to the solid phase the Fc binding protein including the amino acid sequence described in any one of SEQ ID NOs: 114, 118, 130, 134, 148, 154, 164, 170, 174, and 176, the pH of the buffer solution used as the eluate is in the range of pH 3.0 to pH 4.5. In addition, the buffer solution used as the eluate, if necessary, may contain an additive, including, for example, surfactants, salts, and carbohydrates for stabilizing the target protein.

The target protein isolated and purified using the adsorbent of the present embodiment can also be further highly purified by column chromatography. Exemplary chromatographies to be used include ion exchange chromatography, hydrophobic interaction chromatography, gel filtration chromatography, and hydroxyapatite chromatography.

EXAMPLES

Although the following provides a detailed explanation of the present invention with reference to Examples, the present invention is not limited to these Examples.

Example 1

Cloning of Polynucleotide Encoding Human Fc Receptor FcγRI (1) An amino acid sequence of a human Fc receptor FcγRI described in SEQ ID NO: 1 in an extracellular region, a cell transmembrane region, and an intracellular region (region at positions 16 to 374) was converted using an *E. coli* codon into a nucleotide sequence.

(2) Based on the nucleotide sequence, 52 types of oligonucleotides were synthesized to produce a polynucleotide encoding the human FcγRI. The synthesized oligonucleotides are shown in SEQ ID NOs: 10 to 61.

(3) Two-step PCR described below was carried out to produce a full-length polynucleotide encoding the human FcγRI from the oligonucleotide synthesized in (2).

(3-1) A first PCR was carried out by heating for 5 minutes at 94° C., carrying out 25 cycles consisting of 30 seconds at 94° C. in the first step, 30 seconds at 62° C. in the second step, and 1 minute at 72° C. in the third step, and finally heating for 7 minutes at 72° C. using a reaction solution shown in Table 1.

TABLE 1

| Composition | Volume |
| --- | --- |
| 10 × Pyrobest buffer(Takara Bio) | 5 μL |
| 2.5 mM dNTPs | 5 μL |
| DNA mixture | 1 μL |
| 5 U/μL Pyrobest (Takara Bio) | 0.5 μL |
| H₂O | 38.5 μL |

A DNA mixture described in Table 1 represents a solution obtained by weighting each of 52 types of 50 pmol/μL synthesized oligonucleotides in the same amount and mixing them.

(3-2) A second PCR was carried out by heating for 5 minutes at 94° C., carrying out 25 cycles consisting of 30 seconds at 94° C. in the first step, 30 seconds at 65° C. in the second step, and 1 minute at 72° C. in the third step, and finally heating for 7 minutes at 72° C. using a reaction solution shown in Table 2.

TABLE 2

| Composition | Volume |
| --- | --- |
| 10 × Pyrobest buffer (Takara Bio) | 5 μL |
| 2.5 mM dNTPs | 5 μL |
| 10 pmol/μL Oligonucleotide of SEQ ID NO: 61 | 2 μL |
| 10 pmol/μL Oligonucleotide of SEQ ID NO: 10 | 2 μL |
| PCR reaction solution in first step | 1 μL |
| Pyrobest (Takara Bio) | 0.5 μL |
| H₂O | 34.5 μL |

Among a composition shown in Table 2, a polynucleotide in the first PCR solution was used as a template. Further, an oligonucleotide having a sequence shown in SEQ ID NO: 10 (5'-ATGTGGTTTCTGACCACGCTGTTGCTGTGGGT-GCCGGT-3') and an oligonucleotide having a sequence shown in SEQ ID NO: 61 (5'-GGTCGCGCCCTGCG-GCTCCTTACGATGCAC-3') were used as PCR primers. After completion of the reaction, a product was subjected to 0.9% agarose gel electrophoresis, and DNA band with a designed size (about 1.1 kbp) was confirmed.

(4) The DNA band was extracted (by QIAquick Gel extraction kit, QIAGEN), the 5'-terminal of the extracted DNA was phosphorylated (by TaKaRa BKL Kit, Takara Bio), and the DNA was inserted in a pUC19 plasmid vector digested with a restriction enzyme SmaI.

(5) E. coli strain JM109 (TakaraBio) was transformed with the plasmid vector prepared in (4).

Figure 2:
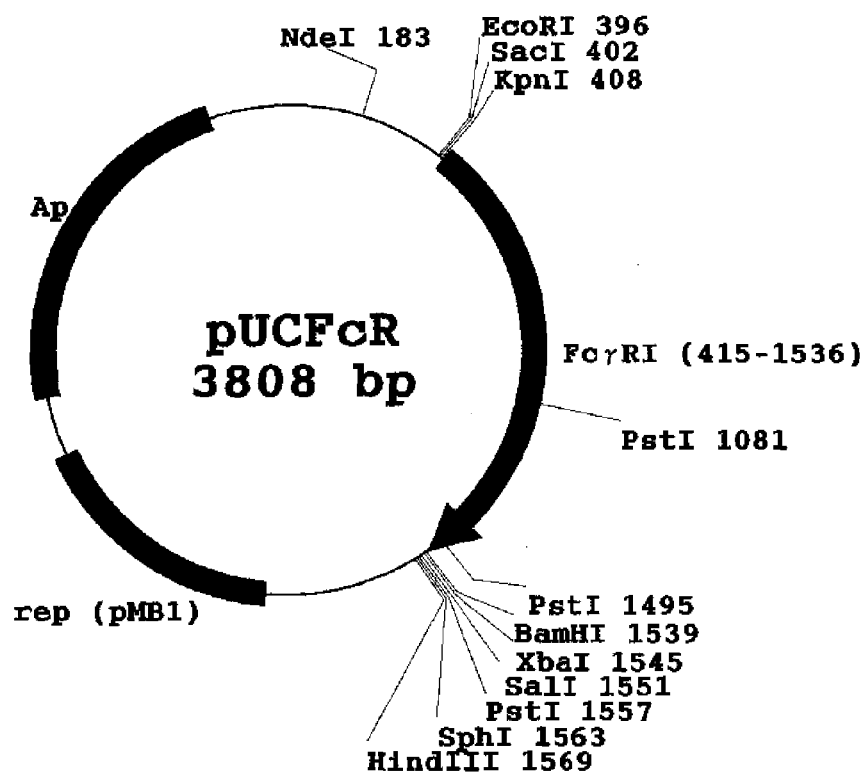
FIG. 2 is a schematic diagram of the structure of the plasmid pUCFcR inserted with the polynucleotide encoding the human FcγRI.

(6) A plasmid was extracted from the transformant in accordance with ordinary methods (by QIAprep Spin Miniprep kit, QIAGEN) to obtain a plasmid pUCFcR. The outline of a structure is shown in FIG. 2.

Example 2

Production of Expression Vector of Fc Binding Protein

Figure 3:
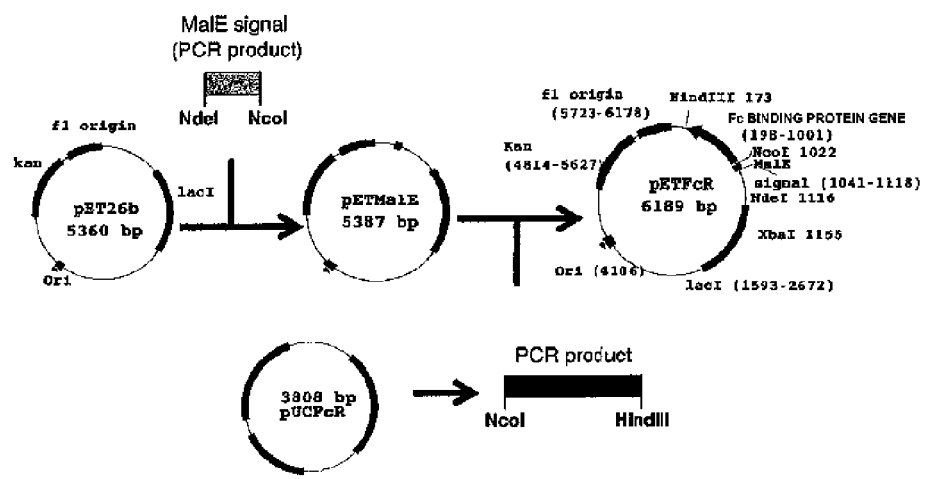
FIG. 3 is a schematic diagram of production of the plasmid pETFcR inserted with the polynucleotide encoding the Fc binding protein.

A system using MalE signal peptide (amino acid sequence; MKIKTGARILALSALTTMMFSASALA, SEQ ID NO: 182) was constructed to express an Fc binding protein in E. coli. The outline of a production process is shown in FIG. 3.

(1) Oligonucleotides shown below were ligated by the PCR method in order to produce a polynucleotide encoding the MalE signal peptide.

An oligonucleotide having a sequence shown in SEQ ID NO: 62 (5'-TATA[CATATG]AAAATAAAAACAGGTG-CACGCATCC-3'; bases in square brackets represent a restriction enzyme NdeI site)

An oligonucleotide having a sequence shown in SEQ ID NO: 63 (5'-GCATTAACGACGATGATGTTTTCCGC-CTCGGCTCTCGCC-3')

An oligonucleotide having a sequence shown in SEQ ID NO: 64 (5'-ATCGTCGTTAATGCGGATAATGCGAGGAT-GCGTGCACCTG-3')

An oligonucleotide having a sequence shown in SEQ ID NO: 65 (5'-TTGTC[CCATGG]CTTCTTCGATTTTGGC-GAGAGCCG-3'; bases in square brackets represent a restriction enzyme NcoI site)

A PCR was carried out for 5 cycles consisting of 10 seconds at 98° C. in the first step, 5 seconds at 55° C. in the second step, and 1 minute at 72° C. in the third step using a reaction solution shown in Table 3.

TABLE 3

| Composition | Concentration/Volume |
| --- | --- |
| Oligonucleotides | Each 2.5 mM |
| 2.5 U/μL PrimeSTAR HS (Takara Bio) | 0.5 μL |
| 5 × PrimeSTAR buffer (Takara Bio) | 10 μL |
| 2.5 mM dNTPs | 4 μL |
| H₂O | up to 50 μL |

(2) The PCR was carried out using the PCR product obtained in (1) as a template to produce a polynucleotide encoding the MalE signal peptide. In the PCR, the oligonucleotide including the sequence shown in SEQ ID NO: 62 and the oligonucleotide including the sequence shown in SEQ ID NO: 65 were used as PCR primers. Further, the PCR was carried out for 30 cycles consisting of 10 seconds at 98° C. in the first step, 5 seconds at 55° C. in the second step, and 1 minute at 72° C. in the third step using a reaction solution shown in Table 4.

TABLE 4

| Composition | Volume |
| --- | --- |
| Template DNA | Proper quantity |
| 10 pmol/μL PCR Primers | Each 2 μL |
| 2.5 U/μL PrimeSTAR HS (Takara Bio) | 0.5 μL |
| 5 × PrimeSTAR buffer (Takara Bio) | 10 μL |
| dNTPS | 4 μL |
| H₂O | up to 50 μL |

(3) The polynucleotide encoding the MalE signal peptide produced in (2) was digested with restriction enzymes NdeI and NcoI. This product was ligated into pET26b(+) plasmid vector (Novagen) digested with the restriction enzymes NdeI and NcoI, and E. coli strain BL21 (DE3) was transformed by a heat-shock method.

Figure 4:
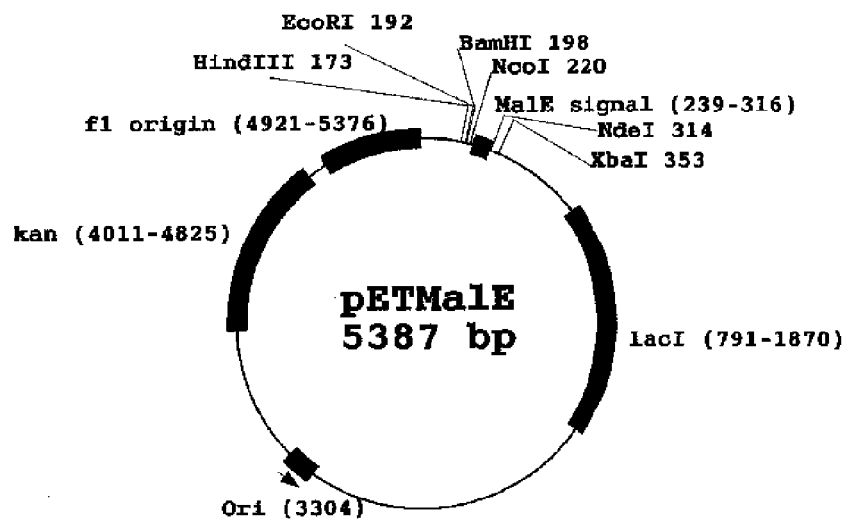
FIG. 4 is a schematic diagram of the structure of the plasmid pETMalE.

(4) The obtained transformant was cultured in LB medium containing 50 μg/mL of kanamycin. Subsequently, plasmid DNA was extracted from the cultured transformant to prepare a plasmid pETMalE. The outline of a structure is shown in FIG. 4.

(5) A polynucleotide encoding a polypeptide containing an Fc binding protein was produced by the PCR using pUCFcR (FIG. 2) produced in Example 1 as a template. In the PCR reaction, oligonucleotides described below were each used as a PCR primer.

An oligonucleotide having a sequence shown in SEQ ID NO: 66 (5'-TCAG[CCATGG]GACAAGTAGATACCAC- CAAAGCTGTGATTA-3'; bases in square brackets represent a restriction enzyme NcoI site)

An oligonucleotide having a sequence shown in SEQ ID NO: 67 (5'-CC[AAGCTT]AATGATGATGATGATGATGGACCGGGGTCGGCAGTTGAAGACCCAG-3'; bases in square brackets represent a restriction enzyme HindIII site)

Further, the PCR was carried out for 30 cycles consisting of 10 seconds at 98° C. in the first step, 5 seconds at 55° C. in the second step, and 1 minute at 72° C. in the third step using the reaction solution composition shown in Table 4.

(6) The polynucleotide obtained in (5) was digested with the restriction enzymes NcoI and HindIII and ligated into the plasmid pETMalE (FIG. 4) which had been digested with the restriction enzymes NcoI and HindIII and produced in Example 2, and *E. coli* strain BL21 (DE3) was transformed by the heat-shock method.

Figure 5:
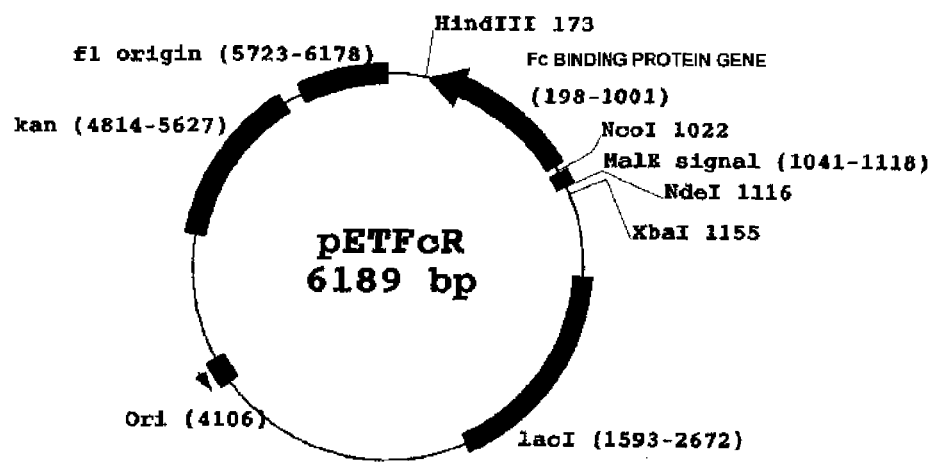
FIG. 5 is a schematic diagram of the structure of the plasmid pETFcR.

(7) The obtained transformant was cultured in LB medium containing 50 µg/mL of kanamycin. Plasmid DNA was extracted from cultured bacteria cells (transformant), to prepare a plasmid pETFcR in which a polynucleotide encoding an Fc binding protein was inserted. The outline of a structure thereof is shown in FIG. 5.

Example 3

Analysis of Nucleotide Sequence

The sequences of the polynucleotides inserted in pUCFcR (FIG. 2) produced in Example 1 and pETFcR (FIG. 5) produced in Example 2 were subjected to a cycle sequencing reaction using a Big Dye Terminator Cycle Sequencing FS read Reaction kit (PE Applied Biosystems) on the basis of a chain termination method, and analyzed using a fully automated DNA sequencer ABI Prism 3700 DNA analyzer (PE Applied Biosystems). Further, an oligonucleotide having a sequence shown in SEQ ID NO: 68 (5'-TAATACGACTCACTATAGGG-3') and an oligonucleotide having a sequence shown in SEQ ID NO: 69 (5'-TATGCTAGTTATTGCTCAG-3') were used as primers for sequencing.

From results of the analysis, the sequences of the polynucleotides inserted in pUCFcR and pETFcR were confirmed to be as designed. The sequence of the polynucleotide inserted in pUCFcR is shown in SEQ ID NO: 70, and an amino acid sequence of an Fc binding protein translated from the polynucleotide is shown in SEQ ID NO: 71. Further, the sequence of the polynucleotide inserted in pETFcR is shown in SEQ ID NO: 72, and an amino acid sequence of an Fc binding protein translated from the polynucleotide is shown in SEQ ID NO: 73.

Example 4

Preparation of Fc Binding Protein and Measurement of Antibody Binding Activity (1) *E. coli* strain BL21 (DE3) transformed with pETFcR (FIG. 5) was cultured in LB medium containing 50 µg/mL of kanamycin (at 37° C. for 18 hours). And then the culture broth was inoculated into a fresh LB medium containing prepared 50 µg/mL of kanamycin.

(2) When the turbidity (Optical Density at 600 nm) of the culture broth reached 0.5, the culture temperature was changed into 20° C. and the culture broth was cultured for 30 minutes. Thereafter, IPTG was added to the culture broth so as to have a concentration of 0.01 mM and was cultured (at 20° C. for 18 hours).

(3) After completion of the culturing, bacterial cells were recovered by centrifugal separation, and a protein was prepared from the cells using a BugBuster Protein extraction kit (Takara Bio).

(4) The antibody binding activity of the prepared protein was evaluated by an ELISA method described below.

(4-1) A γ-globulin formulation (KAKETSUKEN) that was a human antibody was immobilized in wells of a 96-well microplate (at 4° C. for 18 hours) in a concentration of 1 µg/well. After completion of the immobilization, the well was blocked with Starting Block Blocking Buffers (PIERCE).

(4-2) The well was washed with a wash buffer (10 mM Tris-HCl buffer (pH 8.0) containing 0.2% (w/v) Tween 20 and 150 mM NaCl), and a prepared protein extract was appropriately diluted with 50 mM Tris-HCl buffer (pH 8.0) and reacted with the immobilized γ-globulin (at 30° C. for 2 hours).

(4-3) After completion of the reaction, the resultant was washed with the wash buffer again, and a Horse radish Peroxidase (HRP) labeled anti-His-Tag antibody reagent (BETHYL) was added.

(4-4) After a reaction at 30° C. for 2 hours, the resultant was washed with the wash buffer, and TMB Peroxidase Substrate (KPL) was added thereto. The absorbance at 450 nm of the mixture was measured.

Figure 6:
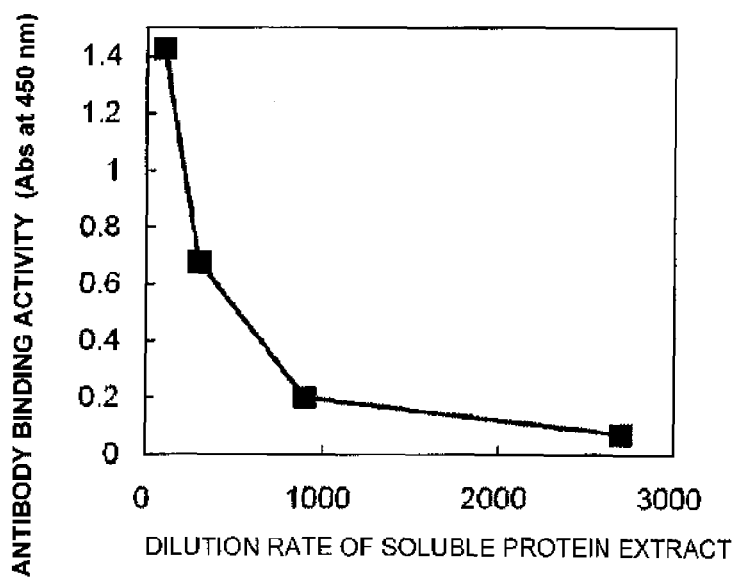
FIG. 6 is a graph for evaluating the antibody binding activity of the Fc binding protein expressed in a plasmid pETFcR transformant.

The measurement results are shown in FIG. 6. In FIG. 6, an x axis (horizontal axis) represents the dilution rate of a sample and a y axis (vertical axis) represents absorbance at 450 nm (unit is optional). The antibody binding activity can be confirmed on the basis of the absorbance. As shown in FIG. 6, as the concentration of a soluble protein extract obtained from the transformant is increased (the dilution rate is decreased), the absorbance is increased. Namely, the transformant obtained by transforming *E. coli* by pETFcR (FIG. 5) that is a recombinant plasmid can be confirmed to express an Fc binding protein.

Example 5

Mutation Introduction into Fc Binding Protein and Production of Library (1) A mutation was randomly introduced into a polynucleotide site encoding the Fc binding protein by the error-prone PCR. A reaction solution composition in the error-prone PCR is shown in the Table 5.

TABLE 5

| Composition | Concentration |
| --- | --- |
| Template DNA (pETFcR) | 0.05 ng/µL |
| PCR primer (SEQ ID NO: 66) | 0.4 µM |
| PCR primer (SEQ ID NO: 67) | 0.4 µM |
| MnCl$_2$ | 0.4 mM |
| dATP | 0.2 mM |
| dGTP | 0.2 mM |
| dCTP | 1 mM |
| dTTP | 1 mM |
| Buffer (Adjust MnCl$_2$ to 5 mM) | ×1 |
| GoTaq polymerase (Promega K.K.) | 0.05 U/µL |
| H$_2$O | up to 50 µL |

A PCR was carried out by heating for 2 minutes at 95° C., carrying out 30 cycles consisting of 30 seconds at 95° C. in the first step, 30 seconds at 60° C. in the second step, and 90 seconds at 72° C. in the third step, and finally heating for 7 minutes at 72° C. The mutation was introduced well into the polynucleotide encoding the Fc binding protein by the error-prone PCR, and the average mutation introduction rate was 0.14%.

(2) The PCR product obtained in (1) was purified, digested with the restriction enzymes NcoI and HindIII, and inserted in pETMalE (FIG. 4), which had been digested with the same restriction enzymes and produced in Example 2, by a ligation reaction.

(3) After completion of the reaction, a reaction solution was introduced into the cells of *E. coli* strain JM109 by an electroporation method. The cells were cultured on LB agar plates containing 50 μg/mL of kanamycin (at 37° C. for 18 hours).

After the culturing, about 50,000 colonies were formed on the plates. Plasmid DNA was extracted from mixed colonies obtained by mixing the colonies to obtain a plasmid library.

Example 6

Screening of Fc Binding Protein with Improved Stability (1) *E. coli* strain BL21 (DE3) was transformed using the plasmid library produced in Example 5.

(2) The transformant obtained in (1) was inoculated into 200 μL of 2YT broth medium (16 g/L Tryptone, 10 g/L Yeast extract, and 5 g/L NaCl) containing 50 μg/mL of kanamycin, and was shake-cultured using a 96-deep well plate at 30° C. overnight.

(3) After the culturing, 50 μL of culture broth was subcultured into 500 μL of 2YT broth medium (containing 0.05 mM IPTG, 0.3% glycine, and 50 μg/mL of kanamycin), and was shake-cultured using a 96-deep well plate at 20° C. overnight.

(4) After the culturing, a culture supernatant obtained by centrifugation was diluted with 50 mM Tris-HCl buffer (pH 8.0) five times, and the antibody binding activity was measured by the ELISA method described in Example 4(4). The culture supernatant was heated for 10 minutes at 43° C., and the antibody binding activity was measured by the ELISA method in the same manner. About 2,500 transformants were evaluated. A transformant expressing an Fc binding protein having improved thermal stability in comparison with the Fc binding protein expressed in the transformant by pETFcR was obtained.

(5) A plasmid was prepared from a transformant expressing an Fc binding protein with improved thermal stability or increased expression amount. The sequence of a polynucleotide region encoding an Fc binding protein inserted in the obtained plasmid was analyzed to identify mutation sites of the amino acid.

From results of analysis of nucleotide sequence, sites of amino acid substitution in the Fc binding protein with improved thermal stability or increased expression amount are as follows.

Specifically, in the amino acid sequence described in SEQ ID NO: 1, substitution shown as Thr20Pro, Thr25Lys, Thr38Ala, Thr38Ser, Leu46Arg, Leu46Pro, Ala62Val, Thr63Ile, Ser69Phe, Ser69Thr, Arg71His, Val77Ala, Val77Glu, Asn78Asp, Asp94Glu, Ile100Val, Ser110Asn, Phe114Leu, His125Arg, Leu131Arg, Leu131Pro, Trp149Leu, Leu156Pro, Ile160Met, Asn163Ser, Asn195Thr, Thr199Ser, Asn206Lys, Asn206Ser, Asn206Thr, Leu207Pro, Leu218Val, Asn240Asp, Leu248Ser, Leu283His, or Leu285Gln was caused. The residual rate (remaining activity) of antibody binding activity after heating and results of analysis of the amino acid substitutions are shown in Table 6. Table 6 reveals that when an Fc binding protein is subjected to amino acid substitution (mutation), the Fc binding protein has improved thermal stability.

TABLE 6

| Amino acid substitution | Remaining Activity (%) |
|---|---|
| Thr20Pro | 38.5 |
| Thr25Lys | 58.5 |
| Thr38Ala | 51.8 |
| Thr38Ser | 49.5 |
| Leu46Arg | 25.5 |
| Leu46Pro | 73.4 |
| Ala62Val | 40.1 |
| Thr63Ile | 40.4 |
| Ser69Phe | 38.7 |
| Ser69Thr | 66.7 |
| Arg71His | 58.1 |
| Val77Ala | 40.8 |
| Val77Glu | 45.1 |
| Asn78Asp | 49.3 |
| Asp94Glu | 36.6 |
| Ile100Val | 65.3 |
| Ser110Asn | 44.0 |
| Phe114Leu | 73.4 |
| His125Arg | 49.4 |
| Leu131Arg | 30.6 |
| Leu131Pro | 68.5 |
| Trp149Leu | 37.5 |
| Leu156Pro | 52.6 |
| Ile160Met | 53.0 |
| Asn163Ser | 58.3 |
| Asn195Thr | 35.6 |
| Thr199Ser | 41.1 |
| Asn206Lys | 52.6 |
| Asn206Ser | 39.1 |
| Asn206Thr | 26.5 |
| Leu207Pro | 52.2 |
| Leu218Val | 36.3 |
| Asn240Asp | 36.5 |
| Leu248Ser | 31.2 |
| Leu283His | 50.5 |
| Leu285Gln | 33.5 |
| Wild-type | 25.5 |

Example 7

Production of Amino Acid-Substituted Fc Binding Protein

Amino acid substitutions involved in improved stability of a structure of the Fc binding protein shown in Example 6 were integrated and the stability was tried to be further improved. The integration of substituted amino acids was carried out mainly by the PCR method, and 4 types of Fc binding proteins shown below were produced.
(a) FcRm4 with four amino acid substitutions
(b) FcRm6 with six amino acid substitutions obtained by substituting two amino acids of FcRm4 with amino acids
(c) FcRm8 with eight amino acid substitutions obtained by substituting two amino acids of FcRm6 with amino acids
(d) FcRm19 with 19 amino acid substitutions obtained by substituting 11 amino acids of FcRm8 with amino acids
Hereinafter, a method for producing each Fc binding protein will be described in detail.
(a) FcRm4
From the amino acid substitutions involved in improved stability of the Fc binding protein shown in Example 6, Leu46Pro, Thr63Ile, Phe114Leu, and Asn240Asp were selected. The selected substitutions were integrated in a wild-type Fc binding protein (Fc binding protein with no amino acid substitution) to produce FcRm4. The integration of the amino acid substitutions shown as Leu46Pro, Thr63Ile, Phe114Leu, and Asn240Asp was carried out using the polynucleotide encoding the Fc binding protein inserted in pETFcR of the transformant expressing each amino acid-substituted Fc binding protein which was obtained by screening.

(a-1) The PCR was carried out using as a template the plasmid pETFcR containing the polynucleotide encoding the Fc binding protein with the substitution shown as Leu46Pro which had been obtained by screening. In the PCR, the oligonucleotide including the sequence shown in SEQ ID NO: 68 and an oligonucleotide having a sequence shown in SEQ ID NO: 74 (5'-AGGAACCATTGGGTT-GAACTTGACCCA-3') were used as PCR primers. The PCR was carried out for 30 cycles consisting of 10 seconds at 98° C. in the first step, 5 seconds at 55° C. in the second step, and 1 minute at 72° C. in the third step using the reaction solution composition shown in Table 4.

(a-2) The PCR was carried out using as a template the plasmid pETFcR containing the polynucleotide encoding the Fc binding protein with Thr63Ile which had been obtained by screening. This PCR was carried out in the same manner as in (a-1) except that an oligonucleotide having a sequence shown in SEQ ID NO: 75 (5'-TGGGTCAAGT-TCAACCCAATGGTTCCT-3') and an oligonucleotide having a sequence shown in SEQ ID NO: 76 (5'-AGCAGC-CAGCCACGATGAATTTCAAGTTGTATCGGATCGC-3') were used as PCR primers.

(a-3) The PCR was carried out using as a template the plasmid pETFcR containing the polynucleotide encoding the Fc binding protein with substitution shown as Phe114Leu which had been obtained by screening. This PCR was carried out in the same manner as in (a-1) except that an oligonucleotide having a sequence shown in SEQ ID NO: 77 (5'-GTGGCCTGAGCGGCCGTAGCGATCCGA-TACAACTTGAAAT-3') and an oligonucleotide having a sequence shown in SEQ ID NO: 78 (5'-CCGCGCA-GGGTTTTGCTGCCCATATAGAACGAGAAATACA-3') were used as PCR primers.

(a-4) The PCR was carried out using as a template the plasmid pETFcR containing the polynucleotide encoding the Fc binding protein with Asn240Asp which had been obtained by screening. This PCR was carried out in the same manner as in (a-1) except that an oligonucleotide having a sequence shown in SEQ ID NO: 79 (5'-CGTCCCGGCCT-GCAGCTGTATTTCTCGTTCTATATGGGCA-3') and the oligonucleotide including the sequence shown in SEQ ID NO: 69 were used as PCR primers.

(a-5) Four types of PCR products obtained in (a-1), (a-2), (a-3), and (a-4) were purified. The purified PCR products were mixed, the PCR was carried out for 5 cycles consisting of 10 seconds at 98° C. in the first step, 5 seconds at 55° C. in the second step, and 1 minute at 72° C. in the third step using reaction solution composition shown in Table 7, and the PCR products were ligated.

TABLE 7

| Composition | Concentration/Volume |
| --- | --- |
| PCR product | Each equimolar |
| 2.5 U/μL PrimeSTAR HS (Takara Bio) | 0.5 μL |
| 5 × PrimeSTAR buffer (Takara Bio) | 10 μL |
| 2.5 mM dNTPs | 4 μL |
| H$_2$O | up to 50 μL |

(a-6) The PCR was carried out using the PCR product obtained in (a-5) as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 55° C. in the second step, and 1 minute at 72° C. in the third step using the reaction solution composition shown in Table 4. Thus, a polynucleotide encoding FcRm4 with four amino acid substitutions was produced.

(a-7) The polynucleotide obtained in (a-6) was digested with the restriction enzymes NcoI and HindIII, and ligated into the expression vector pETMalE digested with the restriction enzymes NcoI and HindIII. E. coli strain BL21 (DE3) was transformed with this product.

(a-8) The obtained transformant was cultured in LB medium containing 50 μg/mL of kanamycin. A plasmid was extracted from the cultured bacterial cells (transformant) to obtain a plasmid pETFcRm4 containing the polynucleotide encoding polypeptide FcRm4 in which four amino acids of a wild-type Fc binding protein were substituted with amino acids.

(a-9) The nucleotide sequence of pETFcRm4 was analyzed in the same manner as in Example 3.

The amino acid sequence of FcRm4 plus a signal sequence and a polyhistidine tag is shown in SEQ ID NO: 2, and the sequence of the polynucleotide encoding the FcRm4 is shown in SEQ ID NO: 6. In SEQ ID NO: 2, the MalE signal peptide is from methionine at position 1 to alanine at position 26, the linker peptide is from lysine at position 27 to glycine at position 33, the amino acid sequence of FcRm4 is from glutamine at position 34 to valine at position 307, and the polyhistidine tag is histidine at positions 308 to 313. Further, in SEQ ID NO: 2, proline of Leu46Pro is at position 64, isoleucine of Thr63Ile is at position 81, leucine of Phe114Leu is at position 132, and aspartic acid of Asn240Asp is at position 258.

(b) FcRm6

From the amino acid substitutions involved in improved stability of the Fc binding protein shown in Example 6, Thr38Ser, Leu46Pro, Thr63Ile, Ile100Val, Phe114Leu, and Asn240Asp were selected. The selected substitutions were integrated in a wild-type Fc binding protein to produce FcRm6. Specifically, nucleotide sequence substitutions causing the produced plasmid pETFcRm4 to amino acid substitutions of Thr38Ser and Ile100Val were carried out to integrate Thr38Ser and Ile100Val in the pETFcRm4. The nucleotide sequence substitution causing the amino acid substitution of Thr38Ser was carried out using an oligonucleotide having a sequence shown in SEQ ID NO: 80 (5'-TGCAACGTCACGGATTCTTCCTGGAA-3') and an oligonucleotide having a sequence shown in SEQ ID NO: 81 (5'-TTCCAGGAAGAATCCGTGACGTTGCA-3'). Further, the nucleotide sequence substitution causing the amino acid substitution of Ile100Val was carried out using an oligonucleotide having a sequence shown in SEQ ID NO: 82 (5'-CAGCCAGCCACGATGAACTTCAAGTT-3') and an oligonucleotide having a sequence shown in SEQ ID NO: 83 (5'-AACTTGAAGTTCATCGTGGCTGGCTG-3').

(b-1) The PCR was carried out using the plasmid pET-FcRm4 as a template and the oligonucleotide including the sequence shown in SEQ ID NO: 68 and the oligonucleotide including the sequence shown in SEQ ID NO: 80 as PCR primers. The PCR was carried out for 30 cycles consisting of 10 seconds at 98° C. in the first step, 5 seconds at 55° C. in the second step, and 1 minute at 72° C. in the third step using the reaction solution composition shown in Table 4.

(b-2) The PCR was carried out using the plasmid pET-FcRm4 as a template. This PCR was carried out in the same manner as in (b-1) except that the oligonucleotide including the sequence shown in SEQ ID NO: 81 and the oligonucleotide including the sequence shown in SEQ ID NO: 82 were used as PCR primers.

(b-3) The PCR was carried out using the plasmid pET-FcRm4 as a template. This PCR was carried out in the same manner as in (b-1) except that the oligonucleotide including the sequence shown in SEQ ID NO: 83 and the oligonucleotide including the sequence shown in SEQ ID NO: 69 were used as PCR primers.

(b-4) Three types of the PCR products obtained in (b-1), (b-2), and (b-3) were purified. The purified PCR products were mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated.

(b-5) The PCR was carried out using the PCR product obtained in (b-4) as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 55° C. in the second step, and 1 minute at 72° C. in the third step using the reaction solution composition shown in Table 4. Thus, a polynucleotide encoding FcRm6 with six amino acid substitutions was produced.

(b-6) The polynucleotide obtained in (b-5) was digested with the restriction enzymes NcoI and HindIII, and ligated into the expression vector pETMalE digested with the restriction enzymes NcoI and HindIII. E. coli strain BL21 (DE3) was transformed with this product.

(b-7) The obtained transformant was cultured in LB medium containing 50 μg/mL of kanamycin. A plasmid was extracted from cultured bacteria cells (transformant) to obtain a plasmid pETFcRm6 containing the polynucleotide encoding polypeptide FcRm6 in which six amino acids of a wild-type Fc binding protein were substituted with amino acids.

(b-8) The sequence of pETFcRm6 was analyzed in the same manner as in Example 3.

The amino acid sequence of FcRm6 plus a signal sequence and a polyhistidine tag is shown in SEQ ID NO: 3, and the sequence of the polynucleotide encoding the FcRm6 is shown in SEQ ID NO: 7. In SEQ ID NO: 3, the MalE signal peptide is from methionine at position 1 to alanine at position 26, the linker peptide is from lysine at position 27 to glycine at position 33, the amino acid sequence of FcRm6 is from glutamine at position 34 to valine at position 307, and the polyhistidine tag is histidine at positions 308 to 313. Further, in SEQ ID NO: 3, serine of Thr38Ser is at position 56, proline of Leu46Pro is at position 64, isoleucine of Thr63Ile is at position 81, valine of Ile100Val is at position 118, leucine of Phe114Leu is at position 132, and aspartic acid of Asn240Asp is at position 258.

(c) FcRm8

From the amino acid substitutions involved in improved stability of the Fc binding protein shown in Example 6, Thr38Ser, Leu46Pro, Thr63Ile, Ile100Val, Phe114Leu, Ile160Met, Asn163Ser, and Asn240Asp were selected. The selected substitutions were accumulated in a wild-type Fc binding protein to produce FcRm8. Specifically, nucleotide sequence substitutions causing amino acid substitutions of Ile160Met and Asn163Ser in the produced plasmid pET-FcRm6 were carried out to integrate Ile160Met and Asn163Ser in the pETFcRm6. The nucleotide sequence substitutions causing the amino acid substitutions of Ile160Met and Asn163Ser were carried out using the oligonucleotide including the sequence shown in SEQ ID NO: 84 (5'-TACGTCCCGCTGTGGGACATGTTCGTCTTCAGA-3') and an oligonucleotide having a sequence shown in SEQ ID NO: 85 (5'-TCTGAAGACGAACATGTCCCACAGCGGGACGTA-3').

(c-1) The PCR was carried out using the plasmid pET-FcRm6 as a template and the oligonucleotide including the sequence shown in SEQ ID NO: 68 and an oligonucleotide having a sequence shown in SEQ ID NO: 84 as PCR primers. The PCR was carried out for 30 cycles consisting of 10 seconds at 98° C. in the first step, 5 seconds at 55° C. in the second step, and 1 minute at 72° C. in the third step using the reaction solution composition shown in Table 4.

(c-2) The PCR was carried out in the same manner as in (c-1) using the plasmid pETFcRm6 as a template and the oligonucleotide including the sequence shown in SEQ ID NO: 85 and the oligonucleotide including the sequence shown in SEQ ID NO: 69 as PCR primers.

(c-3) Two types of the PCR products obtained in (c-1) and (b-2) were purified. The purified PCR products were mixed, the PCR was carried out for a reaction cycle consisting of 10 seconds at 98° C. in the first step, 5 seconds at 55° C. in the second step, and 1 minute at 72° C. in the third step using the reaction solution composition shown in Table 7, and the PCR products were ligated.

(c-4) The PCR was carried out using the PCR product obtained in (c-3) as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 55° C. in the second step, and 1 minute at 72° C. in the third step using the reaction solution composition shown in Table 4. Thus, a polynucleotide encoding FcRm8 with eight amino acid substitutions was produced.

(c-5) The polynucleotide obtained in (c-4) was digested with the restriction enzymes NcoI and HindIII, and ligated into the expression vector pETMalE digested with the restriction enzymes NcoI and HindIII. E. coli strain BL21 (DE3) was transformed with this product.

(c-6) The obtained transformant was cultured in LB medium containing 50 μg/mL of kanamycin. A plasmid was extracted from cultured bacteria cells (transformant) to obtain a plasmid pETFcRm8 containing the polynucleotide encoding polypeptide FcRm8 in which eight amino acids of a wild-type Fc binding protein were substituted with amino acids.

(c-7) The nucleotide sequence of pETFcRm8 was analyzed in the same manner as in Example 3.

The amino acid sequence of FcRm8 plus a signal sequence and a polyhistidine tag is shown in SEQ ID NO: 4, and the sequence of the polynucleotide encoding the FcRm8 is shown in SEQ ID NO: 8. In SEQ ID NO: 4, the MalE signal peptide is from methionine at position 1 to alanine at position 26, the linker peptide is from lysine at position 27 to glycine at position 33, the amino acid sequence of FcRm8 is from glutamine at position 34 to valine at position 307, and the polyhistidine tag is histidine at positions 308 to 313. Further, in SEQ ID NO: 4, serine of Thr38Ser is at position 56, proline of Leu46Pro is at position 64, isoleucine of Thr63Ile is at position 81, valine of Ile100Val is at position 118, leucine of Phe114Leu is at position 132, methionine of Ile160Met is at position 178, serine of Asn163Ser is at position 181, and aspartic acid of Asn240Asp is at position 258.

(d) FcRm19

From the amino acid substitutions involved in improved stability of the Fc binding protein shown in Example 6, Thr20Pro, Thr25Lys, Thr38Ser, Leu46Pro, Thr63Ile, Ser69Thr, Arg71His, Val77Glu, Asn78Asp, Ile100Val, Phe114Leu, Ile160Met, Asn163Ser, Asn195Thr, Asn206Thr, Leu207Pro, Asn240Asp, Leu283His, and Leu285Gln were selected. The selected substitutions were integrated in a wild-type Fc binding protein to produce FcRm19.

Specifically, nucleotide sequence substitutions causing the produced plasmid pETFcRm8 to amino acid substitutions of Thr20Pro, Thr25Lys, Ser69Thr, Arg71His, Val77Glu, Asn78Asp, Asn195Thr, Asn206Thr, Leu207Pro, Leu283His, and Leu285Gln were carried out. Due to the nucleotide sequence substitutions, Thr20Pro, Thr25Lys, Ser69Thr, Arg71His, Val77Glu, Asn78Asp, Asn195Thr, Asn206Thr, Leu207Pro, Leu283His, and Leu285Gln were integrated in the pETFcRm8.

Further, the nucleotide sequence substitution causing two amino acid substitutions of Thr20Pro and Thr25Lys was carried out using an oligonucleotide having a sequence shown in SEQ ID NO: 86 (5'-TGCAGCTTAATCACA-GCTTTGGGGGTAT-3') and an oligonucleotide having a sequence shown in SEQ ID NO: 87 (5'-ATAC-CCCCAAAGCTGTGATTAAGCTGCA-3'). The nucleotide sequence substitution causing four amino acid substitutions of Ser69Thr, Arg71His, Val77Glu, and Asn78Asp was carried out using an oligonucleotide having a sequence shown in SEQ ID NO: 88 (5'-CGCTCGCGGAGGTAATGTGG-TAAGTCGGGGT-3') and an oligonucleotide having a sequence shown in SEQ ID NO: 89 (5'-ATTACCTCCGC-GAGCGAAGACGATTCG-T).

The nucleotide sequence substitution causing three amino acid substitutions of Asn195Thr, Asn206Thr, and Leu207Pro was carried out using an oligonucleotide having a sequence shown in SEQ ID NO: 90 (5'-TCAAGCA-GCGGGCTTGTCACACTCGCAGTCAGCA-T) and an oligonucleotide having a sequence shown in SEQ ID NO: 91 (5'-ACAAGCCCGCTGCTTGAAGGCACTCCGGTGA-3').

The nucleotide sequence substitution causing two amino acid substitutions of Leu283His and Leu285Gln was carried out using an oligonucleotide having a sequence shown in SEQ ID NO: 92 (5'-TCGGCTGTTGATGACCCAGCACT-TGCAA-3') and an oligonucleotide having a sequence shown in SEQ ID NO: 93 (5'-TTGCAAGTGCTGGGTCAT-CAACAGCCGA-3').

(d-1) The PCR was carried out using the plasmid pET-FcRm8 as a template and the oligonucleotide including the sequence shown in SEQ ID NO: 68 and the oligonucleotide including the sequence shown in SEQ ID NO: 86 as PCR primers. The PCR was carried out for 30 cycles consisting of 10 seconds at 98° C. in the first step, 5 seconds at 55° C. in the second step, and 1 minute at 72° C. in the third step using the reaction solution composition shown in Table 4.

(d-2) The PCR was carried out using the plasmid pET-FcRm8 as a template. This PCR was carried out in the same manner as in (d-1) except that the oligonucleotide including the sequence shown in SEQ ID NO: 87 and the oligonucleotide including the sequence shown in SEQ ID NO: 88 were used as PCR primers.

(d-3) The PCR was carried out using the plasmid pET-FcRm8 as a template. This PCR was carried out in the same manner as in (d-1) except that the oligonucleotide including the sequence shown in SEQ ID NO: 89 and the oligonucleotide including the sequence shown in SEQ ID NO: 90 were used as PCR primers.

(d-4) The PCR was carried out using the plasmid pET-FcRm8 as a template. This PCR was carried out in the same manner as in (d-1) except that the oligonucleotide including the sequence shown in SEQ ID NO: 91 and the oligonucleotide including the sequence shown in SEQ ID NO: 92 were used as PCR primers.

(d-5) The PCR was carried out using the plasmid pET-FcRm8 as a template. This PCR was carried out in the same manner as in (d-1) except that the oligonucleotide including the sequence shown in SEQ ID NO: 93 and the oligonucleotide including the sequence shown in SEQ ID NO: 69 as PCR primers.

(d-6) Five types of PCR products obtained in (d-1), (d-2), (d-3), (d-4), and (d-5) were purified.

The purified PCR products were mixed, the PCR was carried out for a reaction cycle consisting of 10 seconds at 98° C. in the first step, 5 seconds at 55° C. in the second step, and 1 minute at 72° C. in the third step using the reaction solution composition shown in Table 7, and the PCR products were ligated.

(d-7) The PCR was carried out using the PCR product obtained in (d-6) as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 55° C. in the second step, and 1 minute at 72° C. in the third step using the reaction solution composition shown in Table 4. Thus, a polynucleotide encoding FcRm19 with 19 amino acid substitutions was produced.

(d-8) The polynucleotide obtained in (d-7) was digested with the restriction enzymes NcoI and HindIII, and ligated into the plasmid DNA pETMalE digested with the restriction enzymes NcoI and HindIII. *E. coli* strain BL21 (DE3) was transformed with this product.

(d-9) The obtained transformant was cultured in LB medium containing 50 μg/mL of kanamycin. A plasmid was extracted from cultured bacteria cells (transformant) to obtain a plasmid pETFcRm19 containing the polynucleotide encoding polypeptide FcRm19 in which 19 amino acids of a wild-type Fc binding protein were substituted with amino acids.

(d-10) The nucleotide sequence of pETFcRm19 was analyzed in the same manner as in Example 3.

The amino acid sequence of FcRm19 plus a signal sequence and a polyhistidine tag is shown in SEQ ID NO: 5, and the sequence of the polynucleotide encoding the FcRm19 is shown in SEQ ID NO: 9. In SEQ ID NO: 5, the MalE signal peptide is from methionine at position 1 to alanine at position 26, the linker peptide is from lysine at position 27 to glycine at position 33, the amino acid sequence of FcRm19 is from glutamine at position 34 to valine at position 307, and the polyhistidine tag is histidine at positions 308 to 313. In SEQ ID NO: 5, proline of Thr20Pro is at position 38, lysine of Thr25Lys is at position 43, serine of Thr38Ser is at position 56, proline of Leu46Pro is at position 64, isoleucine of Thr63Ile is at position 81, threonine of Ser69Thr is at position 87, histidine of Arg71His is at position 89, glutamic acid of Val77Glu is at position 95, aspartic acid of Asn78Asp is at position 96, valine of Ile100Val is at position 118, leucine of Phe114Leu is at position 132, methionine of Ile160Met is at position 178, serine of Asn163Ser is at position 181, threonine of Asn195Thr is at position 213, threonine of Asn206Thr is at position 224, proline of Leu207Pro is at position 225, aspartic acid of Asn240Asp is at position 258, histidine of Leu283His is at position 301, and glutamine of Leu285Gln is at position 303.

Example 8

Evaluation of Productivity of Fc Binding Proteins Accumulating Amino Acid Substitution (1) Each of the transformants obtained in Examples 2 and 7 was inoculated into 2YT broth medium containing 50 μg/mL of kanamycin. The precultures were carried out by shake-culturing at 37° C. overnight.

(2) Each of preculture broths was inoculated into 2YT broth medium containing 50 μg/mL of kanamycin, followed by shake-culturing at 37° C. After 1.5 hours from the starting of the culturing, the culture temperature was changed to 20° C. followed by shake-culturing for 30 minutes. IPTG was added so that the final concentration was 0.01 mM, followed by shake-culturing at 20° C. overnight.

(3) Soluble proteins were extracted from the cultured bacterial cells, and each protein concentration of the extracted Fc binding protein was measured using human FcγRI in the known concentration as a control by the ELISA method described in Example 4.

Figure 7:
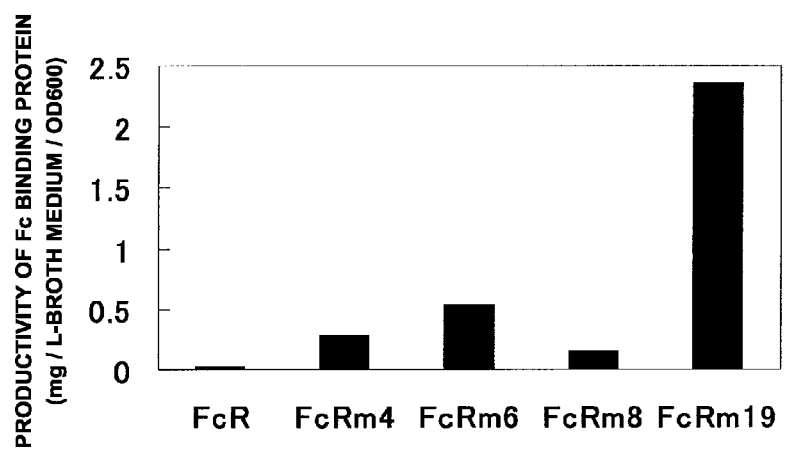
FIG. 7 is a graph for evaluating the productivity of the Fc binding proteins (FcRm4, FcRm6, FcRm8, FcRm19).

FIG. 7 shows a result of comparison of productivities of Fc binding proteins expressed by the transformants produced in Examples 2 and 7 as the production amount (mg/L-broth medium/OD600) per turbidity (Optical Density at 600 nm, OD600) of the culture broth. FcR in FIG. 7 shows a (wild-type) Fc binding protein with no amino acid substitution expressed by the transformant in Example 2. The FcRm4, FcRm6, FcRm8, and FcRm19 that were Fc binding proteins expressed by the transformants produced in Example 7 were confirmed to have higher productivity than this Fc binding protein. The result in FIG. 7 reveals that the productivity of the Fc binding protein is improved by integration of amino acid substitutions involved in improved stability.

Example 9

Production of Fc Binding Protein (1) Each of the transformants produced in Examples 2 and 7 was precultured in the same manner as in Example 8.

(2) Each of preculture broths was inoculated into 2YT broth medium containing 50 μg/mL of kanamycin followed by shake-culturing at 37° C.

(3) When the turbidity (OD600) of each of the culture broth was from 1.5 to 2.0, the culture broth was cooled to 15° C., and 0.1 mM IPTG was added, followed by shake-culturing at 15° C. overnight.

(4) After completion of culturing, each of the bacterial cells obtained by centrifugal separation was suspended in 20 mM Tris-HCl buffer (pH 8.0) containing 150 mM NaCl and 0.1 mM PMSF (phenylmethylsulfonyl fluoride), and disintegrated by ultrasonic waves with cooling to 6° C. Centrifugation separation was carried out to recover each supernatant.

(5) From each of the recovered supernatants, an Fc binding protein was purified by a method described below.

(5-1) Imidazole was added to each of the recovered supernatants so that the final concentration was 10 mM, and was applied to a nickel chelate column equilibrated by a 20 mM Tris-HCl buffer (pH 8.0) containing 150 mM NaCl precedently (His•Bind Resin: Novagen). The column was then washed with the 20 mM Tris-HCl buffer (pH 8.0) containing 150 mM NaCl, and an Fc binding protein was eluted with PBS (137 mM NaCl, 8.10 mM disodium hydrogen phosphate, 2.68 mM potassium chloride, 1.47 mM potassium hydrogen phosphate) (pH 7.0) containing 500 mM imidazole.

(5-2) The elute containing the Fc binding protein obtained in (5-1) was applied to IgG Sepharose (registered trademark) 6 Fast Flow (GE Healthcare Biosciences, hereinafter referred to as FF) equilibrated by PBS (pH 7.0) in advance. Subsequently, FF was washed with PBS (pH 7.0), and an Fc binding protein was eluted in 20 mM citric acid buffer (pH 3.0) containing 150 mM NaCl and 10% glycerol. Herein, the elution was carried out in a container charging a 1M Tris-HCl buffer (pH 8.0) in a volume equal to ¼ of the eluted volume.

Example 10

Evaluation of Thermal Stability of Fc Binding Protein

The purified solution of each Fc binding protein was dialyzed using PBS (pH 7.0) at 4° C., and the transition midpoint (Tm) was measured by a differential scanning calorimetry (DSC) (VP capillary DSC platform, Nihon SiberHegner) under conditions of a temperature increasing rate of 60° C./hour. The results are shown in Table 8.

TABLE 8

| Fc binding protein | Transition midpoint (Tm)(° C.) |
|---|---|
| FcR | 48.5 |
| FcRm4 | 56.0 |
| FcRm6 | 60.4 |
| FcRm8 | 60.2 |
| FcRm19 | 65.6 |

FcR in Table 8 shows a wild-type Fc binding protein expressed by the transformant produced in Example 2. The FcRm4, FcRm6, FcRm8, and FcRm19 that were the Fc binding proteins expressed by the transformant produced in Example 7 were confirmed to have increased Tm and improved thermal stability in comparison with this Fc binding protein. Further, the thermal stability of the Fc binding protein was improved by integration of amino acid substitutions involved in improved stability.

Example 11

Mutation Introduction into Fc Binding Protein (FcRm8) and Production of Library (1) A mutation was randomly introduced into the polynucleotide encoding the FcRm8 produced in Example 7(c) by the error-prone PCR. A reaction solution composition in the error-prone PCR is shown in the Table 9. The plasmid pETFcRm8 described in Example 7(c) was used as a template DNA and the oligonucleotide including the sequence shown in SEQ ID NO: 66 and the oligonucleotide including the sequence shown in SEQ ID NO: 67 were used as PCR primers.

TABLE 9

| Composition | Concentration |
|---|---|
| Template DNA | 0.05 ng/μL |
| Each PCR primer | 0.4 μM |
| MnCl$_2$ | 0.4 mM |
| dATP | 0.2 mM |
| dGTP | 0.2 mM |
| dCTP | 1 mM |
| dTTP | 1 mM |
| Buffer (Adjust MnCl$_2$ to 5 mM) | ×1 |
| GoTaq polymerase (Promega K.K.) | 0.05 U/μL |
| H$_2$O | up to 50 μL |

A PCR was carried out by heating for 2 minutes at 95° C., carrying out 30 cycles consisting of 30 seconds at 95° C. in the first step, 30 seconds at 60° C. in the second step, and 90 seconds at 72° C. in the third step, and finally heating for 7 minutes at 72° C.

(2) The PCR product obtained in (1) was purified, digested with the restriction enzymes NcoI and HindIII, and inserted in the plasmid pETMalE (FIG. 4), which had been digested with the restriction enzymes NcoI and HindIII and produced in Example 2, by a ligation reaction.

(3) After completion of the reaction, the cells of *E. coli* strain JM109 were transformed using the obtained ligation product by the electroporation method, and were cultured on LB agar plates containing 50 μg/mL of kanamycin (at 37° C. for 18 hours). After the culturing, about 4,000 colonies were formed on the plates. Plasmid DNA was extracted from mixed colonies obtained by mixing the colonies to obtain an FcRm8 random mutation plasmid library.

(4) *E. coli* strain BL21 (DE3) was transformed using the plasmid library produced in (3), and colonies were formed in LB agar medium containing 50 μg/mL of kanamycin. Thereby, an FcRm8 random mutation transformant library was produced.

Example 12

Screening of Fc Binding Protein (FcRm8) Library (1) The FcRm8 random mutation transformant library produced in Example 11 was inoculated into 200 μL of an LB broth medium containing 50 μg/mL of kanamycin, and was shake-cultured using a 96-deep well plate at 37° C. overnight.

(2) After the culturing, 5 μl of culture broth was subcultured into 500 μL of 2YT broth medium (containing 0.05 mM IPTG, 0.3% glycine, and 50 μg/mL of kanamycin), and was shake-cultured using a 96-deep well plate at 20° C. overnight.

(3) After the culturing, a culture supernatant obtained by centrifugation was diluted with pure water ten times, and the diluted supernatant and a 0.1 M glycine-sodium hydroxide buffer (pH 10.0) were mixed in equal volumes. The mixture was heated at 53° C. for 20 minutes, and neutralized with a 1M Tris-HCl buffer (pH 8.0).

(4) The antibody binding activities of the Fc binding proteins obtained from about 3,000 transformants were measured by the ELISA method described below.

(4-1) A γ-globulin formulation (KAKETSUKEN) that was a human antibody was immobilized in wells of a 96-well microplate (at 4° C. for 18 hours) in a concentration of 1 μg/well. After completion of the immobilization, the well was blocked with a 50 mM Tris-HCl buffer (pH 8.0) containing 2% (w/v) skim milk.

(4-2) The γ-globulin was washed with a wash buffer (10 mM Tris-HCl buffer (pH 8.0) containing 0.2% (w/v) Tween 20 and 150 mM NaCl), and a prepared protein extract was appropriately diluted with 50 mM Tris-HCl buffer (pH 8.0) and reacted with the immobilized γ-globulin (at 30° C. for 1 hour).

(4-3) After completion of the reaction, the resultant was washed with the wash buffer, and a Horse radish Peroxidase (HRP) labeled anti-His-Tag antibody reagent (BETHYL) was added.

(4-4) After a reaction at 30° C. for 1 hour, the resultant was washed with the wash buffer, and TMB Peroxidase Substrate (KPL) was added. The absorbance at 450 nm of the mixture was measured.

(5) The antibody binding activities of the Fc binding proteins heated (at 53° C. for 20 minutes) was divided by the antibody binding activities of unheated Fc binding proteins to obtain percentages of remaining activity.

(6) A plasmid was prepared from a transformant expressing an Fc binding protein with improved stability in comparison with the FcRm8. The sequence of a polynucleotide region encoding an Fc binding protein inserted in the obtained plasmid was analyzed through the method described in Example 3 to identify mutation sites of amino acid existing in the Fc binding protein with improved stability in comparison with the FcRm8.

As shown from the results of analysis of the nucleotide sequence, the substitutions of amino acid in the Fc binding protein with improved stability in comparison with the FcRm8 are as follows (provided that the substitution of amino acid existing in the FcRm8 is not included.)

Specifically, in the amino acid sequence described in SEQ ID NO: 1, a substitution shown as Thr20Ile, Glu36Gly, Glu44Asp, Val45Ala, Pro49Ser, Gly60Asp, Thr63Leu, Thr65Ala, Ser66Thr, Ser69Thr, Thr73Ala, Val77Glu, Asn78Ser, Arg102Ser, His125Arg, Leu131Pro, Tyr133His, Arg139His, Lys142Glu, Phe147Ser, His148Arg, His148Gln, Trp149Arg, Asn152Ile, Asn152Thr, Leu156His, Leu156Pro, Ile160Thr, Ile160Val, Ile160Leu, Met171Thr, Lys173Arg, Ile181Thr, Leu203His, Asn206Ser, Leu207Gln, Gln219Pro, Leu225Gln, Met231Lys, Arg251Ser, Leu257Arg, Leu257Gln, Gly282Asp, Leu285Gln, Leu285Arg, or Val289Asp was caused. The residual rate (remaining activity) of antibody binding activity after heating and results of analysis of the amino acid substitutions are shown in Table 10. Table 10 reveals that when the FcRm8 is further subjected to the amino acid substitution, the Fc binding protein has improved stability.

TABLE 10

| Amino acid substitution | Remaining activity (%) |
|---|---|
| Glu36Gly | 66.4 |
| Glu44Asp | 34.0 |
| Pro49Ser | 30.7 |
| Ala62Val | 27.5 |
| Thr63Leu | 54.7 |
| Gln64Lys | 24.0 |
| Thr65Ala | 55.9 |
| Ser66Thr | 30.8 |
| Ser69Thr | 49.5 |
| Thr73Ala | 41.7 |
| Val77Glu | 55.9 |
| Asn78Ser | 43.3 |
| Arg102Ser | 44.0 |
| Val109Ala | 16.8 |
| Leu131Pro | 40.1 |
| Tyr133His | 36.1 |

TABLE 10-continued

| Amino acid substitution | Remaining activity (%) |
|---|---|
| Lys142Glu | 39.2 |
| Phe147Ser | 38.9 |
| His148Gln | 44.2 |
| Trp149Arg | 63.9 |
| Asn152Ile | 56.5 |
| Leu156His | 49.5 |
| Leu156Pro | 33.6 |
| Ile160Thr | 54.3 |
| Ile160Val | 39.0 |
| Met171Thr | 37.4 |
| Leu203Pro | 28.4 |
| Leu203His | 77.3 |
| Asn206Ser | 33.8 |
| Leu207Gln | 37.8 |
| Gln219Pro | 40.3 |
| Leu225Gln | 45.5 |
| Ser228Thr | 28.7 |
| Gln244Arg | 28.8 |
| Arg252His | 24.8 |
| Leu257Arg | 46.3 |
| Leu257Gln | 46.7 |
| Pro274Gln | 28.2 |
| Gly282Asp | 40.3 |
| Leu285Gln | 70.2 |
| Leu285Arg | 37.3 |
| Val289Asp | 36.6 |
| Thr20Ile, Met231Lys | 56.1 |
| Gly60Asp, Arg139His | 59.7 |
| His125Arg, Met171Thr | 35.4 |
| His148Arg, Arg251Ser | 61.7 |
| Trp149Arg, Asn152Thr | 68.2 |
| Ile181Thr, Leu285Gln | 85.1 |
| Val45Ala, Ile160Leu, Lys173Arg | 98.9 |
| FcRm8 | 30.6 |

Example 13

Production of Fc Binding Protein (FcRm32)

From the amino acid substitutions involved in improved stability of the Fc binding protein shown in Example 12, Glu36Gly, Val45Ala, Pro49Ser, Gly60Asp, Thr65Ala, Tyr133His, Arg139His, Trp149Arg, Leu156Pro, Ile160Thr, Lys173Arg, Ile181Thr, Leu203His, Leu207Gln, and Met231Lys that were amino acid substitutions involved in improved stability were selected. The substitutions were integrated with respect to the FcRm19 described in Example 7(d) to produce an Fc binding protein FcRm32 in which 32 amino acids of a wild-type Fc binding protein were substituted with amino acids. Thus, stability was further improved. Further, the amino acid substitutions shown as Glu36Gly, Val45Ala, Pro49Ser, Gly60Asp, Thr65Ala, Tyr133His, Arg139His, Trp149Arg, Leu156Pro, Ile160Thr, Lys173Arg, Ile181Thr, Leu203His, Leu207Gln, and Met231Lys were carried out using oligonucleotides described below.

(i) amino acid substitution Glu36Gly: an oligonucleotide having a sequence shown in SEQ ID NO: 94 (5'-ACGTCACGGATTCTCCCTGGAACACGCTCA-3') and an oligonucleotide having a sequence shown in SEQ ID NO: 95 (5'-TGAGCGTGTTCCAGGGAGAATCCGTGACGT-3')

(ii) amino acid substitution Val45Ala: an oligonucleotide having a sequence shown in SEQ ID NO: 96 (5'-AGACAGATGCGGTGCTTCGCAGTGCAA-3') and an oligonucleotide having a sequence shown in SEQ ID NO: 97 (5'-TTGCACTGCGAAGCACCGCATCTGTCT-3')

(iii) amino acid substitution Pro49Ser: an oligonucleotide having a sequence shown in SEQ ID NO: 98 (5'-AACTTGACCCAGACAGATGCGGTACTT-3') and an oligonucleotide having a sequence shown in SEQ ID NO: 99 (5'-AAGTACCGCATCTGTCTGGGTCAAGTT-3')

(iv) amino acid substitutions Gly60Asp and Thr65Ala: an oligonucleotide having a sequence shown in SEQ ID NO: 100 (5'-GGGTGGAGGCCTGGATCGCGGTGTCATTCAGGA-3') and an oligonucleotide having a sequence shown in SEQ ID NO: 101 (5'-TCCTGAATGACACCGCGATCCAGGCCTOCACCC-3')

(v) amino acid substitutions Tyr133His and Arg139His: an oligonucleotide having a sequence shown in SEQ ID NO: 102 (5'-TTGTGGTAGTAAAGCACGTTGTGCACCAGCTT-3') and an oligonucleotide having a sequence shown in SEQ ID NO: 103 (5'-TGCACAACGTGCTTTACTACCACAACGGCAA-3')

(vi) amino acid substitution Trp149Arg: an oligonucleotide having a sequence shown in SEQ ID NO: 104 (5'-AGGTTGGAGTTCCGGTGGAAGAACTTAA-3') and an oligonucleotide having a sequence shown in SEQ ID NO: 105 (5'-TTAAGTTCTTCCACCGGAACTCCAACCT-3')

(viii) amino acid substitutions Leu156Pro and Ile160Thr: an oligonucleotide having a sequence shown in SEQ ID NO: 106 (5'-TGTGGGACGTGTTCGTCTTCGGAATGGTCA-3') and an oligonucleotide having a sequence shown in SEQ ID NO: 107 (5'-TGACCATTCCGAAGACGAACACGTCCCACA-3')

(ix) amino acid substitution Lys173Arg: an oligonucleotide having a sequence shown in SEQ ID NO: 108 (5'-TCCCGCCGACGTATAACGATGTCTGCCCAT-3')

(x) amino acid substitution Ile181Thr: an oligonucleotide having a sequence shown in SEQ ID NO: 109 (5'-ACATCGTTATACGTCGGCGGGAACCTCGGTCA-3')

(xi) amino acid substitutions Leu203His and Leu207Gln: an oligonucleotide having a sequence shown in SEQ ID NO: 110 (5'-AGGGTCACCTGAGTGCCTTCATGCAGCGG-3') and an oligonucleotide having a sequence shown in SEQ ID NO: 111 (5'-CCGCTGCATGAAGGCACTCAGGTGACCCT-3')

(xii) amino acid substitution Met231Lys: an oligonucleotide having a sequence shown in SEQ ID NO: 112 (5'-CGCAGGGTTTTGCTGCCCTTATAGAACGA-3') and an oligonucleotide having a sequence shown in SEQ ID NO: 113 (5'-TCGTTCTATAAGGGCAGCAAAACCCTGCG-3')

(1) The PCR was carried out using the plasmid pET-FcRm19 described in Example 7 (d) as a template and the oligonucleotide including the sequence shown in SEQ ID NO: 68 and the oligonucleotide including the sequence shown in SEQ ID NO: 94 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m32p1.

(2) The PCR was carried out using the plasmid pET-FcRm19 described in Example 7 (d) as a template and the oligonucleotide including the sequence shown in SEQ ID NO: 95 and the oligonucleotide including the sequence shown in SEQ ID NO: 106 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m32p2.

(3) The PCR was carried out using the plasmid pET-FcRm19 described in Example 7 (d) as a template and the oligonucleotide including the sequence shown in SEQ ID NO: 107 and the oligonucleotide including the sequence shown in SEQ ID NO: 110 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m32p3.

(4) The PCR was carried out using the plasmid pET-FcRm19 described in Example 7 (d) as a template and the oligonucleotide including the sequence shown in SEQ ID NO: 111 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m32p4.

(5) Four types of the PCR products m32 µl, m32p2, m32p3, and m32p4 were purified. The purified m32 µl, m32p2, m32p3, and m32p4 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated.

(6) The PCR was carried out using the PCR product obtained in (5) as a template and the oligonucleotide including the sequence shown in SEQ ID NO: 68 and the oligonucleotide including the sequence shown in SEQ ID NO: 69 as PCR primers.

The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m32p5.

(7) The m32p5 was purified. The PCR was carried out using the purified m32p5 as a template and the oligonucleotide including the sequence shown in SEQ ID NO: 68 and the oligonucleotide including the sequence shown in SEQ ID NO: 98 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m32p6.

(8) The m32p5 was purified. The PCR was carried out using the purified m32p5 as a template and the oligonucleotide including the sequence shown in SEQ ID NO: 99 and the oligonucleotide including the sequence shown in SEQ ID NO: 104 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m32p7.

(9) The m32p5 was purified. The PCR was carried out using the purified m32p5 as a template and the oligonucleotide including the sequence shown in SEQ ID NO: 105 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m32p8.

(10) Three types of the PCR products m32p6, m32p7, and m32p8 were purified. The purified m32p6, m32p7, and m32p8 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR reaction was carried out using this PCR product as a template and the oligonucleotide including the sequence shown in SEQ ID NO: 68 and the oligonucleotide including the sequence shown in SEQ ID NO: 69 as PCR primers. The PCR reaction was carried out for 30 cycles consisting of 10 seconds at 98° C. in the first step, 5 seconds at 50° C. in the second step, and 1 minute at 72° C. in the third step using the to reaction solution composition shown in Table 4. The PCR product was designated as m32p9.

(11) The m32p9 was purified. The PCR was carried out using the purified m32p9 as a template and the oligonucleotide including the sequence shown in SEQ ID NO: 68 and the oligonucleotide including the sequence shown in SEQ ID NO: 100 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m32p10.

(12) The m32p9 was purified. The PCR was carried out using the purified m32p9 as a template and the oligonucleotide including the sequence shown in SEQ ID NO: 101 and the oligonucleotide including the sequence shown in SEQ ID NO: 108 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m32p11.

(13) The m32p9 was purified. The PCR was carried out using the purified m32p9 as a template and the oligonucleotide including the sequence shown in SEQ ID NO: 109 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m32p12.

(14) Three types of the PCR products, m32p10, m32p11, and m32p12 were purified. The purified m32p10, m32p11, and m32p12 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m32p13.

(15) The m32p13 was purified. The PCR was carried out using the purified m32p13 as a template and the oligonucleotide including the sequence shown in SEQ ID NO: 68 and the oligonucleotide including the sequence shown in SEQ ID NO: 96 as PCR primers. The PCR was carried out for 30 cycles consisting of 10 seconds at 98° C. in the first step, 5 seconds at 50° C. in the second step, and 1 minute at 72° C.

in the third step using the reaction solution composition shown in Table 4. The PCR product was designated as m32p14.

(16) The m32p13 was purified. The PCR was carried out using the purified m32p13 as a template and the oligonucleotide including the sequence shown in SEQ ID NO: 97 and the oligonucleotide including the sequence shown in SEQ ID NO: 102 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m32p15.

(17) The m32p13 was purified. The PCR was carried out using the purified m32p13 as a template and the oligonucleotide including the sequence shown in SEQ ID NO: 103 and the oligonucleotide including the sequence shown in SEQ ID NO: 112 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m32p16.

(18) The m32p13 was purified. The PCR was carried out using the purified m32p13 as a template and the oligonucleotide including the sequence shown in SEQ ID NO: 113 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m32p17.

(19) Four types of the PCR products, m32p14, m32p15, m32p16, and m32p17 were purified. The purified m32p14, m32p15, m32p16, and m32p17 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated.

(20) The PCR was carried out using the PCR product obtained in (19) as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4.

(21) The PCR product obtained in (20) was purified to obtain a polynucleotide encoding the Fc binding protein FcRm32 in which 32 amino acids of a wild-type Fc binding protein were substituted with amino acids.

(22) The polynucleotide encoding the FcRm32 was digested with the restriction enzymes NcoI and HindIII, and ligated into the expression vector pETMalE (FIG. 4) which had been digested with the restriction enzymes NcoI and HindIII and described in Example 2. *E. coli* strain BL21 (DE3) was transformed with this product.

(23) The obtained transformant was cultured in LB medium containing 50 µg/mL of kanamycin. A plasmid was extracted from the cultured bacterial cells (transformant) to obtain a plasmid pETFcRm32 containing the polynucleotide encoding the FcRm32.

(24) The nucleotide sequence of pETFcRm32 was analyzed in the same manner as in Example 3.

The amino acid sequence of FcRm32 plus a signal sequence and a polyhistidine tag is shown in SEQ ID NO: 114, and the sequence of the polynucleotide encoding the FcRm32 is shown in SEQ ID NO: 115. In SEQ ID NO: 114, the MalE signal peptide is from methionine at position 1 to alanine at position 26, the linker peptide is from lysine at position 27 to glycine at position 33, the amino acid sequence of FcRm32 is from glutamine at position 34 to valine at position 307, and the polyhistidine tag is histidine at positions 308 to 313. Further, in SEQ ID NO: 114, proline of Thr20Pro that is a substituted amino acid is at position 38, lysine of Thr25Lys is at position 43, glycine of Glu36Gly is at position 54, serine of Thr38Ser is at position 56, alanine of Val45Ala is at position 63, proline of Leu46Pro is at position 64, serine of Pro49Ser is at position 67, aspartic acid of Gly60Asp is at position 78, isoleucine of Thr63Ile is at position 81, alanine of Thr65Ala is at position 83, threonine of Ser69Thr is at position 87, histidine of Arg71His is at position 89, glutamic acid of Val77Glu is at position 95, aspartic acid of Asn78Asp is at position 96, valine of Ile100Val is at position 118, leucine of Phe114Leu is at position 132, histidine of Tyr133His is at position 151, histidine of Arg139His is at position 157, arginine of Trp149Arg is at position 167, praline of Leu156Pro is at position 174, threonine of Ile160Thr is at position 178, serine of Asn163Ser is at position 181, arginine of Lys173Arg is at position 191, threonine of Ile181Thr is at position 199, threonine of Asn195Thr is at position 213, histidine of Leu203His is at position 221, threonine of Asn206Thr is at position 224, glutamine of Leu207Gln is at position 225, lysine of Met231Lys is at position 249, aspartic acid of Asn240Asp is at position 258, histidine of Leu283His is at position 301, and glutamine of Leu285Gln is at position 303.

Example 14

Evaluation of Productivity of Fc Binding Protein (FcRm32)

(1) The transformant produced in Example 13 was inoculated into an LB broth medium containing 50 µg/mL of kanamycin. The precultures were carried out by shake-culturing at 37° C. overnight.

(2) A preculture broth was inoculated into an LB broth medium containing 50 µg/mL of kanamycin followed by shake-culturing at 37° C. After 1.5 hours from the start of culturing, the culture temperature was changed to 20° C. followed by shake-culturing for 30 minutes. IPTG was added so that the final concentration was 0.01 mM followed by shake-culturing at 20° C. overnight.

(3) After completion of the culturing, bacterial cells were recovered by centrifugal separation, and a protein was prepared from the cells using a BugBuster Protein extraction kit (Takara Bio).

Figure 8:
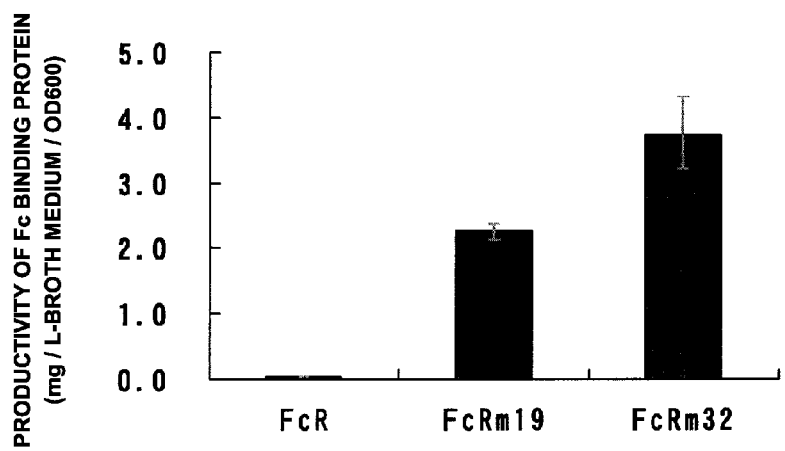
FIG. 8 is a graph for evaluating the productivity of the Fc binding protein (FcRm32).

(4) The antibody binding activity of the prepared protein was evaluated by the ELISA method described in Example 12 (4), and thus the productivity of the Fc binding protein was measured. FIG. 8 shows a result of comparison of productivity of the Fc binding protein as the production amount (mg/L-broth medium/OD600) per turbidity (Optical Density at 600 nm, OD600) of the culture broth. FcR in FIG. 8 shows the wild-type Fc binding protein expressed by the transformant in Example 2. FcRm19 shows the Fc binding protein expressed by the transformant in Example 7 (d). FcRm32 that was the Fc binding protein expressed by the transformant produced in Example 13 was confirmed to have higher productivity than these Fc binding proteins. The result in FIG. 8 reveals that the productivity of the Fc binding protein is improved by integration of amino acid substitutions (mutation) involved in improved stability.

Example 15

Evaluation of Stability of Fc Binding Protein (FcRm32) Against Alkali (1) The Fc binding proteins (FcRm19 and FcRm32) and a wild-type Fc binding protein were prepared by the method described in Example 14, and the concentrations thereof were measured by the ELISA method described in Example 12(4).

(2) The proteins used for the concentration measurement were diluted so that the concentration was 5 µg/mL. To each of the resultant, an equal amount of a 600 mM sodium hydroxide solution was added and the mixture was allowed to stand at 25° C. for 5 minutes.

(3) After standing, the pH was adjusted to a neutral region with 1M Tris-HCl buffer (pH 8.0), and the antibody binding activities of alkali-treated and untreated samples were measured by the ELISA method described in Example 12(4).

(4) The antibody binding activities of the alkali-treated samples were divided by the antibody binding activities of the untreated samples to obtain a percentage of remaining activity of each of Fc binding proteins by alkali treatment.

Figure 9:
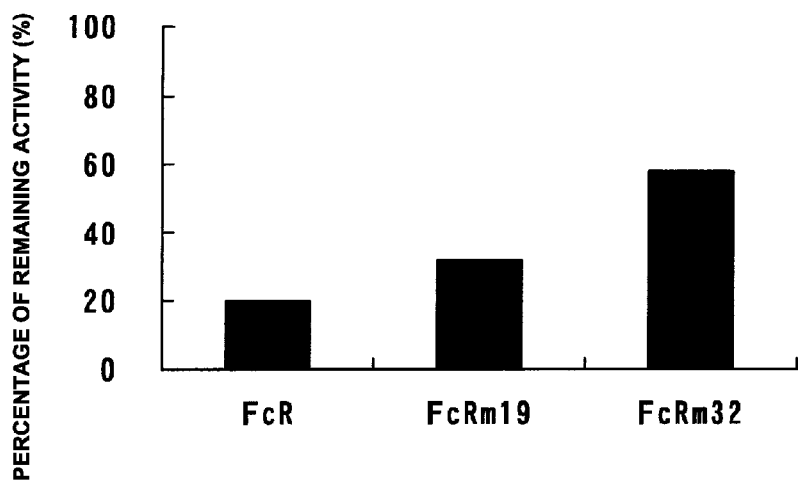
FIG. 9 is a graph for evaluating the alkali stability of the Fc binding protein (FcRm32).

FIG. 9 shows a result of comparison of stability against alkali. FcR in FIG. 9 shows the wild-type Fc binding protein expressed by the transformant in Example 2. FcRm19 shows the Fc binding protein expressed by the transformant in Example 7 (d). As compared to these Fc binding proteins, FcRm32 that was the Fc binding protein expressed by the transformant produced in Example 13 was confirmed to have higher stability against alkali than the FcR and FcRm19. The result in FIG. 9 reveals that the stability of the Fc binding protein against alkali is improved by integration of amino acid substitutions (mutation) involved in improved stability.

Example 16

Mutation Introduction into Fc Binding Protein (FcRm32) and Production of Library (1) A mutation was randomly introduced into the polynucleotide encoding the FcRm32 produced in Example 13 by an error-prone PCR. Reaction solution composition in the error-prone PCR is shown in the Table 9. The plasmid pETFcRm32 described in Example 13 was used as a template DNA and the oligonucleotide including the sequence shown in SEQ ID NO: 66 and the oligonucleotide including the sequence shown in SEQ ID NO: 67 were used as PCR primers. A PCR was carried out by heating for 2 minutes at 95° C., carrying out 30 cycles consisting of 30 seconds at 95° C. in the first step, 30 seconds at 60° C. in the second step, and 90 seconds at 72° C. in the third step, and finally heating for 7 minutes at 72° C.

(2) The PCR product obtained in (1) was purified, digested with the restriction enzymes NcoI and HindIII, and inserted in the plasmid pETMalE (FIG. 4), which had been digested with the restriction enzymes NcoI and HindIII and produced in Example 2, by a ligation reaction.

(3) After completion of the reaction, the cells of *E. coli* strain JM109 were transformed using the resulting ligation product by the electroporation method, and cultured on an LB agar plates containing 50 µg/mL of kanamycin (at 37° C. for 18 hours). After the culturing, about 19,000 colonies were formed on the plates. Plasmid DNA was extracted from mixed colonies obtained by mixing the colonies to obtain an FcRm32 random mutation plasmid library.

(4) *E. coli* strain BL21 (DE3) was transformed using the plasmid library produced in (3), and colonies were formed on LB agar medium containing 50 µg/mL of kanamycin. Thus, an FcRm32 random mutation transformant library was produced.

Example 17

Screening of Library of Fc Binding Protein (FcRm32) with Improved Stability (1) The FcRm32 random mutation transformant library produced in Example 16 was inoculated into 200 µL of an LB broth medium containing 50 µg/mL of kanamycin, and was shake-cultured using a 96-deep well plate at 37° C. overnight.

(2) After the culturing, 5 µL of culture broth was subcultured into 500 µL of 2YT broth medium (containing 0.05 mM IPTG, 0.3% glycine, and 50 µg/mL of kanamycin), and was shake-cultured using a 96-deep well plate at 20° C. overnight.

(3) After the culturing, a culture supernatant obtained by centrifugation was diluted with pure water ten times, and the diluted supernatant and a 0.1 M glycine-sodium hydroxide buffer (pH 10.0) were mixed in equal volumes. The mixture was heated at 70° C. for 20 minutes, and neutralized with a 1M Tris-HCl buffer (pH 8.0).

(4) The antibody binding activities of the Fc binding proteins obtained from about 3,000 transformants were measured by the ELISA method described in Example 12(4). The antibody binding activities of the Fc binding proteins heated (at 70° C. for 20 minutes) were divided by the antibody binding activities of unheated Fc binding proteins to obtain percentages of remaining activity.

(5) A plasmid was prepared from the transformant expressing the Fc binding protein with improved stability in comparison with the FcRm32. The sequence of a polynucleotide region encoding an Fc binding protein inserted in the obtained plasmid was analyzed through the method described in Example 3 to identify mutation sites of amino acid existing in the Fc binding protein with improved stability in comparison with the FcRm32.

As shown from the results of analysis of the nucleotide sequence, positions of substitutions of amino acid in the Fc binding protein areas follows (provided that the substitution of amino acid existing in the FcRm32 is not included).

Specifically, in the amino acid sequence described in SEQ ID NO: 1, substitution shown as Gln27Pro, Gln35Leu, Leu41Met, Ser51Thr, Ser51Pro, Ser52Gly, Ser53Leu, Gly60Gly, Thr63Leu, Gln64Pro, Thr73Ser, Val77Asp, Ser80Ala, Leu89Gln, Arg92Cys, Gln97Leu, Asp129Gly, Leu131Gln, Leu131Pro, Tyr133Arg, Asn134Ser, Tyr138His, Phe144Ile, His148Arg, Asn152Thr, Lys157Arg, Ser182Thr, Val193Leu, Val198Gly, Ser200Gly, Ser200Arg, Leu207Pro, Leu207His, Ser211Arg, Leu223Arg, Asn240Gly, Gln246Arg, Ala250Val, Thr264Ser, Asn268Ser, Glu277Val, or Thr287Ile was caused. Further, substitution (for example, Gly60Gly) in which specified amino acids are not changed represents that a substituted (mutated) amino acid returns to a wild-type amino acid (same as above). The residual rate (remaining activity) of antibody binding activity after heating and results of analysis of the amino acid substitutions are shown in Table 11. Table 11 reveals that when the FcRm32 was further substituted with amino acids, the Fc binding protein has improved stability.

TABLE 11

| Amino acid substitution | Remaining activity (%) |
| --- | --- |
| Gln35Leu | 72.1 |
| Leu41Met | 63.4 |
| Ser52Gly | 77.5 |
| Gln64Arg | 10.9 |
| Thr73Ser | 38.6 |
| Val77Asp | 18.1 |
| Leu89Gln | 38.7 |
| Asp129Gly | 92.6 |
| Leu131Gln | 40.7 |
| Leu131Pro | 23.9 |
| Tyr133Arg | 63.3 |
| Asn134Ser | 33.1 |
| Tyr138His | 16.5 |
| Asn152Thr | 93.7 |
| Lys157Arg | 21.0 |
| Val198Gly | 31.4 |
| Ser200Gly | 13.1 |
| Leu207Pro | 45.6 |
| Asn240Gly | 23.8 |
| Ala250Val | 28.3 |
| Gln35Leu, Ser51Thr | 17.7 |
| Ser51Thr, Thr63Leu | 40.0 |
| Gln64Pro, His133Arg | 46.5 |
| Gly60Gly, Ser182Thr | 18.5 |
| Ser80Ala, Tyr133Arg, Glu277Val | 44.7 |
| His148Arg, Asn268Ser | 26.4 |
| Ser200Arg, Thr287Ile | 56.9 |
| Gln27Pro, Ser51Pro, Arg92Cys | 31.1 |
| Gln97Leu, Ser211Arg, Thr264Ser | 42.7 |
| Gln35Leu, Asp129Gly, His148Arg, Gln246Arg | 50.0 |
| Ser53Leu, Phe144Ile, Val193Leu, Leu207His, Leu223Arg | 43.1 |
| FcRm32 | 11.7 |

Example 18

Production of Fc Binding Protein (FcRm36b)

From the amino acid substitutions involved in improved stability of the Fc binding protein shown in Example 17, Gln35Leu, Leu41Met, Ser52Gly, and Asn152Thr that were amino acid substitutions involved in improved stability were selected. The substitutions were integrated with respect to the FcRm32 described in Example 13 to produce an Fc binding protein FcRm36b in which 36 amino acids of a wild-type Fc binding protein were substituted with amino acids. Thus, stability was further improved. Further, an oligonucleotide including the sequence shown in SEQ ID NO: 116 (5'-ATGCGGTGCTTCGCAGTGCATCGT-CACGGATTCTCCCAGGAACA-3') and an oligonucleotide including the sequence shown in SEQ ID NO: 117 (5'-GACGATGCACTGCGAAGCACCGCATCT-GTCTGGGTCAGGTTCAA-3') were used for amino acid substitutions shown as Gln35Leu, Leu41Met, and Ser52Gly.

(1) The PCR was carried out using the plasmid pET-FcRm32 described in Example 13 as a template and the oligonucleotide including the sequence shown in SEQ ID NO: 68 and the oligonucleotide including the sequence shown in SEQ ID NO: 116 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m36 bp1.

(2) The PCR was carried out using as a template the plasmid containing the polynucleotide encoding the Fc binding protein in which the Fc binding protein FcRm32 obtained by screening in Example 17 was subjected to an additional substitution shown as Asn152Thr. The PCR was carried out using the oligonucleotide including the sequence shown in SEQ ID NO: 117 and the oligonucleotide including the sequence shown in SEQ ID NO: 92 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m36 bp2.

(3) The PCR was carried out using the plasmid pET-FcRm32 described in Example 13 as a template and the oligonucleotide including the sequence shown in SEQ ID NO: 93 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m36 bp3.

(4) Three types of the PCR products, m36 bp1, m36 bp2, and m36 bp3 were purified. The purified m36 bp1, m36 bp2, and m36 bp3 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The resulting PCR product obtained was purified to obtain a polynucleotide encoding the Fc binding protein FcRm36b in which 36 amino acids of a wild-type Fc binding protein were substituted with amino acids.

(5) The polynucleotide encoding the FcRm36b was digested with the restriction enzymes NcoI and HindIII, and ligated into the expression vector pETMalE (FIG. 4) which had been digested with the restriction enzymes NcoI and HindIII and described in Example 2. *E. coli* strain BL21 (DE3) was transformed with this product.

(6) The obtained transformant was cultured in LB medium containing 50 µg/mL of kanamycin. A plasmid was extracted from the cultured bacterial cells (transformant) to obtain a plasmid pETFcRm36b containing the polynucleotide encoding the FcRm36b.

(7) The nucleotide sequence of pETFcRm36b was analyzed in the same manner as in Example 3.

The amino acid sequence of FcRm36b plus a signal sequence and a polyhistidine tag is shown in SEQ ID NO: 118, and the sequence of the polynucleotide encoding the FcRm36b is shown in SEQ ID NO: 119. In SEQ ID NO: 118, the MalE signal peptide is from methionine at position 1 to alanine at position 26, the linker peptide is from lysine at position 27 to glycine at position 33, the amino acid sequence of FcRm36b is from glutamine at position 34 to valine at position 307, and the polyhistidine tag is histidine at positions 308 to 313. Further, in SEQ ID NO: 118, proline of Thr20Pro that is a substituted amino acid is at position 38, lysine of Thr25Lys is at position 43, leucine of Gln35Leu is at position 53, glycine of Glu36Gly is at position 54, serine of Thr38Ser is at position 56, methionine of Leu41Met is at position 59, alanine of Val45Ala is at position 63, proline of Leu46Pro is at position 64, serine of Pro49Ser is at position 67, glycine of Ser52Gly is at position 70, aspartic acid of Gly60Asp is at position 78, isoleucine of Thr63Ile is at position 81, alanine of Thr65Ala is at position 83, threonine of Ser69Thr is at position 87, histidine of Arg71His is at position 89, glutamic acid of Val77Glu is at position 95, aspartic acid of Asn78Asp is at position 96, valine of Ile100Val is at position 118, leucine of Phe114Leu is at position 132, histidine of Tyr133His is at position 151, histidine of Arg139His is at position 157, arginine of Trp149Arg is at position 167, threonine of Asn152Thr is at position 170, proline of Leu156Pro is at position 174, threonine of Ile160Thr is at position 178, serine of Asn163Ser is at position 181, arginine of Lys173Arg is at position 191, threonine of Ile181Thr is at position 199, threonine of Asn195Thr is at position 213, histidine of Leu203His is at position 221, threonine of Asn206Thr is at position 224, glutamine of Leu207Gln is at position 225, lysine of Met231Lys is at position 249, aspartic acid of Asn240Asp is at position 258, histidine of Leu283His is at position 301, and glutamine of Leu285Gln is at position 303.

Example 19

Evaluation of Productivity of Fc Binding Protein (FcRm36b)

The transformants produced in Examples 18 and 2 were prepared in the same manner as in Example 14. The productivities of Fc binding proteins measured by the ELISA method described in Example 12(4) were compared as the production amount (mg/L-broth medium/OD600) per turbidity (Optical Density at 600 nm, OD600) of the culture broth.

Figure 10:
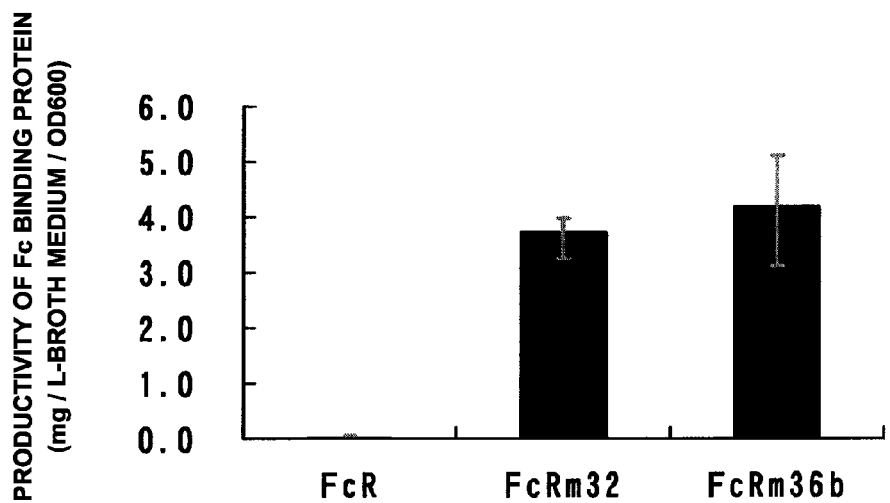
FIG. 10 is a graph for evaluating the productivity of the Fc binding protein (FcRm36b).

The results are shown in FIG. 10. FcR in FIG. 10 shows the wild-type Fc binding protein expressed by the transformant in Example 2. FcRm32 in FIG. 10 shows the Fc binding protein expressed by the transformant in Example 13. The FcRm36b that was the Fc binding protein expressed by the transformant produced in Example 18 was confirmed to have higher productivity than these Fc binding proteins. The results in FIG. 10 reveal that the productivity of the Fc binding protein is improved by integration of amino acid substitutions (mutation) involved in improved stability.

Example 20

Evaluation of Stability of Fc Binding Protein (FcRm36b) Against Alkali (1) The Fc binding proteins (FcRm32 and FcRm36b) and a wild-type Fc binding protein were prepared by the method described in Example 14, and the concentrations thereof were measured by the ELISA method described in Example 12(4).

(2) The proteins used for the concentration measurement were diluted so that the concentration was 5 μg/mL. To each of the resultant, an equal amount of a 600 mM sodium hydroxide solution was added and the mixture was allowed to stand at 25° C. for 5 minutes.

(3) After standing, the pH was adjusted to a neutral region with 1M Tris-HCl buffer (pH 8.0), and the antibody binding activities of the alkali-treated sample in (2) and a sample which was not alkali-treated in (2) for comparison were measured by the ELISA method described in Example 12(4).

(4) The antibody binding activity of the alkali-treated sample was divided by the antibody binding activity of the sample not alkali-treated to obtain a percentage of remaining activity of each of Fc binding proteins by alkali treatment.

Figure 11:
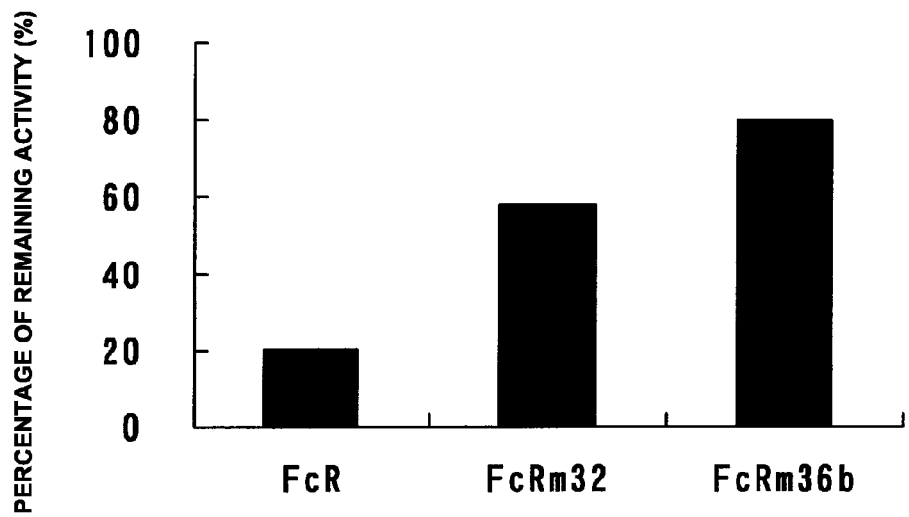
FIG. 11 is a graph for evaluating the alkali stability of the Fc binding protein (FcRm36b).

FIG. 11 shows a result of comparison of stability against alkali. FcR in FIG. 11 shows the wild-type Fc binding protein expressed by the transformant in Example 2. FcRm32 in FIG. 11 shows the Fc binding protein expressed by the transformant in Example 13. The FcRm36b that was the Fc binding protein expressed by the transformant produced in Example 18 was confirmed to have higher stability against alkali than the FcR and FcRm32. The results in FIG. 11 reveal that the stability of the Fc binding protein against alkali is improved by integration of amino acid substitutions (mutation) involved in improved stability.

Example 21

Mutation Introduction into Fc Binding Protein (FcRm36b) and Production of Library (1) A mutation was randomly introduced into the polynucleotide encoding the FcRm36b produced in Example 18 by the error-prone PCR. The reaction solution composition in the error-prone PCR is shown in the Table 9. The plasmid pETFcRm36b described in Example 18 was used as a template DNA. Further, an oligonucleotide including the sequence shown in SEQ ID NO: 120 (5'-TCAGC-CATGGGACAAGTAGATACCCCCAAAGCTGTGATTA-3') and an oligonucleotide including the sequence shown in SEQ ID NO: 121 (5'-CCAAGCTTAATGATGATGATGAT-GATGGACCGGGGTCGGCTGTTGATGACCCAG-3') were used as PCR primers. A PCR was carried out by heating for 2 minutes at 95° C., carrying out 30 cycles consisting of 30 seconds at 95° C. in the first step, 30 seconds at 60° C. in the second step, and 90 seconds at 72° C. in the third step, and finally heating for 7 minutes at 72° C.

(2) The PCR product obtained in (1) was purified, digested with the restriction enzymes NcoI and HindIII, and inserted in the plasmid pETMalE (FIG. 4), which had been digested with the restriction enzymes NcoI and HindIII and produced in Example 2, by a ligation reaction.

(3) After completion of the reaction, *E. coli* strain BL21 (DE3) was transformed using the resulting ligation product by the electroporation method, and cultured in LB agar medium containing 50 μg/mL of kanamycin to form colonies. Thus, an FcRm36b random mutation transformant library was produced.

Example 22

Screening of Fc Binding Protein (FcRm36b) Library (1) The FcRm36b random mutation transformant library produced in Example 21 was inoculated into 200 μL of an LB broth medium containing 50 μg/mL of kanamycin, and was shake-cultured using a 96-deep well plate at 37° C. overnight.

(2) After the culturing, 5 μL of culture broth was subcultured into 500 μL of 2YT broth medium (containing 0.05 mM IPTG, 0.3% glycine, and 50 μg/mL of kanamycin), and was shake-cultured using a 96-deep well plate at 20° C. overnight.

(3) After the culturing, a culture supernatant obtained by centrifugation was diluted with pure water five times, and the diluted supernatant and a 400 mM sodium hydroxide solution were mixed in equal volumes. The mixture was alkali-treated at 30° C. for 60 minutes, and the pH was adjusted to a neutral region with 1M Tris-HCl buffer (pH 8.0).

(4) The antibody binding activities of the Fc binding proteins obtained from about 3,000 transformants were measured by the ELISA method described in Example 12(4). The antibody binding activities of the Fc binding proteins alkali-treated in (3) were divided by the antibody binding activities of Fc binding proteins not alkali-treated in (3) to determine percentages of remaining activity.

(5) A plasmid was prepared from a transformant expressing an Fc binding protein with improved stability in comparison with the FcRm36b. The sequence of a polynucleotide region encoding an Fc binding protein inserted in the obtained plasmid was analyzed through the method described in Example 3 to identify mutation sites of amino acid existing in the Fc binding protein with improved stability in comparison with the FcRm36b.

As shown from the results of analysis of the nucleotide sequence, positions of substitutions of amino acid in the Fc binding protein are accumulated as follows (provided that the substitution of amino acid existing in the FcRm36b is not included).

Specifically, in the amino acid sequence described in SEQ ID NO: 1, substitution shown as Thr25Met, Gln35Met, His42Leu, Ser53Thr, Gln64His, Thr67Ala, Thr67Ser, Val77Lys, Leu89Pro, Ser90Gly, Gln97Leu, Gln97Lys, Arg102Leu, Gly103Asp, Thr115Ile, Glu118Asp, Lys128Arg, Asp129Gly, Leu131Gln, Tyr133Tyr, Lys142Arg, Asn152Pro, Lys157Arg, Ser182Thr, Ser182Leu, Thr199Ala, Leu203Leu, Glu213Val, Lys215Arg, Lys215Glu, Leu218Ile, Gln224Arg, Tyr230His, Ser233Gly, Lys234Glu, Glu244Val, Thr249Ala, Thr249Ser, Glu253Gly, Glu261Val, Ala262Val, Ala263Ser, Glu265Ala, Glu265Gly, Leu270His, Lys271Arg, Gln279Arg, Gln279His, Leu283Pro, Pro286Gln, Thr287Ile, Thr287Pro, Val289Ala, Val289Asp, or Val289Gly was caused. Further, among the substitutions, substitution (for example, Tyr133Tyr) in which specified amino acids are not changed represents that a substituted (mutated) amino acid returns to a wild-type amino acid. Results of analysis of amino acid substitutions are shown in Table 12. Table 12 reveals that when the FcRm36b was further substituted with amino acids, the Fc binding protein has improved stability.

TABLE 12

| Amino acid substitution | Remaining activity (%) |
|---|---|
| His42Leu | 8.3 |
| Gln55His | 7.4 |
| Thr67Ser | 8.9 |
| Asp129Gly | 14.8 |
| Leu131Gln | 13.2 |
| Tyr133Tyr | 11.8 |
| Ser182Thr | 10.2 |
| Thr199Ala | 9.9 |
| Leu203Leu | 11.5 |
| Tyr230His | 11.9 |
| Ser233Gly | 89.0 |
| Lys234Glu | 8.3 |

TABLE 12-continued

| Amino acid substitution | Remaining activity (%) |
|---|---|
| Glu244Val | 10.4 |
| Thr249Ser | 13.2 |
| Glu261Val | 14.1 |
| Glu265Gly | 17.7 |
| Glu265Ala | 12.5 |
| Lys271Arg | 13.0 |
| Pro286Gln | 7.6 |
| Val289Asp | 13.1 |
| Val289Ile | 7.3 |
| Thr25Met, Gln64His | 8.5 |
| Thr25Met, Thr115Ile | 12.1 |
| Arg71Tyr, Val289Ala | 6.8 |
| Val77Lys, Ala263Ser | 13.8 |
| Leu89Pro, Gln97Lys | 9.2 |
| Ser90Gly, Lys271Arg | 9.9 |
| Gln97Leu, Glu261Val | 17.0 |
| Lys128Arg, Thr249Ala | 20.2 |
| Tyr133Tyr, Ala262Val | 10.9 |
| Tyr133Tyr, Leu270His | 10.1 |
| Lys157Arg, Leu218Ile | 21.3 |
| Ser182Leu, Glu213Val | 23.2 |
| Ser182Thr, Val289Gly | 10.2 |
| Lys215Arg, Gln224Arg | 13.3 |
| Lys215Glu, Lys271Arg | 10.3 |
| Gln224Arg, Gln279Arg | 13.0 |
| Glu253Gly, Val289Asp | 13.9 |
| Leu283Pro, Thr287Ile | 8.3 |
| Thr25Met, Lys142Arg, Thr287Pro | 14.4 |
| Gln35Met, Thr249Ser, Gln279His | 11.0 |
| Ser53Thr, Asn152Pro, Val289Ala | 16.8 |
| Thr67Ala, Thr199Ala, Val289Asp | 11.9 |
| Arg102Leu, Gly103Asp, Glu244Val | 18.6 |
| Glu118Asp, Asp129Gly, Ser233Gly | 29.2 |
| FcRm36b | 7.5 |

Example 23

Production of Fc Binding Protein (FcRm44)

From the amino acid substitutions involved in improved stability of the Fc binding protein shown in Example 22, Gln97Leu, Lys128Arg, Lys157Arg, Ser182Leu, Glu213Val, Leu218Ile, Thr249Ala, and Glu261Val that were amino acid substitutions involved in improved stability were selected. The substitutions were accumulated with respect to the FcRm36b described in Example 18 to produce an Fc binding protein FcRm44 in which 44 amino acids of a wild-type Fc binding protein were substituted with amino acids. Thus, stability was further improved. Further, the amino acid substitutions shown as Lys128Arg, Lys157Arg, Glu213Val, Leu218Ile, and Thr249Ala were carried out using oligonucleotides described below.

(i) amino acid substitution Lys128Arg: an oligonucleotide including the sequence shown in SEQ ID NO: 122 (5'-CAGCTTATCTCTCCATGCGTGGCAA-3') and an oligonucleotide including the sequence shown in SEQ ID NO: 123 (5'-TTGCCACGCATGGAGAGATAAGCTG-3')

(ii) amino acid substitution Lys157Arg: an oligonucleotide including the sequence shown in SEQ ID NO: 124 (5'-ACGTGTTCGTCCTCGGAATGGTCAGGGT-3') and an oligonucleotide including the sequence shown in SEQ ID NO: 125 (5'-ACCCTGACCATTCCGAGGACGAACACGT-3')

(iii) amino acid substitutions Glu213Val and Leu218Ile: an oligonucleotide including the sequence shown in SEQ ID NO: 126 (5'-ACGCTGTATCAGCAGTTTGGTTACGCAGCTCA-3') and an oligonucleotide including the sequence shown in SEQ ID NO: 127 (5'-TGAGCTGCGTAAC-CAAACTGCTGATACAGCGT-3')

(iv) amino acid substitution Thr249Ala: an oligonucleotide including the sequence shown in SEQ ID NO: 128 (5'-ACGACGCGCGGCTAAAATCTGATACT-3') and an oligonucleotide including the sequence shown in SEQ ID NO: 129 (5'-AGTATCAGATTTTAGCCGCGCGTCGT-3')

(1) The PCR was carried out using as a template a plasmid containing the polynucleotide encoding the Fc binding protein in which the Fc binding protein FcRm36b obtained by screening in Example 22 was subjected to additional substitutions shown as Gln97Leu and Glu261Val. The oligonucleotide including the sequence shown in SEQ ID NO: 68 and the oligonucleotide including the sequence shown in SEQ ID NO: 122 were used as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m44p1.

(2) The PCR was carried out using as a template a plasmid containing a polynucleotide encoding an Fc binding protein in which the Fc binding protein FcRm36b obtained by screening in Example 22 was subjected to additional substitutions shown as Gln97Leu and Glu261Val. The oligonucleotide including the sequence shown in SEQ ID NO: 123 and the oligonucleotide including the sequence shown in SEQ ID NO: 128 were used as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m44p2.

(3) The PCR was carried out using as a template a plasmid containing a polynucleotide encoding an Fc binding protein in which the Fc binding protein FcRm36b obtained by screening in Example 22 was subjected to additional substitutions shown as Gln97Leu and Glu261Val. The PCR was carried out using the oligonucleotide including the sequence shown in SEQ ID NO: 129 and the oligonucleotide including the sequence shown in SEQ ID NO: 69 were used as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m44p3.

(4) Three types of the PCR products, m44 p1, m44p2, and m44p3 were purified, and mixed. The PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m44p4.

(5) The m44p4 was purified. The PCR was carried out using the purified m44p4 as a template and the oligonucleotide including the sequence shown in SEQ ID NO: 68 and the oligonucleotide including the sequence shown in SEQ ID NO: 124 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m44p5.

(6) The PCR was carried out using as a template a plasmid containing a polynucleotide encoding an Fc binding protein in which the Fc binding protein FcRm36b obtained by screening in Example 22 was subjected to additional substitutions shown as Ser182Leu and Glu213Val. The PCR was carried out using the oligonucleotide including the sequence shown in SEQ ID NO: 125 and the oligonucleotide including the sequence shown in SEQ ID NO: 126 were used as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m44p6.

(7) The m44p4 was purified. The PCR was carried out using the purified m44p4 as a template and the oligonucleotide including the sequence shown in SEQ ID NO: 127 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m44p7.

(8) Three types of the PCR products, m44p5, m44p6, and m44p7 were purified. The purified m44p5, m44p6, and m44p7 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR was carried out using the PCR product as a template. The oligonucleotide including the sequence shown in SEQ ID NO: 68 and the oligonucleotide including the sequence shown in SEQ ID NO: 69 were used as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The resulting PCR product obtained was purified to obtain a polynucleotide encoding the Fc binding protein FcRm44 in which 44 amino acids of a wild-type Fc binding protein were substituted with amino acids.

(9) The polynucleotide encoding the FcRm44 was digested with the restriction enzymes NcoI and HindIII, and ligated into the expression vector pETMalE (FIG. 4) which had been digested with the restriction enzymes NcoI and HindIII and described in Example 2. *E. coli* strain BL21 (DE3) was transformed with this product.

(10) The obtained transformant was cultured in LB medium containing 50 μg/mL of kanamycin. A plasmid was extracted from the cultured bacterial cells (transformant) to obtain a plasmid pETFcRm44 containing the polynucleotide encoding the FcRm44.

(11) The nucleotide sequence of pETFcRm44 was analyzed in the same manner as in Example 3.

The amino acid sequence of FcRm44 plus a signal sequence and a polyhistidine tag is shown in SEQ ID NO: 130, and the sequence of the polynucleotide encoding the FcRm44 is shown in SEQ ID NO: 131. In SEQ ID NO: 130, the MalE signal peptide is from methionine at position 1 to alanine at position 26, the linker peptide is from lysine at position 27 to glycine at position 33, the amino acid sequence of FcRm44 is from glutamine at position 34 to valine at position 307, and the polyhistidine tag is histidine at positions 308 to 313. Further, in SEQ ID NO: 130, proline of Thr20Pro that is a substituted amino acid is at position 38, lysine of Thr25Lys is at position 43, leucine of Gln35Leu is at position 53, glycine of Glu36Gly is at position 54, serine of Thr38Ser is at position 56, methionine of Leu41Met is at position 59, alanine of Val45Ala is at position 63, proline of Leu46Pro is at position 64, serine of Pro49Ser is at position 67, glycine of Ser52Gly is at position 70, aspartic acid of Gly60Asp is at position 78, isoleucine of Thr63Ile is at position 81, alanine of Thr65Ala is at position 83, threonine of Ser69Thr is at position 87, histidine of Arg71His is at position 89, glutamic acid of Val77Glu is at position 95, aspartic acid of Asn78Asp is at position 96, leucine of Gln97Leu is at position 115, valine of Ile100Val is at position 118, leucine of Phe114Leu is at position 132, arginine of Lys128Arg is at position 146, histidine of Tyr133His is at position 151, histidine of Arg139His is at position 157, arginine of Trp149Arg is at position 167, threonine of Asn152Thr is at position 170, proline of Leu156Pro is at position 174, arginine of Lys157Arg is at position 175, threonine of Ile160Thr is at position 178, serine of Asn163Ser is at position 181, arginine of Lys173Arg is at position 191, threonine of Ile181Thr is at position 199, leucine of Ser182Leu is at position 200, threonine of Asn195Thr is at position 213, histidine of Leu203His is at position 221, threonine of Asn206Thr is at position 224, glutamine of Leu207Gln is at position 225, valine of Glu213Val is at position 231, isoleucine of Leu218Ile is at position 236, lysine of Met231Lys is at position 249, aspartic acid of Asn240Asp is at position 258, alanine of Thr249Ala is at position 267, valine of Glu261Val is at position 279, histidine of Leu283His is at position 301, and glutamine of Leu285Gln is at position 303.

Example 24

Evaluation of Productivity of Fc Binding Protein (FcRm44)

The transformants produced in Examples 23 and 2 were prepared in the same manner as in Example 14. The productivities of Fc binding proteins measured by the ELISA method described in Example 12(4) were compared as the production amount (mg/L-broth medium/OD600) per turbidity (Optical Density at 600 nm, OD600) of the culture broth.

Figure 12:
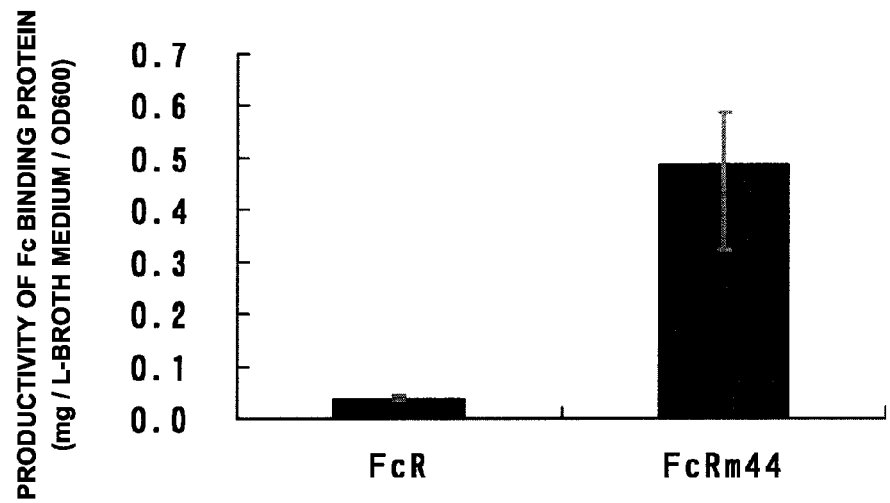
FIG. 12 is a graph for evaluating the productivity of the Fc binding protein (FcRm44).

The results are shown in FIG. 12. FcR in FIG. 12 shows the wild-type Fc binding protein expressed by the transformant in Example 2. The FcRm44 that was the Fc binding protein expressed by the transformant produced in Example 23 was confirmed to have higher productivity than the wild-type Fc binding protein. The results in FIG. 12 reveal that the productivity of the Fc binding protein is improved by integration of amino acid substitutions (mutation) involved in improved stability.

Example 25

Evaluation of Stability of Fc Binding Protein (FcRm44) Against Alkali (1) The Fc binding proteins (FcRm36b and FcRm44) and a wild-type Fc binding protein were prepared by the method described in Example 14, and the concentrations thereof were measured by the ELISA method described in Example 12(4).

(2) Each of the Fc binding proteins was diluted so that the concentration was 5 µg/mL. To each of the resultant, an equal amount of a 600 mM sodium hydroxide solution was added and the mixture was allowed to stand at 25° C. for 10 minutes.

(3) After standing, the pH was adjusted to a neutral region with 1M Tris-HCl buffer (pH 8.0), and the antibody binding activities of the alkali-treated sample in (2) and a sample which was not alkali-treated in (2) for comparison were measured by the ELISA method described in Example 12(4).

(4) The antibody binding activity of the alkali-treated sample was divided by the antibody binding activity of the sample not alkali-treated to obtain a percentage of remaining activity of each of Fc binding proteins by alkali treatment.

Figure 13:
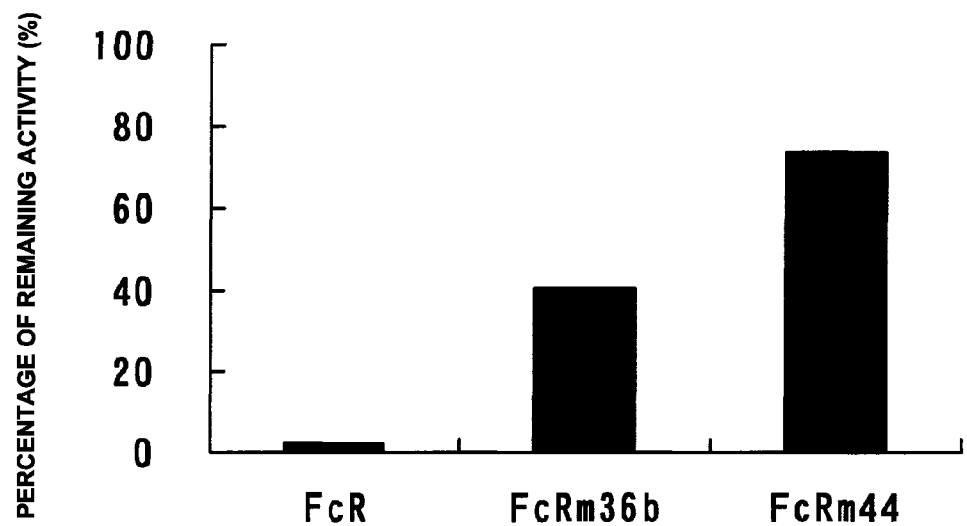
FIG. 13 is a graph for evaluating the alkali stability of the Fc binding protein (FcRm44).

FIG. 13 shows a result of comparison of stability against alkali. FcR in FIG. 13 shows the wild-type Fc binding protein expressed by the transformant in Example 2. FcRm36b in FIG. 13 shows the Fc binding protein expressed by the transformant in Example 18. FcRm44 that was the Fc binding protein expressed by the transformant produced in Example 23 was confirmed to have higher stability against alkali than these Fc binding proteins. The result in FIG. 13 reveals that the stability of the Fc binding protein against alkali is improved by integration of amino acid substitutions (mutation) involved in improved stability.

Example 26

Mutation Introduction into Fc Binding Protein (FcRm44) and Production of Library (1) A mutation was randomly introduced into the polynucleotide encoding the FcRm44 produced in Example 23 by the error-prone PCR. The reaction solution composition in the error-prone PCR is shown in the Table 9. The plasmid pETFcRm44 described in Example 23 was used as a template DNA. The oligonucleotide including the sequence shown in SEQ ID NO: 120 and the oligonucleotide including the sequence shown in SEQ ID NO: 121 were used as PCR primers. A PCR was carried out by heating for 2 minutes at 95° C., carrying out 30 cycles consisting of 30 seconds at 95° C. in the first step, 30 seconds at 60° C. in the second step, and 90 seconds at 72° C. in the third step, and finally heating for 7 minutes at 72° C.

(2) The PCR product obtained in (1) was purified, digested with the restriction enzymes NcoI and HindIII, and inserted in the plasmid pETMalE (FIG. 4), which had been digested with the restriction enzymes NcoI and HindIII and produced in Example 2, by a ligation reaction.

(3) After completion of the reaction, E. coli strain BL21 (DE3) was transformed using the resulting ligation product by the electroporation method, and cultured in LB agar medium containing 50 µg/mL of kanamycin to form colonies. Thus, an FcRm44 random mutation transformant library was produced.

Example 27

Screening of Fc Binding Protein (FcRm44) Library (1) The FcRm44 random mutation transformant library produced in Example 26 was inoculated into 200 µL of an LB broth medium containing 50 µg/mL of kanamycin, and was shake-cultured using a 96-deep well plate at 37° C. overnight.

(2) After the culturing, 5 W, of culture broth was subcultured into 500 μL of 2YT broth medium (containing 0.05 mM IPTG, 0.3% glycine, and 50 μg/mL of kanamycin), and was shake-cultured using a 96-deep well plate at 20° C. overnight.

(3) After the culturing, a culture supernatant obtained by centrifugation was diluted with pure water five times, and the diluted supernatant and a 400 mM sodium hydroxide solution were mixed in equal volumes. The mixture was alkali-treated at 30° C. for 120 minutes, and the pH was adjusted to a neutral region with 1M Tris-HCl buffer (pH 8.0).

(4) The antibody binding activities of the Fc binding proteins obtained from about 3,000 transformants were measured by the ELISA method described in Example 12(4). The antibody binding activities of the Fc binding proteins alkali-treated in (3) were divided by the antibody binding activities of Fc binding proteins not alkali-treated in (3) to obtain percentages of remaining activity.

(5) A plasmid was prepared from a transformant expressing an Fc binding protein with improved stability in comparison with the FcRm44. The sequence of a polynucleotide region encoding an Fc binding protein inserted in the plasmid was analyzed through the method described in Example 3 to identify mutation sites of amino acid existing in the Fc binding protein with improved stability in comparison with the FcRm44.

As shown from the results of analysis of the nucleotide sequences, positions of substitutions of amino acid in the Fc binding protein are accumulated as follows (provided that the substitution of amino acid existing in the FcRm44 is not included).

Specifically, in the amino acid sequence described in SEQ ID NO: 1, substitution shown as Val17Gly, Thr19Ile, Thr25Met, Thr25Arg, Gln35Met, Glu44Asp, Leu46Ser, His47Gln, His47Leu, Pro49Ala, Gly50Arg, Ser51Thr, Ser51Leu, Ser51Pro, Gln55Arg, Ala62Val, Gln64Leu, Ser69Ala, Thr73Ala, Asn78Gly, Ser80Ala, Gly88Ser, Ser90Gly, His101Leu, Gly103Ser, Ala121Thr, Ala121Val, Lys128Gly, Leu131Gln, Asn134Ser, Tyr137Phe, Ser151Thr, Asn159Thr, Thr165Met, Thr184Ser, Asn195Asn, Asn195Ala, Ala196Ser, Thr199Ser, Leu203Gln, Glu204Val, Ser211Gly, Gln219Arg, Gln224Arg, Phe227Ile, Ser233Asn, Lys234Glu, Gln246Arg, Leu248Ile, Arg252His, Leu257Gln, Asn268Ile, Gln279Arg, Gly282Asp, Pro286Arg, Thr287Pro, Thr287Ala, Thr287Val, Val289Ala, Val289Asp, or Val289Leu was caused. Further, among the substitutions, substitution (for example, Asn195Asn) in which the represented amino acids are not changed represents that a substituted (mutated) amino acid returns to a wild-type amino acid. Results of analysis of amino acid substitutions are shown in Table 13. Table 13 reveals that when the FcRm44 was further substituted with amino acids, the Fc binding protein has improved stability.

TABLE 13

| Amino acid substitution | Remaining activity (%) |
| --- | --- |
| Val17Gly | 29.9 |
| Thr19Ile | 26.2 |
| Thr25Met | 41.3 |
| Thr25Arg | 32.2 |
| Leu46Ser | 35.9 |
| His47Gln | 43.7 |
| His47Leu | 16.4 |
| Gln55Arg | 19.6 |

TABLE 13-continued

| Amino acid substitution | Remaining activity (%) |
| --- | --- |
| Ser69Ala | 27.2 |
| Ser80Ala | 31.7 |
| His101Leu | 21.7 |
| Lys128Gly | 48.2 |
| Leu131Gln | 47.4 |
| Asn134Ser | 27.6 |
| Asn159Thr | 30.3 |
| Thr165Met | 19.8 |
| Asn195Ser | 15.1 |
| Ser200Gly | 14.9 |
| Leu203Gln | 17.1 |
| Gln224Arg | 27.5 |
| Phe227Ile | 16.5 |
| Leu248Ile | 17.0 |
| Trp259Arg | 12.8 |
| Gln279Arg | 19.8 |
| Gly282Asp | 31.2 |
| Thr287Pro | 28.6 |
| Val289Ala | 28.1 |
| Val289Asp | 18.9 |
| Gln35Met, Arg252His | 22.6 |
| Glu44Asp, Ala62Val | 33.1 |
| Pro49Ala, Gly88ser | 22.9 |
| Gly50Arg, Ser51Pro | 19.4 |
| Asn78Gly, Val289Leu | 22.8 |
| Ser90Gly, Asn268Ile | 26.5 |
| Gly103Ser, Leu257Gln | 29.7 |
| Asn195Asn, Lys234Glu | 30.4 |
| Ser211Gly, Ser233Asn | 16.2 |
| Gln219Arg, Thr287Val | 34.8 |
| His47Leu, Asn195Ala, Gln246Arg | 25.3 |
| Ser51Leu, Ala121Thr, Thr199Ser | 50.5 |
| Ser51Thr, Tyr137Phe, Thr184Ser | 65.6 |
| Gln64Leu, Ala196Ser, Pro286Arg | 27.8 |
| Thr73Ala, Ala121Val, Thr287Ala | 40.5 |
| Thr73Ala, Ser151Thr, Thr199Ser, Glu204Val | 30 0 |
| FcRm44 | 16.0 |

Example 28

Production of Fc Binding Protein (FcRm48)

From the amino acid substitutions involved in improved stability of the Fc binding protein shown in Example 27, Ser51Thr, Leu131Gln, Tyr137Phe and Thr184Ser that were amino acid substitutions involved in improved stability were selected. The substitutions were integrated with respect to the FcRm44 described in Example 23 to produce an Fc binding protein FcRm48 in which 48 amino acids of a wild-type Fc binding protein were substituted with amino acids. Thus, stability was further improved. Further, an oligonucleotide including the sequence shown in SEQ ID NO: 132 (5'-GTGCACCTGCTTATCTCTCCATGCGT-3') and an oligonucleotide including the sequence shown in SEQ ID NO: 133 (5'-ACGCATGGAGAGATAAGCAGGT-GCAC-3') were used for amino acid substitution shown as Leu131Gln.

(1) The PCR was carried out using as a template a plasmid containing a polynucleotide encoding an Fc binding protein in which the Fc binding protein FcRm44 obtained by screening in Example 27 was subjected to additional substitutions shown as Ser51Thr, Tyr137Phe, and Thr184Ser. The oligonucleotide including the sequence shown in SEQ ID NO: 68 and the oligonucleotide including the sequence shown in SEQ ID NO: 132 were used as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m48p1.

(2) The PCR was carried out using as a template a plasmid containing a polynucleotide encoding an Fc binding protein in which the Fc binding protein FcRm44 obtained by screening in Example 27 was subjected to additional substitutions shown as Ser51Thr, Tyr137Phe, and Thr184Ser. The oligonucleotide including the sequence shown in SEQ ID NO: 133 and the oligonucleotide including the sequence shown in SEQ ID NO: 69 were used as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m48p2.

(3) Two types of the PCR products m48 µl and m48p2 were purified. The purified m48 µl and m48p2 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was purified to obtain a polynucleotide encoding the Fc binding protein FcRm48 in which 48 amino acids of a wild-type Fc binding protein were substituted with amino acids.

(4) The polynucleotide encoding the FcRm48 was digested with the restriction enzymes NcoI and HindIII, and ligated into the expression vector pETMalE (FIG. 4) digested with the restriction enzymes NcoI and HindIII and produced in Example 2. *E. coli* strain BL21 (DE3) was transformed with this product.

(5) The obtained transformant was cultured in LB medium containing 50 µg/mL of kanamycin. A plasmid was extracted from the cultured bacterial cells (transformant) to obtain a plasmid pETFcRm48 containing the polynucleotide encoding the FcRm48.

(6) The nucleotide sequence of pETFcRm48 was analyzed in the same manner as in Example 3.

The amino acid sequence of FcRm48 plus a signal sequence and a polyhistidine tag is shown in SEQ ID NO: 134, and the sequence of the polynucleotide encoding the FcRm48 is shown in SEQ ID NO: 135. In SEQ ID NO: 134, the MalE signal peptide is from methionine at position 1 to alanine at position 26, the linker peptide is from lysine at position 27 to glycine at position 33, the amino acid sequence of FcRm48 is from glutamine at position 34 to valine at position 307, and the polyhistidine tag is histidine at positions 308 to 313. Further, in SEQ ID NO: 134, proline of Thr20Pro that is a substituted amino acid is at position 38, lysine of Thr25Lys is at position 43, leucine of Gln35Leu is at position 53, glycine of Glu36Gly is at position 54, serine of Thr38Ser is at position 56, methionine of Leu41Met is at position 59, alanine of Val45Ala is at position 63, proline of Leu46Pro is at position 64, serine of Pro49Ser is at position 67, threonine of Ser51Thr is at position 69, glycine of Ser52Gly is at position 70, aspartic acid of Gly60Asp is at position 78, isoleucine of Thr63Ile is at position 81, alanine of Thr65Ala is at position 83, threonine of Ser69Thr is at position 87, histidine of Arg71His is at position 89, glutamic acid of Val77Glu is at position 95, aspartic acid of Asn78Asp is at position 96, leucine of Gln97Leu is at position 115, valine of Ile100Val is at position 118, leucine of Phe114Leu is at position 132, arginine of Lys128Arg is at position 146, glutamine of Leu131Gln is at position 149, histidine of Tyr133His is at position 151, phenylalanine of Tyr137Phe is at position 155, histidine of Arg139His is at position 157, arginine of Trp149Arg is at position 167, threonine of Asn152Thr is at position 170, proline of Leu156Pro is at position 174, arginine of Lys157Arg is at position 175, threonine of Ile160Thr is at position 178, serine of Asn163Ser is at position 181, arginine of Lys173Arg is at position 191, threonine of Ile181Thr is at position 199, leucine of Ser182Leu is at position 200, serine of Thr184Ser is at position 202, threonine of Asn195Thr is at position 213, histidine of Leu203His is at position 221, threonine of Asn206Thr is at position 224, glutamine of Leu207Gln is at position 225, valine of Glu213Val is at position 231, isoleucine of Leu218Ile is at position 236, lysine of Met231Lys is at position 249, aspartic acid of Asn240Asp is at position 258, alanine of Thr249Ala is at position 267, valine of Glu261Val is at position 279, histidine of Leu283His is at position 301, and glutamine of Leu285Gln is at position 303.

Example 29

Evaluation of Productivity of Fc Binding Protein (FcRm48)

The transformants produced in Examples 28 and 2 were prepared in the same manner as in Example 14. The productivities of Fc binding proteins measured by the ELISA method described in Example 12(4) were compared as the production amount (mg/L-broth medium/OD600) per turbidity (Optical Density at 600 nm, OD600) of the culture broth.

Figure 14:
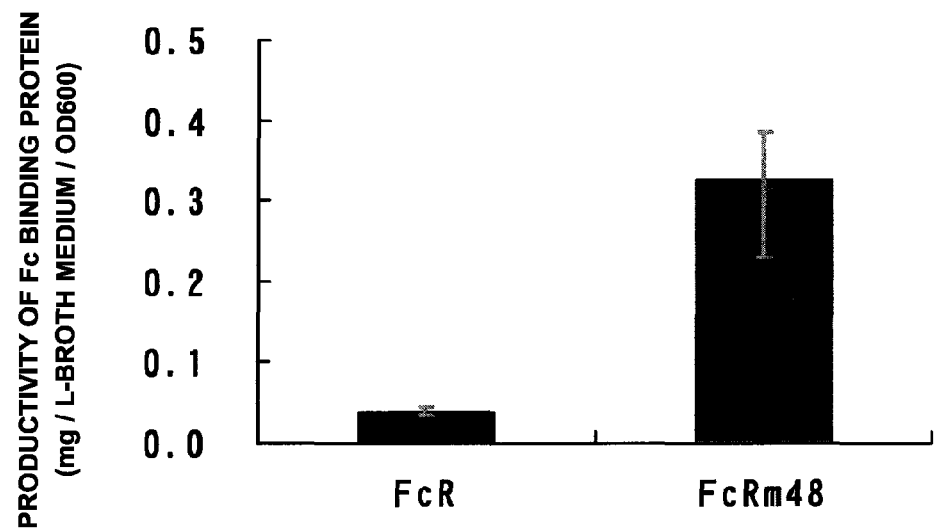
FIG. 14 is a graph for evaluating the productivity of the Fc binding protein (FcRm48).

The results are shown in FIG. 14. FcR in FIG. 14 shows the wild-type Fc binding protein expressed by the transformant in Example 2.

The FcRm48 that was the Fc binding protein expressed by the transformant produced in Example 28 was confirmed to have higher productivity than the wild-type Fc binding protein. The results in FIG. 14 reveal that the productivity of the Fc binding protein is improved by integration of amino acid substitutions (mutation) involved in improved stability.

Example 30

Evaluation of Stability of Fc Binding Protein (FcRm48) Against Alkali (1) The Fc binding proteins (FcRm44 and FcRm48) and a wild-type Fc binding protein were prepared by the method described in Example 14, and the concentrations thereof were measured by the ELISA method described in Example 12(4).

(2) Each of the Fc binding proteins was diluted so that the concentration was 5 µg/mL. To each of the resultant, an equal amount of a 600 mM sodium hydroxide solution was added and the mixture was allowed to stand at 25° C. for 50 minutes.

(3) After standing, the pH was adjusted to a neutral region with 1M Tris-HCl buffer (pH 8.0), and the antibody binding activities of the alkali-treated sample in (2) and a sample which was not alkali-treated in (2) for comparison were measured by the ELISA method described in Example 12(4).

(4) The antibody binding activity of the alkali-treated sample was divided by the antibody binding activity of the sample not alkali-treated to obtain a percentage of remaining activity of each of Fc binding proteins by alkali treatment.

Figure 15:
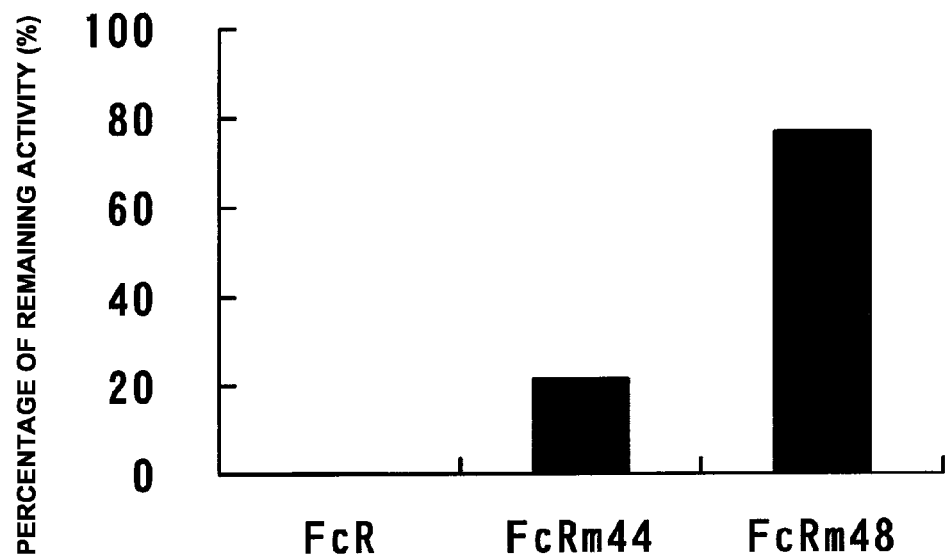
FIG. 15 is a graph for evaluating the alkali stability of the Fc binding protein (FcRm48).

FIG. 15 shows a result of comparison of stability against alkali. FcR in FIG. 15 shows the wild-type Fc binding protein expressed by the transformant in Example 2. FcRm44 in FIG. 15 shows the Fc binding protein expressed by the transformant in Example 23. The FcRm48 that was the Fc binding protein expressed by the transformant produced in Example 28 was confirmed to have higher stability against alkali than these Fc binding proteins. The result in FIG. 15 reveals that the alkali stability of the Fc binding protein is improved by integration of amino acid substitutions (mutation) involved in improved stability.

Example 31

Mutation Introduction into Fc Binding Protein (FcRm48) and Production of Library (1) A mutation was randomly introduced into the polynucleotide encoding the FcRm48 produced in Example 28 by the error-prone PCR. The reaction solution composition in the error-prone PCR is shown in the Table 9. The plasmid pETFcRm48 described in Example 28 was used as a template DNA. The oligonucleotide including the sequence shown in SEQ ID NO: 120 and the oligonucleotide including the sequence shown in SEQ ID NO: 121 were used as PCR primers. A PCR was carried out by heating for 2 minutes at 95° C., carrying out 30 cycles consisting of 30 seconds at 95° C. in the first step, 30 seconds at 60° C. in the second step, and 90 seconds at 72° C. in the third step, and finally heating for 7 minutes at 72° C.

(2) The PCR product obtained in (1) was purified, digested with the restriction enzymes NcoI and HindIII, and inserted in the plasmid pETMalE (FIG. 4), which had been digested with the restriction enzymes NcoI and HindIII and produced in Example 2, by a ligation reaction.

(3) After completion of the reaction, E. coli strain BL21 (DE3) was transformed using the resulting ligation product by the electroporation method, and cultured in LB agar medium containing 50 μg/mL of kanamycin to form colonies. Thus, an FcRm48 random mutation transformant library was produced.

Example 32

Screening of Library of Fc Binding Protein (FcRm48) with Improved Stability (1) The FcRm48 random mutation transformant library produced in Example 31 was inoculated into 200 μL of an LB broth medium containing 50 μg/mL of kanamycin, and was shake-cultured using a 96-deep well plate at 37° C. overnight.

(2) After the culturing, 5 μL of culture broth was subcultured into 500 μL of 2YT broth medium (containing 0.05 mM IPTG, 0.3% glycine, and 50 μg/mL of kanamycin), and was shake-cultured using a 96-deep well plate at 20° C. overnight.

(3) After the culturing, a culture supernatant obtained by centrifugation was diluted with pure water five times, and the diluted supernatant and a 600 mM sodium hydroxide solution were mixed in equal volumes. The mixture was alkali-treated at 30° C. for 120 minutes, and the pH was adjusted to a neutral region with 1M Tris-HCl buffer (pH 8.0).

(4) The antibody binding activities of the Fc binding proteins obtained from about 3,000 transformants were measured by the ELISA method described in Example 12(4). The antibody binding activities of the Fc binding proteins alkali-treated in (3) were divided by the antibody binding activities of Fc binding proteins not alkali-treated in (3) to obtain percentages of remaining activity.

(5) A plasmid was prepared from the transformant expressing the Fc binding protein with improved stability in comparison with the FcRm48. The sequence of a polynucleotide region encoding an Fc binding protein inserted in the obtained plasmid was analyzed through the method described in Example 3 to identify mutation sites of amino acid existing in the Fc binding protein with improved stability in comparison with the FcRm48.

As shown from the results of analysis of the nucleotide sequence, positions of substitutions of amino acid in the Fc binding protein are integrated as follows (provided that the substitution of amino acid existing in the FcRm48 is not included).

Specifically, in the amino acid sequence described in SEQ ID NO: 1, substitution shown as Thr25Met, Gln35Arg, His42Leu, Val45Val, His47Asn, Ser51Ala, Ser53Pro, Gln64Lys, Arg71Tyr, Val77Val, Ile96Val, Ser151Thr, Asn159Asp, Thr199Ser, Thr199Ala, Leu207Arg, Thr209Ala, Glu213Ile, Lys215Glu, Leu223Arg, Leu223Gln, Lys234Glu, Asn240Gly, Glu261Ala, Asn268Thr, Leu270Arg, Leu270Val, Arg272Gln, Pro286Glu, Pro286Gln, Thr287Pro, Thr287Ser, Pro288Ala, Pro288Ser, Val289Ala, Val289Asp, or Val289Gly was caused. Further, substitution (for example, Val77Val) in which specified amino acids are not changed represents that a substituted (mutated) amino acid returns to a wild-type amino acid. Results of analysis of amino acid substitutions are shown in Table 14. Table 14 reveals that when the FcRm48 was further substituted with amino acids, the Fc binding protein has improved stability.

TABLE 14

| Amino acid substitution | Remaining activity (%) |
|---|---|
| Gln35Arg | 41.8 |
| His47Asn | 34.4 |
| Leu55Gln | 19.2 |
| Ser69Ala | 24.4 |
| His101Arg | 20.1 |
| Ser151Thr | 52.5 |
| Asn159Asp | 39.9 |
| Thr199Ala | 40.3 |
| Thr199Ser | 36.2 |
| Leu207Arg | 35.9 |
| Leu223Arg | 37.7 |
| Leu223Gln | 35.2 |
| Leu248Ile | 25.7 |
| Asn268Thr | 36.1 |
| Asn268Ser | 32.7 |
| Leu270Val | 48.2 |
| Leu270Arg | 43.6 |
| Pro286Ser | 33.3 |
| Pro286Gln | 43.2 |
| Thr287Pro | 40.1 |
| Pro288Ala | 39.4 |
| Val289Ala | 43.9 |
| Val289Asp | 41.0 |
| Val289Gly | 43.6 |
| Thr25Met, Ser151Thr | 42.5 |
| His42Leu, Lys234Glu | 36.0 |

TABLE 14-continued

| Amino acid substitution | Remaining activity (%) |
|---|---|
| Ser53Pro, Pro286Glu | 37.5 |
| Gln64Lys, Val289Ala | 51.6 |
| Thr67Ser, Leu218Leu | 32.8 |
| Arg71Tyr, Lys215Glu | 34.5 |
| Val77Val, Ser151Thr | 47.6 |
| Gly103Asp, Leu131Arg | 33.6 |
| Thr199Ala, Glu213Glu | 23.8 |
| Pro286Gln, Val289Asp | 41.5 |
| Thr19Ile, Thr25Met, Ser52Val | 34.1 |
| Val45Val, Ser51Ala, Thr199Ala | 55.0 |
| His47Gln, Arg71Leu, Gly238Glu | 21.7 |
| Val109Ala, Trp149Gln, Val289Phe | 33.8 |
| Glu261Ala, Leu270Arg, Pro288Ser | 37.7 |
| Arg272Gln, Thr287Ser, Val289Asp | 39.5 |
| Ile96Val, Thr209Ala, Glu213Ile, Asn240Gly | 35.6 |
| FcRm48 | 34.3 |

Example 33

Production of Fc Binding Protein (FcRm54b)

From the amino acid substitutions involved in improved stability of the Fc binding protein shown in Example 32, His42Leu, Ser51Ala, Ser151Thr, Thr199Ala, Lys234Glu, and Leu270Val that were amino acid substitutions involved in improved stability were selected. From the amino acid substitutions involved in improved stability of the Fc binding protein shown in Example 27, Thr73Ala and Ala121Val that were amino acid substitutions involved in improved stability were selected. The selected substitutions were integrated with respect to the FcRm48 described in Example 28, and the amino acid of the amino acid substitution shown as Val45Ala was substituted with valine to produce an Fc binding protein FcRm54b in which 54 amino acids of a wild-type Fc binding protein were substituted with amino acids. Thus, stability was further improved. Further, the amino acid substitutions shown as His42Leu, Thr73Ala, Ala121Val, Ser151Thr, Lys234Glu, and Leu270Val were carried out using oligonucleotides described below.

(i) amino acid substitution His42Leu: an oligonucleotide including the sequence shown in SEQ ID NO: 136 (5'-CTTCGCAGAGCATCGTCACGGATTCT-3') and an oligonucleotide including the sequence shown in SEQ ID NO: 137 (5'-AGAATCCGTGACGATGCTCTGCGAAG-3'

(ii) amino acid substitution Thr73Ala: an oligonucleotide including the sequence shown in SEQ ID NO: 138 (5'-TCGCTCGCGGAGGCAATGTGGTAAGT-3') and an oligonucleotide including the sequence shown in SEQ ID NO: 139 (5'-ACTTACCACATTGCCTCCGCGAGCGA-3')

(iii) amino acid substitution Ala121Val: an oligonucleotide including the sequence shown in SEQ ID NO: 140 (5'-TGGCAACGTAATACAAGCGGTTCGCCT-3') and an oligonucleotide including the sequence shown in SEQ ID NO: 141 (5'-AGGCGAACCGCTTGTATTACGTTGCCA-3')

(iv) amino acid substitution Ser151Thr: an oligonucleotide including the sequence shown in SEQ ID NO: 142 (5'-TGGTCAGGGTTGTGTTCCGGTGGAAGAA-3') and an oligonucleotide including the sequence shown in SEQ ID NO: 143 (5'-TTCTTCCACCGGAACACAACCCTGACCA-3')

(v) amino acid substitution Lys234Glu: an oligonucleotide including the sequence shown in SEQ ID NO: 144 (5'-TCCGCGCAGGGTTTCGCTGCCCTTATA-3') and an oligonucleotide including the sequence shown in SEQ ID NO: 145 (5'-TATAAGGGCAGCGAAACCCTGCGCGGA-3')

(vi) amino acid substitution Leu270Val: an oligonucleotide including the sequence shown in SEQ ID NO: 146 (5'-TGGGCTCCGTTTAACCACATTGCCAT-3') and an oligonucleotide including the sequence shown in SEQ ID NO: 147 (5'-ATGGCAATGTGGTTAAACGGAGCCCA-3')

(1) The PCR was carried out using as a template a plasmid containing a polynucleotide encoding an Fc binding protein in which the Fc binding protein FcRm48 obtained by screening in Example 32 was subjected to additional amino acid substitutions shown as Ser51Ala and Thr199Ala, and the amino acid of the amino acid substitution shown as Val45Ala was changed to valine. The oligonucleotide including the sequence shown in SEQ ID NO: 68 and the oligonucleotide including the sequence shown in SEQ ID NO: 138 were used as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m54 bp1.

(2) The PCR was carried out using as a template a plasmid containing a polynucleotide encoding an Fc binding protein in which the Fc binding protein FcRm48 obtained by screening in Example 32 was subjected to additional amino acid substitutions shown as Ser51Ala and Thr199Ala, and the amino acid shown as Val45Ala was changed to valine. The oligonucleotide including the sequence shown in SEQ ID NO: 139 and the oligonucleotide including the sequence shown in SEQ ID NO: 140 were used as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m54 bp2.

(3) The PCR was carried out using as a template a plasmid containing a polynucleotide encoding an Fc binding protein in which the Fc binding protein FcRm48 obtained by screening in Example 32 was subjected to additional amino acid substitutions shown as Ser51Ala and Thr199Ala, and the amino acid of the amino acid substitution shown as Val45Ala was changed to valine. The oligonucleotide including the sequence shown in SEQ ID NO: 141 and the oligonucleotide including the sequence shown in SEQ ID NO: 69 were used as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m54 bp3.

(4) Three types of the PCR products, m54 bp1, m54 bp2, and m54 bp3 were purified. The purified m54 bp1, m54 bp2, and m54 bp3 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m54 bp4.

(5) The m54 bp4 was purified. The PCR was carried out using the purified m54 bp4 as a template and the oligonucleotide including the sequence shown in SEQ ID NO: 68 and the oligonucleotide including the sequence shown in SEQ ID NO: 142 as PCR primers. The PCR was carried out for 30 cycles consisting of 10 seconds at 98° C. in the first step, 5 seconds at 50° C. in the second step, and 1 minute at 72° C. in the third step reaction solution composition shown in Table 4. The PCR product was designated as m54 bp5.

(6) The m54 bp4 was purified. The PCR was carried out using the purified m54 bp4 as a template and the oligonucleotide including the sequence shown in SEQ ID NO: 143 and the oligonucleotide including the sequence shown in SEQ ID NO: 146 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m54 bp6.

(7) The m54 bp4 was purified. The PCR was carried out using the purified m54 bp4 as a template and the oligonucleotide including the sequence shown in SEQ ID NO: 147 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m54 bp7.

(8) Three types of the PCR products, m54 bp5, m54 bp6, and m54 bp7 were purified. The m54 bp5, m54 bp6, and m54 bp7 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m54 bp8.

(9) The m54 bp8 was purified. The PCR was carried out using the purified m54 bp8 as a template and the oligonucleotide including the sequence shown in SEQ ID NO: 68 and the oligonucleotide including the sequence shown in SEQ ID NO: 136 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m54 bp9.

(10) The m54 bp8 was purified. The PCR was carried out using the purified m54 bp8 as a template and the oligonucleotide including the sequence shown in SEQ ID NO: 137 and the oligonucleotide including the sequence shown in SEQ ID NO: 144 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m54 bp10.

(11) The m54 bp8 was purified. The PCR was carried out using the purified m54 bp8 as a template and the oligonucleotide including the sequence shown in SEQ ID NO: 145 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m54 bp11.

(12) Three types of the PCR products, m54 bp9, m54 bp10, and m54 bp11 were purified. The purified m54 bp9, m54 bp10, and m54 bp11 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was purified to obtain a polynucleotide encoding an Fc binding protein FcRm54b in which 54 amino acids of a wild-type Fc binding protein were substituted with amino acids.

(13) The polynucleotide encoding the FcRm54b was digested with the restriction enzymes NcoI and HindIII, and ligated into the expression vector pETMalE (FIG. 4) digested with the restriction enzymes NcoI and HindIII and produced in Example 2. *E. coli* strain BL21 (DE3) was transformed with this product.

(14) The obtained transformant was cultured in LB medium containing 50 μg/mL of kanamycin. A plasmid was extracted from the cultured bacterial cells to obtain a plasmid pETFcRm54b containing the polynucleotide encoding the FcRm54b.

(15) The nucleotide sequence of pETFcRm54b was analyzed in the same manner as in Example 3.

The amino acid sequence of FcRm54b plus a signal sequence and a polyhistidine tag is shown in SEQ ID NO: 148, and the sequence of the polynucleotide encoding the FcRm54b is shown in SEQ ID NO: 149. In SEQ ID NO: 148, the MalE signal peptide is from methionine at position 1 to alanine at position 26, the linker peptide is from lysine at position 27 to glycine at position 33, the amino acid sequence of FcRm54b is from glutamine at position 34 to valine at position 307, and the polyhistidine tag is histidine at positions 308 to 313. Further, in SEQ ID NO: 148, proline of Thr20Pro that is a substituted amino acid is at position 38, lysine of Thr25Lys is at position 43, leucine of Gln35Leu is at position 53, glycine of Gln35Leu is at position 54, serine of Thr38Ser is at position 56, methionine of Leu41Met is at position 59, leucine of His42Leu is at position 60, proline of Leu46Pro is at position 64, serine of Pro49Ser is at position 67, alanine of Ser51Ala is at position 69, glycine of Ser52Gly is at position 70, aspartic acid of Gly60Asp is at position 78, isoleucine of Thr63Ile is at position 81, alanine of Thr65Ala is at position 83, threonine of Ser69Thr is at position 87, histidine of Arg71His is at position 89, alanine of Thr73Ala is at position 91, glutamic acid of Val77Glu is at position 95, aspartic acid of Asn78Asp is at position 96, leucine of Gln97Leu is at position 115, valine of Ile100Val is at position 118, leucine of Phe114Leu is at position 132, valine of Ala121Val is at position 139, arginine of Lys128Arg is at position 146, glutamine of Leu131Gln is at position 149, histidine of Tyr133His is at position 151, phenylalanine of Tyr137Phe is at position 155, histidine of Arg139His is at position 157, arginine of Trp149Arg is at position 167, threonine of Ser151Thr is at position 169, threonine of Asn152Thr is at position 170, proline of Leu156Pro is at position 174, arginine of Lys157Arg is at position 175, threonine of Ile160Thr is at position 178, serine of Asn163Ser is at position 181, arginine of Lys173Arg is at position 191, threonine of Ile181Thr is at position 199, leucine of Ser182Leu is at position 200, serine of Thr184Ser is at position 202, threonine of Asn195Thr is at position 213, alanine of Thr199Ala is at position 217, histidine of Leu203His is at position 221, threonine of Asn206Thr is at position 224, glutamine of Leu207Gln is at position 225, valine of Glu213Valis at position 231, isoleucine of Leu218Ile is at position 236, lysine of Met231Lys is at position 249, glutamic acid of Lys234Glu is at position 252, aspartic acid of Asn240Asp is at position 258, alanine of Thr249Ala is at position 267, valine of Glu261Val is at position 279, valine of Leu270Val is at position 288, histidine of Leu283His is at position 301, and glutamine of Leu285Gln is at position 303.

Example 34

Evaluation of Productivity of Fc Binding Protein (FcRm54b)

Figure 16:
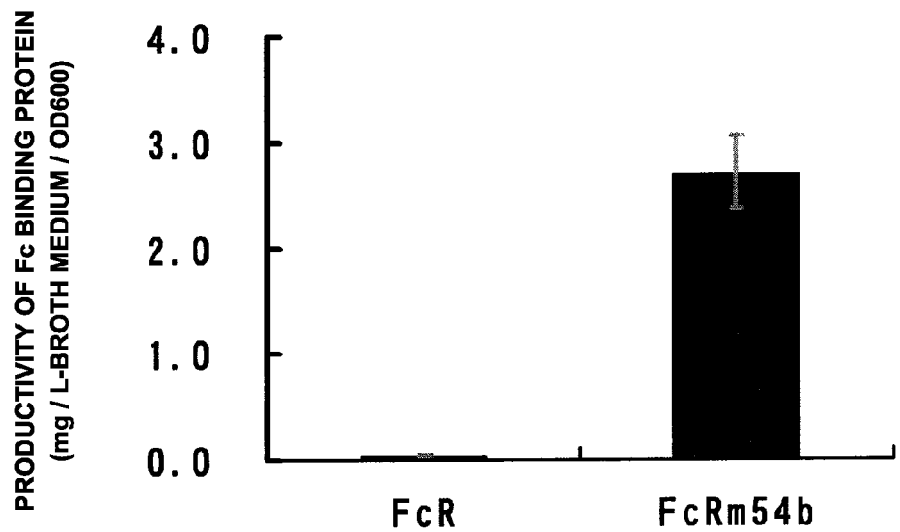
FIG. 16 is a graph for evaluating the productivity of the Fc binding protein (FcRm54b).

The transformants produced in Examples 33 and 2 were prepared in the same manner as in Example 14. The productivities of Fc binding proteins measured by the ELISA method described in Example 12(4) were compared as the production amount (mg/L-broth medium/OD600) per turbidity (Optical Density at 600 nm, OD600) of the culture broth.
The results are shown in FIG. 16. FcR in FIG. 16 shows the wild-type Fc binding protein expressed by the transformant in Example 2.
The FcRm54b that was the Fc binding protein expressed by the transformant produced in Example 33 was confirmed to have higher productivity than the wild-type Fc binding protein. The results in FIG. 16 reveal that the productivity of the Fc binding protein is improved by integration of amino acid substitutions (mutation) involved in improved stability.

Example 35

Evaluation of Stability of Fc Binding Protein (FcRm54b) Against Alkali (1) The Fc binding proteins (FcRm48 and FcRm54b) and a wild-type Fc binding protein were prepared by the method described in Example 14, and the concentrations thereof were measured by the ELISA method described in Example 12(4).
(2) Each of the Fc binding proteins was diluted so that the concentration was 5 μg/mL. To each of the resultant, an equal amount of a 600 mM sodium hydroxide solution was added and the mixture was allowed to stand at 25° C. for 120 minutes.
(3) After standing, the pH was adjusted to a neutral region with 1M Tris-HCl buffer (pH 8.0), and the antibody binding activities of the alkali-treated sample in (2) and a sample which was not alkali-treated in (2) for comparison were measured by the ELISA method described in Example 12(4).

Figure 17:
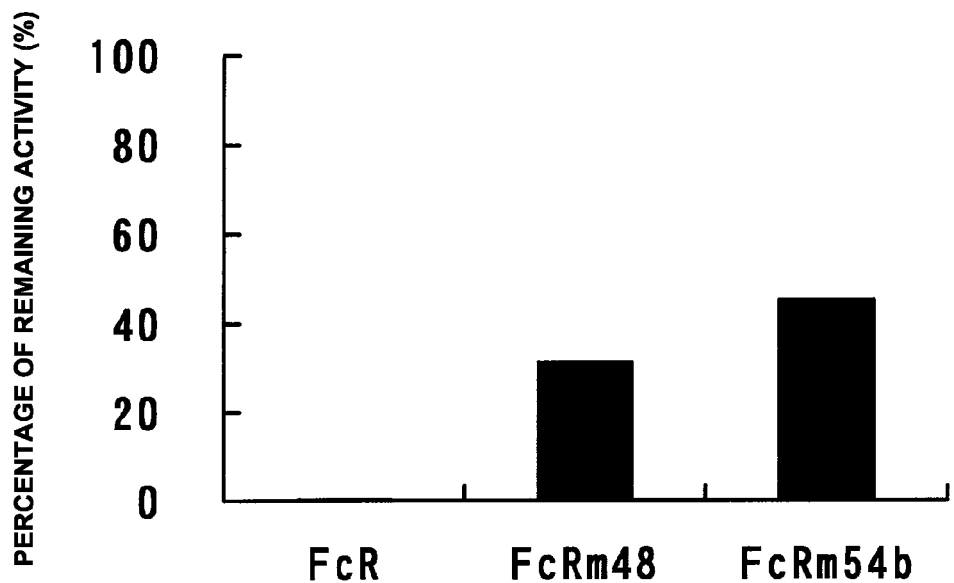
FIG. 17 is a graph for evaluating the alkali stability of the Fc binding protein (FcRm54b).

(4) The antibody binding activity of the alkali-treated sample was divided by the antibody binding activity of the sample not alkali-treated to obtain a percentage of remaining activity of each of Fc binding proteins by alkali treatment.
FIG. 17 shows a result of comparison of stability against alkali. FcR in FIG. 17 shows the wild-type Fc binding protein expressed by the transformant in Example 2. FcRm48 in FIG. 17 shows the Fc binding protein expressed by the transformant in Example 28. FcRm54b that was the Fc binding protein expressed by the transformant produced in Example 33 was confirmed to have higher stability against alkali than these Fc binding proteins. The result in FIG. 17 reveals that the alkali stability of the Fc binding protein is improved by integration of amino acid substitutions (mutation) involved in improved stability.

Example 36

Mutation Introduction into Fc Binding Protein (FcRm54b) and Production of Library (1) A mutation was randomly introduced into the polynucleotide encoding the FcRm54b produced in Example 33 by the error-prone PCR. The reaction solution composition in the error-prone PCR is shown in the Table 9. The plasmid pETFcRm54b described in Example 33 was used as a template DNA. The oligonucleotide including the sequence shown in SEQ ID NO: 120 and the oligonucleotide including the sequence shown in SEQ ID NO: 121 were used as PCR primers. A PCR was carried out by heating for 2 minutes at 95° C., carrying out 30 cycles consisting of 30 seconds at 95° C. in the first step, 30 seconds at 60° C. in the second step, and 90 seconds at 72° C. in the third step, and finally heating for 7 minutes at 72° C.
(2) The PCR product obtained in (1) was purified, digested with the restriction enzymes NcoI and HindIII, and inserted in the plasmid pETMalE (FIG. 4), which had been digested with the restriction enzymes NcoI and HindIII and produced in Example 2, by a ligation reaction. After completion of the reaction, E. coli strain BL21 (DE3) was transformed using the resulting ligation product by the electroporation method, and cultured in LB agar medium containing 50 μg/mL of kanamycin to form colonies. Thus, an FcRm54b random mutation transformant library was produced.

Example 37

Screening of Library of Fc Binding Protein (FcRm54b) with Improved Stability (1) The FcRm54b random mutation transformant library produced in Example 36 was inoculated into 200 μL of an LB broth medium containing 50 μg/mL of kanamycin, and was shake-cultured using a 96-deep well plate at 37° C. overnight.
(2) After the culturing, 5 μL of culture broth was subcultured into 500 μL of 2YT broth medium (containing 0.05 mM IPTG, 0.3% glycine, and 50 μg/mL of kanamycin), and was shake-cultured using a 96-deep well plate at 20° C. overnight.
(3) After the culturing, a culture supernatant obtained by centrifugation was diluted with pure water five times, and the diluted supernatant and a 700 mM sodium hydroxide solution were mixed in equal volumes. The mixture was alkali-treated at 30° C. for 120 minutes, and the pH was adjusted to a neutral region with 1M Tris-HCl buffer (pH 8.0).

(4) The antibody binding activities of the Fc binding proteins obtained from about 3,000 transformants were measured by the ELISA method described in Example 12(4). The antibody binding activities of the Fc binding proteins alkali-treated in (3) were divided by the antibody binding activities of Fc binding proteins not alkali-treated in (3) to obtain percentages of remaining activity.

(5) A plasmid was prepared from a transformant expressing an Fc binding protein with improved stability in comparison with the FcRm54b. The sequence of a polynucleotide region encoding an Fc binding protein inserted in the obtained plasmid was analyzed through the method described in Example 3 to identify mutation sites of amino acid existing in the Fc binding protein with improved stability in comparison with the FcRm54b.

As shown from the results of analysis of the nucleotide sequence, positions of substitutions of amino acid in the Fc binding protein are accumulated as follows (provided that the substitution of amino acid existing in the FcRm54b is not included).

Specifically, in the amino acid sequence described in SEQ ID NO: 1, substitution shown as Thr25Met, Gln35Gln, Leu41Leu, His47Gln, His47Asn, Ser53Pro, Phe57Tyr, Leu58Arg, Ala62Glu, Tyr70His, Arg92Leu, Ser111Ala, Thr115Ile, Glu118Asp, Tyr133Tyr, Gly141Asp, Gly141Val, Thr154Ser, Ser182Val, Thr184Thr, Pro190Ser, Leu202Met, Leu203Tyr, Leu207Pro, Glu213Glu, Leu217Arg, Leu218Met, Leu218Lys, Gln219Arg, Met231Arg, Glu244Val, Tyr245His, Leu248Ser, Glu261Glu, Ala263Ser, Pro286Gln, Thr287Ala, Pro288Thr, Val289Gly, Val289Asp, or Val289Leu was caused. Further, among the substitutions, substitution (for example, Gln35Gln) in which specified amino acids are not changed represents that a to substituted (mutated) amino acid returns to a wild-type amino acid. Results of analysis of amino acid substitutions are shown in Table 15. Table 15 reveals that when the FcRm54b was substituted with amino acids, the Fc binding protein has improved stability.

TABLE 15

| Amino acid substitution | Remaining activity (%) |
| --- | --- |
| Leu41Leu | 55.0 |
| Glu44Asp | 35.7 |
| His47Gln | 45.3 |
| Phe57Tyr | 39.2 |
| Arg92Leu | 45.8 |
| Gly141Asp | 45.0 |
| Ser182Val | 59.3 |
| Pro190Ser | 51.0 |
| Glu213Glu | 44.5 |
| Gln219Arg | 51.5 |
| Tyr245His | 46.7 |
| Leu248Ser | 47.9 |
| Glu261Glu | 39.6 |
| Pro286Gln | 49.9 |
| Thr287Asn | 37.1 |
| Val289Gly | 57.8 |
| Val289Asp | 57.6 |
| Thr25Met, Pro286Gln | 50.3 |
| His47Asn, Pro286Gln | 51.3 |
| Ser53Pro, Val289Leu | 40.6 |
| Leu58Arg, Thr115Ile | 72.3 |
| Thr61Ser, Gly88Ser | 38.4 |
| Ala62Glu, Leu217Arg | 50.8 |
| Ser111Ala, Val289Asp | 57.9 |

TABLE 15-continued

| Amino acid substitution | Remaining activity (%) |
| --- | --- |
| Glu118Asp, Tyr133Tyr | 45.9 |
| Met171Lys, Val289Ala | 35.2 |
| Thr184Thr, Leu218Met | 44.0 |
| Leu203Tyr, Leu218Lys | 38.9 |
| Leu207Pro, Val289Asp | 56.0 |
| Thr287Ala, Pro288Thr | 39.0 |
| Gln35Gln, Tyr70His, Leu202Met | 41.4 |
| Gly141Val, Thr154Ser, Met231Arg, Glu244Val, Ala263Ser | 43.7 |
| FcRm54b | 38.6 |

Example 38

Production of Fc Binding Protein (FcRm56b)

From the amino acid substitutions involved in improved stability of the Fc binding protein shown in Example 37, Leu58Arg, Ser111Ala, and Thr115Ile that were amino acid substitutions involved in improved stability were selected. The selected substitutions were integrated with respect to the FcRm54b described in Example 33, and the amino acid of the amino acid substitution shown as Glu261Val was changed to glutamine to produce an Fc binding protein FcRm56b in which 56 amino acids of a wild-type Fc binding protein were substituted with amino acids. Thus, stability was further improved. Further, in order to cause amino acid substitution shown as Ser111Ala and change the amino acid of the amino acid substitution shown as Glu261Val to previous glutamine (Glu), oligonucleotides described below were used.

(i) amino acid substitution Ser111Ala: an oligonucleotide including the sequence shown in SEQ ID NO: 150 (5'-AAACGCGGGCGCTAACCTGTAAAAGCA-3') and an oligonucleotide including the sequence shown in SEQ ID NO: 151 (5'-TGCTTTTACAGGTTAGCGCCCGCGTTT-3')

(ii) change of amino acid of amino acid substitution Glu261Val to previous glutamine (Glu): an oligonucleotide including the sequence shown in SEQ ID NO: 152 (5'-TCGGTCGCCGCTTCACACCAGTACA-3') and an oligonucleotide including the sequence shown in SEQ ID NO: 153 (5'-TGTACTGGTGTGAAGCGGCGACCGA-3')

(1) The PCR was carried out using as a template a plasmid containing a polynucleotide encoding an Fc binding protein in which the Fc binding protein FcRm54b obtained by screening in Example 37 was subjected to additional substitutions shown as Leu58Arg and Thr115Ile. The oligonucleotide including the sequence shown in SEQ ID NO: 68 and the oligonucleotide including the sequence shown in SEQ ID NO: 152 were used as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m56 bp1.

(2) The PCR was carried out using as a template a plasmid containing a polynucleotide encoding an Fc binding protein in which the Fc binding protein FcRm54b obtained by screening in Example 37 was subjected to additional substitutions shown as Leu58Arg and Thr115Ile. The oligonucleotide including the sequence shown in SEQ ID NO: 153 and the oligonucleotide including the sequence shown in SEQ ID NO: 69 were used as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m56 bp2.

(3) Two types of the PCR products m56 bp1 and m56 bp2 were purified. The purified m56 bp1 and m56 bp2 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m56 bp3.

(4) The m56 bp3 was purified. The PCR was carried out using the purified m56 bp3 as a template and the oligonucleotide including the sequence shown in SEQ ID NO: 68 and the oligonucleotide including the sequence shown in SEQ ID NO: 150 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m56 bp4.

(5) The m56 bp3 was purified. The PCR was carried out using the purified m56 bp3 as a template and the oligonucleotide including the sequence shown in SEQ ID NO: 151 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m56 bp5.

(6) Two types of the PCR products m56 bp4 and m56 bp5 were purified. The purified m56 bp4 and m56 bp5 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was purified to obtain a polynucleotide encoding tan Fc binding protein FcRm56b in which 56 amino acids of a wild-type Fc binding protein were substituted with amino acids.

(7) The polynucleotide encoding the FcRm56b was digested with the restriction enzymes NcoI and HindIII, and ligated into the expression vector pETMalE (FIG. 4) which had been digested with the restriction enzymes NcoI and HindIII and described in Example 2. E. coli strain BL21 (DE3) was transformed with this product.

(8) The obtained transformant was cultured in LB medium containing 50 μg/mL of kanamycin. A plasmid was extracted from the cultured bacterial cells (transformant) to obtain a plasmid pETFcRm56b containing the polynucleotide encoding the FcRm56b.

(9) The nucleotide sequence of pETFcRm56b was analyzed in the same manner as in Example 3.

The amino acid sequence of FcRm56b plus a signal sequence and a polyhistidine tag is shown in SEQ ID NO: 154, and the sequence of the polynucleotide encoding the FcRm56b is shown in SEQ ID NO: 155. In SEQ ID NO: 154, the MalE signal peptide is from methionine at position 1 to alanine at position 26, the linker peptide is from lysine at position 27 to glycine at position 33, the amino acid sequence of FcRm56b is from glutamine at position 34 to valine at position 307, and the polyhistidine tag is histidine at positions 308 to 313. Further, in SEQ ID NO: 154, proline of Thr20Pro that is a substituted amino acid is at position 38, lysine of Thr25Lys is at position 43, leucine of Gln35Leu is at position 53, glycine of Glu36Gly is at position 54, serine of Thr38Ser is at position 56, methionine of Leu41Met is at position 59, leucine of His42Leu is at position 60, proline of Leu46Pro is at position 64, serine of Pro49Ser is at position 67, alanine of Ser51Ala is at position 69, glycine of Ser52Gly is at position 70, arginine of Leu58Arg is at position 76, aspartic acid of Gly60Asp is at position 78, isoleucine of Thr63Ile is at position 81, alanine of Thr65Ala is at position 83, threonine of Ser69Thr is at position 87, histidine of Arg71His is at position 89, alanine of Thr73Ala is at position 91, glutamic acid of Val77Glu is at position 95, aspartic acid of Asn78Asp is at position 96, leucine of Gln97Leu is at position 115, valine of Ile100Val is at position 118, alanine of Ser111Ala is at position 129, leucine of Phe114Leu is at position 132, isoleucine of Thr115Ile is at position 133, valine of Ala121Val is at position 139, arginine of Lys128Arg is at position 146, glutamine of Leu131Gln is at position 149, histidine of Tyr133His is at position 151, phenylalanine of Tyr137Phe is at position 155, histidine of Arg139His is at position 157, arginine of Trp149Arg is at position 167, threonine of Ser151Thr is at position 169, threonine of Asn152Thr is at position 170, proline of Leu156Pro is at position 174, arginine of Lys157Arg is at position 175, threonine of Ile160Thr is at position 178, serine of Asn163Ser is at position 181, arginine of Lys173Arg is at position 191, threonine of Ile181Thr is at position 199, leucine of Ser182Leu is at position 200, serine of Thr184Ser is at position 202, threonine of Asn195Thr is at position 213, alanine of Thr199Ala is at position 217, histidine of Leu203His is at position 221, threonine of Asn206Thr is at position 224, glutamine of Leu207Gln is at position 225, valine of Glu213Val is at position 231, isoleucine of Leu218Ile is at position 236, lysine of Met231Lys is at position 249, glutamic acid of Lys234Glu is at position 252, aspartic acid of Asn240Asp is at position 258, alanine of Thr249Ala is at position 267, valine of Leu270Val is at position 288, histidine of Leu283His is at position 301, and glutamine of Leu285Gln is at position 303.

Example 39

Evaluation of Productivity of Fc Binding Protein (FcRm56b)

The transformants produced in Examples 38 and 2 were prepared in the same manner as in Example 14. The productivities of Fc binding proteins measured by the ELISA method described in Example 12(4) were compared as the production amount (mg/L-broth medium/OD600) per turbidity (Optical Density at 600 nm, OD600) of the culture broth.

Figure 18:
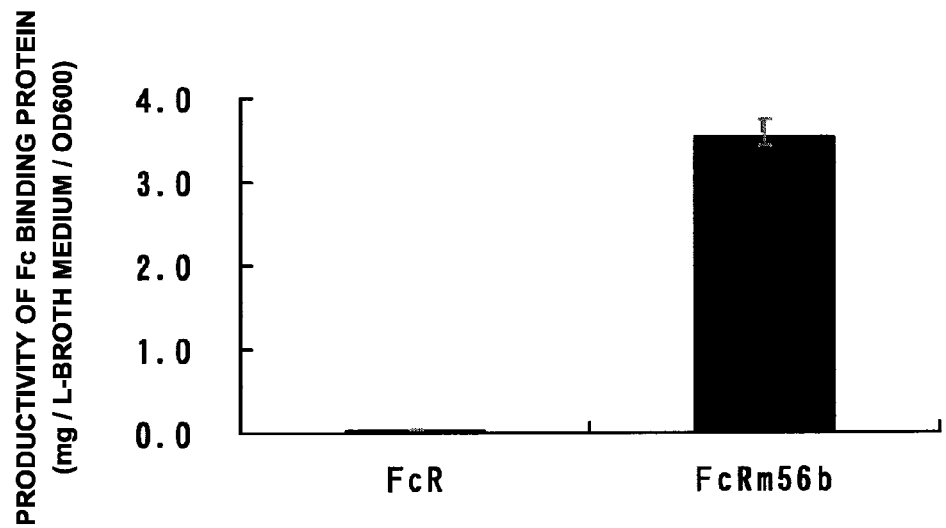
FIG. 18 is a graph for evaluating the productivity of the Fc binding protein (FcRm56b).

The results are shown in FIG. 18. FcR in FIG. 18 shows the wild-type Fc binding protein expressed by the transformant in Example 2. The FcRm56b that was the Fc binding protein expressed by the transformant produced in Example 38 was confirmed to have higher productivity than the wild-type Fc binding protein. The result in FIG. 18 reveals that the productivity of the Fc binding protein is improved by integration of amino acid substitutions (mutation) involved in improved stability.

Example 40

Evaluation of Stability of Fc Binding Protein (FcRm56b) Against Alkali (1) The Fc binding proteins (FcRm54b and FcRm56b) and a wild-type Fc binding protein were prepared by the method described in Example 14, and the concentrations thereof were measured by the ELISA method described in Example 12(4).

(2) Each of the Fc binding proteins was diluted so that the concentration was 5 μg/mL. To each of the resultant, an equal amount of a 600 mM sodium hydroxide solution was added and the mixture was allowed to stand at 25° C. for 180 minutes.

(3) After standing, the pH was adjusted to a neutral region with 1M Tris-HCl buffer (pH 8.0), and the antibody binding activities of the alkali-treated sample in (2) and a sample which was not alkali-treated in (2) for comparison were measured by the ELISA method described in Example 12(4).

(4) The antibody binding activity of the alkali-treated sample was divided by the antibody binding activity of the sample not alkali-treated to obtain a percentage of remaining activity of each of Fc binding proteins by alkali treatment.

Figure 19:
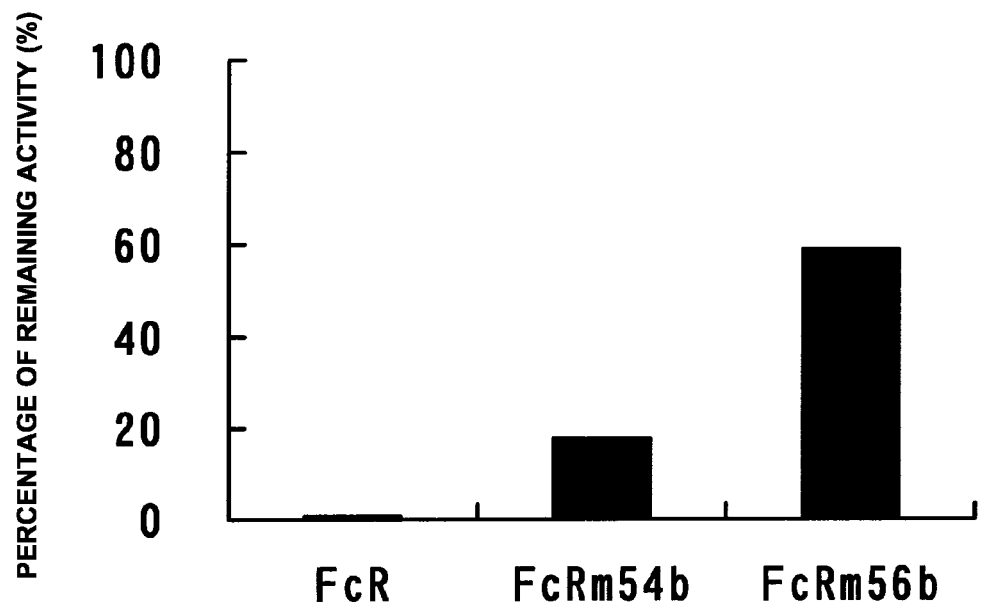
FIG. 19 is a graph for evaluating the alkali stability of the Fc binding protein (FcRm56b).

FIG. 19 shows a result of comparison of stability against alkali. FcR in FIG. 19 shows the wild-type Fc binding protein expressed by the transformant in Example 2. FcRm54b in FIG. 19 shows the Fc binding protein expressed by the transformant in Example 33. The FcRm56b that was the Fc binding protein expressed by the transformant produced in Example 38 was confirmed to have higher stability against alkali than these Fc binding proteins. The result in FIG. 19 reveals that the alkali stability of the Fc binding protein is improved by integration of amino acid substitutions (mutation) involved in improved stability.

Example 41

Mutation Introduction into Fc Binding Protein (FcRm56b) and Production of Library (1) A mutation was randomly introduced into the polynucleotide encoding the FcRm56b produced in Example 38 by the error-prone PCR. The reaction solution composition in the error-prone PCR is shown in the Table 9. The plasmid pETFcRm56b described in Example 38 was used as a template DNA. The oligonucleotide including the sequence shown in SEQ ID NO: 120 and the oligonucleotide including the sequence shown in SEQ ID NO: 121 were used as PCR primers. A PCR was carried out by heating for 2 minutes at 95° C., carrying out 30 cycles consisting of 30 seconds at 95° C. in the first step, 30 seconds at 60° C. in the second step, and 90 seconds at 72° C. in the third step, and finally heating for 7 minutes at 72° C.

(2) The PCR product was purified, digested with the restriction enzymes NcoI and HindIII, and inserted in the plasmid pETMalE (FIG. 4), which had been digested with the restriction enzymes NcoI and HindIII and produced in Example 2, by a ligation reaction. After completion of the reaction, E. coli strain BL21 (DE3) was transformed using the resulting ligation product by the electroporation method, and cultured in LB agar medium containing 50 μg/mL of kanamycin to form colonies. Thus, an FcRm56b random mutation transformant library was produced.

Example 42

Screening of Library of Fc Binding Protein (FcRm56b) with Improved Stability (1) The FcRm56b random mutation transformant library produced in Example 41 was inoculated into 200 μL of an LB broth medium containing 50 μg/mL of kanamycin, and was shake-cultured using a 96-deep well plate at 37° C. overnight.

(2) After the culturing, 5 μL of culture broth was subcultured into 500 μL of 2YT broth medium (containing 0.05 mM IPTG, 0.3% glycine, and 50 μg/mL of kanamycin), and was shake-cultured using a 96-deep well plate at 20° C. overnight.

(3) After the culturing, a culture supernatant obtained by centrifugation was diluted with pure water five times, and the diluted supernatant and a 800 mM sodium hydroxide solution were mixed in equal volumes. The mixture was alkali-treated at 30° C. for 180 minutes, and the pH was adjusted to a neutral region with 1M Tris-HCl buffer (pH 8.0).

(4) The antibody binding activities of the Fc binding proteins obtained from about 3,000 transformants were measured by the ELISA method described in Example 12(4). The antibody binding activities of the Fc binding proteins alkali-treated in (3) were divided by the antibody binding activities of Fc binding proteins not alkali-treated in (3) to obtain percentages of remaining activity.

(5) A plasmid was prepared from the transformant expressing the Fc binding protein with improved stability in comparison with the FcRm56b. The sequence of a polynucleotide region encoding an Fc binding protein inserted in the obtained plasmid was analyzed through the method described in Example 3 to identify mutation sites of amino acid existing in the Fc binding protein with improved stability in comparison with the FcRm56b.

As shown from the results of analysis of the nucleotide sequence, positions of substitutions of amino acid in the Fc binding protein are accumulated as follows (provided that the substitution of amino acid existing in the FcRm56b is not included).

Specifically, in the amino acid sequence described in SEQ ID NO: 1, substitution shown as Thr19Ile, Thr25Thr, Thr25Met, Thr38Ala, Ser53Thr, Thr61Ala, Thr63Phe, Tyr70Phe, Asn78Gly, Leu131Leu, Asn140Asp, Thr154Ser, Ser161Thr, Thr177Ser, Leu203Leu, Leu203Arg, Leu207Pro, Lys215Arg, Tyr230Phe, Ser233Gly, Asn268Ser, Leu283Leu, Leu285His, Pro286Ser, Thr287Pro, Val289Ala, Val289Asp, Val289Leu, or Val289Ile was caused. Further, among the substitutions, substitution (for example, Thr25Thr) in which a specified amino acid is not changed represents that a substituted (mutated) amino acid returns to a wild-type amino acid. The results of analysis of amino acid substitutions are shown in Table 16. Table 16 reveals that when the FcRm56b was substituted with amino acids, the Fc binding protein has improved stability.

TABLE 16

| Amino acid substitution | Remaining activity (%) |
|---|---|
| Thr19Ile | 47.4 |
| Thr25Thr | 47.9 |
| Thr38Ala | 40.8 |
| Ser53Thr | 41.1 |
| Thr61Ser | 38.1 |
| Thr63Phe | 41.4 |
| Tyr70Phe | 59.3 |
| His101Tyr | 39.6 |
| Asn140Asp | 41.9 |
| Leu203Arg | 50.7 |
| Leu207pro | 51.6 |
| Tyr230Phe | 60.6 |
| Ser233Gly | 50.8 |
| Leu283Leu | 42.5 |
| Leu285His | 46.7 |
| Thr287Pro | 48.1 |
| Thr287Asn | 37.9 |
| Val289Leu | 47.7 |
| Thr25Met, Asn268Ser | 44.6 |
| Glu44Val, Thr67Ala | 38.7 |
| Tyr70Phe, Lys215Arg | 58.8 |
| Asn78Gly, Val289Asp | 43.6 |
| Leu131Leu, Leu203Leu | 54.7 |
| Thr154Ser, Ser233Gly | 43.6 |
| Ser161Thr, Val289Asp | 42.5 |
| Thr177Ser, Asn268Ser | 41.2 |
| Leu203Arg, Ser233Gly | 56.3 |
| Pro286Ser, Val289Ala | 42.3 |
| Thr61Ala, Asn268Ser, Val289Ile | 42.3 |
| FcRm56b | 40.2 |

Example 43

Production of Fc Binding Protein (FcRm57b)

From the amino acid substitutions involved in improved stability of the Fc binding protein shown in Example 42, Tyr70Phe, Leu207Pro, Tyr230Phe, and Ser233Gly that were amino acid substitutions involved in improved stability were selected. The selected substitutions were integrated with respect to the FcRm56b described in Example 38, and the amino acids of the amino acid substitutions shown as Leu131Gln and Leu203His were substituted with leucine to produce an Fc binding protein FcRm57b in which 57 amino acids of a wild-type Fc binding protein were substituted with amino acids. Further, the amino acid substitutions shown as Tyr70Phe, Leu207Pro, Tyr230Phe, and Ser233Gly were carried out using oligonucleotides described below.

(i) amino acid substitution Tyr70Phe: an oligonucleotide including the sequence shown in SEQ ID NO: 156 (5'-AGGCAATGTGGAAAGTCGGGGTGGA-3') and an oligonucleotide including the sequence shown in SEQ ID NO: 157 (5'-TCCACCCCGACTTTCCACATTGCCT-3')

(ii) amino acid substitution Leu207Pro: an oligonucleotide including the sequence shown in SEQ ID NO: 158 (5'-AGCTCAGGGTCACCGGAGTGCCTTCA-3') and an oligonucleotide including the sequence shown in SEQ ID NO: 159 (5'-TGAAGGCACTCCGGTGACCCTGAGCT-3')

(iii) amino acid substitution Tyr230Phe: an oligonucleotide including the sequence shown in SEQ ID NO: 160 (5'-GCCCTTAAAGAACGAGAAATACAGCT-3') and an oligonucleotide including the sequence shown in SEQ ID NO: 161 (5'-AGCTGTATTTCTCGTTCTTTAAGGGC-3')

(iv) amino acid substitution Ser233Gly: an oligonucleotide including the sequence shown in SEQ ID NO: 162 (5'-TCCGCGCAGGGTTTCGCCGCCCTTA-3') and an oligonucleotide including the sequence shown in SEQ ID NO: 163 (5'-TAAGGGCGGCGAAACCCTGCGCGGA-3')

(1) The PCR was carried out using as a template a plasmid containing a polynucleotide encoding an Fc binding protein in which each amino acid of the amino acid substitutions Leu131Gln and Leu203His of the Fc binding protein FcRm56b obtained by screening in Example 42 was changed to leucine. The oligonucleotide including the sequence shown in SEQ ID NO: 68 and the oligonucleotide including the sequence shown in SEQ ID NO: 156 were used as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m57 bp1.

(2) The PCR was carried out using as a template a plasmid containing a polynucleotide encoding an Fc binding protein in which each amino acid of the amino acid substitutions Leu131Gln and Leu203His of the Fc binding protein FcRm56b obtained by screening in Example 42 was changed to leucine. The oligonucleotide including the sequence shown in SEQ ID NO: 157 and the oligonucleotide including the sequence shown in SEQ ID NO: 162 were used as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m57 bp2.

(3) The PCR was carried out using as a template a plasmid containing a polynucleotide encoding an Fc binding protein in which each amino acid of the amino acid substitutions Leu131Gln and Leu203His of the Fc binding protein FcRm56b obtained by screening in Example 42 was changed to leucine. The oligonucleotide including the sequence shown in SEQ ID NO: 163 and the oligonucleotide including the sequence shown in SEQ ID NO: 69 were used as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m57 bp3.

(4) Three types of the PCR products, m57 bp1, m57 bp2, and m57 bp3 were purified. The purified m57 bp1, m57 bp2, and m57 bp3 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m57 bp4.

(5) The m57 bp4 was purified. The PCR was carried out using the purified m57 bp4 as a template and the oligonucleotide including the sequence shown in SEQ ID NO: 68 and the oligonucleotide including the sequence shown in SEQ ID NO: 158 as PCR primers. The PCR was carried out for 30 cycles consisting of 10 seconds at 98° C. in the first step, 5 seconds at 50° C. in the second step, and 1 minute at 72°

C. in the third step using the reaction solution composition shown in Table 4. The PCR product was designated as m57 bp5.

(6) The m57 bp4 was purified. The PCR was carried out using the purified m57 bp4 as a template and the oligonucleotide including the sequence shown in SEQ ID NO: 159 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m57 bp6.

(7) Two types of the PCR products m57 bp5 and m57 bp6 were purified. The purified m57 bp5 and m57 bp6 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m57 bp7.

(8) The m57 bp7 was purified. The PCR was carried out using the purified m57 bp7 as a template and the oligonucleotide including the sequence shown in SEQ ID NO: 68 and the oligonucleotide including the sequence shown in SEQ ID NO: 160 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m57 bp8.

(9) The m57 bp7 was purified. The PCR was carried out using the purified m57 bp7 as a template and the oligonucleotide including the sequence shown in SEQ ID NO: 161 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m57 bp9.

(10) Two types of the PCR products m57 bp8 and m57 bp9 were purified. The purified m57 bp8 and m57 bp9 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was purified to obtain a polynucleotide encoding an Fc binding protein FcRm57b in which 57 amino acids of a wild-type Fc binding protein were substituted with amino acids.

(11) The polynucleotide encoding the FcRm57b was digested with the restriction enzymes NcoI and HindIII, and ligated into the expression vector pETMalE (FIG. 4) which had been digested with the restriction enzymes NcoI and HindIII and described in Example 2. E. coli strain BL21 (DE3) was transformed with this product.

(12) The obtained transformant was cultured in LB medium containing 50 µg/mL of kanamycin. A plasmid was extracted from the cultured bacterial cells (transformant) to obtain a plasmid pETFcRm57b containing the polynucleotide encoding the FcRm57b.

(13) The nucleotide sequence of pETFcRm57b was analyzed in the same manner as in Example 3.

The amino acid sequence of FcRm57b plus a signal sequence and a polyhistidine tag is shown in SEQ ID NO: 164, and the sequence of the polynucleotide encoding the FcRm57b is shown in SEQ ID NO: 165. In SEQ ID NO: 164, the MalE signal peptide is from methionine at position 1 to alanine at position 26, the linker peptide is from lysine at position 27 to glycine at position 33, the amino acid sequence of FcRm57b is from glutamine at position 34 to valine at position 307, and the polyhistidine tag is histidine at positions 308 to 313. Further, in SEQ ID NO: 154, proline of Thr20Pro that is a substituted amino acid is at position 38, lysine of Thr25Lys is at position 43, leucine of Gln35Leu is at position 53, glycine of Glu36Gly is at position 54, serine of Thr38Ser is at position 56, methionine of Leu41Met is at position 59, leucine of His42Leu is at position 60, proline of Leu46Pro is at position 64, serine of Pro49Ser is at position 67, alanine of Ser51Ala is at position 69, glycine of Ser52Gly is at position 70, arginine of Leu58Arg is at position 76, aspartic acid of Gly60Asp is at position 78, isoleucine of Thr63Ile is at position 81, alanine of Thr65Ala is at position 83, threonine of Ser69Thr is at position 87, phenylalanine of Tyr70Phe is at position 88, histidine of Arg71His is at position 89, alanine of Thr73Ala is at position 91, glutamic acid of Val77Glu is at position 95, aspartic acid of Asn78Asp is at position 96, leucine of Gln97Leu is at position 115, valine of Ile100Val is at position 118, alanine of Ser111Ala is at position 129, leucine of Phe114Leu is at position 132, isoleucine of Thr115Ile is at position 133, valine of Ala121Val is at position 139, arginine of Lys128Arg is at position 146, histidine of Tyr133His is at position 151, phenylalanine of Tyr137Phe is at position 155, histidine of Arg139His is at position 157, arginine of Trp149Arg is at position 167, threonine of Ser151Thr is at position 169, threonine of Asn152Thr is at position 170, proline of Leu156Pro is at position 174, arginine of Lys157Arg is at position 175, threonine of Ile160Thr is at position 178, serine of Asn163Ser is at position 181, arginine of Lys173Arg is at position 191, threonine of Ile181Thr is at position 199, leucine of Ser182Leu is at position 200, serine of Thr184Ser is at position 202, threonine of Asn195Thr is at position 213, alanine of Thr199Ala is at position 217, threonine of Asn206Thr is at position 224, proline of Leu207Pro is at position 225, valine of Glu213Val is at position 231, isoleucine of Leu218Ile is at position 236, phenylalanine of Tyr230Phe is at position 248, lysine of Met231Lys is at position 249, glycine of Ser233Gly is at position 251, glutamic acid of Lys234Glu is at position 252, aspartic acid of Asn240Asp is at position 258, alanine of Thr249Ala is at position 267, valine of Leu270Val is at position 288, histidine of Leu283His is at position 301, and glutamine of Leu285Gln is at position 303.

Example 44

Evaluation of Productivity of Fc Binding Protein (FcRm57b)

The transformants produced in Examples 43 and 2 were prepared in the same manner as in Example 14. The productivities of Fc binding proteins measured by the ELISA method described in Example 12(4) were compared as the production amount (mg/L-broth medium/OD600) per turbidity (Optical Density at 600 nm, OD600) of the culture broth.

Figure 20:
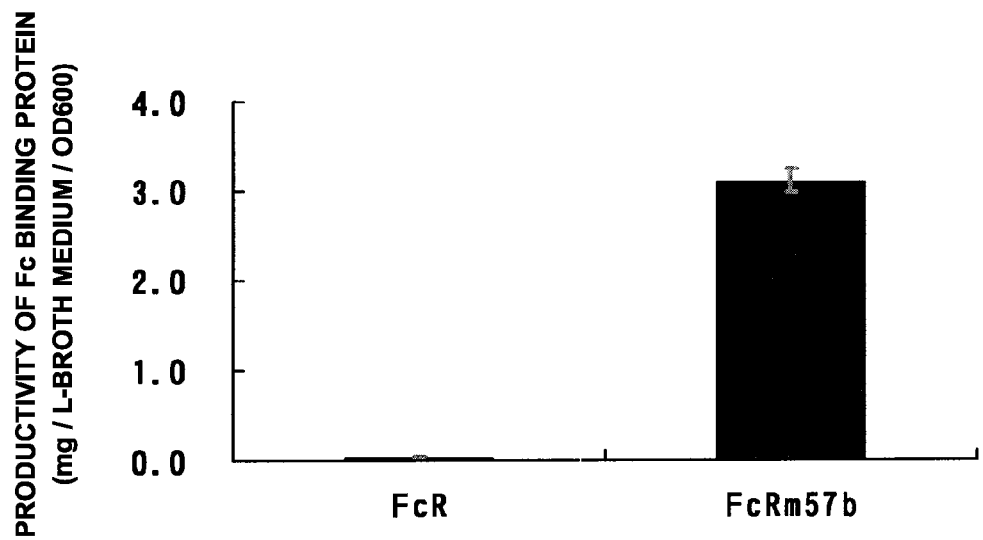
FIG. 20 is a graph for evaluating the productivity of the Fc binding protein (FcRm57b).

The results are shown in FIG. 20. FcR in FIG. 20 shows the wild-type Fc binding protein expressed by the transformant in Example 2.
The FcRm57b that was the Fc binding protein expressed by the transformant produced in Example 43 was confirmed to have higher productivity than the wild-type Fc binding protein. The result in FIG. 20 reveals that the productivity of the Fc binding protein is improved by integration of amino acid substitutions (mutation) involved in improved stability.

Example 45

Evaluation of Stability of Fc Binding Protein (FcRm57b) Against Alkali (1) The Fc binding proteins (FcRm56b and FcRm57b) and a wild-type Fc binding protein were prepared by the method described in Example 14, and the concentrations thereof were measured by the ELISA method described in Example 12(4).

(2) Each of the Fc binding proteins was diluted so that the concentration was 5 µg/mL. To each of the resultant, an equal amount of a 600 mM sodium hydroxide solution was added and the mixture was allowed to stand at 25° C. for 120 minutes.

(3) After standing, the pH was adjusted to a neutral region with 1M Tris-HCl buffer (pH 8.0), and the antibody binding activities of the alkali-treated sample in (2) and a sample which was not alkali-treated in (2) for comparison were measured by the ELISA method described in Example 12(4).

(4) The antibody binding activity of the alkali-treated sample was divided by the antibody binding activity of the sample not alkali-treated to obtain a percentage of remaining activity of each of Fc binding proteins by alkali treatment.

Figure 21:
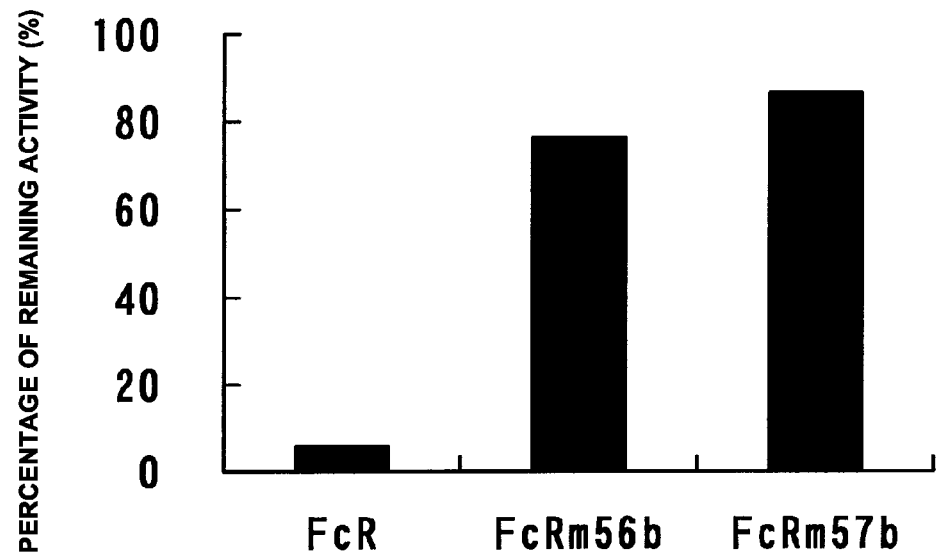
FIG. 21 is a graph for evaluating the alkali stability of the Fc binding protein (FcRm57b).

FIG. 21 shows a result of comparison of stability against alkali. FcR in FIG. 21 shows the wild-type Fc binding protein expressed by the transformant in Example 2. FcRm56b in FIG. 21 shows the Fc binding protein expressed by the transformant in Example 38. FcRm57b that was the Fc binding protein expressed by the transformant produced in Example 43 was confirmed to have higher stability against alkali than these Fc binding proteins. The result in FIG. 21 reveals that the alkali stability of the Fc binding protein is improved by integration of amino acid substitutions (mutation) involved in improved stability.

Example 46

Mutation Introduction into Fc Binding Protein (FcRm57b) and Production of Library (1) A mutation was randomly introduced into the polynucleotide encoding the FcRm57b produced in Example 43 by the error-prone PCR. The reaction solution composition in the error-prone PCR is shown in the Table 9. The plasmid pETFcRm57b described in Example 43 was used as a template DNA and the oligonucleotide including the sequence shown in SEQ ID NO: 120 and the oligonucleotide including the sequence shown in SEQ ID NO: 121 were used as PCR primers. A PCR was carried out by heating for 2 minutes at 95° C., carrying out 30 cycles consisting of 30 seconds at 95° C. in the first step, 30 seconds at 60° C. in the second step, and 90 seconds at 72° C. in the third step, and finally heating for 7 minutes at 72° C.

(2) The PCR product was purified, digested with the restriction enzymes NcoI and HindIII, and inserted in the plasmid pETMalE (FIG. 4), which had been digested with the restriction enzymes NcoI and HindIII and produced in Example 2, by a ligation reaction.

(3) After completion of the reaction, *E. coli* strain BL21 (DE3) was transformed using the resulting ligation product by the electroporation method, and cultured in LB agar medium containing 50 µg/mL of kanamycin to form colonies. Thus, an FcRm57b random mutation transformant library was produced.

Example 47

Screening of Library of Fc Binding Protein (FcRm57b) with Improved Stability (1) The FcRm57b random mutation transformant library produced in Example 46 was inoculated into 200 µL of an LB broth medium containing 50 µg/mL of kanamycin, and was shake-cultured using a 96-deep well plate at 37° C. overnight.

(2) After the culturing, 5 µL of culture broth was subcultured into 500 µL of 2YT broth medium (containing 0.05 mM IPTG, 0.3% glycine, and 50 µg/mL of kanamycin), and was shake-cultured using a 96-deep well plate at 20° C. overnight.

(3) After the culturing, a culture supernatant obtained by centrifugation was diluted with pure water five times, and the diluted supernatant and a 1000 mM sodium hydroxide solution were mixed in equal volumes. The mixture was alkali-treated at 30° C. for 180 minutes, and the pH was adjusted to a neutral region with 1M Tris-HCl buffer (pH 8.0).

(4) The antibody binding activities of the Fc binding proteins obtained from about 3,000 transformants were measured by the ELISA method described in Example 12(4). The antibody binding activities of the Fc binding proteins alkali-treated in (3) were divided by the antibody binding activities of Fc binding proteins not alkali-treated in (3) to obtain percentages of remaining activity.

(5) A plasmid was prepared from a transformant expressing an Fc binding protein with improved stability in comparison with the FcRm57b. The sequence of a polynucleotide region encoding an Fc binding protein inserted in the obtained plasmid was analyzed through the method described in Example 3 to identify mutation sites of amino acid existing in the Fc binding protein with improved stability in comparison with the FcRm57b.

As shown from the results of analysis of the nucleotide sequence, positions of substitutions of amino acid in the Fc binding protein are accumulated as follows (provided that the substitution of amino acid existing in the FcRm57b is not included).

Specifically, in the amino acid sequence described in SEQ ID NO: 1, substitution shown as Val17Glu, Gln27Lys, Leu41Leu, Gly50Glu, Ser51Val, Ser53Leu, Thr61Ser, Thr65Val, Ser74Phe, Ser76Asn, Arg84Ser, Gly88Ser, Leu89Pro, Ile96Lys, Thr115Phe, Glu118Asp, Asp129Gly, Gly141Asp, Asn159Asp, Thr165Met, Lys173Lys, His174Gln, Ser182Glu, Val198Met, Leu202Met, Leu203Pro, Glu213Ile, Leu217Gln, Leu223Met, Tyr245Glu, Gln246Lys, Leu248Ile, Gln279Arg, Pro286Gln, Thr287Pro, Val289Ala, Val289Asp, or Val289Gly was caused. Further, substitution (for example, Leu41Leu) in which specified amino acid is not changed represents that a substituted (mutated) amino acid returns to a wild-type amino acid. Results of analysis of amino acid substitutions are shown in Table 17. Table 17 reveals that when the FcRm57b was further substituted with amino acids, the Fc binding protein has improved stability.

TABLE 17

| Amino acid substitution | Remaining activity (%) |
| --- | --- |
| Val17Glu | 63.2 |
| Lys25Met | 54.6 |
| Leu41Leu | 63.7 |
| Gln55Leu | 58.6 |
| Phe57Leu | 38.9 |
| Ser74Phe | 65.3 |
| Ser76Asn | 65.3 |
| Gly88Ser | 69.9 |
| Glu118Asp | 71.0 |
| Lys157Lys | 57.7 |
| Thr165Met | 75.5 |
| Lys173Lys | 71.8 |
| His174Gln | 63.1 |
| Leu202Met | 67.4 |
| Ser211Gly | 53.6 |
| Leu223Met | 67.8 |
| Tyr245Glu | 63.7 |
| Gln246Lys | 76.2 |
| Pro286Gln | 66.5 |
| Thr287Ser | 60.1 |
| Thr287Pro | 69.4 |
| Val289Asp | 69.6 |
| Val289Gly | 69.5 |
| Lys25Met, Phe144Ile | 59.2 |
| Lys25Met, Ala250Thr | 56.9 |
| Lru46Ser, Asp94Glu | 59.5 |
| Gly50Glu, Thr65Val | 62.7 |
| Ser51Val, Leu203Pro | 68.8 |
| Arg84Ser, Gln279Arg | 61.8 |
| Leu89Pro, Val289Gly | 71.3 |
| Ile96Lys, Thr287Pro | 62.8 |
| Gly141Asp, Val198Met | 64.5 |
| Ser182Glu, Glu213Ile | 65.0 |
| Leu217Gln, Val289Asp | 75.5 |
| Gln27Lys, Thr115Phe, Asp129Gly | 62.6 |
| Ser53Leu, Leu248Ile, Val289Ala | 68.8 |
| Thr61Ser, Asn159Asp, Val289Ala | 67.1 |
| FcRm57b | 61.7 |

Example 48

Production of Fc Binding Protein (FcRm61)

From the amino acid substitutions involved in improved stability of the Fc binding protein shown in Example 47, Glu118Asp, Thr165Met, Gln246Lys, and Val289Asp that were amino acid substitutions involved in improved stability were selected.

The substitutions were integrated with respect to the FcRm57b described in Example 43 to produce an Fc binding protein FcRm61 in which 61 amino acids of a wild-type Fc binding protein were substituted with amino acids. Thus, stability was further improved. Further, in order to cause amino acid substitutions shown as Glu118Asp and Gln246Lys, oligonucleotides described below were used.

(i) amino acid substitution Glu118Asp: an oligonucleotide including the sequence shown in SEQ ID NO: 166 (5'-TACAAGCGGGTCGCCTTCGATTAAA-3') and an oligonucleotide including the sequence shown in SEQ ID NO: 167 (5'-TTTAATCGAAGGCGACCCGCTTGTA-3')

(ii) amino acid substitution Gln246Lys: an oligonucleotide including the sequence shown in SEQ ID NO: 168 (5'-GGCTAAAATCTTATACTCACTCGAG-3') and an oligonucleotide including the sequence shown in SEQ ID NO: 169 (5'-CTCGAGTGAGTATAAGATTTTAGCC-3')

(1) The PCR was carried out using as a template a plasmid containing a polynucleotide encoding an Fc binding protein in which the Fc binding protein FcRm57b produced by screening in Example 47 was subjected to an additional substitution shown as Thr165Met. The oligonucleotide including the sequence shown in SEQ ID NO: 68 and the oligonucleotide including the sequence shown in SEQ ID NO: 168 were used as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m61p1.

(2) The PCR was carried out using as a template a plasmid containing a polynucleotide encoding an Fc binding protein in which the Fc binding protein FcRm57b obtained by screening in Example 47 was subjected to additional substitutions shown as Leu217Gln and Val289Asp. The oligonucleotide including the sequence shown in SEQ ID NO: 169 and the oligonucleotide including the sequence shown in SEQ ID NO: 69 were used as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m61p2.

(3) Two types of the PCR products m61p1 and m61p2 were purified and mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m61p3.

(4) The m61p3 was purified. The PCR was carried out using the purified m61p3 as a template and the oligonucleotide including the sequence shown in SEQ ID NO: 68 and the oligonucleotide including the sequence shown in SEQ ID NO: 166 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m61p4.

(5) The m61p3 was purified. The PCR was carried out using the purified m61p3 as a template and the oligonucleotide including the sequence shown in SEQ ID NO: 167 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m61p5.

(6) Two types of the PCR products m61p4 and m61p5 were purified and mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was purified to obtain a polynucleotide encoding an Fc binding protein FcRm61 in which 61 amino acids of a wild-type Fc binding protein were substituted with amino acids.

(7) The polynucleotide encoding the FcRm61 was digested with the restriction enzymes NcoI and HindIII, and ligated into the expression vector pETMalE (FIG. 4) which had been digested with the restriction enzymes NcoI and HindIII and described in Example 2. *E. coli* strain BL21 (DE3) was transformed with this product.

(8) The obtained transformant was cultured in LB medium containing 50 μg/mL of kanamycin. A plasmid was extracted from the cultured bacterial cells to obtain a plasmid pETFcRm61 containing the polynucleotide encoding the FcRm61.

(9) The nucleotide sequence of pETFcRm61 was analyzed in the same manner as in Example 3. The amino acid sequence of FcRm61 plus a signal sequence and a polyhistidine tag is shown in SEQ ID NO: 170, and the sequence of the polynucleotide encoding the FcRm61 is shown in SEQ ID NO: 171. In SEQ ID NO: 170, the MalE signal peptide is from methionine at position 1 to alanine at position 26, the linker peptide is from lysine at position 27 to glycine at position 33, the amino acid sequence of FcRm61 is from glutamine at position 34 to valine at position 307, and the polyhistidine tag is histidine at positions 308 to 313. Further, in SEQ ID NO: 170, proline of Thr20Pro that is a substituted amino acid is at position 38, lysine of Thr25Lys is at position 43, leucine of Gln35Leu is at position 53, glycine of Glu36Gly is at position 54, serine of Thr38Ser is at position 56, methionine of Leu41Met is at position 59, leucine of His42Leu is at position 60, proline of Leu46Pro is at position 64, serine of Pro49Ser is at position 67, alanine of Ser51Ala is at position 69, glycine of Ser52Gly is at position 70, arginine of Leu58Arg is at position 76, aspartic acid of Gly60Asp is at position 78, isoleucine of Thr63Ile is at position 81, alanine of Thr65Ala is at position 83, threonine of Ser69Thr is at position 87, phenylalanine of Tyr70Phe is at position 88, histidine of Arg71His is at position 89, alanine of Thr73Ala is at position 91, glutamic acid of Val77Glu is at position 95, aspartic acid of Asn78Asp is at position 96, leucine of Gln97Leu is at position 115, valine of Ile100Val is at position 118, alanine of Ser111Ala is at position 129, leucine of Phe114Leu is at position 132, isoleucine of Thr115Ile is at position 133, aspartic acid of Glu118Asp is at position 136, valine of Ala121Val is at position 139, arginine of Lys128Arg is at position 146, histidine of Tyr133His is at position 151, phenylalanine of Tyr137Phe is at position 155, histidine of Arg139His is at position 157, arginine of Trp149Arg is at position 167, threonine of Ser151Thr is at position 169, threonine of Asn152Thr is at position 170, proline of Leu156Pro is at position 174, arginine of Lys157Arg is at position 175, threonine of Ile160Thr is at position 178, serine of Asn163Ser is at position 181, methionine of Thr165Met is at position 183, arginine of Lys173Arg is at position 191, threonine of Ile181Thr is at position 199, leucine of Ser182Leu is at position 200, serine of Thr184Ser is at position 202, threonine of Asn195Thr is at position 213, alanine of Thr199Ala is at position 217, threonine of Asn206Thr is at position 224, proline of Leu207Pro is at position 225, valine of Glu213Val is at position 231, isoleucine of Leu218Ile is at position 236, phenylalanine of Tyr230Phe is at position 248, lysine of Met231Lys is at position 249, glycine of Ser233Gly is at position 251, glutamic acid of Lys234Glu is at position 252, aspartic acid of Asn240Asp is at position 258, lysine of Gln246Lys is at position 264, alanine of Thr249Ala is at position 267, valine of Leu270Val is at position 288, histidine of Leu283His is at position 301, glutamine of Leu285Gln is at position 303, and aspartic acid of Val289Asp is at position 307.

Example 49

Production of Fc Binding Protein (FcRm60c)

From the amino acid substitutions involved in improved stability of the Fc binding protein shown in Example 47, Thr165Met, Leu217Gln, and Val289Asp that were amino acid substitutions involved in improved stability were selected. The selected substitutions were integrated with respect to the FcRm57b described in Example 43 to produce an Fc binding protein FcRm60c in which 60 amino acids of a wild-type Fc binding protein were substituted with amino acids. Thus, stability was further improved. Further, an oligonucleotide including the sequence shown in SEQ ID NO: 172 (5'-AGCAATGGTACATCCCGCTGTGGGA-3') and an oligonucleotide including the sequence shown in SEQ ID NO: 173 (5'-TCCCACAGCGGGATGTACCATT-GCT-3') were used for amino acid substitution shown as Thr165Met.

(1) The PCR was carried out using as a template a plasmid containing a polynucleotide encoding an Fc binding protein in which the Fc binding protein FcRm57b obtained by screening in Example 47 was subjected to additional substitutions shown as Leu217Gln and Val289Asp. The oligonucleotide including the sequence shown in SEQ ID NO: 68 and the oligonucleotide including the sequence shown in SEQ ID NO: 172 were used as PCR primers to carry out the PCR. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m60 cp1.

(2) The PCR was carried out using as a template a plasmid containing a polynucleotide encoding an Fc binding protein in which the Fc binding protein FcRm57b obtained by screening in Example 47 was subjected to additional substitutions shown as Leu217Gln and Val289Asp, and as PCR primers the oligonucleotide including the sequence shown in SEQ ID NO: 173 and the oligonucleotide including the sequence shown in SEQ ID NO: 69. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m60 cp2.

(3) Two types of the PCR products m60 cp1 and m60 cp2 were purified. The purified m60 cp1 and m60 cp2 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was purified to obtain a polynucleotide encoding the Fc binding protein FcRm60c in which 60 amino acids of a wild-type Fc binding protein were substituted with amino acids.

(4) The polynucleotide encoding the FcRm60c was digested with the restriction enzymes NcoI and HindIII, and ligated into the expression vector pETMalE (FIG. 4) which had been digested with the restriction enzymes NcoI and HindIII and described in Example 2. *E. coli* strain BL21 (DE3) was transformed with this product.

(5) The obtained transformant was cultured in LB medium containing 50 μg/mL of kanamycin. A plasmid was extracted from the cultured bacterial cells to obtain a plasmid pETFcRm60c containing the polynucleotide encoding the FcRm60c.

(6) The nucleotide sequence of pETFcRm60c was analyzed in the same manner as in Example 3.

The amino acid sequence of FcRm60c plus a signal sequence and a polyhistidine tag is shown in SEQ ID NO: 174, and the sequence of the polynucleotide encoding the FcRm60c is shown in SEQ ID NO: 175. In SEQ ID NO: 174, the MalE signal peptide is from methionine at position 1 to alanine at position 26, the linker peptide is from lysine at position 27 to glycine at position 33, the amino acid sequence of FcRm60c is from glutamine at position 34 to valine at position 307, and the polyhistidine tag is histidine at positions 308 to 313. Further, in SEQ ID NO: 174, proline of Thr20Pro that is a substituted amino acid is at position 38, lysine of Thr25Lys is at position 43, leucine of Gln35Leu is at position 53, glycine of Glu36Gly is at position 54, serine of Thr38Ser is at position 56, methionine of Leu41Met is at position 59, leucine of His42Leu is at position 60, proline of Leu46Pro is at position 64, serine of Pro49Ser is at position 67, alanine of Ser51Ala is at position 69, glycine of Ser52Gly is at position 70, arginine of Leu58Arg is at position 76, aspartic acid of Gly60Asp is at position 78, isoleucine of Thr63Ile is at position 81, alanine of Thr65Ala is at position 83, threonine of Ser69Thr is at position 87, phenylalanine of Tyr70Phe is at position 88, histidine of Arg71His is at position 89, alanine of Thr73Ala is at position 91, glutamic acid of Val77Glu is at position 95, aspartic acid of Asn78Asp is at position 96, leucine of Gln97Leu is at position 115, valine of Ile100Val is at position 118, alanine of Ser111Ala is at position 129, leucine of Phe114Leu is at position 132, isoleucine of Thr115Ile is at position 133, valine of Ala121Val is at position 139, arginine of Lys128Arg is at position 146, histidine of Tyr133His is at position 151, phenylalanine of Tyr137Phe is at position 155, histidine of Arg139His is at position 157, arginine of Trp149Arg is at position 167, threonine of Ser151Thr is at position 169, threonine of Asn152Thr is at position 170, proline of Leu156Pro is at position 174, arginine of Lys157Arg is at position 175, threonine of Ile160Thr is at position 178, serine of Asn163Ser is at position 181, methionine of Thr165Met is at position 183, arginine of Lys173Arg is at position 191, threonine of Ile181Thr is at position 199, leucine of Ser182Leu is at position 200, serine of Thr184Ser is at position 202, threonine of Asn195Thr is at position 213, alanine of Thr199Ala is at position 217, threonine of Asn206Thr is at position 224, proline of Leu207Pro is at position 225, valine of Glu213Val is at position 231, glutamine of Leu217Gln is at position 235, isoleucine of Leu218Ile is at position 236, phenylalanine of Tyr230Phe is at position 248, lysine of Met231Lys is at position 249, glycine of Ser233Gly is at position 251, glutamic acid of Lys234Glu is at position 252, aspartic acid of Asn240Asp is at position 258, alanine of Thr249Ala is at position 267, valine of Leu270Val is at position 288, histidine of Leu283His is at position 301, glutamine of Leu285Gln is at position 303, and aspartic acid of Val289Asp is at position 307.

Example 50

Production of Fc Binding Protein (FcRm62)

From the amino acid substitutions involved in improved stability of the Fc binding protein shown in Example 47, Glu118Asp, Thr165Met, Leu217Gln, Gln246Lys, and Val289Asp that were amino acid substitutions involved in improved stability were selected. The selected substitutions were integrated with respect to the FcRm57b described in Example 43 to produce an Fc binding protein FcRm62 in which 62 amino acids of a wild-type Fc binding protein were substituted with amino acids. Thus, stability was further improved. Further, in order to cause amino acid substitution shown as Glu118Asp, the oligonucleotide including the sequence shown in SEQ ID NO: 167 was used. Further, in order to cause amino acid substitution shown as Gln246Lys, the oligonucleotide including the sequence shown in SEQ ID NO: 168 was used.

(1) The PCR was carried out using the plasmid pETFcRm60c of Example 49 as a template and the oligonucleotide including the sequence shown in SEQ ID NO: 167 and the oligonucleotide including the sequence shown in SEQ ID NO: 168 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was designated as m62p1.

(2) The PCR product m62 μl was purified and mixed in each of purified PCR products m61p4 and m61p2 of Example 48. The PCR was carried out for 5 cycles consisting of 10 seconds at 98° C. in the first step, 5 seconds at 55° C. in the second step, and 1 minute at 72° C. in the third step using the reaction solution composition shown in Table 7, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 50° C. in the second step, and 1 minute at 72° C. in the third step using the reaction solution composition shown in Table 4. The PCR product was purified to obtain a polynucleotide encoding the Fc binding protein FcRm62 in which 62 amino acids of a wild-type Fc binding protein were substituted with amino acids.

(3) The polynucleotide encoding the FcRm62 was digested with the restriction enzymes NcoI and HindIII, and ligated into the expression vector pETMalE (FIG. 4) which had been digested with the restriction enzymes NcoI and HindIII and described in Example 2. *E. coli* strain BL21 (DE3) was transformed with this product.

(4) The obtained transformant was cultured in LB medium containing 50 μg/mL of kanamycin. A plasmid was extracted from the cultured bacterial cells (transformant) to obtain a plasmid pETFcRm62 containing the polynucleotide encoding the FcRm62.

(5) The nucleotide sequence of pETFcRm62 was analyzed in the same manner as in Example 3.

The amino acid sequence of FcRm62 plus a signal sequence and a polyhistidine tag is shown in SEQ ID NO: 176, and the sequence of the polynucleotide encoding the FcRm62 is shown in SEQ ID NO: 177. In SEQ ID NO: 176, the MalE signal peptide is from methionine at position 1 to alanine at position 26, the linker peptide is from lysine at position 27 to glycine at position 33, the amino acid sequence of FcRm62 is from glutamine at position 34 to valine at position 307, and the polyhistidine tag is histidine at positions 308 to 313. Further, in SEQ ID NO: 176, proline of Thr20Pro that is a substituted amino acid is at position 38, lysine of Thr25Lys is at position 43, leucine of Gln35Leu is at position 53, glycine of Glu36Gly is at position 54, serine of Thr38Ser is at position 56, methionine of Leu41Met is at position 59, leucine of His42Leu is at position 60, proline of Leu46Pro is at position 64, serine of Pro49Ser is at position 67, alanine of Ser51Ala is at position 69, glycine of Ser52Gly is at position 70, arginine of Leu58Arg is at position 76, aspartic acid of Gly60Asp is at position 78, isoleucine of Thr63Ile is at position 81, alanine of Thr65Ala is at position 83, threonine of Ser69Thr is at position 87, phenylalanine of Tyr70Phe is at position 88, histidine of Arg71His is at position 89, alanine of Thr73Ala is at position 91, glutamic acid of Val77Glu is at position 95, aspartic acid of Asn78Asp is at position 96, leucine of Gln97Leu is at position 115, valine of Ile100Val is at position 118, alanine of Ser111Ala is at position 129, leucine of Phe114Leu is at position 132, isoleucine of Thr115Ile is at position 133, aspartic acid of Glu118Asp is at position 136, valine of Ala121Val is at position 139, arginine of Lys128Arg is at position 146, histidine of Tyr133His is at position 151, phenylalanine of Tyr137Phe is at position 155, histidine of Arg139His is at position 157, arginine of Trp149Arg is at position 167, threonine of Ser151Thr is at position 169, threonine of Asn152Thr is at position 170, proline of Leu156Pro is at position 174, arginine of Lys157Arg is at position 175, threonine of Ile160Thr is at position 178, serine of Asn163Ser is at position 181, methionine of Thr165Met is at position 183, arginine of Lys173Arg is at position 191, threonine of Ile181Thr is at position 199, leucine of Ser182Leu is at position 200, serine of Thr184Ser is at position 202, threonine of Asn195Thr is at position 213, alanine of Thr199Ala is at position 217, threonine of Asn206Thr is at position 224, proline of Leu207Pro is at position 225, valine of Glu213Val is at position 231, glutamine of Leu217Gln is at position 235, isoleucine of Leu218Ile is at position 236, phenylalanine of Tyr230Phe is at position 248, lysine of Met231Lys is at position 249, glycine of Ser233Gly is at position 251, glutamic acid of Lys234Glu is at position 252, aspartic acid of Asn240Asp is at position 258, lysine of Gln246Lys is at position 264, alanine of Thr249Ala is at position 267, valine of Leu270Val is at position 288, histidine of Leu283His is at position 301, glutamine of Leu285Gln is at position 303, and aspartic acid of Val289Asp is at position 307.

Example 51

Evaluation of Productivity of Fc Binding Protein (FcRm61, FcRm60c, and FcRm62)

The transformants produced in Examples 2 and 48 to 50 were prepared in the same manner as in Example 14. The productivities of Fc binding proteins measured by the ELISA method described in Example 12 (4) were compared as the production amount (mg/L-broth medium/OD600) per turbidity (Optical Density at 600 nm, OD600) of the culture broth.

Figure 22:
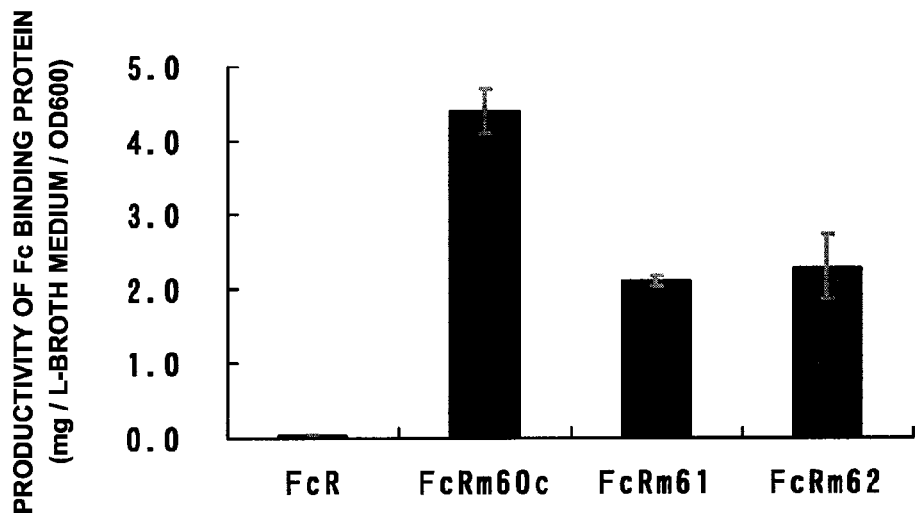
FIG. 22 is a graph for evaluating the productivity of the Fc binding proteins (FcRm60c, FcRm61, FcRm62).

The results are shown in FIG. 22. FcR in FIG. 22 shows the wild-type Fc binding protein expressed by the transformant in Example 2.

The FcRm61, FcRm60c, and FcRm62 that were the Fc binding protein expressed by the transformants produced in Examples 48 to 50 was confirmed to have higher productivity than the wild-type Fc binding protein. The results in FIG. 22 reveal that the productivity of the Fc binding protein is improved by integration of amino acid substitutions (mutation) involved in improved stability.

Example 52

Evaluation of Stability of Fc Binding Protein (FcRm61, FcRm60c, and FcRm62) Against Alkali (1) The Fc binding proteins (FcRm61, FcRm60c, and FcRm62) and a wild-type Fc binding protein were prepared by the method described in Example 14, and the concentrations thereof were measured by the ELISA method described in Example 12(4).

(2) Each of the Fc binding proteins was diluted so that the concentration was 5 μg/mL. To each of the resultant, an equal amount of a 600 mM sodium hydroxide solution was added and the mixture was allowed to stand at 25° C. for 180 minutes.

(3) After standing, the pH was adjusted to a neutral region with 1M Tris-HCl buffer (pH 8.0), and the antibody binding activities of the alkali-treated sample in (2) and a sample which was not alkali-treated in (2) for comparison were measured by the ELISA method described in Example 12(4).

(4) The antibody binding activity of the alkali-treated sample was divided by the antibody binding activity of the sample not alkali-treated to obtain a percentage of remaining activity of each of Fc binding proteins by alkali treatment.

Figure 23:
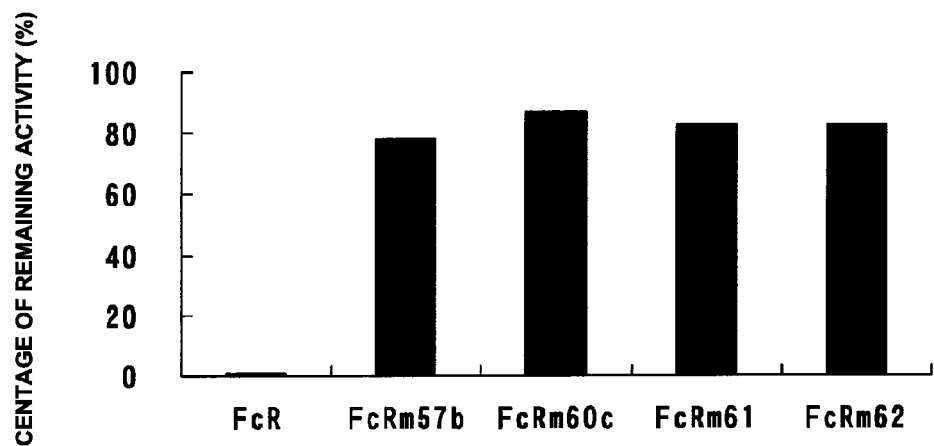
FIG. 23 is a graph for evaluating the alkali stability of the Fc binding proteins (FcRm60c, FcRm61, FcRm62).

FIG. 23 shows a result of comparison of stability against alkali. FcR in FIG. 23 shows the wild-type Fc binding protein expressed by the transformant in Example 2. FcRm57b in FIG. 23 shows the Fc binding protein expressed by the transformant in Example 43. The FcRm61, FcRm60c, and FcRm62 that were the Fc binding proteins expressed by the transformants produced in Examples 48 to 50 were confirmed to have higher stability against alkali than the FcR and FcRm57b. The result in FIG. 23 reveals that the alkali stability of the Fc binding protein is improved by integration of amino acid substitutions (mutation) involved in improved stability.

Example 53

Evaluation of Thermal Stability of Fc Binding Proteins (FcRm32, FcRm36b, FcRm44, FcRm48, FcRm54b, FcRm56b, and FcRm57b)

The Fc binding proteins (FcRm32, FcRm36b, FcRm44, FcRm48, FcRm54b, FcRm56b, and FcRm57b) produced in Examples 13, 18, 23, 28, 33, 38, and 43 were prepared by the method described in Example 9. The transition midpoints (Tm) of the prepared Fc binding proteins were measured by the method same as in Example 10. The results thus obtained are shown in Table 18.

TABLE 18

| Fc binding protein | Transition midpoint (Tm)(° C.) |
| --- | --- |
| FcR | 48.5 |
| FcRm32 | 73.0 |
| FcRm36b | 77.3 |
| FcRm44 | 78.1 |
| FcRm48 | 78.2 |
| FcRm54b | 80.0 |
| FcRm56b | 81.9 |
| FcRm57b | 79.4 |

FcR in FIG. 18 shows an Fc binding protein with no amino acid substitution (Fc receptor) expressed by the transformant produced in Example 2. The Fc binding proteins (FcRm32, FcRm36b, FcRm44, FcRm48, FcRm54b, FcRm56b, and FcRm57b) produced in Examples 13, 18, 23, 28, 33, 38, and 43 were confirmed to have increased Tm and improved thermal stability in comparison with this wild-type Fc binding protein.

Example 54

Evaluation of Acid Stability of Fc Binding Proteins (FcRm19, FcRm32, FcRm36b, FcRm44, FcRm48, FcRm54b, FcRm56b, FcRm57b, FcRm60c, FcRm61, and FcRm62)

(1) The wild-type Fc binding protein and Fc binding proteins produced in Examples 2, 7(d), 13, 18, 23, 28, 33, 38, 43, 48, 49, and 50 were prepared by the method described in Example 14, and the concentrations thereof were measured by the ELISA method described in Example 12(4).

(2) Each of the Fc binding proteins was diluted so that the concentration was 2 μg/mL. To each resultant, an equal amount of a 100 mM citric acid buffer (pH 3.0) was added and the mixture was allowed to stand at 25° C. for 24 hours.

(3) After standing, the pH was adjusted to a neutral region with 1M Tris-HCl buffer (pH 8.0), and the antibody binding activities of the alkali-treated sample in (2) and a sample which was not acid-treated (2) for comparison were measured by the ELISA method described in Example 12(4).

(4) The antibody binding activities of the acid-treated samples were divided by the antibody binding activities of the samples not treated with acid to obtain percentages of remaining activity of each Fc binding proteins by acid treatment.

Figure 24:
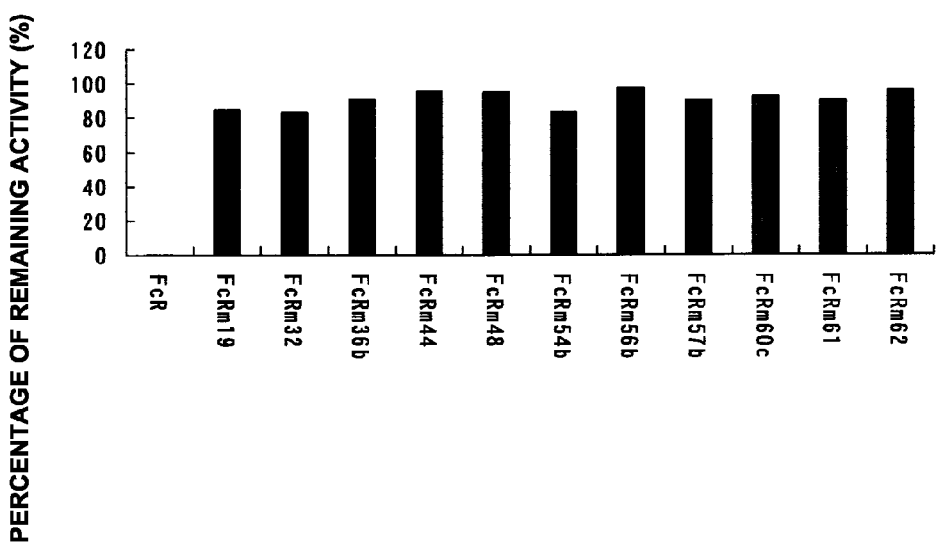
FIG. 24 is a graph for evaluating the acid stability of the Fc binding proteins.

FIG. 24 shows a result of comparison of stability against acid. FcR in FIG. 24 shows the wild-type Fc binding protein expressed by the transformant in Example 2. FcRm19, FcRm32, FcRm36b, FcRm44, FcRm48, FcRm54b, FcRm56b, FcRm57b, FcRm60c, FcRm61, and FcRm62 in FIG. 24 show the Fc binding proteins expressed by the transformants produced in Examples 7(d), 13, 18, 23, 28, 33, 38, 43, 49, 48, and 50. The Fc binding proteins were confirmed to have higher stability against acid than that of the wild-type Fc binding protein.

Example 55

Production of Fc Binding Protein Having Leu46 Substituted with Amino Acid

From the amino acid substitutions involved in improved thermal stability of the Fc binding protein shown in Example 5, the substitution of leucine at position 46 (Leu46) in the amino acid sequence described in SEQ ID NO: 1 with proline (Pro) has particularly remarkably improved thermal stability (Table 6). In order to reevaluate the availability of substitution of leucine at position 46, a plasmid containing a polynucleotide encoding an Fc binding protein in which leucine at position 46 was substituted with another amino acid and a transformant thereof was produced. Further, an oligonucleotide including the sequence shown in SEQ ID NO: 178 (5'-ACGTTGCACTGCGAAGTANNKCATCT-GCCTGGG-3') and an oligonucleotide including the sequence shown in SEQ ID NO: 179 (5'-ACTTGACCCA-GGCAGATGMNNTACTTCGCAGTG-3') were used to substitute the leucine at position 46 with an arbitrary amino acid.

(1) The PCR was carried out using as a template the plasmid pETFcR containing the polynucleotide encoding the wild-type Fc binding protein produced in Example 2. The oligonucleotide including the sequence shown in SEQ ID NO: 68 and the oligonucleotide including the sequence shown in SEQ ID NO: 179 were used as PCR primers. The PCR was carried out for 30 cycles consisting of 10 seconds at 98° C. in the first step, 5 seconds at 55° C. in the second step, and 1 minute at 72° C. in the third step using a reaction solution composition shown in Table 19. The PCR product was designated as L46p1.

TABLE 19

| Composition | Concentration |
| --- | --- |
| Template DNA | Proper quantity |
| 100 pmol/μL PCR primer | Each 1 μL |
| 2.5 U/μL PrimeSTAR HS (Takara Bio) | 0.5 μL |
| 5 × PrimeSTAR buffer (Takara Bio) | 10 μL |
| 2.5 mM dNTPs | 4 μL |
| H$_2$O | up to 50 μL |

(2) The PCR was carried out using as a template the plasmid pETFcR containing the polynucleotide encoding the wild-type Fc binding protein produced in Example 2. The oligonucleotide including the sequence shown in SEQ ID NO: 178 and the oligonucleotide including the sequence shown in SEQ ID NO: 69 were used as PCR primers. The PCR was carried out for 30 cycles consisting of 10 seconds at 98° C. in the first step, 5 seconds at 55° C. in the second step, and 1 minute at 72° C. in the third step using the reaction solution composition shown in Table 19. The PCR product was designated as L46p2.

(3) Two types of the PCR products L46 μl and L46p2 were purified. The purified L46 μl and L46p2 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 20, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 55° C. in the second step, and 1 minute at 72° C. in the third step using the reaction solution composition shown in Table 19. A polynucleotide encoding the Fc binding protein in which the amino acid at position 46 of the wild-type Fc binding protein was substituted with an arbitrary amino acid was obtained. The PCR product was designated as L46p3.

TABLE 20

| Composition | Concentration |
| --- | --- |
| PCR Product | Each equimolar |
| 2.5 U/μL PrimeSTAR HS (Takara Bio) | 0.5 μL |
| 5 × PrimeSTAR buffer (Takara Bio) | 6 μL |
| 2.5 mM dNTPs | 2.4 μL |
| H$_2$O | up to 30 μL |

(4) The L46p3 was purified and digested with the restriction enzymes NcoI and HindIII, and ligated into the expression vector pETMalE (FIG. 4) which had been digested with the restriction enzymes NcoI and HindIII and described in Example 2. *E. coli* strain BL21 (DE3) was transformed with this product.

(5) The obtained transformant was cultured in LB medium containing 50 μg/mL of kanamycin. A plasmid was extracted from the cultured bacterial cells (transformant) and sequence analysis was carried out by the method described in Example 3. As a result, a transformant expressing an Fc binding protein in which the leucine (Leu) at position 46 was substituted with alanine (Ala), arginine (Arg), asparagine (Asn), aspartic acid (Asp), glutamine (Gln), glycine (gly), histidine (His), isoleucine (ILe), lysine (Lys), proline (Pro), serine (Ser), or tryptophan (Trp) was obtained.

Example 56

Evaluation of Activity of Fc Binding Protein Having Leu46 Substituted with Amino Acid (1) The transformant was inoculated into 200 W, of an LB broth medium containing 50 μg/mL of kanamycin, and was shake-cultured using a 96-deep well plate at 37° C. overnight.

(2) After the culturing, 50 W, of the culture broth was subcultured into 500 μL of 2YT broth medium (containing 0.05 mM IPTG, 0.3% glycine, and 50 μg/mL of kanamycin), and was shake-cultured using a 96-deep well plate at 20° C. overnight.

(3) After the culturing, a culture supernatant obtained by centrifugation was diluted with 50 mM Tris-HCl buffer (pH 8.0) five times, and the antibody binding activity was measured by the ELISA method described in Example 12(4).

The results are shown in Table 21. Table 21 reveals that the activity is improved by substituting the leucine (Leu) at position 46 in the amino acid sequence described in SEQ ID NO: 1 with Ala, Arg, Asn, Asp, Gln, Gly, His, Lys, Pro, Ser, or Trp. The substitution with Asp, Pro, or Ser is preferable, and the substitution with Pro is more preferable.

TABLE 21

| Amino acid substitution | OD450 nm |
| --- | --- |
| Ala | 0.39 |
| Arg | 0.35 |
| Asn | 0.38 |
| Asp | 0.45 |
| Gln | 0.29 |
| Gly | 0.31 |
| His | 0.29 |
| Ile | 0.14 |
| Lys | 0.35 |
| Pro | 0.53 |
| Ser | 0.43 |
| Trp | 0.29 |
| Leu | 0.22 |

Example 57

Production of Fc Binding Protein Having Phe114 Substituted with Amino Acid

From the amino acid substitutions involved in improved thermal stability of the Fc binding protein shown in Example 5, the substitutions of phenylalanine at position 114 (Phe114) in the amino acid sequence described in SEQ ID NO: 1 with leucine (Leu) has particularly remarkably improved thermal stability (Table 6). In order to reevaluate the availability of substitution of phenylalanine at position 114, a plasmid containing a polynucleotide encoding a modified Fc binding protein in which phenylalanine at position 114 was substituted with another amino acid and a transformant thereof was produced. Further, an oligonucleotide including the sequence shown in SEQ ID NO: 180 (5'-CAGGTTAGCTCCCGCGTTNNKACCGAAGGCGA-3') and an oligonucleotide including the sequence shown in SEQ ID NO: 181 (5'-AAGCGGTTCGCCTTCGGTMN-NAACGCGGGAGC-3') were used to substitute the phenylalanine at position 114 with an arbitrary amino acid.

(1) The PCR was carried out using as a template the plasmid pETFcR containing the polynucleotide encoding the wild-type Fc binding protein produced in Example 2. The oligonucleotide including the sequence shown in SEQ ID NO: 68 and the oligonucleotide including the sequence shown in SEQ ID NO: 181 were used as PCR primers. The PCR was carried out for 30 cycles consisting of 10 seconds at 98° C. in the first step, 5 seconds at 55° C. in the second step, and 1 minute at 72° C. in the third step using the reaction solution composition shown in Table 19. The PCR product was designated as F114p1.

(2) The PCR was carried out using as a template the plasmid pETFcR containing the polynucleotide encoding the wild-type Fc binding protein produced in Example 2. The oligonucleotide including the sequence shown in SEQ ID NO: 180 and the oligonucleotide including the sequence shown in SEQ ID NO: 69 were used as PCR primers. The PCR was carried out for 30 cycles consisting of 10 seconds at 98° C. in the first step, 5 seconds at 55° C. in the second step, and 1 minute at 72° C. in the third step using the reaction solution composition shown in Table 19. The PCR product was designated as F114p2.

(3) Two types of the PCR products F114 μl and F114p2 were purified. The purified F114 μl and F114p2 were mixed, the PCR was carried out for 5 cycles consisting of 10 seconds at 98° C. in the first step, 5 seconds at 55° C. in the second step, and 1 minute at 72° C. in the third step using the reaction solution composition shown in Table 20, and the PCR products were ligated. The PCR was carried out using this PCR product as a template and the oligonucleotide including the sequence shown in SEQ ID NO: 68 and the oligonucleotide including the sequence shown in SEQ ID NO: 69 as PCR primers. The PCR was carried out for 30 cycles consisting of 10 seconds at 98° C. in the first step, 5 seconds at 55° C. in the second step, and 1 minute at 72° C. in the third step using the reaction solution composition shown in Table 19. A polynucleotide encoding the Fc binding protein in which the amino acid at position 114 of the wild-type Fc binding protein was substituted with an arbitrary amino acid was obtained. The PCR product was designated as F114p3.

(4) The F114p3 was purified and digested with the restriction enzymes NcoI and HindIII, and ligated into the expression vector pETMalE which had been digested with the restriction enzymes NcoI and HindIII and described in Example 2. *E. coli* strain BL21 (DE3) was transformed with this product.

(5) The obtained transformant was cultured in LB medium containing 50 µg/mL of kanamycin. A plasmid was extracted from the cultured bacterial cells (transformant) and sequence analysis was carried out by the method described in Example 3. As a result, a transformant expressing an Fc binding protein in which the phenylalanine (Phe) at position 114 was substituted with alanine (Ala), arginine (Arg), aspartic acid (Asp), cysteine (Cys), glutamine (Gln), glutamic acid (Glu), glycine (gly), histidine (His), isoleucine (ILe), leucine (Leu), lysine (Lys), methionine (Met), proline (Pro), serine (Ser), threonine (Thr), tryptophan (Trp), tyrosine (Tyr), or valine (Val) was obtained.

Example 58

Evaluation of Activity of Fc Binding Protein Having Phe114 Substituted with Amino Acid (1) The transformant was inoculated into 200 µL of an LB broth medium containing 50 µg/mL of kanamycin, and was shake-cultured using a 96-deep well plate at 37° C. overnight.

(2) After the culturing, 50 µL of the culture broth was subcultured into 500 µL of 2YT broth medium (containing 0.05 mM IPTG, 0.3% glycine, and 50 µg/mL of kanamycin), and was shake-cultured using a 96-deep well plate at 20° C. overnight.

(3) After the culturing, a culture supernatant obtained by centrifugation was diluted with 50 mM Tris-HCl buffer (pH 8.0) five times, and the antibody binding activity was measured by the ELISA method described in Example 12(4).

The results are shown in Table 22. As shown from Table 22, the activity was confirmed to be improved by substituting the phenylalanine (Phe) at position 114 in the amino acid sequence described in SEQ ID NO: 1 with Ala, Ile, Leu, Met, Pro, Thr, or Val. The substitution with Ile, Leu, Met, or Val is preferable, and the substitution with Ile, Leu, or Val is more preferable.

TABLE 22

| Amino acid substitution | OD450 nm |
| --- | --- |
| Ala | 0.19 |
| Arg | 0.08 |
| Asp | 0.05 |

TABLE 22-continued

| Amino acid substitution | OD450 nm |
| --- | --- |
| Cys | 0.05 |
| Gln | 0.13 |
| Glu | 0.09 |
| Gly | 0.06 |
| His | 0.06 |
| Ile | 0.87 |
| Leu | 0.50 |
| Lys | 0.07 |
| Met | 0.43 |
| Pro | 0.16 |
| Ser | 0.10 |
| Thr | 0.24 |
| Trp | 0.05 |
| Tyr | 0.08 |
| Val | 0.74 |
| Phe | 0.14 |

Example 59

Immobilization of Fc Binding Protein (FcRm19) in Gel (1) An Fc binding protein FcRm19 was prepared using the transformant produced in Example 7(d) by the method described in Example 9.

(2) 0.4 mL of the obtained 6.9 mg/mL FcRm19 solution and 0.1 mL of Toyopearl gel (Tosoh Corp.) with epoxy groups introduced were mixed, and a potassium phosphate buffer was added so that the final concentration was 0.6 M, to cause a reaction at 20° C. for 14 hours.

(3) After the reaction, a reaction residue was removed from the gel by filtration through a filter (pore size: 10 µm), and the gel was washed with 20 mM PBS (pH 7.0) to prepare a gel with immobilized FcRm19.

(4) The amount of an Fc binding protein as the reaction residue was determined by the Bradford method (protein assay kit, BioRad). An immobilization rate was calculated by dividing the amount by the amount of charged Fc binding protein.

As a result, an immobilization rate of 83.3% and an amount of immobilized FcRm19 per mL of the gel of 23.0 mg were confirmed.

Example 60

Evaluation of Adsorption of Antibody in Gel with Immobilized Fc Binding Protein (FcRm19)

(1) 0.5 mL of 10 mg/mL γ-globulin formulation (KAKETSUKEN, hereinafter referred to as IgG) dissolved in 20 mM PBS (pH 7.0) was added to 0.1 mL of the gel with immobilized Fc binding protein (FcRm19) prepared in Example 59, followed by shaking at 15° C. for 1 hour.

(2) After the shaking, the IgG solution was removed from the gel by filtration through a filter (pore size: 10 µm), and the gel was washed with 0.2 mL of 20 mM PBS (pH 7.0) five times.

(3) The gel was finally rinsed with 0.2 mL of 100 mM citric acid buffer (pH 3.0) three times to elute the IgG adsorbed by the gel.

The amount of the eluted IgG was determined to be 2.10 mg by measurement of absorbance at 280 nm (calculated as an absorbance of 1% IgG solution of 14 using a 10-mm cell).

As a result, the amount of adsorbed IgG per mL of the gel with immobilized FcRm19 prepared in Example 59 was confirmed to be 21.0 mg.

Example 61

Evaluation of Elution of Antibody from Gel with Immobilized Fc Binding Protein (FcRm19)

(1) A column was packed with 0.1 mL of the gel with immobilized Fc binding protein (FcRm19) prepared in Example 59, and 3 mg/mL IgG dissolved in 2 mL of 20 mM PBS (pH 7.0) was added to allow the gel to adsorb IgG.

(2) The column was sufficiently washed with 20 mM PBS (pH 7.0), and 2 mL of 100 mM citric acid buffer having an arbitrary pH within a range of 3.0 to 4.2 was passed through the column to elute IgG (referred to as an eluate 1).

(3) 2 mL of 100 mM citric acid buffer (pH 3.0) was finally passed to completely elute the IgG adsorbed by the gel (referred to as an eluate 2).

(4) The amounts of IgG in the eluates 1 and 2 were determined by the measurement of absorbance at 280 nm described in Example 60, and percentages of IgG elution in the eluates with various pHs were determined on the basis of the following equation 1:

$$R=A/(A+B)\times 100 \qquad (1)$$

In the equation 1,
R: percentage of IgG elution (%)
A: amount of IgG in eluate 1
B: amount of IgG in eluate 2

Figure 25:
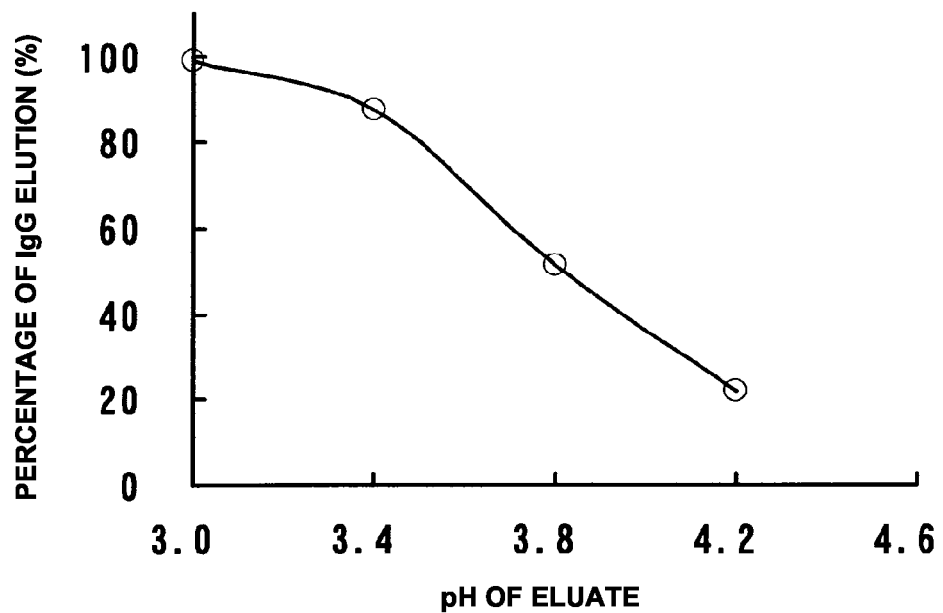
FIG. 25 is a graph for evaluating the antibody elution of the Fc binding protein (FcRm19)-immobilized gel.

As a result, the percentages of antibody elution at pHs of 3.0, 3.4, 3.8, and 4.2 were 99.1%, 87.4%, 51.3%, and 22.0%, respectively. FIG. 25 shows the results of percentages of antibody elution at each pH.

Example 62

Immobilization of Fc Binding Protein (FcRm32) in Gel (1) An Fc binding protein FcRm32 was prepared using the transformant produced in Example 13 by the method described in Example 9

(2) 0.3 mL of the obtained 8.1 mg/mL Fc binding protein (FcRm32) solution and 0.1 mL of Toyopearl gel (Tosoh Corp.) with an epoxy group introduced were mixed, and a potassium phosphate buffer was added so that the final concentration was 1.0 M, to cause a reaction at 20° C. for 14 hours.

(3) After the reaction, a reaction residue was removed from the gel by filtration through a filter (pore size: 10 µm), and the gel was washed with 20 mM PBS (pH 7.0) to prepare a gel with immobilized FcRm32.

(4) The amount of FcRm32 as the reaction residue was determined by the Bradford method, and an immobilization rate was calculated by dividing the amount by the amount of charged Fc binding protein.

As a result, an immobilization rate of 79.3% and an amount of immobilized FcRm32 per mL of the gel of 19.3 mg were confirmed.

Example 63

Evaluation of Adsorption of Antibody in Gel with Immobilized Fc Binding Protein (FcRm32)

(1) 0.5 mL of 10 mg/mL IgG dissolved in 20 mM PBS (pH 7.0) was added to 0.1 mL of the gel with immobilized Fc binding protein (FcRm32) prepared in Example 62 followed by shaking at 15° C. for 1 hour.

(2) After the shaking, the IgG solution was removed from the gel by filtration through a filter (pore size: 10 µm), and the gel was washed with 0.2 mL of 20 mM PBS (pH 7.0) five times.

(3) The gel was finally rinsed with 0.2 mL of 100 mM citric acid buffer (pH 3.0) three times to elute the IgG adsorbed by the gel.

The amount of eluted IgG was determined to be 1.98 mg by the measurement of absorbance at 280 nm described in Example 60. As a result, the amount of adsorbed IgG per mL of the gel with immobilized FcRm32 prepared in Example 62 was confirmed to be 19.8 mg.

Example 64

Evaluation of Elution of Antibody from Gel with Immobilized Fc Binding Protein (FcRm32)

(1) A column was packed with 0.1 mL of the gel with immobilized Fc binding protein (FcRm32) prepared in Example 62, and 3 mg/mL IgG (KAKETSUKEN) dissolved in 2 mL of 20 mM PBS (pH 7.0) was passed through the column to adsorb IgG by the gel.

(2) The column was sufficiently washed with 20 mM PBS (pH 7.0), and 2 mL of 100 mM citric acid buffer having an arbitrary pH within a range of 3.0 to 4.2 was passed through the column to elute IgG (referred to as an eluate 1).

(3) 2 mL of 100 mM citric acid buffer (pH 3.0) was finally passed to completely elute the IgG adsorbed by the gel (referred to as an eluate 2).

(4) The amounts of IgG in the eluates 1 and 2 were determined by the measurement of absorbance at 280 nm described in Example 60, and percentages of IgG elution in the eluates with various pHs were determined on the basis of the equation 1 described in Example 61.

Figure 26:
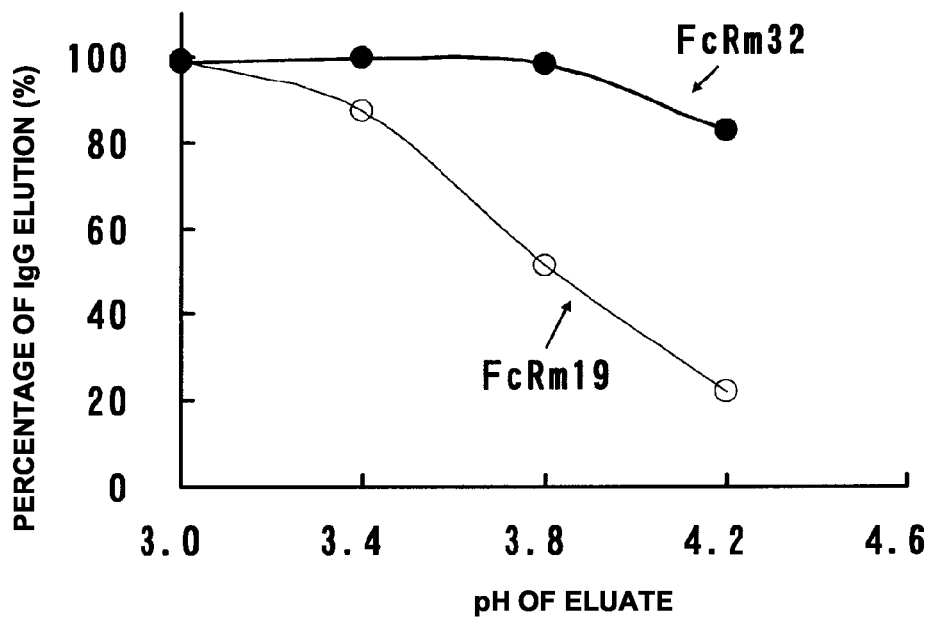
FIG. 26 is a graph for evaluating the antibody elution of the Fc binding protein (FcRm32)-immobilized gel.

As a result, the percentages of antibody elution at pHs of 3.0, 3.4, 3.8, and 4.2 were 98.7%, 99.3%, 97.9%, and 82.8%, respectively. The elution of IgG in a buffer having higher pH (more neutral) was confirmed to be largely improved as compared with the evaluation of elution of an antibody in the gel with immobilized FcRm19 carried out in Example 59. FIG. 26 shows a comparison of percentages of antibody elution in the gel with immobilized FcRm32 at each pH with those in the gel with immobilized FcRm19.

Example 65

Immobilization of Fc Binding Protein (FcRm36b) in Gel (1) An Fc binding protein FcRm36b was prepared using the transformant produced in Example 18 by the method described in Example 9.

(2) 0.1 mL of obtained 15.5 mg/mL FcRm36b solution and 0.05 mL of Toyopearl gel (Tosoh Corp.) with epoxy groups introduced were mixed, and a potassium phosphate buffer was added so that the final concentration was 0.8 M, to cause a reaction at 35° C. for 5 hours.

(3) After the reaction, a reaction residue was removed from the gel by filtration through a filter (pore size: 10 µm), and the gel was washed with 20 mM PBS (pH 7.0) to prepare a gel with immobilized FcRm36b.

(4) The amount of the Fc binding protein as the reaction residue was determined by the Bradford method. An immobilization rate was calculated by dividing the amount by the amount of charged Fc binding protein.

As a result, an immobilization rate of 67.7% and an amount of immobilized FcRm36b per mL of the gel of 21.0 mg were confirmed.

Example 66

Evaluation of Adsorption of Antibody in Gel with immobilized Fc Binding Protein (FcRm36b)

(1) 0.5 mL of 10 mg/mL IgG dissolved in 20 mM PBS (pH 7.0) was added to 0.05 mL of the gel with immobilized Fc binding protein (FcRm36b) prepared in Example 65 followed by shaking at 15° C. for 1 hour.

(2) After the shaking, the IgG solution was removed from the gel by filtration through a filter (pore size: 10 μm), and the gel was washed with 0.2 mL of 20 mM PBS (pH 7.0) five times.

(3) The gel was finally rinsed with 0.2 mL of 100 mM citric acid buffer (pH 3.0) three times to elute the IgG adsorbed by the gel.

The amount of eluted IgG was determined to be 1.44 mg by the measurement of absorbance at 280 nm described in Example 60. As a result, the amount of adsorbed IgG per mL of the gel with immobilized FcRm36b prepared in Example 65 was confirmed to be 28.8 mg.

Example 67

Evaluation of Elution of Antibody from Gel with Immobilized Fc Binding Protein (FcRm36b)

(1) A column was packed with 0.05 mL of the gel with immobilized Fc binding protein (FcRm36b) prepared in Example 65, and 3 mg/mL IgG (KAKETSUKEN) dissolved in 2 mL of 20 mM PBS (pH 7.0) was passed through the column to allow the gel to adsorb IgG.

(2) The column was sufficiently washed with 20 mM PBS (pH 7.0), and 2 mL of 100 mM citric acid buffer having an arbitrary pH within a range of 3.0 to 4.2 was passed through the column to elute IgG (referred to as an eluate 1).

(3) 2 mL of 100 mM citric acid buffer (pH 3.0) was finally passed to completely elute the IgG adsorbed by the gel (referred to as an eluate 2).

(4) The amounts of IgG in the eluates 1 and 2 were determined by the measurement of absorbance at 280 nm described in Example 60, and percentages of IgG elution in the eluates with various pHs were determined on the basis of the equation 1 described in Example 61.

Figure 27:
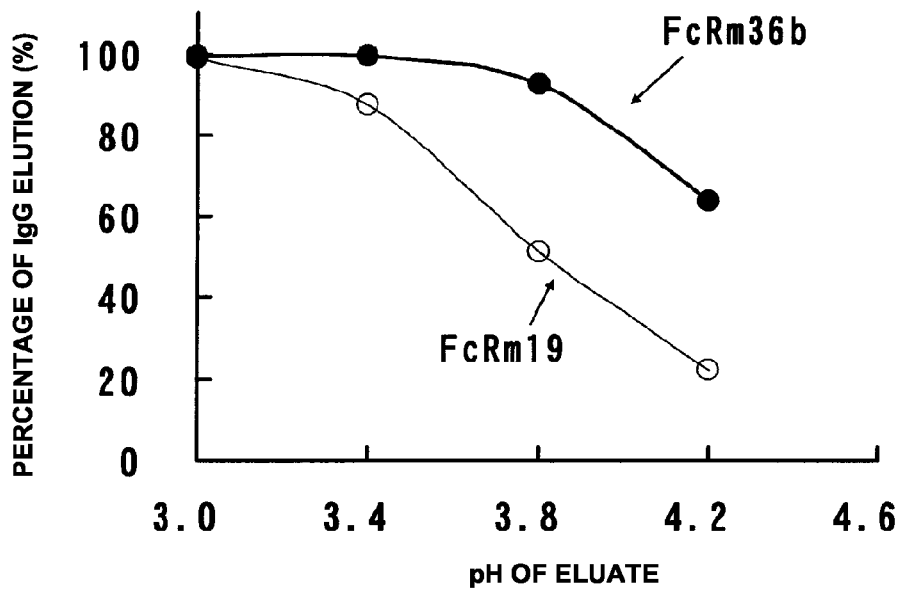
FIG. 27 is a graph for evaluating the antibody elution of the Fc binding protein (FcRm36b)-immobilized gel.

As a result, the percentages of antibody elution at pHs of 3.0, 3.4, 3.8, and 4.2 were 99.5%, 99.4%, 92.2%, and 64.0%, respectively. As a result, the elution of IgG in a buffer having higher pH (more neutral) was confirmed to be largely improved as compared with the evaluation of elution of an antibody in the gel with immobilized FcRm19 carried out in Example 59. FIG. 27 shows a comparison of percentages of antibody elution in the gel with immobilized FcRm36b at each pH with those in the gel with immobilized FcRm19.

Example 68

Immobilization of Fc Binding Protein (FcRm48) in Gel (1) An Fc binding protein FcRm48 was prepared using the transformant produced in Example 28 by the method described in Example 9.

(2) 0.1 mL of obtained 8.8 mg/mL FcRm48 solution and 0.05 mL of Toyopearl gel (Tosoh Corp.) with epoxy groups introduced were mixed, and a potassium, phosphate buffer was added so that the final concentration was 0.8 M, to cause a reaction at 35° C. for 5 hours.

(3) After the reaction, a reaction residue was removed from the gel by filtration through a filter (pore size: 10 μm), and the gel was washed with 20 mM PBS (pH 7.0) to prepare a gel with immobilized Fc binding protein (FcRm48).

(4) The amount of an Fc binding protein as the reaction residue was determined by the Bradford method, and an immobilization rate was calculated by dividing the amount by the amount of charged Fc binding protein.

As a result, an immobilization rate of 77.3% and an amount of immobilized FcRm48 per mL of the gel of 13.6 mg were confirmed.

Example 69

Evaluation of Adsorption of Antibody in Gel with Immobilized Fc Binding Protein (FcRm48)

(1) 0.5 mL of 10 mg/mL IgG dissolved in 20 mM PBS (pH 7.0) was added to 0.05 mL of the gel with immobilized Fc binding protein (FcRm48) prepared in Example 68 followed by shaking at 15° C. for 1 hour.

(2) After that, the IgG solution was removed from the gel by filtration through a filter (pore size: 10 μm), and the gel was washed with 0.2 mL of 20 mM PBS (pH 7.0) five times.

(3) The gel was finally rinsed with 0.2 mL of 100 mM citric acid buffer (pH 3.0) three times to elute the IgG adsorbed by the gel.

The amount of eluted IgG was determined to be 0.94 mg by the measurement of absorbance at 280 nm described in Example 60. As a result, the amount of adsorbed IgG per mL of the gel with immobilized FcRm48 prepared in Example 68 was confirmed to be 18.8 mg.

Example 70

Evaluation of Elution of Antibody from Gel with Immobilized Fc Binding Protein (FcRm48)

(1) A column was packed with 0.05 mL of the gel with immobilized Fc binding protein (FcRm48) prepared in Example 68, and 3 mg/mL IgG (KAKETSUKEN) dissolved in 2 mL of 20 mM PBS (pH 7.0) was passed through the column to allow the gel to adsorb IgG.

(2) The column was sufficiently washed with 20 mM PBS (pH 7.0), and 2 mL of 100 mM citric acid buffer having an arbitrary pH within a range of 3.0 to 4.2 was passed through the column to elute IgG (referred to as an eluate 1).

(3) 2 mL of 100 mM citric acid buffer (pH 3.0) was finally passed to completely elute the IgG adsorbed by the gel (referred to as an eluate 2).

(4) The amounts of IgG in the eluates 1 and 2 were determined by the measurement of absorbance at 280 nm described in Example 60, and a percentage of IgG elution in the eluates with various pHs was determined on the basis of the equation 1 described in Example 61.

Figure 28:
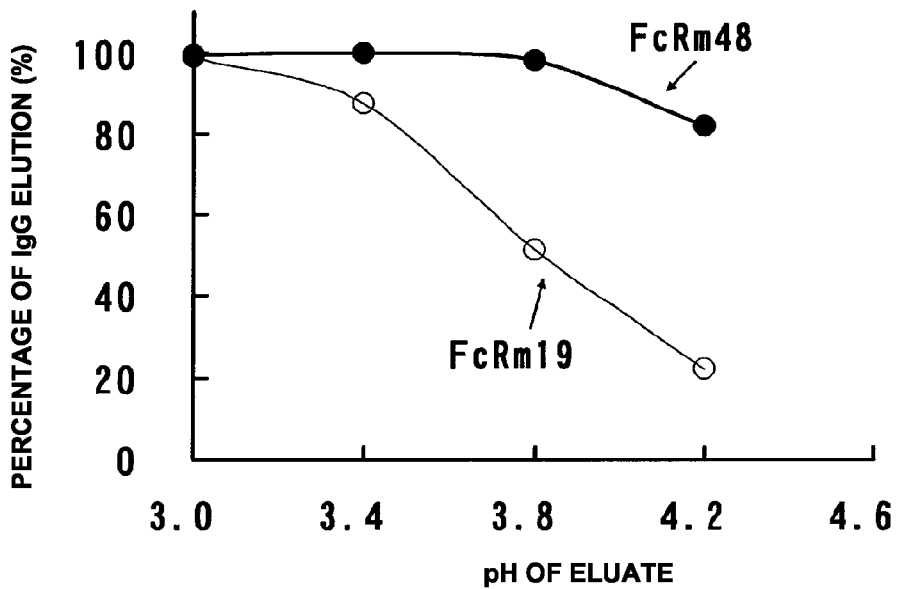
FIG. 28 is a graph for evaluating the antibody elution of the Fc binding protein (FcRm48)-immobilized gel.

As a result, the percentages of antibody elution at pHs of 3.0, 3.4, 3.8, and 4.2 were 99.2%, 100.0%, 98.2%, and 81.9%, respectively. As a result, the elution of IgG in a buffer having higher pH (more neutral) was confirmed to be largely improved as compared with the evaluation of elution of an antibody in the gel with immobilized FcRm19 carried out in Example 59. FIG. 28 shows a comparison of percentages of antibody elution in the gel with immobilized FcRm48 at each pH with those in the gel with immobilized FcRm19.

Example 71

Immobilization of Fc Binding Protein (FcRm56b) in Gel (1) An Fc binding protein FcRm56b was prepared using the transformant produced in Example 38 by the method described in Example 9.

(2) 1.0 mL of obtained 13.2 mg/mL FcRm56b solution and 0.5 mL of Toyopearl gel (Tosoh Corp.) with epoxy groups introduced were mixed, and a potassium phosphate buffer was added so that the final concentration was 0.8 M, to cause a reaction at 35° C. for 5 hours.

(3) After the reaction, a reaction residue was removed from the gel by filtration through a filter (pore size: 10 μm), and the gel was washed with 20 mM PBS (pH 7.0) to prepare a gel with immobilized Fc binding protein (FcRm56b).

(4) The amount of an Fc binding protein as the reaction residue was determined by the Bradford method. An immobilization rate was calculated by dividing the amount by the amount of charged Fc binding protein.

As a result, an immobilization rate of 70.8% and an amount of immobilized FcRm56b per mL of the gel of 18.7 mg were confirmed.

Example 72

Evaluation of Adsorption of Antibody in Gel with Immobilized Fc Binding Protein (FcRm56b)

(1) 3.0 mL of 10 mg/mL IgG dissolved in 20 mM PBS (pH 7.0) was added to 0.5 mL of the gel with immobilized Fc binding protein (FcRm56b) prepared in Example 71 followed by shaking at 15° C. for 1 hour.

(2) After the shaking, the IgG solution was removed from the gel by filtration through a filter (pore size: 10 μm), and the gel was washed with 1.0 mL of 20 mM PBS (pH 7.0) five times.

(3) The gel was finally rinsed with 1.0 mL of 100 mM citric acid buffer (pH 3.0) three times to elute the IgG adsorbed by the gel.

The amount of eluted IgG was determined to be 11.5 mg by the measurement of absorbance at 280 nm described in Example 60. As a result, the amount of adsorbed IgG per mL of the gel with immobilized FcRm56b prepared in Example 71 was confirmed to be 23.0 mg.

Example 73

Evaluation of Elution of Antibody from Gel with Immobilized Fc Binding Protein (FcRm56b)

(1) A column was packed with 0.1 mL of the gel with immobilized Fc binding protein (FcRm56b) prepared in Example 71, and 3 mg/mL IgG (KAKETSUKEN) dissolved in 2 mL of 20 mM PBS (pH 7.0) was passed through the column to allow the gel to adsorb IgG.

(2) The column was sufficiently washed with 20 mM PBS (pH 7.0), and 2 mL of 100 mM citric acid buffer having an arbitrary pH within a range of 3.0 to 4.2 was passed through the column to elute IgG (referred to as an eluate 1).

(3) 2 mL of 100 mM citric acid buffer (pH 3.0) was finally passed to completely elute the IgG adsorbed by the gel (referred to as an eluate 2).

(4) The amounts of IgG in the eluates 1 and 2 were determined by the measurement of absorbance at 280 nm described in Example 60, and percentages of IgG elution in the eluates with various pHs were determined on the basis of the equation 1 described in Example 61.

Figure 29:
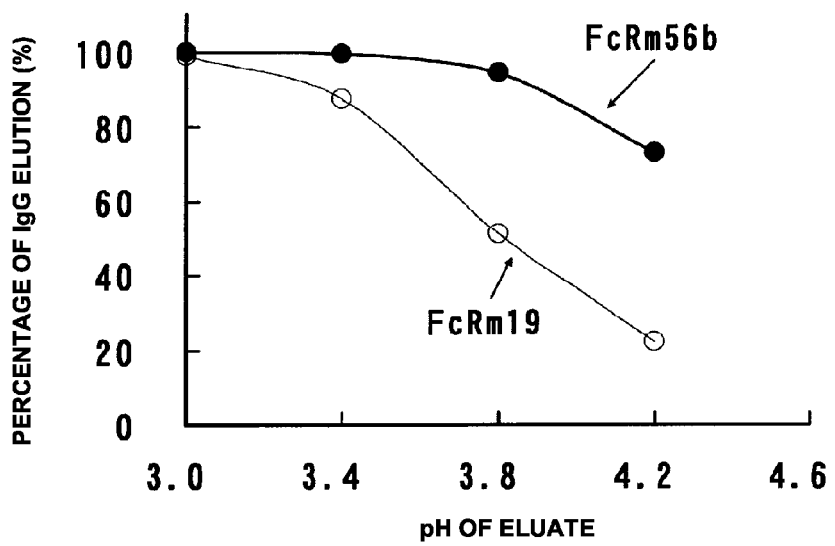
FIG. 29 is a graph for evaluating the antibody elution of the Fc binding protein (FcRm56b)-immobilized gel.

As a result, the percentages of antibody elution at pHs of 3.0, 3.4, 3.8, and 4.2 were 99.7%, 99.5%, 94.5%, and 73.0%, respectively. As a result, the elution of IgG in a buffer having higher pH (more neutral) was confirmed to be largely improved as compared with the evaluation of elution of an antibody in the gel with immobilized FcRm19 carried out in Example 59. FIG. 29 shows a comparison of percentages of antibody elution in the gel with immobilized FcRm56b at each pH with those in the gel with immobilized FcRm19.

Example 74

Immobilization of Fc Binding Protein (FcRm57b) in Gel (1) An Fc binding protein FcRm57b was prepared using the transformant produced in Example 43 by the method described in Example 9.

(2) 1.0 mL of obtained 8.9 mg/mL FcRm57b solution and 0.4 mL of Toyopearl gel (Tosoh Corp.) with epoxy groups introduced were mixed, and a potassium phosphate buffer was added so that the final concentration was 0.8 M, to cause a reaction at 35° C. for 5 hours.

(3) After the reaction, a reaction residue was removed from the gel by filtration through a filter (pore size: 10 μm), and the gel was washed with 20 mM PBS (pH 7.0) to prepare a gel with immobilized Fc binding protein (FcRm57b).

(4) The amount of an Fc binding protein as the reaction residue was determined by the Bradford method. An immobilization rate was calculated by dividing the amount by the amount of charged Fc binding protein.

As a result, an immobilization rate of 64.0% and an amount of immobilized FcRm57b per mL of the gel of 14.2 mg were confirmed.

Example 75

Evaluation of Adsorption of Antibody in Gel with Immobilized Fc Binding Protein (FcRm57b)

(1) 3.0 mL of 10 mg/mL IgG dissolved in 20 mM PBS (pH 7.0) was added to 0.4 mL of the gel with immobilized Fc binding protein (FcRm57b) prepared in Example 74 followed by shaking at 15° C. for 1 hour.

(2) After that, the IgG solution was removed from the gel by filtration through a filter (pore size: 10 μm), and the gel was washed with 1.0 mL of 20 mM PBS (pH 7.0) five times.

(3) The gel was finally rinsed with 1.0 mL of 100 mM citric acid buffer (pH 3.0) three times to elute the IgG adsorbed by the gel.

The amount of eluted IgG was determined to be 6.67 mg by the measurement of absorbance at 280 nm described in Example 60. As a result, the amount of adsorbed IgG per mL of the gel with immobilized FcRm56b prepared in Example 74 was confirmed to be 16.7 mg.

Example 76

Evaluation of Elution of Antibody from Gel with Immobilized Fc Binding Protein (FcRm57b)

(1) A column was packed with 0.1 mL of the gel with immobilized Fc binding protein (FcRm57b) prepared in Example 74, and 3 mg/mL IgG (KAKETSUKEN) dissolved in 2 mL of 20 mM PBS (pH 7.0) was passed through the column to allow the gel to adsorb IgG.

(2) The column was sufficiently washed with 20 mM PBS (pH 7.0), and 2 mL of 100 mM citric acid buffer having an arbitrary pH within a range of 3.0 to 4.2 was passed through the column to elute IgG (referred to as an eluate 1).

(3) 2 mL of 100 mM citric acid buffer (pH 3.0) was finally passed to completely elute the IgG adsorbed by the gel (referred to as an eluate 2).

(4) The amounts of IgG in the eluates 1 and 2 were determined by the measurement of absorbance at 280 nm described in Example 60, and percentages of IgG elution in the eluates with various pHs were determined on the basis of the equation 1 described in Example 61.

Figure 30:
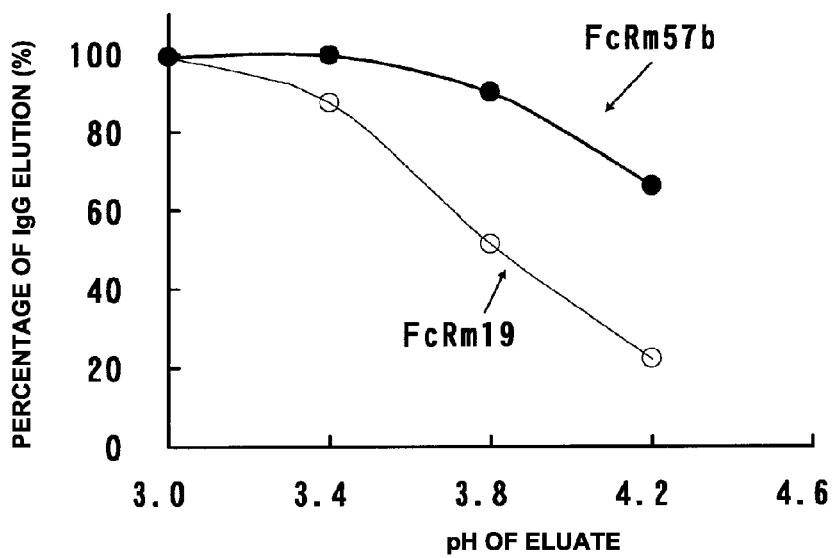
FIG. 30 is a graph for evaluating the antibody elution of the Fc binding protein (FcRm57b)-immobilized gel.

As a result, the percentages of antibody elution at pHs of 3.0, 3.4, 3.8, and 4.2 were 99.3%, 99.6%, 90.2%, and 66.2%, respectively. As a result, the elution of IgG in a buffer having higher pH (more neutral) was confirmed to be largely improved as compared with the evaluation of elution of an antibody in the gel with immobilized FcRm19 carried out in Example 59. FIG. 30 shows a comparison of percentages of antibody elution in the gel with immobilized FcRm57b at each pH with those in the gel with immobilized FcRm19.

Example 77

Evaluation of Stability of Fc Binding Protein (FcRm32, FcRm36b, and FcRm56b) Against Alkali (1) Each of the gels with immobilized Fc binding proteins produced in Examples 62, 65, and 71 was diluted with 20 mM PBS (pH 7.0) to make a 20% slurry. 50 µL of each slurry was dispensed in each of four spin columns with filter (micro bio-spin column, BioRad).

(2) In three of the columns produced in (1), PBS was removed from the gel slurry by filtration through a filter, the gel was washed with 0.15 mL of 0.1 M sodium hydroxide solution one time, and 0.15 mL of sodium hydroxide solution was added again.

(3) After the columns were each allowed to stand at 20° C. for 1 hour, 3 hours, and 24 hours, the columns were washed with 0.2 mL of 20 mM PBS (PH 7.0) three times.

(4) To each of the resulting columns (alkali-treating time: 0, 1, 3, and 24 hours), 10 mg/mL IgG (KAKETSUKEN) dissolved in 20 mM PBS (pH 7.0) was added followed by shaking at 15° C. for 1 hour.

(5) After the shaking, the IgG solution was removed from the respective gels by filtration through a filter, and the respective gels were washed with 0.2 mL of 20 mM PBS (pH 7.0) five times.

(6) The respective gels were finally rinsed with 0.1 mL of 100 mM citric acid buffer (pH 3.0) three times to elute the IgG adsorbed by the respective gels.

(7) The amount of eluted IgG was determined by the measurement of absorbance at 280 nm described in Example 60 to calculate the amount of adsorbed IgG in each gel.

Figure 31:
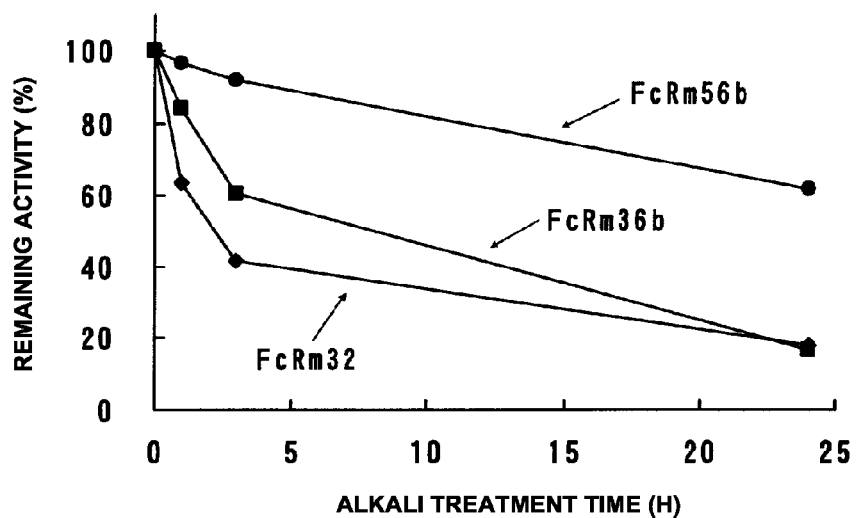
FIG. 31 is a graph for evaluating the alkali stability of the Fc binding protein (FcRm32, FcRm36b, FcRm56b)-immobilized gels.

When the amount of bound IgG in a gel not alkali-treated was assumed to be 100% activity, those in the gel with immobilized FcRm32 (Example 62) which had been treated for 1, 3, and 24 hours were 63.6%, 41.8%, and 18.2%, respectively. Those in the gel with immobilized FcRm36b (Example 65) which had been treated for 1, 3, and 24 hours were 84.2%, 60.4%, and 16.8%, respectively. Those in the gel with immobilized FcRm56b (Example 71) which had been treated for 1, 3, and 24 hours were 96.8%, 92.1%, and 61.9%, respectively. This reveals that the stability against alkali is improved by Fc binding proteins accumulating amino acid substitutions (mutations) involved in improved stability. FIG. 31 shows the results of stability of the gel with each immobilized Fc binding protein against alkali.

Example 78

Evaluation of Repeated Stability of Gel with Immobilized Fc Binding Protein (FcRm56b)

A column was packed with 0.2 mL of the gel with immobilized Fc binding protein (FcRm56b) prepared in Example 71, and buffers were passed repeatedly through a cycle shown in Table 23. Further, buffers and an IgG solution were passed at first, 30th, 50th, 70th, 90th, 110th, 130th, and 150th passings through a cycle shown in Table 24, and the amount of adsorbed IgG in the column was calculated.

TABLE 23

| Name of solution | Amount passed | Flow rate |
| --- | --- | --- |
| 20 mM PBS (pH 7.2) | 1.0 mL | 0.5 mL/min |
| 100 mM Citric acid buffer (pH 3.5) | 2.0 mL | 0.5 mL/min |
| 20 mM PBS (pH 7.2) | 1.0 mL | 0.5 mL/min |
| 100 mM NaOH | 3.0 mL | 0.2 mL/min |
| H$_2$O | 1.0 mL | 0.5 mL/min |
| 20 mM PBS (pH 7.2) | 2.0 mL | 0.5 mL/min |

TABLE 24

| Name of solution | Amount passed | Flow rate |
| --- | --- | --- |
| 20 mM PBS (pH 7.2) | 0.4 mL | 0.5 mL/min |
| 3 mg/mL IgG in 20 mM PBS (pH 7.2) | 2.0 mL | 0.5 mL/min |
| 20 mM PBS (pH 7.2) | 3.0 mL | 0.5 mL/min |
| 100 mM Citric acid buffer (pH 3.5) | 2.0 mL | 0.5 mL/min |
| 100 mM NaOH | 3.0 mL | 0.2 mL/min |
| H$_2$O | 1.0 mL | 0.5 mL/min |
| 20 mM PBS (pH 7.2) | 0.8 mL | 0.5 mL/min |

Measurement was carried out with time. When the amount of adsorbed IgG at the first passing is assumed to be 100%, the amount of adsorbed IgG in the column at 30th, 50th, 70th, 90th, 110th, 130th, and 150th passings are 98.9%, 94.7%, 89.0%, 84.9%, 84.9%, 80.2%, and 80.7%, respectively.

Figure 32:
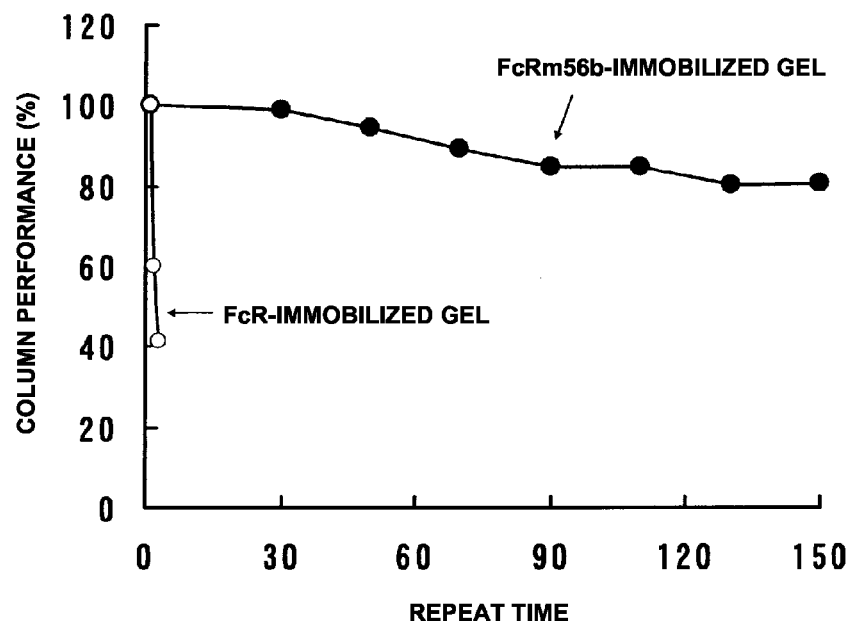
FIG. 32 is a graph for evaluating the repeat stability of the Fc binding protein (FcRm56b)-immobilized gel.

As a comparative example, a wild-type Fc binding protein (FcR) was prepared using the transformant prepared in Example 2 by the method described in Example 9, FcR was immobilized in 0.2 mL of gel in the same manner as in Example 59, and a column was packed with the gel. Further, buffers and an IgG solution were passed through the column through the cycle shown in Table 24, and change of amount of adsorbed IgG in the column was confirmed. The amount of adsorbed IgG in the column was measured with time. When the amount of adsorbed IgG at the first passing is regarded as 100%, the amount decreases by 60.0% at the second passing and by 41.5% at the third passing. This shows that it is actually difficult that a gel with immobilized FcR is recycled by washing with alkali. FIG. 32 shows a comparison of repeatable stability of the gel with each immobilized Fc binding protein by washing with alkali.

The invention claimed is:

1. An Fc binding protein which comprises a human FcγRI α-chain region modified by substitution, wherein the unmodified human FcγRI a-chain region comprises residues 16-289 of SEQ ID NO: 1, and wherein said substitutions comprise substitution of phenylalanine at position 114 of SEQ ID NO: 1 with leucine.

2. An Fc binding protein, wherein said Fc binding protein comprises the amino acid sequence of residues 34 to 307 of any one of SEQ ID NOS: 2, 3, 4, 5, 114, 118, 130, 134, 148, 154, 164, 170, 174, and 176.

3. An Fc binding protein, wherein said Fc binding protein comprises the amino acid sequence of any one of SEQ ID NOS: 2, 3, 4, 5, 114, 118, 130, 134, 148, 154, 164, 170, 174, and 176.

4. An adsorbent for a protein containing an Fc binding protein binding site, the adsorbent obtained by immobilizing to a solid phase the Fc binding protein according to claim 1.

5. An antibody purification method comprising:
(1) adding a solution containing an antibody to an adsorbent, the adsorbent obtained by immobilizing to a solid phase an Fc binding protein, wherein said Fc binding protein comprises the amino acid sequence of any one of SEQ ID NOS: 114, 118, 130, 134, 148, 154, 164, 170, 174, and 176; and
(2) eluting the antibody adsorbed to the adsorbent with a buffer solution of pH 3.0 to pH 4.5.

6. An Fc binding protein which comprises a human FcγRI α-chain region modified by substitution, wherein the unmodified human FcγRI α-chain region comprises residues 16-289 of SEQ ID NO: 1, and wherein the substitution(s) are selected from the group consisting of (1) to (167), with the proviso that at least phenylalanine at position 114 of SEQ ID NO: 1 is substituted by leucine:

(1) threonine at position 20 of SEQ ID NO: 1 is substituted by proline;
(2) threonine at position 25 of SEQ ID NO: 1 is substituted by lysine;
(3) threonine at position 38 of SEQ ID NO: 1 is substituted by alanine or serine;
(4) leucine at position 46 of SEQ ID NO: 1 is substituted by arginine or proline;
(5) alanine at position 62 of SEQ ID NO: 1 is substituted by valine;
(6) threonine at position 63 of SEQ ID NO: 1 is substituted by isoleucine;
(7) serine at position 69 of SEQ ID NO: 1 is substituted by phenylalanine or threonine;
(8) arginine at position 71 of SEQ ID NO: 1 is substituted by histidine;
(9) valine at position 77 of SEQ ID NO: 1 is substituted by alanine or glutamic acid;
(10) asparagine at position 78 of SEQ ID NO: 1 is substituted by aspartic acid;
(11) aspartic acid at position 94 of SEQ ID NO: 1 is substituted by glutamic acid;
(12) isoleucine at position 100 of SEQ ID NO: 1 is substituted by valine;
(13) serine at position 110 of SEQ ID NO: 1 is substituted by asparagine;
(14) phenylalanine at position 114 of SEQ ID NO: 1 is substituted by leucine;
(15) histidine at position 125 of SEQ ID NO: 1 is substituted by arginine;
(16) leucine at position 131 of SEQ ID NO: 1 is substituted by arginine or proline;
(17) tryptophan at position 149 of SEQ ID NO: 1 is substituted by leucine;
(18) leucine at position 156 of SEQ ID NO: 1 is substituted by proline;
(19) isoleucine at position 160 of SEQ ID NO: 1 is substituted by methionine;
(20) asparagine at position 163 of SEQ ID NO: 1 is substituted by serine;
(21) asparagine at position 195 of SEQ ID NO: 1 is substituted by threonine;
(22) threonine at position 199 of SEQ ID NO: 1 is substituted by serine;
(23) asparagine at position 206 of SEQ ID NO: 1 is substituted by lysine, serine, or threonine;
(24) leucine at position 207 of SEQ ID NO: 1 is substituted by proline;
(25) leucine at position 218 of SEQ ID NO: 1 is substituted by valine;

(26) asparagine at position 240 of SEQ ID NO: 1 is substituted by aspartic acid;
(27) leucine at position 248 of SEQ ID NO: 1 is substituted by serine;
(28) leucine at position 283 of SEQ ID NO: 1 is substituted by histidine;
(29) leucine at position 285 of SEQ ID NO: 1 is substituted by glutamine;
(30) valine at position 17 of SEQ ID NO: 1 is substituted by glycine or glutamic acid;
(31) threonine at position 19 of SEQ ID NO: 1 is substituted by isoleucine;
(32) threonine at position 20 of SEQ ID NO: 1 is substituted by isoleucine;
(33) threonine at position 25 of SEQ ID NO: 1 is substituted by methionine or arginine;
(34) glutamine at position 27 of SEQ ID NO: 1 is substituted by proline or lysine;
(35) glutamine at position 35 of SEQ ID NO: 1 is substituted by leucine, methionine, or arginine;
(36) glutamic acid at position 36 of SEQ ID NO: 1 is substituted by glycine;
(37) leucine at position 41 of SEQ ID NO: 1 is substituted by methionine;
(38) histidine at position 42 of SEQ ID NO: 1 is substituted by leucine;
(39) glutamic acid at position 44 of SEQ ID NO: 1 is substituted by aspartic acid;
(40) valine at position 45 of SEQ ID NO: 1 is substituted by alanine;
(41) leucine at position 46 of SEQ ID NO: 1 is substituted by alanine, asparagine, aspartic acid, glutamine, glycine, histidine, lysine, serine, or tryptophan;
(42) histidine at position 47 of SEQ ID NO: 1 is substituted by glutamine, leucine, or asparagine;
(43) proline at position 49 of SEQ ID NO: 1 is substituted by serine or alanine;
(44) glycine at position 50 of SEQ ID NO: 1 is substituted by arginine or glutamic acid;
(45) serine at position 51 of SEQ ID NO: 1 is substituted by alanine, threonine, leucine, proline, or valine;
(46) serine at position 52 of SEQ ID NO: 1 is substituted by glycine;
(47) serine at position 53 of SEQ ID NO: 1 is substituted by leucine, threonine, or proline;
(48) glutamine at position 55 of SEQ ID NO: 1 is substituted by arginine;
(49) phenylalanine at position 57 of SEQ ID NO: 1 is substituted by tyrosine;
(50) leucine at position 58 of SEQ ID NO: 1 is substituted by arginine;
(51) glycine at position 60 of SEQ ID NO: 1 is substituted by aspartic acid;
(52) threonine at position 61 of SEQ ID NO: 1 is substituted by alanine or serine;
(53) alanine at position 62 of SEQ ID NO: 1 is substituted by glutamic acid;
(54) threonine at position 63 of SEQ ID NO: 1 is substituted by leucine, or phenylalanine;
(55) glutamine at position 64 of SEQ ID NO: 1 is substituted by proline, histidine, leucine, or lysine;
(56) threonine at position 65 of SEQ ID NO: 1 is substituted by alanine or valine;
(57) serine at position 66 of SEQ ID NO: 1 is substituted by threonine;
(58) threonine at position 67 of SEQ ID NO: 1 is substituted by alanine or serine;
(59) serine at position 69 of SEQ ID NO: 1 is substituted by alanine;
(60) tyrosine at position 70 of SEQ ID NO: 1 is substituted by histidine or phenylalanine;
(61) arginine at position 71 of SEQ ID NO: 1 is substituted by tyrosine;
(62) threonine at position 73 of SEQ ID NO: 1 is substituted by alanine or serine;
(63) serine at position 74 of SEQ ID NO: 1 is substituted by phenylalanine;
(64) serine at position 76 of SEQ ID NO: 1 is substituted by asparagine;
(65) valine at position 77 of SEQ ID NO: 1 is substituted by aspartic acid or lysine;
(66) asparagine at position 78 of SEQ ID NO: 1 is substituted by serine or glycine;
(67) serine at position 80 of SEQ ID NO: 1 is substituted by alanine;
(68) arginine at position 84 of SEQ ID NO: 1 is substituted by serine;
(69) glycine at position 88 of SEQ ID NO: 1 is substituted by serine;
(70) leucine at position 89 of SEQ ID NO: 1 is substituted by glutamine or proline;
(71) serine at position 90 of SEQ ID NO: 1 is substituted by glycine;
(72) arginine at position 92 of SEQ ID NO: 1 is substituted by cysteine or leucine;
(73) isoleucine at position 96 of SEQ ID NO: 1 is substituted by valine or lysine;
(74) glutamine at position 97 of SEQ ID NO: 1 is substituted by leucine or lysine;
(75) histidine at position 101 of SEQ ID NO: 1 is substituted by leucine;
(76) arginine at position 102 of SEQ ID NO: 1 is substituted by serine or leucine;
(77) glycine at position 103 of SEQ ID NO: 1 is substituted by aspartic acid or serine;
(78) serine at position 111 of SEQ ID NO: 1 is substituted by alanine;
(79) threonine at position 115 of SEQ ID NO: 1 is substituted by isoleucine or phenylalanine;
(80) glutamic acid at position 118 of SEQ ID NO: 1 is substituted by aspartic acid;
(81) alanine at position 121 of SEQ ID NO: 1 is substituted by threonine or valine;
(82) lysine at position 128 of SEQ ID NO: 1 is substituted by arginine or glycine;
(83) aspartic acid at position 129 of SEQ ID NO: 1 is substituted by glycine;
(84) leucine at position 131 of SEQ ID NO: 1 is substituted by glutamine;
(85) tyrosine at position 133 of SEQ ID NO: 1 is substituted by histidine or arginine;
(86) asparagine at position 134 of SEQ ID NO: 1 is substituted by serine;
(87) tyrosine at position 137 of SEQ ID NO: 1 is substituted by phenylalanine;
(88) tyrosine at position 138 of SEQ ID NO: 1 is substituted by histidine;
(89) arginine at position 139 of SEQ ID NO: 1 is substituted by histidine;
(90) asparagine at position 140 of SEQ ID NO: 1 is substituted by aspartic acid;
(91) glycine at position 141 of SEQ ID NO: 1 is substituted by aspartic acid or valine;

(92) lysine at position 142 of SEQ ID NO: 1 is substituted by glutamic acid or arginine;
(93) phenylalanine at position 144 of SEQ ID NO: 1 is substituted by isoleucine;
(94) phenylalanine at position 147 of SEQ ID NO: 1 is substituted by serine;
(95) histidine at position 148 of SEQ ID NO: 1 is substituted by arginine or glutamine;
(96) tryptophan at position 149 of SEQ ID NO: 1 is substituted by arginine;
(97) serine at position 151 of SEQ ID NO: 1 is substituted by threonine;
(98) asparagine at position 152 of SEQ ID NO: 1 is substituted by threonine, isoleucine, or proline;
(99) threonine at position 154 of SEQ ID NO: 1 is substituted by serine;
(100) leucine at position 156 of SEQ ID NO: 1 is substituted by histidine;
(101) lysine at position 157 of SEQ ID NO: 1 is substituted by arginine;
(102) asparagine at position 159 of SEQ ID NO: 1 is substituted by threonine or aspartic acid;
(103) isoleucine at position 160 of SEQ ID NO: 1 is substituted by threonine, valine, or leucine;
(104) serine at position 161 of SEQ ID NO: 1 is substituted by threonine;
(105) threonine at position 165 of SEQ ID NO: 1 is substituted by methionine;
(106) methionine at position 171 of SEQ ID NO: 1 is substituted by threonine;
(107) lysine at position 173 of SEQ ID NO: 1 is substituted by arginine;
(108) histidine at position 174 of SEQ ID NO: 1 is substituted by glutamine;
(109) threonine at position 177 of SEQ ID NO: 1 is substituted by serine;
(110) isoleucine at position 181 of SEQ ID NO: 1 is substituted by threonine;
(111) serine at position 182 of SEQ ID NO: 1 is substituted by threonine, leucine, valine, or glutamic acid;
(112) threonine at position 184 of SEQ ID NO: 1 is substituted by serine;
(113) proline at position 190 of SEQ ID NO: 1 is substituted by serine;
(114) valine at position 193 of SEQ ID NO: 1 is substituted by leucine;
(115) asparagine at position 195 of SEQ ID NO: 1 is substituted by alanine;
(116) alanine at position 196 of SEQ ID NO: 1 is substituted by serine;
(117) valine at position 198 of SEQ ID NO: 1 is substituted by glycine or methionine;
(118) threonine at position 199 of SEQ ID NO: 1 is substituted by alanine;
(119) serine at position 200 of SEQ ID NO: 1 is substituted by glycine or arginine;
(120) leucine at position 202 of SEQ ID NO: 1 is substituted by methionine;
(121) leucine at position 203 of SEQ ID NO: 1 is substituted by histidine, glutamine, tyrosine, arginine, or proline;
(122) glutamic acid at position 204 of SEQ ID NO: 1 is substituted by valine;
(123) leucine at position 207 of SEQ ID NO: 1 is substituted by glutamine, histidine, or arginine;
(124) threonine at position 209 of SEQ ID NO: 1 is substituted by alanine;
(125) serine at position 211 of SEQ ID NO: 1 is substituted by arginine or glycine;
(126) glutamic acid at position 213 of SEQ ID NO: 1 is substituted by valine or isoleucine;
(127) lysine at position 215 of SEQ ID NO: 1 is substituted by arginine or glutamic acid;
(128) leucine at position 217 of SEQ ID NO: 1 is substituted by arginine or glutamine;
(129) leucine at position 218 of SEQ ID NO: 1 is substituted by isoleucine, methionine, or lysine;
(130) glutamine at position 219 of SEQ ID NO: 1 is substituted by proline or arginine;
(131) leucine at position 223 of SEQ ID NO: 1 is substituted by arginine, glutamine, or methionine;
(132) glutamine at position 224 of SEQ ID NO: 1 is substituted by arginine;
(133) leucine at position 225 of SEQ ID NO: 1 is substituted by glutamine;
(134) phenylalanine at position 227 of SEQ ID NO: 1 is substituted by isoleucine;
(135) tyrosine at position 230 of SEQ ID NO: 1 is substituted by histidine or phenylalanine;
(136) methionine at position 231 of SEQ ID NO: 1 is substituted by lysine or arginine;
(137) serine at position 233 of SEQ ID NO: 1 is substituted by glycine or asparagine;
(138) lysine at position 234 of SEQ ID NO: 1 is substituted by glutamic acid;
(139) asparagine at position 240 of SEQ ID NO: 1 is substituted by glycine;
(140) glutamic acid at position 244 of SEQ ID NO: 1 is substituted by valine;
(141) tyrosine at position 245 of SEQ ID NO: 1 is substituted by histidine or glutamic acid;
(142) glutamine at position 246 of SEQ ID NO: 1 is substituted by arginine or lysine;
(143) leucine at position 248 of SEQ ID NO: 1 is substituted by isoleucine;
(144) threonine at position 249 of SEQ ID NO: 1 is substituted by alanine or serine;
(145) alanine at position 250 of SEQ ID NO: 1 is substituted by valine;
(146) arginine at position 251 of SEQ ID NO: 1 is substituted by serine;
(147) arginine at position 252 of SEQ ID NO: 1 is substituted by histidine;
(148) glutamic acid at position 253 of SEQ ID NO: 1 is substituted by glycine;
(149) leucine at position 257 of SEQ ID NO: 1 is substituted by arginine or glutamine;
(150) glutamic acid at position 261 of SEQ ID NO: 1 is substituted by valine or alanine;
(151) alanine at position 262 of SEQ ID NO: 1 is substituted by valine;
(152) alanine at position 263 of SEQ ID NO: 1 is substituted by serine;
(153) threonine at position 264 of SEQ ID NO: 1 is substituted by serine;
(154) glutamic acid at position 265 of SEQ ID NO: 1 is substituted by alanine or glycine;
(155) asparagine at position 268 of SEQ ID NO: 1 is substituted by serine, isoleucine, or threonine;
(156) leucine at position 270 of SEQ ID NO: 1 is substituted by histidine, arginine, or valine;
(157) lysine at position 271 of SEQ ID NO: 1 is substituted by arginine;

(158) arginine at position 272 of SEQ ID NO: 1 is substituted by glutamine;
(159) glutamic acid at position 277 of SEQ ID NO: 1 is substituted by valine;
(160) glutamine at position 279 of SEQ ID NO: 1 is substituted by arginine or histidine;
(161) glycine at position 282 of SEQ ID NO: 1 is substituted by aspartic acid;
(162) leucine at position 283 of SEQ ID NO: 1 is substituted by proline;
(163) leucine at position 285 of SEQ ID NO: 1 is substituted by arginine or histidine;
(164) proline at position 286 of SEQ ID NO: 1 is substituted by glutamine, arginine, or glutamic acid;
(165) threonine at position 287 of SEQ ID NO: 1 is substituted by isoleucine, proline, alanine, or valine;
(166) proline at position 288 of SEQ ID NO: 1 is substituted by alanine, serine, or threonine; and
(167) valine at position 289 of SEQ ID NO: 1 is substituted by alanine, aspartic acid, glycine, leucine, or isoleucine.

\* \* \* \* \*